(12) United States Patent
Alonso-de Diego et al.

(10) Patent No.: US 10,519,162 B2
(45) Date of Patent: *Dec. 31, 2019

(54) 6,7-DIHYDROPYRAZOLO[1,5-a]PYRAZIN-4(5H)-ONE COMPOUNDS AND THEIR USE AS NEGATIVE ALLOSTERIC MODULATORS OF MGLUR2 RECEPTORS

(71) Applicant: Janssen Pharmaceutica NV, New Brunswick, NJ (US)

(72) Inventors: Sergio-Alvar Alonso-de Diego, Toledo (ES); Michiel Luc Maria Van Gool, Madrid (ES); Maria Luz Martin-Martin, Toledo (ES); Susana Conde-Ceide, Toledo (ES); José Ignacio Andrés-Gil, Madrid (ES); Óscar Delgado-González, Madrid (ES); Gary John Tresadern, Toledo (ES); Andrés Avelino Trabanco-Suárez, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,223

(22) Filed: May 10, 2018

(65) Prior Publication Data

US 2018/0258096 A1 Sep. 13, 2018

Related U.S. Application Data

(63) Continuation of application No. 15/500,319, filed as application No. PCT/EP2015/067572 on Jul. 30, 2015, now Pat. No. 10,005,785.

(30) Foreign Application Priority Data

Aug. 1, 2014 (EP) .................................... 14179600
Dec. 3, 2014 (EP) .................................... 14196083

(51) Int. Cl.
| | | |
|---|---|---|
| *A61K 31/4985* | (2006.01) | |
| *C07D 487/04* | (2006.01) | |
| *A61K 9/00* | (2006.01) | |
| *A61K 9/06* | (2006.01) | |
| *A61K 9/10* | (2006.01) | |
| *A61K 9/20* | (2006.01) | |
| *A61K 31/501* | (2006.01) | |
| *A61K 31/506* | (2006.01) | |

(52) U.S. Cl.
CPC .......... *C07D 487/04* (2013.01); *A61K 9/0019* (2013.01); *A61K 9/06* (2013.01); *A61K 9/10* (2013.01); *A61K 9/20* (2013.01); *A61K 31/4985* (2013.01); *A61K 31/501* (2013.01); *A61K 31/506* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| | | | |
|---|---|---|---|
| 9,392,612 B2 | 7/2016 | Kondo | |
| 9,527,831 B2 | 12/2016 | Brodney et al. | |
| 10,005,786 B2 | 6/2018 | Alonso-de Diego | |
| 2001/0011087 A1 | 8/2001 | Wehner et al. | |
| 2003/0027807 A1 | 2/2003 | Wehner et al. | |
| 2005/0107412 A1 | 5/2005 | Maw et al. | |
| 2013/0310555 A1 | 11/2013 | Chong | |

FOREIGN PATENT DOCUMENTS

| | | |
|---|---|---|
| EP | 0756200 B1 | 1/1997 |
| EP | 2327704 A1 | 6/2011 |
| EP | 2666775 A1 | 11/2013 |
| WO | 2002096873 A1 | 12/2002 |
| WO | 2005002552 A2 | 1/2005 |
| WO | 2005061507 A1 | 7/2005 |
| WO | 2006030847 A1 | 3/2006 |
| WO | 2006050803 A1 | 5/2006 |

(Continued)

OTHER PUBLICATIONS

International Search Report for PCT/EP2015/067533 dated Oct. 19, 2015.
International Search Report for PCT/EP2015/067572 dated Sep. 9, 2015.
International Search Report for PCT/EP2015/067534 dated Sep. 10, 2015.
International Search Report for PCT/EP2015/067538 dated Sep. 9, 2015.
International Search Report for PCT/US2015/067530, dated Nov. 2, 2015.
Alfonso R Gennaro, 18th edition Remington's—Pharmaceutical Sciences, 18th edition Remington's—Pharmaceutical Sciences, 1990, Part 8_ Pharmaceutical preparations and their Manufacture_ pp. 1435-1714, Part 8.

(Continued)

*Primary Examiner* — Douglas M Willis

(57) ABSTRACT

The present invention relates to novel 6,7-dihydropyrazolo [1,5-a]pyrazin-4(5H)-one derivatives of Formula (I)

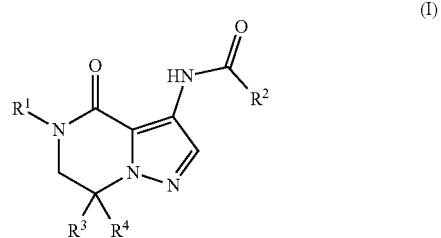

as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

20 Claims, 1 Drawing Sheet

(56) References Cited

FOREIGN PATENT DOCUMENTS

| WO | 2007084314 A2 | 7/2007 |
|---|---|---|
| WO | 2007092416 A2 | 8/2007 |
| WO | 2008001115 A2 | 1/2008 |
| WO | 2008141239 A1 | 11/2008 |
| WO | 2009095872 A2 | 8/2009 |
| WO | 2009/130232 A1 | 10/2009 |
| WO | 2009118292 A1 | 10/2009 |
| WO | 2010130423 A1 | 11/2010 |
| WO | 2010130424 | 11/2010 |
| WO | 2012035078 A1 | 3/2012 |
| WO | 2012062752 A1 | 5/2012 |
| WO | 2012083224 A1 | 6/2012 |
| WO | 2012143726 A1 | 10/2012 |
| WO | 2013012915 A1 | 1/2013 |
| WO | 2013012918 A1 | 1/2013 |
| WO | 2013066736 A1 | 5/2013 |
| WO | 2013154878 A1 | 10/2013 |
| WO | 2013156869 A1 | 10/2013 |
| WO | 2013174822 A1 | 11/2013 |
| WO | 2013192343 A1 | 12/2013 |
| WO | 2013192347 A1 | 12/2013 |
| WO | 2013192350 A1 | 12/2013 |
| WO | 2014064028 A1 | 5/2014 |
| WO | 2014/207082 A1 | 12/2014 |
| WO | 2014195311 A1 | 12/2014 |
| WO | 016380 | 2/2016 |
| WO | 016395 A1 | 2/2016 |
| WO | 2016016381 A1 | 2/2016 |
| WO | 2016016382 A1 | 2/2016 |
| WO | 2016016383 A1 | 2/2016 |
| WO | WO 16/016395 * | 2/2016 |
| WO | 2016087487 A1 | 6/2016 |
| WO | 2016087489 A1 | 6/2016 |
| WO | 2017103179 A1 | 6/2017 |
| WO | 2017103182 A1 | 6/2017 |

OTHER PUBLICATIONS

Alper R. et al, Agonist-Stimulated [35S]GTBgS Binding, Current Protocols in Pharmacology, 1998, suppl.2.
Celia Goeldner, Cognitive impairment in major depression and the mGlu2 receptor as a therapeutic target, Neuropharmacology, Aug. 3, 2013, pp. 337-346, 64.
Cid Jose Maria et al, Discovery of 3-Cyclopropylmethyl-7-(4-phenylpiperidin-1-yl)-8-trifluoromethyl[1,2,4]triazolo[4,3-a]pyridine (JNJ-42153605): A Positive Allosteric Modulator of the Metabotropic Glutamate 2 Receptor, Journal of Medicinal Chemistry, Oct. 16, 2012, pp. 8770-8789, 55.
Dinklo Theo et al, Characterization of 2-[[4-Fluoro-3-(trifluoromethyl)phenyl]amino]-4-(4-pyridinyl)-5-thiazolemethanol (JNJ-1930942), a Novel Positive Allosteric Modulator of the 7 Nicotinic Acetylcholine Receptor S, The Journal of Pharmacology and Experimental Therapeutics, 2011, pp. 560-574, vol. 336 No. 2.
Embrechts S. et al, Longitudinal characterisation of the TauPS2APP mouse model of Alzheimer's disease in a two trial discrimination task of visuo-spatial recognition memory, 45th European Brain and Behaviour Society Meeting Sep. 6-9, 2013 Munich, Sep. 6, 2009, p. 202, not applicable.
Ferraguti,et al, Metabotropic glutamate receptors, Cell & Tissue Research, Jul. 18, 2006, pp. 483-504, 326.
Guy A. Higgins et al., Pharmacological manipulation of mGlu2 receptors influences, Neuropharmacology, 2004, pp. 907-917, vol. 46.
Hackam, et al, "Translation of Research Evidence From animals to Humans", JAMA, vol. 296 (14): pp. 1731-1732 (2006).
Hickinbottom, English translation of the relevent from reaction of organic complonents, Reactions of organic aompounds, 1939, pp. 360-362, Page Number.
Hiroyuki Koike et al, Role of BDNF/TrkB signaling in antidepressant-like effects of a group II metabotropic glutamate receptor antagonist in animal models of depression, Behavioural Brain Research, Oct. 23, 2012, pp. 48-52, 238.
Kelmendi et al, The role of the Glutamatergic system in the pathophysiology and treatment of mood disorders, Primary Psychiatry, Oct. 2006, pp. 80-86, vol. 13 No. 10.
Li Jingjie et al, Palladium-Catalyzed Oxidative Rearrangement of Tertiary Allylic Alcohols to Enones with Oxygen in Aqueous Solvent, Organic Letters, Oct. 3, 2014, pp. 5370-5373, No. 16.
Lynne Gilfillian et al, Synthesis and biological evaluation of novel 2,3-dihydro-1H-1,5-benzodiazepin-2-ones; potential imaging agents of the metabotropic glutamate 2 receptor, Med. Chem. Commun., May 29, 2013, pp. 1118-1123, vol. 4 Issue 7.
NCT01457677, View of NCT01457677 on Feb. 18, 2014, ClinicalTrials.gov Archive, Feb. 18, 2014, pp. 1-3, not applicable.
Niswender Colleen M. et al, Metabotropic Glutamate Receptors: Physiology, Pharmacology, and Disease, Annu.Rev.Pharmacol. Toxicol., 2010, pp. 295-322, 50.
Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.
Serena Bigotti et al, Synthesis of C[CH(RF)NH]Gly-peptides: The dramatic effect of a single fluorine atom on the diastereocontrol of the key aza-Michael reaction, Journal of Fluorine Chemistry, Jun. 27, 2008, pp. 767-774, 129.
Shigemoto, et al., Differential Presynaptic Localization of Metabotropic Glutamate Receptor Subtypes in the Rat Hippocampus, The Journal of Neuroscience, Oct. 1, 1997, pp. 7503-7522, vol. 17 Issue 19, Society for Neuroscience.
V. Craig Jordan, "Tamoxifen: A Most Unlikely Pioneering Medicine", Nature Reviews Drug Discovery, 2003, pp. 205-213, vol. 2.
Vippagunta et al, Crystalline solids, Advanced Drug Delivery Reviews, May 16, 2001, pp. 3-26, vol. 48 No. 1.

* cited by examiner

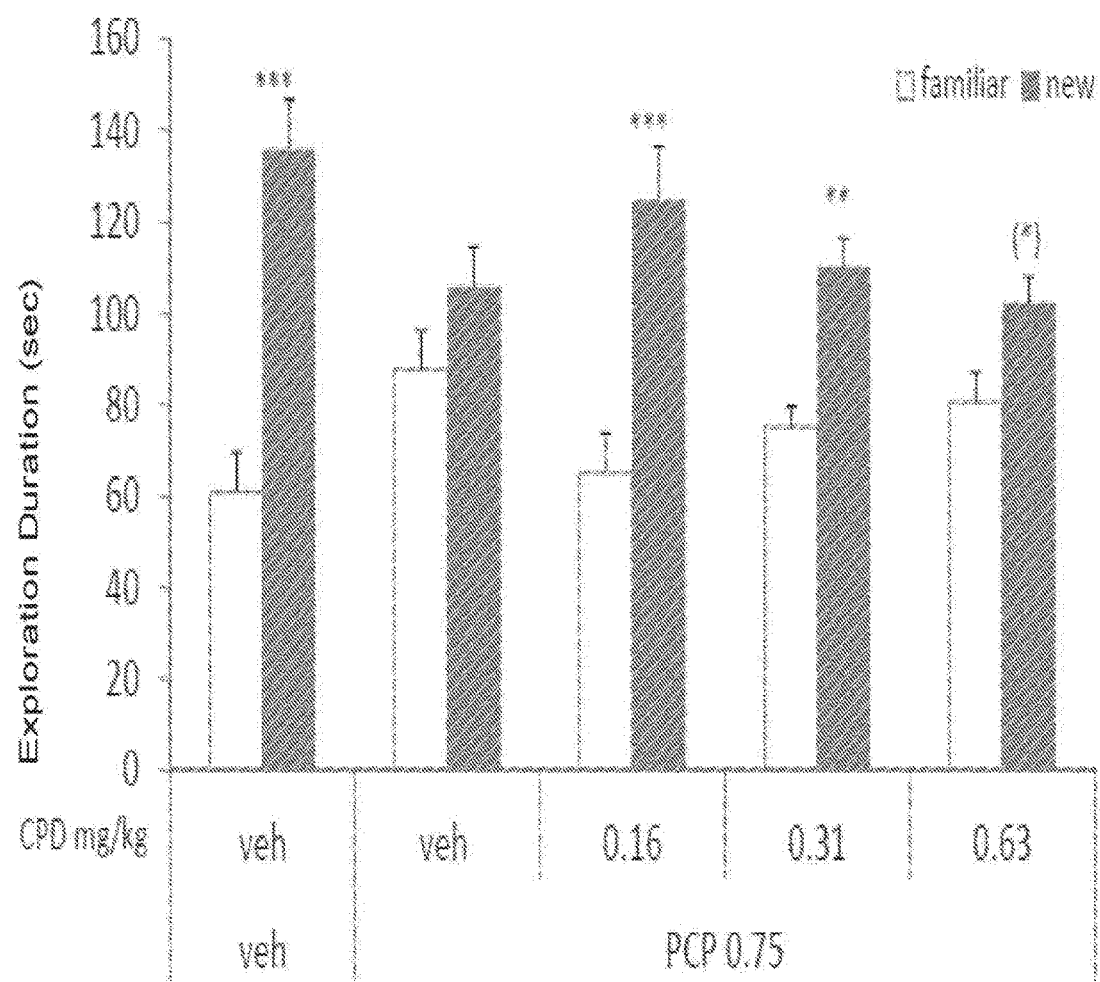

6,7-DIHYDROPYRAZOLO[1,5-α]PYRAZIN-4(5H)-ONE COMPOUNDS AND THEIR USE AS NEGATIVE ALLOSTERIC MODULATORS OF MGLUR2 RECEPTORS

This application is a continuation application of U.S. patent application Ser. No. 15/500,319 filed Jan. 30, 2017, which is a 371 National Stage Application of PCT/EP2015/067572 with an international filing date of Jul. 30, 2015, and claims the benefit of EP 14179600.3 filed Aug. 1, 2014 and EP 14196083.1 filed Dec. 3, 2014, the entire disclosures of each of which are hereby incorporated in their entirety.

FIELD OF THE INVENTION

The present invention relates to novel 6,7-dihydropyrazolo[1,5-a]pyrazin-4(5H)-one derivatives as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer's disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain Therapeutics) describes 4H-pyrazolo[1,5-a]quinazolin-5-ones and 4H-pyrrolo[1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD).

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved in mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

DESCRIPTION OF THE INVENTION

The present invention is directed to 6,7-dihydropyrazolo[1,5-a]pyrazin-4(5H)-one derivatives of Formula (I)

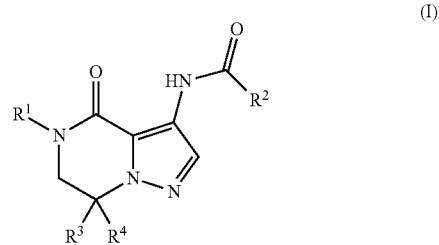

and stereoisomeric forms thereof, wherein
$R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;
$R^2$ is selected from the group consisting of $C_{1-4}$alkyl; $C_{3-7}$cycloalkyl; Het$^1$; Aryl; Het$^2$; and $C_{1-4}$alkyl substituted with one or more substituents each independently selected from the group consisting of halo, $C_{3-7}$cycloalkyl, Aryl, Het$^1$ and Het$^2$; wherein
Aryl is phenyl optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —SO$_2$—$C_{1-4}$alkyl;

Het$^1$ is selected from the group consisting of oxetanyl, tetrahydrofuranyl and tetrahydropyranyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —SO$_2$—$C_{1-4}$alkyl;

or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —SO$_2$—$C_{1-4}$alkyl;

R' and R" are each independently selected from the group consisting of hydrogen, $C_{1-4}$alkyl and —$C_{2-4}$alkyl-OH; and R$^3$ is selected from hydrogen and $C_{1-4}$alkyl;

R$^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;

and the N-oxides and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament, and to a compound of Formula (I) for use in the treatment or in the prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to the use of a compound of Formula (I) in combination with an additional pharmaceutical agent for use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a method of treating or preventing a central nervous system disorder selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder, comprising administering to a subject in need thereof, a therapeutically effective amount of a compound of Formula (I) or a therapeutically effective amount of a pharmaceutical composition according to the invention.

The invention also relates to a product comprising a compound of Formula (I) and an additional pharmaceutical agent, as a combined preparation for simultaneous, separate or sequential use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to 6,7-dihydropyrazolo[1,5-a]pyrazin-4(5H)-one derivatives designed to bind irreversibly to the mGluR2 receptor.

DESCRIPTION OF THE FIGURES

FIGURE shows the effect of Co. No. 8 (mg/kg p.o., 4 h prior to test) on exploration times of the new vs. the familiar arm in the V-maze by rats in the absence or presence of PCP (0 (=veh) or 0.75 mg/kg s.c., 0.5 h prior to test). Data are reported as Mean±SEM, n=12/group; ANOVA with LSD-post hoc, p vs. familiar arm: *** p<0.001, *<0.05. In FIG. 1, veh means vehicle and CPD means Co. No. 8

DETAILED DESCRIPTION OF THE INVENTION

The present invention relates in particular to compounds of Formula (I) as defined hereinabove, wherein R$^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, SF$_5$, $C_{1-4}$alkylthio, monohalo-$C_{1-4}$alkylthio and polyhalo-$C_{1-4}$alkylthio;

R$^2$ is selected from the group consisting of $C_{1-4}$alkyl; $C_{3-7}$cycloalkyl; Het$^1$; Aryl; Het$^2$; and $C_{1-4}$alkyl substituted with one or more substituents each independently selected from the group consisting of halo, $C_{3-7}$cycloalkyl, Aryl, Het$^1$ and Het$^2$; wherein Aryl is phenyl optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —SO$_2$—$C_{1-4}$alkyl;

Het$^1$ is selected from the group consisting of oxetanyl, tetrahydrofuranyl and tetrahydropyranyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —SO$_2$—$C_{1-4}$alkyl;

or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, $C_{1-4}$alkyl, —$C_{1-4}$alkyl-OH, monohalo-$C_{1-4}$alkyl, polyhalo-$C_{1-4}$alkyl, —CN, —O—$C_{1-4}$alkyl, —OH, —$C_{1-4}$alkyl-O—$C_{1-4}$alkyl, —NR'R", —NHC(O)$C_{1-4}$alkyl, —C(O)NR'R", —C(O)NH[C(O)$C_{1-4}$alkyl], —S(O)$_2$NR'R", —S(O)$_2$NH[C(O)$C_{1-4}$alkyl] and —SO$_2$—$C_{1-4}$alkyl;

R' and R" are each independently selected from the group consisting of hydrogen and $C_{1-4}$alkyl; and $R^3$ is selected from hydrogen and $C_{1-4}$alkyl;

$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;

and the N-oxides and the pharmaceutically acceptable salts and the solvates thereof.

The present invention relates in particular to compounds of Formula (I) as defined hereinabove, and stereoisomeric forms thereof, wherein $R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, SF$_5$, $C_{1-4}$alkylthio, monohalo-$C_{1-4}$alkylthio and polyhalo-$C_{1-4}$alkylthio;

$R^2$ is selected from the group consisting of $C_{1-4}$alkyl; $C_{3-7}$cycloalkyl; Het$^1$; Aryl; Het$^2$; and $C_{1-4}$alkyl substituted with one or more substituents each independently selected from the group consisting of halo, $C_{3-7}$cycloalkyl, Aryl, Het$^1$ and Het$^2$; wherein Aryl is phenyl optionally substituted with one or more substituents each independently selected from the group consisting of halo, $C_{1-4}$alkyl, —O—$C_{1-4}$alkyl, —OH, —$C_{1-4}$alkyl-O—$C_{1-4}$alkyl, —SO$_2$—NR'R" and —SO$_2$—$C_{1-4}$alkyl;

Het$^1$ is selected from the group consisting of oxetanyl, tetrahydrofuranyl and tetrahydropyranyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, $C_{1-4}$alkyl, monohalo-$C_{1-4}$alkyl, polyhalo-$C_{1-4}$alkyl, —CN, —OH, —O—$C_{1-4}$alkyl, —$C_{1-4}$alkyl-O—$C_{1-4}$alkyl, —C(O)NR'R", —NHC(O)$C_{1-4}$alkyl and —NR'R";

or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, $C_{1-4}$alkyl, —CN, —OH, —O—$C_{1-4}$alkyl, —C(O)NR'R", —NHC(O)$C_{1-4}$alkyl and —NR'R";

R' and R" are each independently selected from hydrogen and $C_{1-4}$alkyl; and $R^3$ is selected from hydrogen and $C_{1-4}$alkyl;

$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;

and the N-oxides and the pharmaceutically acceptable salts and the solvates thereof.

In an additional embodiment, the invention relates to compounds of Formula (I) as defined hereinabove, and stereoisomeric forms thereof, wherein $R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, —O—$C_{1-4}$alkyl, monohalo-$C_{1-4}$alkyloxy, polyhalo-$C_{1-4}$alkyloxy and —SF$_5$;

$R^2$ is selected from the group consisting of $C_{1-4}$alkyl; Aryl; Het$^2$; and $C_{1-4}$alkyl substituted with one, two or three substituents each independently selected from the group consisting of halo, $C_{3-7}$cycloalkyl and Aryl; wherein Aryl is phenyl optionally substituted with one, two or three substituents each independently selected from the group consisting of halo, $C_{1-4}$alkyl, —O—$C_{1-4}$alkyl, —OH and —$C_{1-4}$alkyl-O—$C_{1-4}$alkyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or two substituents each independently selected from the group consisting of halo, $C_{1-4}$alkyl, —CN, —OH, —O—$C_{1-4}$alkyl, —$C_{1-4}$alkyl-O—$C_{1-4}$alkyl, —C(O)NR'R", —NHC(O)$C_{1-4}$alkyl and —NR'R";

or (b) a 5-membered aromatic heterocyclyl selected from the group consisting of thiazolyl, oxazolyl, 1H-pyrazolyl and 1H-imidazolyl, each of which may be optionally substituted with one or two substituents each independently selected from the group consisting of halo, $C_{1-4}$alkyl and NR'R";

R' and R" are each independently selected from hydrogen and $C_{1-4}$alkyl; and $R^3$ is hydrogen;
$R^4$ is hydrogen, $C_{1-4}$alkyl or —$C_{1-4}$alkyl-O—$C_{1-4}$alkyl;
and the N-oxides and the pharmaceutically acceptable salts and the solvates thereof.

In an additional embodiment, the invention relates to compounds of Formula (I) as defined hereinabove, and stereoisomeric forms thereof, wherein
$R^1$ is phenyl or 2-pyridinyl, each optionally substituted with one, two or three substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, —O—$C_{1-4}$alkyl and monohalo-$C_{1-4}$alkyloxy and polyhalo-$C_{1-4}$alkyloxy;
$R^2$ is selected from the group consisting of $C_{1-4}$alkyl; Aryl; Het$^2$; and $C_{1-4}$alkyl substituted with one, two or three substituents each independently selected from the group consisting of halo, $C_{3-7}$cycloalkyl and Aryl; wherein
Aryl is phenyl optionally substituted with one, two or three substituents each independently selected from the group consisting of halo, $C_{1-4}$alkyl, —O—$C_{1-4}$alkyl, —OH and —$C_{1-4}$alkyl-O—$C_{1-4}$alkyl;
Het$^2$ is (a) a 6-membered aromatic heterocyclyl substituent selected from the group consisting of pyridinyl, pyrimidinyl, pyrazinyl and pyridazinyl, each of which may be optionally substituted with one or two substituents each independently selected from the group consisting of halo, $C_{1-4}$alkyl, —CN, —OH, —O—$C_{1-4}$alkyl, —$C_{1-4}$alkyl-O—$C_{1-4}$alkyl, —C(O)NR'R", —NHC(O)$C_{1-4}$alkyl and —NR'R";
or (b) a 5-membered aromatic heterocyclyl selected from the group consisting of thiazolyl, oxazolyl, 1H-pyrazolyl and 1H-imidazolyl, each of which may be optionally substituted with one or two substituents each independently selected from the group consisting of halo, $C_{1-4}$alkyl and NR'R";
R' and R" are each independently selected from hydrogen and $C_{1-4}$alkyl; and
$R^3$ is hydrogen;
$R^4$ is hydrogen, $C_{1-4}$alkyl or —$C_{1-4}$alkyl-O—$C_{1-4}$alkyl;
and the N-oxides and the pharmaceutically acceptable salts and the solvates thereof.

In an additional embodiment, the invention relates to compounds of Formula (I) as defined hereinabove, and stereoisomeric forms thereof, wherein
$R^1$ is phenyl or 2-pyridinyl, each optionally substituted with one or two substituents each independently selected from the group consisting of halo, $C_{1-4}$alkyl, monohalo-$C_{1-4}$alkyl, polyhalo-$C_{1-4}$alkyl, —CN, —$C_{1-4}$alkyl-O—$C_{1-4}$alkyl, —O—$C_{1-4}$alkyl and monohalo-$C_{1-4}$alkyloxy and polyhalo-$C_{1-4}$alkyloxy;
$R^2$ is selected from the group consisting of $C_{1-4}$alkyl; Aryl; Het$^2$; and $C_{1-4}$alkyl substituted with one, two or three substituents each independently selected from the group consisting of halo, $C_{3-7}$cycloalkyl and Aryl; wherein
Aryl is phenyl optionally substituted with one or two substituents each independently selected from the group consisting of halo, $C_{1-4}$alkyl, —O—$C_{1-4}$alkyl, —OH and —$C_{1-4}$alkyl-O—$C_{1-4}$alkyl;
Het$^2$ is (a) a 6-membered aromatic heterocyclyl substituent selected from the group consisting of pyridinyl, pyrimidinyl, pyrazinyl and pyridazinyl, each of which may be optionally substituted with one or two substituents each independently selected from the group consisting of halo, $C_{1-4}$alkyl, —CN, —OH, —O—$C_{1-4}$alkyl, —C(O)NR'R", —NHC(O)$C_{1-4}$alkyl and —NR'R"; or (b) a 5-membered aromatic heterocyclyl selected from the group consisting of thiazolyl, oxazolyl, 1H-pyrazolyl and 1H-imidazolyl, each of which may be optionally substituted with one or two substituents each independently selected from the group consisting of halo, $C_{1-4}$alkyl and NR'R";
R' and R" are each independently selected from hydrogen and $C_{1-4}$alkyl; and
$R^3$ is hydrogen;
$R^4$ is $C_{1-4}$alkyl or —$C_{1-4}$alkyl-O—$C_{1-4}$alkyl;
and the N-oxides and the pharmaceutically acceptable salts and the solvates thereof.

In an additional embodiment, the invention relates to compounds of Formula (I) as defined hereinabove, and stereoisomeric forms thereof, wherein
$R^1$ is phenyl optionally substituted with one or two substituents each independently selected from the group consisting of halo, $C_{1-4}$alkyl, monohalo-$C_{1-4}$alkyl, polyhalo-$C_{1-4}$alkyl, —CN, —$C_{1-4}$alkyl-O—$C_{1-4}$alkyl, —O—$C_{1-4}$alkyl and monohalo-$C_{1-4}$alkyloxy, polyhalo-$C_{1-4}$alkyloxy; or $R^1$ is 2-pyridinyl, optionally substituted with one or two substituents each independently selected from the group consisting of polyhalo-$C_{1-4}$alkyl and —O—$C_{1-4}$alkyl;
$R^2$ is selected from the group consisting of Aryl and Het$^2$; wherein
Aryl is phenyl optionally substituted with one or two substituents each independently selected from the group consisting of halo, $C_{1-4}$alkyl, —O—$C_{1-4}$alkyl, —OH and —$C_{1-4}$alkyl-O—$C_{1-4}$alkyl;
Het$^2$ is (a) a 6-membered aromatic heterocyclyl substituent selected from the group consisting of pyridinyl and pyrazinyl, each of which may be optionally substituted with one or two substituents each independently selected from the group consisting of halo, $C_{1-4}$alkyl, —O—$C_{1-4}$alkyl, —NHC(O)$C_{1-4}$alkyl and —NR'R";
or (b) a 5-membered aromatic heterocyclyl selected from thiazolyl;
R' and R" are hydrogen; and
$R^3$ is hydrogen;
$R^4$ is $C_{1-4}$alkyl or —$C_{1-4}$alkyl-O—$C_{1-4}$alkyl;
and the N-oxides and the pharmaceutically acceptable salts and the solvates thereof.

In an additional embodiment, the invention relates to compounds of Formula (I) as defined hereinabove, and stereoisomeric forms thereof, wherein
$R^1$ is phenyl optionally substituted with one or two substituents each independently selected from the group consisting of halo, $C_{1-4}$alkyl and polyhalo-$C_{1-4}$alkyl;
$R^2$ is pyridinyl, or pyrazinyl, each of which may be optionally substituted with one or two substituents each independently selected from the group consisting of $C_{1-4}$alkyl, —O—$C_{1-4}$alkyl and $NH_2$;
$R^3$ is hydrogen;
$R^4$ is $C_{1-4}$alkyl or —$C_{1-4}$alkyl-O—$C_{1-4}$alkyl, in particular —$CH_3$ or —$CH_2OCH_3$, more in particular —$CH_3$;
and the N-oxides and the pharmaceutically acceptable salts and the solvates thereof.

In an additional embodiment, the invention relates to compounds of Formula (I) as defined hereinabove, and stereoisomeric forms thereof, wherein
$R^1$ is phenyl optionally substituted with one or two substituents each independently selected from the group consisting of halo and polyhalo-$C_{1-4}$alkyl;
$R^2$ is 3-pyridinyl, optionally substituted with one or two substituents each independently selected from the group consisting of $C_{1-4}$alkyl, —O—$C_{1-4}$alkyl and $NH_2$;
$R^3$ is hydrogen;
$R^4$ is $C_{1-4}$alkyl or —$C_{1-4}$alkyl-O—$C_{1-4}$alkyl, in particular —$CH_3$ or —$CH_2OCH_3$, more in particular —$CH_3$;
and the N-oxides and the pharmaceutically acceptable salts and the solvates thereof.

In an additional embodiment, the invention relates to compounds of Formula (I) as defined hereinabove and stereoisomeric forms thereof, wherein
$R^1$ is phenyl optionally substituted with one or two substituents each independently selected from the group consisting of halo, $C_{1-4}$alkyl, monohalo-$C_{1-4}$alkyl, polyhalo-$C_{1-4}$alkyl, —CN, —$C_{1-4}$alkyl-O—$C_{1-4}$alkyl, —O—$C_{1-4}$alkyl and monohalo-$C_{1-4}$alkyloxy, polyhalo-$C_{1-4}$alkyloxy; or $R^1$ is 2-pyridinyl, optionally substituted with one or two substituents each independently selected from the group consisting of halo, monohalo-$C_{1-4}$alkyl, polyhalo-$C_{1-4}$alkyl and —O—$C_{1-4}$alkyl;
$R^2$ is pyridinyl substituted with —NH—$C_{2-4}$alkyl-OH;
$R^3$ is hydrogen;
$R^4$ is $C_{1-4}$alkyl or —$C_{1-4}$alkyl-O—$C_{1-4}$alkyl;
and the N-oxides and the pharmaceutically acceptable salts and the solvates thereof.

In a further embodiment, the present invention relates to compounds of Formula (I) as defined herein wherein $R^3$ is hydrogen and $R^4$ is a substituent different from hydrogen having a configuration as depicted in the Formula (I') below, wherein the 6,7-dihydropyrazolo[1,5-a]pyrazin-4(5H)-one core, $R^1$ and $R^2$ are in the plane of the drawing and $R^4$ is projected above the plane (bond shown with a bold wedge), and the rest of variables are as defined in Formula (I) herein

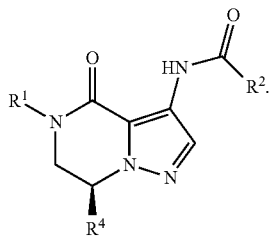

(I')

In a yet further embodiment, the present invention relates to compounds of Formula (I) as defined herein wherein $R^4$ is hydrogen and $R^3$ is a substituent different from hydrogen, for example a $C_{1-4}$alkyl substituent having a configuration as depicted in the Formula (I") below, wherein the 6,7-dihydropyrazolo[1,5-a]pyrazin-4(5R)-one core, $R^1$ and $R^2$ are in the plane of the drawing and $R^3$ is projected above the plane of the drawing (bond shown with a bold wedge), and the rest of variables are as defined in Formula (I) herein

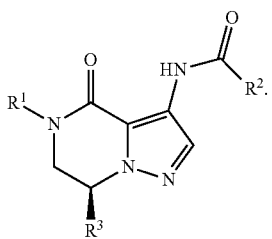

(I")

Specific compounds according to the invention include:
6-amino-N-[(7S)-7-methyl-4-oxo-5-[4-(trifluoromethyl)phenyl]-6,7-dihydropyrazolo[1,5-a]pyrazin-3-yl]pyridine-3-carboxamide;
2-methyl-N-[(7S)-7-methyl-4-oxo-5-[4-(trifluoromethyl)phenyl]-6,7-dihydropyrazolo[1,5-a]pyrazin-3-yl]pyridine-4-carboxamide;
2-methoxy-N-[(7S)-7-methyl-4-oxo-5-[4-(trifluoromethyl)phenyl]-6,7-dihydropyrazolo[1,5-a]pyrazin-3-yl]pyridine-4-carboxamide;
3-methyl-N-[(7S)-7-methyl-4-oxo-5-[4-(trifluoromethyl)phenyl]-6,7-dihydropyrazolo[1,5-a]pyrazin-3-yl]-1H-pyrazole-5-carboxamide;
N-[(7S)-7-methyl-4-oxo-5-[4-(trifluoromethyl)phenyl]-6,7-dihydropyrazolo[1,5-a]pyrazin-3-yl]isoxazole-5-carboxamide;
1-methyl-N-[(7S)-7-methyl-4-oxo-5-[4-(trifluoromethyl)phenyl]-6,7-dihydropyrazolo[1,5-a]pyrazin-3-yl]pyrazole-4-carboxamide;
6-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;
2-amino-N-[(7S)-7-methyl-4-oxo-5-[4-(trifluoromethyl)phenyl]-6,7-dihydropyrazolo[1,5-a]pyrazin-3-yl]pyridine-4-carboxamide;
6-amino-N-[(7S)-5-[3-chloro-4-(trifluoromethyl)phenyl]-7-methyl-4-oxo-6,7-dihydropyrazolo[1,5-a]pyrazin-3-yl]pyridine-3-carboxamide;
N-[(7S)-7-methyl-4-oxo-5-[4-(trifluoromethyl)phenyl]-6,7-dihydropyrazolo[1,5-a]pyrazin-3-yl]benzamide;
N-[(7S)-5-[3-chloro-4-(trifluoromethyl)phenyl]-7-methyl-4-oxo-6,7-dihydropyrazolo[1,5-a]pyrazin-3-yl]benzamide;

N-[(7S)-5-[3-chloro-4-(trifluoromethyl)phenyl]-7-methyl-4-oxo-6,7-dihydropyrazolo[1,5-a]pyrazin-3-yl]-2-methyl-pyridine-4-carboxamide;

N-[(7S)-7-methyl-4-oxo-5-[4-(trifluoromethyl)phenyl]-6,7-dihydropyrazolo[1,5-a]pyrazin-3-yl]pyridine-2-carboxamide;

2-fluoro-N-[(7S)-7-methyl-4-oxo-5-[4-(trifluoromethyl)phenyl]-6,7-dihydropyrazolo[1,5-a]pyrazin-3-yl]benzamide;

4-fluoro-N-[(7S)-7-methyl-4-oxo-5-[4-(trifluoromethyl)phenyl]-6,7-dihydropyrazolo[1,5-a]pyrazin-3-yl]benzamide;

3-fluoro-N-[(7S)-7-methyl-4-oxo-5-[4-(trifluoromethyl)phenyl]-6,7-dihydropyrazolo[1,5-a]pyrazin-3-yl]benzamide;

2-methyl-N-[(7S)-7-methyl-4-oxo-5-[4-(trifluoromethyl)phenyl]-6,7-dihydropyrazolo[1,5-a]pyrazin-3-yl]oxazole-4-carboxamide;

2-cyclopropyl-N-[(7S)-7-methyl-4-oxo-5-[4-(trifluoromethyl)phenyl]-6,7-dihydropyrazolo[1,5-a]pyrazin-3-yl]acetamide;

2-methyl-N-[(7S)-7-methyl-4-oxo-5-[4-(trifluoromethyl)phenyl]-6,7-dihydropyrazolo[1,5-a]pyrazin-3-yl]pyrimidine-5-carboxamide;

N-[(7S)-7-methyl-4-oxo-5-[4-(trifluoromethyl)phenyl]-6,7-dihydropyrazolo[1,5-a]pyrazin-3-yl]-1H-imidazole-4-carboxamide;

3-methyl-N-[(7S)-7-methyl-4-oxo-5-[4-(trifluoromethyl)phenyl]-6,7-dihydropyrazolo[1,5-a]pyrazin-3-yl]imidazole-4-carboxamide;

3-methoxy-N-[(7S)-7-methyl-4-oxo-5-[4-(trifluoromethyl)phenyl]-6,7-dihydropyrazolo[1,5-a]pyrazin-3-yl]benzamide;

4-methoxy-N-[(7S)-7-methyl-4-oxo-5-[4-(trifluoromethyl)phenyl]-6,7-dihydropyrazolo[1,5-a]pyrazin-3-yl]benzamide;

3-methyl-N-[(7S)-7-methyl-4-oxo-5-[4-(trifluoromethyl)phenyl]-6,7-dihydropyrazolo[1,5-a]pyrazin-3-yl]isoxazole-5-carboxamide;

3-methyl-N-[(7S)-7-methyl-4-oxo-5-[4-(trifluoromethyl)phenyl]-6,7-dihydropyrazolo[1,5-a]pyrazin-3-yl]benzamide;

2-methoxy-N-[(7S)-7-methyl-4-oxo-5-[4-(trifluoromethyl)phenyl]-6,7-dihydropyrazolo[1,5-a]pyrazin-3-yl]benzamide;

5-methyl-N-[(7S)-7-methyl-4-oxo-5-[4-(trifluoromethyl)phenyl]-6,7-dihydropyrazolo[1,5-a]pyrazin-3-yl]isoxazole-3-carboxamide;

4-methyl-N-[(7S)-7-methyl-4-oxo-5-[4-(trifluoromethyl)phenyl]-6,7-dihydropyrazolo[1,5-a]pyrazin-3-yl]benzamide;

5-amino-N-[(7S)-7-methyl-4-oxo-5-[4-(trifluoromethyl)phenyl]-6,7-dihydropyrazolo[1,5-a]pyrazin-3-yl]pyrazine-2-carboxamide;

6-hydroxy-N-[(7S)-7-methyl-4-oxo-5-[4-(trifluoromethyl)phenyl]-6,7-dihydropyrazolo[1,5-a]pyrazin-3-yl]pyridazine-3-carboxamide;

N-[(7S)-7-methyl-4-oxo-5-[4-(trifluoromethyl)phenyl]-6,7-dihydropyrazolo[1,5-a]pyrazin-3-yl]-2-phenyl-acetamide;

N-[(7S)-7-methyl-4-oxo-5-[4-(trifluoromethyl)phenyl]-6,7-dihydropyrazolo[1,5-a]pyrazin-3-yl]pyridine-4-carboxamide;

N-[(7S)-7-methyl-4-oxo-5-[4-(trifluoromethyl)phenyl]-6,7-dihydropyrazolo[1,5-a]pyrazin-3-yl]pyridine-3-carboxamide;

6-amino-N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

6-amino-N-[(7S)-5-[3-cyano-4-(trifluoromethyl)phenyl]-7-methyl-4-oxo-6,7-dihydropyrazolo[1,5-a]pyrazin-3-yl]pyridine-3-carboxamide;

N-[(7S)-7-methyl-5-[3-methyl-4-(trifluoromethyl)phenyl]-4-oxo-6,7-dihydropyrazolo[1,5-a]pyrazin-3-yl]benzamide;

5-chloro-N-[(7S)-7-methyl-4-oxo-5-[4-(trifluoromethyl)phenyl]-6,7-dihydropyrazolo[1,5-a]pyrazin-3-yl]pyridine-2-carboxamide;

5-fluoro-N-[(7S)-7-methyl-4-oxo-5-[4-(trifluoromethyl)phenyl]-6,7-dihydropyrazolo[1,5-a]pyrazin-3-yl]pyridine-2-carboxamide;

6-amino-N-[(7S)-5-(4-chlorophenyl)-7-methyl-4-oxo-6,7-dihydropyrazolo[1,5-a]pyrazin-3-yl]pyridine-3-carboxamide;

6-amino-N-[(7S)-7-methyl-4-oxo-5-[5-(trifluoromethyl)-2-pyridyl]-6,7-dihydropyrazolo[1,5-a]pyrazin-3-yl]pyridine-3-carboxamide;

6-amino-N-[(7S)-5-[3-methoxy-4-(trifluoromethyl)phenyl]-7-methyl-4-oxo-6,7-dihydropyrazolo[1,5-a]pyrazin-3-yl]pyridine-3-carboxamide;

5-methoxy-N-[(7S)-7-methyl-4-oxo-5-[4-(trifluoromethyl)phenyl]-6,7-dihydropyrazolo[1,5-a]pyrazin-3-yl]pyrazine-2-carboxamide;

5-cyano-N-[(7S)-7-methyl-4-oxo-5-[4-(trifluoromethyl)phenyl]-6,7-dihydropyrazolo[1,5-a]pyrazin-3-yl]pyridine-2-carboxamide;

N2-[(7S)-7-methyl-4-oxo-5-[4-(trifluoromethyl)phenyl]-6,7-dihydropyrazolo[1,5-a]pyrazin-3-yl]pyridine-2,5-dicarboxamide;

6-methoxy-N-[(7S)-7-methyl-4-oxo-5-[4-(trifluoromethyl)phenyl]-6,7-dihydropyrazolo[1,5-a]pyrazin-3-yl]pyridine-2-carboxamide;

6-amino-N-[(7S)-5-(3,4-dichlorophenyl)-7-methyl-4-oxo-6,7-dihydropyrazolo[1,5-a]pyrazin-3-yl]pyridine-3-carboxamide;

6-amino-N-[(7S)-5-[3-fluoro-4-(trifluoromethyl)phenyl]-7-methyl-4-oxo-6,7-dihydropyrazolo[1,5-a]pyrazin-3-yl]pyridine-3-carboxamide;

2-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;

3-methyl-N-[(7S)-7-methyl-4-oxo-5-[4-(trifluoromethyl)phenyl]-6,7-dihydropyrazolo[1,5-a]pyrazin-3-yl]pyridine-2-carboxamide;

5-amino-N-[(7S)-7-methyl-4-oxo-5-[4-(trifluoromethyl)phenyl]-6,7-dihydropyrazolo[1,5-a]pyrazin-3-yl]pyridine-2-carboxamide;

6-methoxy-N-[(7S)-7-methyl-4-oxo-5-[4-(trifluoromethyl)phenyl]-6,7-dihydropyrazolo[1,5-a]pyrazin-3-yl]pyridine-3-carboxamide;

3-fluoro-N-[(7S)-7-methyl-4-oxo-5-[4-(trifluoromethyl)phenyl]-6,7-dihydropyrazolo[1,5-a]pyrazin-3-yl]pyridine-2-carboxamide;

2-amino-N-[(7S)-7-methyl-4-oxo-5-[4-(trifluoromethyl)phenyl]-6,7-dihydropyrazolo[1,5-a]pyrazin-3-yl]pyrimidine-5-carboxamide;

5-methoxy-N-[(7S)-7-methyl-4-oxo-5-[4-(trifluoromethyl)phenyl]-6,7-dihydropyrazolo[1,5-a]pyrazin-3-yl]pyridine-3-carboxamide;

6-methyl-N-[(7S)-7-methyl-4-oxo-5-[4-(trifluoromethyl)phenyl]-6,7-dihydropyrazolo[1,5-a]pyrazin-3-yl]pyridine-2-carboxamide;

N-[(7S)-5-(5-chloro-6-methoxy-2-pyridyl)-7-methyl-4-oxo-6,7-dihydropyrazolo[1,5-a]pyrazin-3-yl]benzamide;

2-methoxy-N-[(7S)-7-methyl-4-oxo-5-[4-(trifluoromethyl)phenyl]-6,7-dihydropyrazolo[1,5-a]pyrazin-3-yl]pyridine-3-carboxamide;

N-[(7S)-5-[6-methoxy-5-(trifluoromethyl)-2-pyridyl]-7-methyl-4-oxo-6,7-dihydropyrazolo[1,5-a]pyrazin-3-yl]benzamide;

3-methoxy-N-[(7S)-5-[6-methoxy-5-(trifluoromethyl)-2-pyridyl]-7-methyl-4-oxo-6,7-dihydropyrazolo[1,5-a]pyrazin-3-yl]benzamide;

4-methoxy-N-[(7S)-5-[6-methoxy-5-(trifluoromethyl)-2-pyridyl]-7-methyl-4-oxo-6,7-dihydropyrazolo[1,5-a]pyrazin-3-yl]benzamide;

6-amino-N-[(7S)-5-[6-methoxy-5-(trifluoromethyl)-2-pyridyl]-7-methyl-4-oxo-6,7-dihydropyrazolo[1,5-a]pyrazin-3-yl]pyridine-3-carboxamide 6-amino-N-[(7S)-5-[3-(methoxymethyl)-4-(trifluoromethyl)phenyl]-7-methyl-4-oxo-6,7-dihydropyrazolo[1,5-a]pyrazin-3-yl]pyridine-3-carboxamide;

6-amino-N-[(7S)-5-[3-chloro-4-(difluoromethyl)phenyl]-7-methyl-4-oxo-6,7-dihydropyrazolo[1,5-a]pyrazin-3-yl]pyridine-3-carboxamide;

2-methoxy-N-[(7S)-5-[6-methoxy-5-(trifluoromethyl)-2-pyridyl]-7-methyl-4-oxo-6,7-dihydropyrazolo[1,5-a]pyrazin-3-yl]benzamide;

2-methyl-N-[(7S)-7-methyl-4-oxo-5-[4-(trifluoromethyl)phenyl]-6,7-dihydropyrazolo[1,5-a]pyrazin-3-yl]benzamide;

6-amino-N-[(7S)-7-methyl-4-oxo-5-[4-(trifluoromethyl)phenyl]-6,7-dihydropyrazolo[1,5-a]pyrazin-3-yl]pyridazine-3-carboxamide;

N-[(7S)-7-methyl-4-oxo-5-[4-(trifluoromethyl)phenyl]-6,7-dihydropyrazolo[1,5-a]pyrazin-3-yl]oxazole-2-carboxamide;

3-(methoxymethyl)-N-[(7S)-7-methyl-4-oxo-5-[4-(trifluoromethyl)phenyl]-6,7-dihydropyrazolo[1,5-a]pyrazin-3-yl]benzamide;

6-amino-N-[(7S)-5-(5-chloro-6-methoxy-2-pyridyl)-7-methyl-4-oxo-6,7-dihydropyrazolo[1,5-a]pyrazin-3-yl]pyridine-3-carboxamide;

N-[(7S)-7-methyl-4-oxo-5-[4-(trifluoromethyl)phenyl]-6,7-dihydropyrazolo[1,5-a]pyrazin-3-yl]-1H-pyrazole-4-carboxamide;

N-[(7S)-7-methyl-4-oxo-5-[4-(trifluoromethyl)phenyl]-6,7-dihydropyrazolo[1,5-a]pyrazin-3-yl]thiazole-2-carboxamide;

3-fluoro-4-methoxy-N-[(7S)-7-methyl-4-oxo-5-[4-(trifluoromethyl)phenyl]-6,7-dihydropyrazolo[1,5-a]pyrazin-3-yl]benzamide;

4-fluoro-2-methoxy-N-[(7S)-7-methyl-4-oxo-5-[4-(trifluoromethyl)phenyl]-6,7-dihydropyrazolo[1,5-a]pyrazin-3-yl]benzamide;

5-fluoro-2-methoxy-N-[(7S)-7-methyl-4-oxo-5-[4-(trifluoromethyl)phenyl]-6,7-dihydropyrazolo[1,5-a]pyrazin-3-yl]benzamide;

2-fluoro-6-methoxy-N-[(7S)-7-methyl-4-oxo-5-[4-(trifluoromethyl)phenyl]-6,7-dihydropyrazolo[1,5-a]pyrazin-3-yl]benzamide;

2-fluoro-4-methoxy-N-[(7S)-7-methyl-4-oxo-5-[4-(trifluoromethyl)phenyl]-6,7-dihydropyrazolo[1,5-a]pyrazin-3-yl]benzamide;

4-fluoro-3-methoxy-N-[(7S)-7-methyl-4-oxo-5-[4-(trifluoromethyl)phenyl]-6,7-dihydropyrazolo[1,5-a]pyrazin-3-yl]benzamide;

2-fluoro-5-methoxy-N-[(7S)-7-methyl-4-oxo-5-[4-(trifluoromethyl)phenyl]-6,7-dihydropyrazolo[1,5-a]pyrazin-3-yl]benzamide;

3-fluoro-5-methoxy-N-[(7S)-7-methyl-4-oxo-5-[4-(trifluoromethyl)phenyl]-6,7-dihydropyrazolo[1,5-a]pyrazin-3-yl]benzamide;

3-fluoro-2-methoxy-N-[(7S)-7-methyl-4-oxo-5-[4-(trifluoromethyl)phenyl]-6,7-dihydropyrazolo[1,5-a]pyrazin-3-yl]benzamide;

6-amino-N-[(7S)-5-[4-chloro-3-(difluoromethoxy)phenyl]-7-methyl-4-oxo-6,7-dihydropyrazolo[1,5-a]pyrazin-3-yl]pyridine-3-carboxamide;

5-amino-N-[(7S)-7-methyl-4-oxo-5-[4-(trifluoromethyl)phenyl]-6,7-dihydropyrazolo[1,5-a]pyrazin-3-yl]-1H-pyrazole-3-carboxamide;

N-[(7S)-7-methyl-4-oxo-5-[4-(trifluoromethyl)phenyl]-6,7-dihydropyrazolo[1,5-a]pyrazin-3-yl]-1H-imidazole-2-carboxamide;

4-methoxy-N-[(7S)-7-methyl-4-oxo-5-[4-(trifluoromethyl)phenyl]-6,7-dihydropyrazolo[1,5-a]pyrazin-3-yl]pyridine-2-carboxamide;

2-fluoro-3-methoxy-N-[(7S)-7-methyl-4-oxo-5-[4-(trifluoromethyl)phenyl]-6,7-dihydropyrazolo[1,5-a]pyrazin-3-yl]benzamide;

5-fluoro-N-[(7S)-7-methyl-4-oxo-5-[4-(trifluoromethyl)phenyl]-6,7-dihydropyrazolo[1,5-a]pyrazin-3-yl]pyridine-3-carboxamide;

6-amino-N-[7-(methoxymethyl)-4-oxo-5-[4-(trifluoromethyl)phenyl]-6,7-dihydropyrazolo[1,5-a]pyrazin-3-yl]pyridine-3-carboxamide;

N-[(7S)-7-methyl-4-oxo-5-[4-(trifluoromethyl)phenyl]-6,7-dihydropyrazolo[1,5-a]pyrazin-3-yl]pyrazine-2-carboxamide;

2-(methoxymethyl)-N-[(7S)-7-methyl-4-oxo-5-[4-(trifluoromethyl)phenyl]-6,7-dihydropyrazolo[1,5-a]pyrazin-3-yl]benzamide;

6-amino-N-[(7S)-5-[3-(fluoromethyl)-4-(trifluoromethyl)phenyl]-7-methyl-4-oxo-6,7-dihydropyrazolo[1,5-a]pyrazin-3-yl]pyridine-3-carboxamide;

2-amino-N-[(7S)-7-methyl-4-oxo-5-[4-(trifluoromethyl)phenyl]-6,7-dihydropyrazolo[1,5-a]pyrazin-3-yl]thiazole-5-carboxamide;

2-fluoro-N-[7-(methoxymethyl)-4-oxo-5-[4-(trifluoromethyl)phenyl]-6,7-dihydropyrazolo[1,5-a]pyrazin-3-yl]benzamide;

N-[(7S)-5-[3-chloro-4-(trifluoromethyl)phenyl]-7-methyl-4-oxo-6,7-dihydropyrazolo[1,5-a]pyrazin-3-yl]pyridine-3-carboxamide;

5-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;

N-[(7S)-7-methyl-4-oxo-5-[4-(trifluoromethyl)phenyl]-6,7-dihydropyrazolo[1,5-a]pyrazin-3-yl]pyrimidine-2-carboxamide;

2-amino-N-[(7S)-7-methyl-4-oxo-5-phenyl-6,7-dihydropyrazolo[1,5-a]pyrazin-3-yl]pyridine-4-carboxamide;

(7*R)-6-amino-N-[7-(methoxymethyl)-4-oxo-5-[4-(trifluoromethyl)phenyl]-6,7-dihydropyrazolo[1,5-a]pyrazin-3-yl]pyridine-3-carboxamide;

(7*S)-6-amino-N-[7-(methoxymethyl)-4-oxo-5-[4-(trifluoromethyl)phenyl]-6,7-dihydropyrazolo[1,5-a]pyrazin-3-yl]pyridine-3-carboxamide;

2-amino-N-[(7S)-7-methyl-4-oxo-5-[4-(trifluoromethyl)phenyl]-6,7-dihydropyrazolo[1,5-a]pyrazin-3-yl]-1H-imidazole-4-carboxamide;

2,6-dimethyl-N-[(7S)-7-methyl-4-oxo-5-[4-(trifluoromethyl)phenyl]-6,7-dihydropyrazolo[1,5-a]pyrazin-3-yl]pyridine-4-carboxamide;

(7*R)-2-fluoro-N-[7-(methoxymethyl)-4-oxo-5-[4-(trifluoromethyl)phenyl]-6,7-dihydropyrazolo[1,5-a]pyrazin-3-yl]benzamide;

(7*S)-2-fluoro-N-[7-(methoxymethyl)-4-oxo-5-[4-(trifluoromethyl)phenyl]-6,7-dihydropyrazolo[1,5-a]pyrazin-3-yl]benzamide;

3-hydroxy-N-[(7S)-7-methyl-4-oxo-5-[4-(trifluoromethyl)phenyl]-6,7-dihydropyrazolo[1,5-a]pyrazin-3-yl]benzamide;

N-[(7S)-5-[3-chloro-4-(trifluoromethyl)phenyl]-7-methyl-4-oxo-6,7-dihydropyrazolo[1,5-a]pyrazin-3-yl]pyridine-2-carboxamide;

N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]-5-fluoro-pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]-5-methoxy-pyridine-3-carboxamide;

N-[(7S)-5-(3,4-dichlorophenyl)-7-methyl-4-oxo-6,7-dihydropyrazolo[1,5-a]pyrazin-3-yl]-5-methoxy-pyridine-3-carboxamide;

N-[(7S)-5-(3,4-dichlorophenyl)-7-methyl-4-oxo-6,7-dihydropyrazolo[1,5-a]pyrazin-3-yl]pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]pyrazine-2-carboxamide;

N-[(7S)-5-(3,4-dichlorophenyl)-7-methyl-4-oxo-6,7-dihydropyrazolo[1,5-a]pyrazin-3-yl]pyrazine-2-carboxamide;

N-[(7S)-5-(3,4-dichlorophenyl)-7-methyl-4-oxo-6,7-dihydropyrazolo[1,5-a]pyrazin-3-yl]pyridine-2-carboxamide;

N-[(7S)-5-(3,4-dichlorophenyl)-7-methyl-4-oxo-6,7-dihydropyrazolo[1,5-a]pyrazin-3-yl]-2,6-dimethyl-pyridine-4-carboxamide;

5-fluoro-N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

N-[(7S)-5-(3,4-dichlorophenyl)-7-methyl-4-oxo-6,7-dihydropyrazolo[1,5-a]pyrazin-3-yl]-5-methyl-pyridine-3-carboxamide;

N-[(7S)-5-(3,4-dichlorophenyl)-7-methyl-4-oxo-6,7-dihydropyrazolo[1,5-a]pyrazin-3-yl]-5-fluoro-pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]-2,6-dimethyl-pyridine-4-carboxamide;

N-[(7S)-7-methyl-5-[3-methyl-4-(trifluoromethyl)phenyl]-4-oxo-6,7-dihydropyrazolo[1,5-a]pyrazin-3-yl]pyridine-2-carboxamide;

N-[(7S)-5-[3-methoxy-4-(trifluoromethyl)phenyl]-7-methyl-4-oxo-6,7-dihydropyrazolo[1,5-a]pyrazin-3-yl]pyridine-2-carboxamide;

2-methyl-N-[(7S)-7-methyl-5-[3-methyl-4-(trifluoromethyl)phenyl]-4-oxo-6,7-dihydropyrazolo[1,5-a]pyrazin-3-yl]pyridine-4-carboxamide;

2,6-dimethyl-N-[(7S)-7-methyl-5-[3-methyl-4-(trifluoromethyl)phenyl]-4-oxo-6,7-dihydropyrazolo[1,5-a]pyrazin-3-yl]pyridine-4-carboxamide;

N-[(7S)-7-methyl-5-[3-methyl-4-(trifluoromethyl)phenyl]-4-oxo-6,7-dihydropyrazolo[1,5-a]pyrazin-3-yl]pyrazine-2-carboxamide;

N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

N-[(7S)-5-(3,4-dichlorophenyl)-7-methyl-4-oxo-6,7-dihydropyrazolo[1,5-a]pyrazin-3-yl]-2,2,2-trifluoro-acetamide;

5-methoxy-N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

5-methyl-N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

N-[(7S)-5-[3-methoxy-4-(trifluoromethyl)phenyl]-7-methyl-4-oxo-6,7-dihydropyrazolo[1,5-a]pyrazin-3-yl]pyridine-3-carboxamide;

5-methoxy-N-[(7S)-5-[3-methoxy-4-(trifluoromethyl)phenyl]-7-methyl-4-oxo-6,7-dihydropyrazolo[1,5-a]pyrazin-3-yl]pyridine-3-carboxamide;

5-fluoro-N-[(7S)-5-[3-methoxy-4-(trifluoromethyl)phenyl]-7-methyl-4-oxo-6,7-dihydropyrazolo[1,5-a]pyrazin-3-yl]pyridine-3-carboxamide;

N-[(7S)-5-[3-methoxy-4-(trifluoromethyl)phenyl]-7-methyl-4-oxo-6,7-dihydropyrazolo[1,5-a]pyrazin-3-yl]-5-methyl-pyridine-3-carboxamide;

N-[(7S)-5-[3-methoxy-4-(trifluoromethyl)phenyl]-7-methyl-4-oxo-6,7-dihydropyrazolo[1,5-a]pyrazin-3-yl]pyrazine-2-carboxamide;

4-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]-4-methyl-pyridine-3-carboxamide;

2,3-dimethyl-N-[(7S)-7-methyl-4-oxo-5-[4-(trifluoromethyl)phenyl]-6,7-dihydropyrazolo[1,5-a]pyrazin-3-yl]pyridine-4-carboxamide;

N-[(7S)-5-[3-chloro-4-(trifluoromethyl)phenyl]-7-methyl-4-oxo-6,7-dihydropyrazolo[1,5-a]pyrazin-3-yl]-5-methoxy-4-methyl-pyridine-3-carboxamide;

5-methoxy-4-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;

N-[(7S)-5-[3-methoxy-4-(trifluoromethyl)phenyl]-7-methyl-4-oxo-6,7-dihydropyrazolo[1,5-a]pyrazin-3-yl]-2-methyl-pyridine-4-carboxamide;

2,5-dimethyl-N-[(7S)-7-methyl-4-oxo-5-[4-(trifluoromethyl)phenyl]-6,7-dihydropyrazolo[1,5-a]pyrazin-3-yl]pyridine-4-carboxamide;

N-[(7S)-5-[3-chloro-4-(trifluoromethyl)phenyl]-7-methyl-4-oxo-6,7-dihydropyrazolo[1,5-a]pyrazin-3-yl]-2,5-dimethyl-pyridine-4-carboxamide;

N-[(7S)-5-[3-fluoro-4-(trifluoromethyl)phenyl]-7-methyl-4-oxo-6,7-dihydropyrazolo[1,5-a]pyrazin-3-yl]pyridine-3-carboxamide;

N-[(7S)-5-[3-fluoro-4-(trifluoromethyl)phenyl]-7-methyl-4-oxo-6,7-dihydropyrazolo[1,5-a]pyrazin-3-yl]-5-methoxy-pyridine-3-carboxamide;

5-fluoro-N-[(7S)-5-[3-fluoro-4-(trifluoromethyl)phenyl]-7-methyl-4-oxo-6,7-dihydropyrazolo[1,5-a]pyrazin-3-yl]pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]-2,3-dimethyl-pyridine-4-carboxamide;

N-[(7S)-5-[3-methoxy-4-(trifluoromethyl)phenyl]-7-methyl-4-oxo-6,7-dihydropyrazolo[1,5-a]pyrazin-3-yl]-2,6-dimethyl-pyridine-4-carboxamide;

N-[(7S)-5-[3-fluoro-4-(trifluoromethyl)phenyl]-7-methyl-4-oxo-6,7-dihydropyrazolo[1,5-a]pyrazin-3-yl]pyridine-2-carboxamide;
N-[(7S)-5-[3-fluoro-4-(trifluoromethyl)phenyl]-7-methyl-4-oxo-6,7-dihydropyrazolo[1,5-a]pyrazin-3-yl]pyrazine-2-carboxamide;
N-[(7S)-5-(3,4-dichlorophenyl)-7-methyl-4-oxo-6,7-dihydropyrazolo[1,5-a]pyrazin-3-yl]-2-methyl-pyridine-4-carboxamide;
N-[(7S)-5-[3-fluoro-4-(trifluoromethyl)phenyl]-7-methyl-4-oxo-6,7-dihydropyrazolo[1,5-a]pyrazin-3-yl]-5-methyl-pyridine-3-carboxamide;
6-acetamido-N-[(7S)-7-methyl-4-oxo-5-[4-(trifluoromethyl)phenyl]-6,7-dihydropyrazolo[1,5-a]pyrazin-3-yl]pyridine-3-carboxamide;
N-[(7S)-7-methyl-4-oxo-5-[4-(trifluoromethyl)phenyl]-6,7-dihydropyrazolo[1,5-a]pyrazin-3-yl]acetamide;
N-[(7S)-5-[3-fluoro-4-(trifluoromethyl)phenyl]-7-methyl-4-oxo-6,7-dihydropyrazolo[1,5-a]pyrazin-3-yl]-2,6-dimethyl-pyridine-4-carboxamide;
N-[(7S)-5-[3-fluoro-4-(trifluoromethyl)phenyl]-7-methyl-4-oxo-6,7-dihydropyrazolo[1,5-a]pyrazin-3-yl]-2-methyl-pyridine-4-carboxamide;
6-amino-N-[(7S)-5-[3-(hydroxymethyl)-4-(trifluoromethyl)phenyl]-7-methyl-4-oxo-6,7-dihydropyrazolo[1,5-a]pyrazin-3-yl]pyridine-3-carboxamide;
4,5-dimethyl-N-[(7S)-7-methyl-4-oxo-5-[4-(trifluoromethyl)phenyl]-6,7-dihydropyrazolo[1,5-a]pyrazin-3-yl]pyridine-3-carboxamide;
N-[(7S)-5-(4-chlorophenyl)-7-methyl-4-oxo-6,7-dihydropyrazolo[1,5-a]pyrazin-3-yl]-5-methyl-pyridine-3-carboxamide;
2-chloro-N-[(7S)-5-[3-chloro-4-(trifluoromethyl)phenyl]-7-methyl-4-oxo-6,7-dihydropyrazolo[1,5-a]pyrazin-3-yl]-6-methyl-pyridine-4-carboxamide;
2-amino-6-methyl-N-[(7S)-7-methyl-4-oxo-5-[4-(trifluoromethyl)phenyl]-6,7-dihydropyrazolo[1,5-a]pyrazin-3-yl]pyridine-4-carboxamide;
6-amino-4-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;
2-(tert-butylamino)-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide;
N-[(7S)-5-(4-chlorophenyl)-7-methyl-4-oxo-6,7-dihydropyrazolo[1,5-a]pyrazin-3-yl]-2,6-dimethyl-pyridine-4-carboxamide;
2-amino-N-[(7S)-5-[3-chloro-4-(trifluoromethyl)phenyl]-7-methyl-4-oxo-6,7-dihydropyrazolo[1,5-a]pyrazin-3-yl]-6-methyl-pyridine-4-carboxamide;
N-[(7S)-5-[3-chloro-4-(trifluoromethyl)phenyl]-7-methyl-4-oxo-6,7-dihydropyrazolo[1,5-a]pyrazin-3-yl]-4,5-dimethyl-pyridine-3-carboxamide;
6-amino-N-[5-[3-chloro-4-(trifluoromethyl)phenyl]-7-(methoxymethyl)-4-oxo-6,7-dihydropyrazolo[1,5-a]pyrazin-3-yl]pyridine-3-carboxamide;
6-(tert-butylamino)-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide;
N-[(7S)-5-[3-chloro-4-(trifluoromethyl)phenyl]-7-methyl-4-oxo-6,7-dihydropyrazolo[1,5-a]pyrazin-3-yl]-5-fluoro-4-methyl-pyridine-3-carboxamide;
6-amino-N-[(7S)-5-[3-chloro-4-(trifluoromethyl)phenyl]-7-methyl-4-oxo-6,7-dihydropyrazolo[1,5-a]pyrazin-3-yl]-4-methyl-pyridine-3-carboxamide;
2-amino-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide;
6-amino-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide;
5-fluoro-4-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;
N-[(7S)-5-(4-chlorophenyl)-7-methyl-4-oxo-6,7-dihydropyrazolo[1,5-a]pyrazin-3-yl]-5-methoxy-pyridine-3-carboxamide;
5-(methoxymethyl)-N-[(7S)-7-methyl-4-oxo-5-[4-(trifluoromethyl)phenyl]-6,7-dihydropyrazolo[1,5-a]pyrazin-3-yl]pyridine-3-carboxamide;
N-[(7S)-5-[3-chloro-4-(trifluoromethyl)phenyl]-7-methyl-4-oxo-6,7-dihydropyrazolo[1,5-a]pyrazin-3-yl]-5-(methoxymethyl)pyridine-3-carboxamide;
(7S)-6-amino-N-[5-[3-chloro-4-(trifluoromethyl)phenyl]-7-(methoxymethyl)-4-oxo-6,7-dihydropyrazolo[1,5-a]pyrazin-3-yl]pyridine-3-carboxamide;
(7R)-6-amino-N-[5-[3-chloro-4-(trifluoromethyl)phenyl]-7-(methoxymethyl)-4-oxo-6,7-dihydropyrazolo[1,5-a]pyrazin-3-yl]pyridine-3-carboxamide;
2-chloro-6-methyl-N-[(7S)-7-methyl-4-oxo-5-[4-(trifluoromethyl)phenyl]-6,7-dihydropyrazolo[1,5-a]pyrazin-3-yl]pyridine-4-carboxamide;
N-[(7S)-5-[3-chloro-4-(trifluoromethyl)phenyl]-7-methyl-4-oxo-6,7-dihydropyrazolo[1,5-a]pyrazin-3-yl]-5-methyl-1-oxido-pyridin-1-ium-3-carboxamide;
2-bromo-N-[(7S)-7-methyl-4-oxo-5-[4-(trifluoromethyl)phenyl]-6,7-dihydropyrazolo[1,5-a]pyrazin-3-yl]thiazole-5-carboxamide;
N-[(7S)-7-methyl-4-oxo-5-[4-(pentafluoro-$\lambda^6$-sulfanyl)phenyl]-6,7-dihydropyrazolo[1,5-a]pyrazin-3-yl]pyridine-3-carboxamide;
N-[(7S)-7-methyl-4-oxo-5-[4-(trifluoromethyl)phenyl]-6,7-dihydropyrazolo[1,5-a]pyrazin-3-yl]tetrahydropyran-4-carboxamide;
N-[(7S)-7-methyl-4-oxo-5-[4-(trifluoromethyl)phenyl]-6,7-dihydropyrazolo[1,5-a]pyrazin-3-yl]-3-sulfamoyl-benzamide;
N-[(7S)-7-methyl-4-oxo-5-[4-(trifluoromethyl)phenyl]-6,7-dihydropyrazolo[1,5-a]pyrazin-3-yl]-1-oxido-pyridin-1-ium-3-carboxamide;
6-amino-5-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;
N-[(7R)-7-methyl-4-oxo-5-[4-(trifluoromethyl)phenyl]-6,7-dihydropyrazolo[1,5-a]pyrazin-3-yl]pyridine-3-carboxamide;
N-[(7S)-7-methyl-4-oxo-5-[4-(trifluoromethoxy)phenyl]-6,7-dihydropyrazolo[1,5-a]pyrazin-3-yl]pyridine-3-carboxamide;
2-amino-N-[(7S)-5-(4-chlorophenyl)-7-methyl-4-oxo-6,7-dihydropyrazolo[1,5-a]pyrazin-3-yl]-6-methyl-pyridine-4-carboxamide;
2-amino-N-[(7S)-7-methyl-4-oxo-5-[4-(trifluoromethyl)phenyl]-6,7-dihydropyrazolo[1,5-a]pyrazin-3-yl]pyridine-3-carboxamide;
N-[(7S)-7-methyl-4-oxo-5-[4-(trifluoromethylsulfanyl)phenyl]-6,7-dihydropyrazolo[1,5-a]pyrazin-3-yl]pyridine-3-carboxamide;
2-amino-6-methyl-N-[(7S)-7-methyl-4-oxo-5-[4-(trifluoromethyl)phenyl]-6,7-dihydropyrazolo[1,5-a]pyrazin-3-yl]pyrimidine-4-carboxamide;

N-[4-oxo-5-[4-(trifluoromethyl)phenyl]-6,7-dihydropyrazolo[1,5-a]pyrazin-3-yl]pyridine-3-carboxamide;

2-amino-N-[(7S)-5-[3-chloro-4-(trifluoromethyl)phenyl]-7-methyl-4-oxo-6,7-dihydropyrazolo[1,5-a]pyrazin-3-yl]-6-methyl-pyrimidine-4-carboxamide;

2-amino-N-[(7S)-5-[3-chloro-4-(trifluoromethyl)phenyl]-7-methyl-4-oxo-6,7-dihydropyrazolo[1,5-a]pyrazin-3-yl]pyridine-3-carboxamide;

2-amino-5-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;

6-methoxy-N-[(7S)-7-methyl-4-oxo-5-[4-(trifluoromethyl)phenyl]-6,7-dihydropyrazolo[1,5-a]pyrazin-3-yl]pyrazine-2-carboxamide;

2-amino-4-methyl-N-[(7S)-7-methyl-4-oxo-5-[4-(trifluoromethyl)phenyl]-6,7-dihydropyrazolo[1,5-a]pyrazin-3-yl]pyridine-3-carboxamide;

4-amino-N-[(7S)-7-methyl-4-oxo-5-[4-(trifluoromethyl)phenyl]-6,7-dihydropyrazolo[1,5-a]pyrazin-3-yl]benzamide;

2-amino-4-methoxy-N-[(7S)-7-methyl-4-oxo-5-[4-(trifluoromethyl)phenyl]-6,7-dihydropyrazolo[1,5-a]pyrazin-3-yl]pyridine-3-carboxamide;

2-(methylamino)-N-[(7S)-7-methyl-4-oxo-5-[4-(trifluoromethyl)phenyl]-6,7-dihydropyrazolo[1,5-a]pyrazin-3-yl]pyridine-3-carboxamide;

3-amino-N-[(7S)-7-methyl-4-oxo-5-[4-(trifluoromethyl)phenyl]-6,7-dihydropyrazolo[1,5-a]pyrazin-3-yl]pyrazine-2-carboxamide;

N-[(7S)-5-[3-chloro-4-(trifluoromethoxy)phenyl]-7-methyl-4-oxo-6,7-dihydropyrazolo[1,5-a]pyrazin-3-yl]pyridine-3-carboxamide 2-amino-N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

2-amino-N-[(7S)-7-methyl-4-oxo-5-[4-(trifluoromethoxy)phenyl]-6,7-dihydropyrazolo[1,5-a]pyrazin-3-yl]pyridine-3-carboxamide;

2-amino-5-methyl-N-[(7S)-7-methyl-5-[3-methyl-4-(trifluoromethyl)phenyl]-4-oxo-6,7-dihydropyrazolo[1,5-a]pyrazin-3-yl]pyridine-3-carboxamide;

2-amino-N-[(7S)-5-(3,4-dichlorophenyl)-7-methyl-4-oxo-6,7-dihydropyrazolo[1,5-a]pyrazin-3-yl]pyridine-3-carboxamide;

2-amino-N-[(7S)-5-(4-chlorophenyl)-7-methyl-4-oxo-6,7-dihydropyrazolo[1,5-a]pyrazin-3-yl]pyridine-3-carboxamide;

2-amino-N-[(7S)-5-(3,4-dichlorophenyl)-7-methyl-4-oxo-6,7-dihydropyrazolo[1,5-a]pyrazin-3-yl]-5-methyl-pyridine-3-carboxamide;

2-amino-5-methyl-N-[(7S)-7-methyl-4-oxo-5-[4-(pentafluoro-$\lambda^6$-sulfanyl)phenyl]-6,7-dihydropyrazolo[1,5-a]pyrazin-3-yl]pyridine-3-carboxamide;

2-amino-N-[(7S)-5-(4-chlorophenyl)-7-methyl-4-oxo-6,7-dihydropyrazolo[1,5-a]pyrazin-3-yl]-5-methyl-pyridine-3-carboxamide;

2-amino-N-[(7S)-7-methyl-4-oxo-5-[4-(pentafluoro-$\lambda^6$-sulfanyl)phenyl]-6,7-dihydropyrazolo[1,5-a]pyrazin-3-yl]pyridine-3-carboxamide;

2-amino-5-methyl-N-[(7S)-7-methyl-4-oxo-5-[4-(trifluoromethylsulfanyl)phenyl]-6,7-dihydropyrazolo[1,5-a]pyrazin-3-yl]pyridine-3-carboxamide;

2-amino-N-[(7S)-5-(4-chloro-3-methyl-phenyl)-7-methyl-4-oxo-6,7-dihydropyrazolo[1,5-a]pyrazin-3-yl]pyridine-3-carboxamide;

2-(fluoromethyl)-6-methyl-N-[(7S)-7-methyl-4-oxo-5-[4-(trifluoromethyl)phenyl]-6,7-dihydropyrazolo[1,5-a]pyrazin-3-yl]pyridine-4-carboxamide;

2-amino-N-[(7S)-5-[3-(fluoromethyl)-4-(trifluoromethyl)phenyl]-7-methyl-4-oxo-6,7-dihydropyrazolo[1,5-a]pyrazin-3-yl]pyridine-3-carboxamide;

2-amino-N-[(7S)-5-(3-chloro-4-methyl-phenyl)-7-methyl-4-oxo-6,7-dihydropyrazolo[1,5-a]pyrazin-3-yl]pyridine-3-carboxamide;

2-amino-5-methyl-N-[(7S)-7-methyl-4-oxo-5-[4-(trifluoromethoxy)phenyl]-6,7-dihydropyrazolo[1,5-a]pyrazin-3-yl]pyridine-3-carboxamide;

2-(2-hydroxyethylamino)-N-[(7S)-7-methyl-4-oxo-5-[4-(trifluoromethyl)phenyl]-6,7-dihydropyrazolo[1,5-a]pyrazin-3-yl]pyridine-3-carboxamide;

N-[(7S)-5-[3-chloro-4-(trifluoromethyl)phenyl]-7-methyl-4-oxo-6,7-dihydropyrazolo[1,5-a]pyrazin-3-yl]-2-(2-hydroxyethylamino)pyridine-3-carboxamide;

6-chloro-N-[(7S)-7-methyl-4-oxo-5-[4-(trifluoromethyl)phenyl]-6,7-dihydropyrazolo[1,5-a]pyrazin-3-yl]pyridine-3-carboxamide;

2-amino-N-[(7S)-5-[3-(hydroxymethyl)-4-(trifluoromethyl)phenyl]-7-methyl-4-oxo-6,7-dihydropyrazolo[1,5-a]pyrazin-3-yl]pyridine-3-carboxamide;

3-[[(7S)-7-methyl-4-oxo-5-[4-(trifluoromethyl)phenyl]-6,7-dihydropyrazolo[1,5-a]pyrazin-3-yl]carbamoyl]benzenesulfonylfluoride;

4-[[(7S)-7-methyl-4-oxo-5-[4-(trifluoromethyl)phenyl]-6,7-dihydropyrazolo[1,5-a]pyrazin-3-yl]carbamoyl]benzenesulfonyl fluoride;

6-fluoro-N-[(7S)-7-methyl-4-oxo-5-[4-(trifluoromethyl)phenyl]-6,7-dihydropyrazolo[1,5-a]pyrazin-3-yl]pyrazine-2-carboxamide;

N-[(7S)-5-(3,4-dichlorophenyl)-7-methyl-4-oxo-6,7-dihydropyrazolo[1,5-a]pyrazin-3-yl]-6-fluoro-pyrazine-2-carboxamide;

6-chloro-N-[(7S)-7-methyl-4-oxo-5-[4-(trifluoromethyl)phenyl]-6,7-dihydropyrazolo[1,5-a]pyrazin-3-yl]pyrazine-2-carboxamide;

6-chloro-N-[(7S)-5-(3,4-dichlorophenyl)-7-methyl-4-oxo-6,7-dihydropyrazolo[1,5-a]pyrazin-3-yl]pyrazine-2-carboxamide;

and the pharmaceutically acceptable salts and solvates of such compounds.

Further specific compounds according to the invention include:

N-[(7S)-5-(3,4-dichlorophenyl)-7-methyl-4-oxo-6,7-dihydropyrazolo[1,5-a]pyrazin-3-yl]pyridine-3-carboxamide or a hydrochloride salt thereof;

2,3-dimethyl-N-[(7S)-7-methyl-4-oxo-5-[4-(trifluoromethyl)phenyl]-6,7-dihydropyrazolo[1,5-a]pyrazin-3-yl]pyridine-4-carboxamide or a hydrochloride salt thereof;

2-amino-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide or a trifluoroacetate salt thereof;

6-amino-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide or a trifluoroacetate salt thereof;

The present invention further relates to derivatives designed to bind irreversibly to the mGluR2 receptor, in particular to the allosteric pocket thereof.

In an embodiment, these compounds have the Formula (I-a)

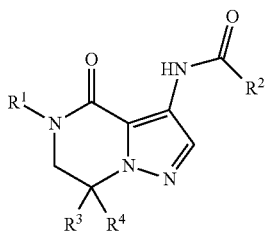

(I-a)

and stereoisomeric forms thereof, wherein $R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio, polyhalo-$C_{1-4}$alkylthio;

$R^2$ is phenyl substituted with —$S(O)_2F$;

$R^3$ is selected from hydrogen and $C_{1-4}$alkyl;

$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;

and the N-oxides and the pharmaceutically acceptable salts and the solvates thereof.

The names of the compounds of the present invention were generated according to the nomenclature rules agreed upon by the International Union of Pure and Applied Chemistry (IUPAC) generated via Accelrys Direct Revision 8.0 SP1 (Microsoft Windows 64-bit Oraclell) (8.0.100.4) OpenEye:1.2.0. In case of tautomeric forms, the name of the depicted tautomeric form of the structure was generated. However it should be clear that the other non-depicted tautomeric form is also included within the scope of the present invention.

Definitions

The notation "$C_{1-4}$alkyl" as used herein alone or as part of another group, defines a saturated, straight or branched, hydrocarbon radical having, unless otherwise stated, from 1 to 4 carbon atoms, such as methyl, ethyl, 1-propyl, 1-methylethyl, butyl, 1-methyl-propyl, 2-methyl-1-propyl, 1,1-dimethylethyl and the like. The notation "—$C_{1-4}$alkyl-OH" as used herein alone or as part of another group, refers to $C_{1-4}$alkyl as defined before, substituted with one OH group at any available carbon atom. The notation "halogen" or "halo" as used herein alone or as part of another group, refers to fluoro, chloro, bromo or iodo, with fluoro or chloro being preferred. The notation "monohalo-$C_{1-4}$alkyl, polyhalo-$C_{1-4}$alkyl" as used herein alone or as part of another group, refers to $C_{1-4}$alkyl as defined before, substituted with 1, 2, 3 or where possible with more halo atoms as defined before. The notation "$C_{3-7}$cycloalkyl" as used herein refers to a saturated, cyclic hydrocarbon radical having from 3 to 7 carbon atoms, such as cyclopropyl, cyclobutyl, cyclopentyl, cyclohexyl and cycloheptyl. A particular $C_{3-7}$cycloalkyl group is cyclopropyl.

The N-oxide forms of the compounds according to Formula (I) are meant to comprise those compounds of Formula (I) wherein one or several nitrogen atoms are oxidized to the so called N-oxide, particularly those N-oxides wherein a nitrogen atom in a pyridinyl radical is oxidized. N-oxides can be formed following procedures known to the skilled person. The N-oxidation reaction may generally be carried out by reacting the starting material of Formula (I) with an appropriate organic or inorganic peroxide. Appropriate inorganic peroxides comprise, for example, hydrogen peroxide, alkali metal or alkaline metal peroxides, e.g. sodium peroxide, potassium peroxide/appropriate organic peroxides may comprise peroxy acids such as, for example, benzenecarboperoxoic acid or halo substituted benzenecarboperoxoic acid, e.g. 3-chloroperoxybenzoic acid (or 3-chloroperbenzoic acid), peroxoalkanoic acids, e.g. peroxoacetic acid, alkylhydroperoxides, e.g. tert-butyl hydroperoxide. Suitable solvents, are for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Whenever the term "substituted" is used in the present invention, it is meant, unless otherwise is indicated or is clear from the context, to indicate that one or more hydrogens, preferably from 1 to 3 hydrogens, more preferably from 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds of Formula (I) and their pharmaceutically acceptable addition salts and solvates thereof may contain one or more centres of chirality and exist as stereoisomeric forms. The term "compounds of the invention" as used herein, is meant to include the compounds of Formula (I), and the salts and solvates thereof. As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers. Hereinbefore and hereinafter, the term "compound of Formula (I)" is meant to include the stereoisomers thereof and the tautomeric forms thereof. The terms "stereoisomers", "stereoisomeric forms" or "stereochemically isomeric forms" hereinbefore or hereinafter are used interchangeably. The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cisor trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible. The meaning of all those terms, i.e. enantiomers, diastereomers, racemates, E isomers, Z isomers, cis isomers, trans isomers and mixtures thereof are known to the skilled person. The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer. Some of the compounds according to Formula (I) may also exist in their tautomeric form. Such forms in so far as they may exist, although not explicitly indicated in the above formula are intended to be included within the scope of the present invention. It follows that a single compound may exist in both stereisomeric and tautomeric forms.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form, for example $^2$H. Radiolabelled compounds of Formula (I) may comprise a radioactive isotope selected from the group consisting of $^3$H, $^{11}$C, $^{14}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group consisting of $^3$H, $^{11}$C and $^{18}$F.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase or chiral supercritical fluid chromatography (SFC). Said pure stereochemically isomeric forms may also be derived from the corresponding pure stereochemically isomeric forms of the appropriate starting materials, provided that the reaction occurs stereospecifically.

The absolute configuration of compounds of the invention reported herein was determined by analysis of the racemic mixture by supercritical fluid chromatography (SFC) followed by SFC comparison of the separate enantiomer(s) which were obtained by asymmetric synthesis, followed by vibrational circular dichroism (VCD) analysis of the particular enantiomer(s).

A. Preparation of the Final Compounds

Experimental Procedure 1

Final compounds according to Formula (I) can be prepared by a coupling reaction of a compound of Formula (III) with a compound of Formula (IIa-1), according to conditions known to the skilled person. Such conditions for example include a suitable coupling agent such as 2-(7-aza-1H-benzotriazole-1-yl)-1,1,3,3-tetramethyluronium hexafluorophosphate (HATU) or benzotriazole-1-yl-oxy-tris(pyrrolidino)phosphonium hexafluorophosphate (PyBOP®) in the presence of a suitable base such as N,N-diisopropylethylamine (DIPEA) or triethylamine (Et₃N) in a suitable solvent such as N,N-dimethylformamide (DMF) or dichloromethane (DCM) under suitable reaction conditions, such as at a convenient temperature, typically room temperature (rt), for a period of time to ensure the completion of the reaction. A compound of Formula (IIa-1) can be obtained commercially or made according to procedures known in the art. In Reaction Scheme 1, all variables are defined as in Formula (I).

Reaction Scheme 1

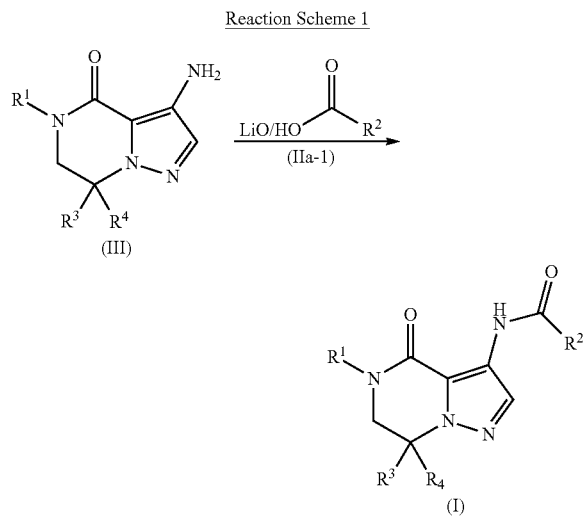

Experimental Procedure 2

Alternatively, final compounds according to Formula (I) can be prepared by a reaction between a compound of Formula (III) with an ester of Formula (IIa-2) wherein $R^y$ is $C_{1-4}$alkyl according to conditions known to the skilled person. Such conditions for example include the use of a suitable base such as lithium bis(trimethylsilyl)amide or isopropylmagnesium chloride, in a suitable solvent such as tetrahydrofuran (THF) under suitable reaction conditions such as at a convenient temperature, typically ranging between 0° C. and 60° C., for a period of time to ensure the completion of the reaction. A compound of Formula (IIa-2) can be obtained commercially or made according to procedures known in the art. In Reaction Scheme 2, $R^y$ is $C_{1-4}$alkyl and all other variables are defined as in Formula (I).

Reaction Scheme 2

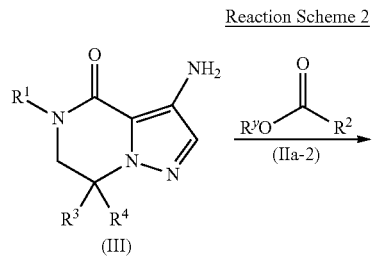

-continued

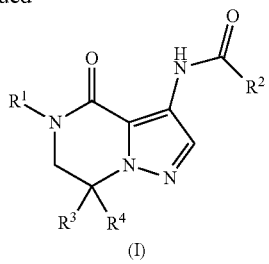

Experimental Procedure 3

Alternatively, final compounds according to Formula (I) can be prepared by a reaction between a compound of Formula (III) with an acid chloride of Formula (IIa-3) according to conditions known to the skilled person. Such conditions for example include the use of a suitable base such as DIPEA, in a suitable solvent such as dichloromethane (DCM) under suitable reaction conditions such as at a convenient temperature, typically ranging between 0° C. and 30° C., for a period of time to ensure the completion of the reaction. A compound of Formula (IIa-3) can be obtained commercially or made according to procedures known in the art. In Reaction Scheme 3, all variables are defined as in Formula (I).

Reaction Scheme 3

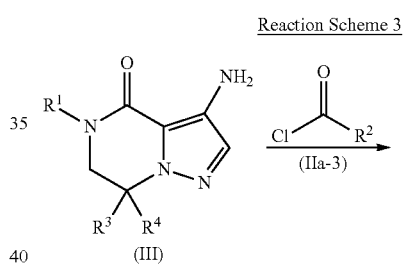

Experimental Procedure 4

Alternatively, final compounds according to Formula (I) can be prepared by a Goldberg coupling reaction of a compound of Formula (IV) with an appropriate amide of Formula (II-b) according to conditions known to the skilled person. Such conditions for example include the use of a suitable copper catalyst such as copper(I) iodide, in the presence of a ligand such as (+/−)-trans-1,2-cyclohexanediamine or N,N'-dimethylethylenediamine, in the presence of a suitable base such as potassium phosphate ($K_3PO_4$) or potassium carbonate ($K_2CO_3$) in a suitable solvent such as 1,4-dioxane or mixture of solvents such as a mixture of toluene and DMF, under suitable reaction conditions, such as at a convenient temperature, typically ranging between 80° C. and 120° C., in particular 100° C., for a period of time to ensure the completion of the reaction. A compound of Formula (II-b) can be obtained commercially or made according to procedures known in the art. In Reaction Scheme 4, halo is defined as iodo or bromo and all other variables are defined as in Formula (I).

Reaction Scheme 4

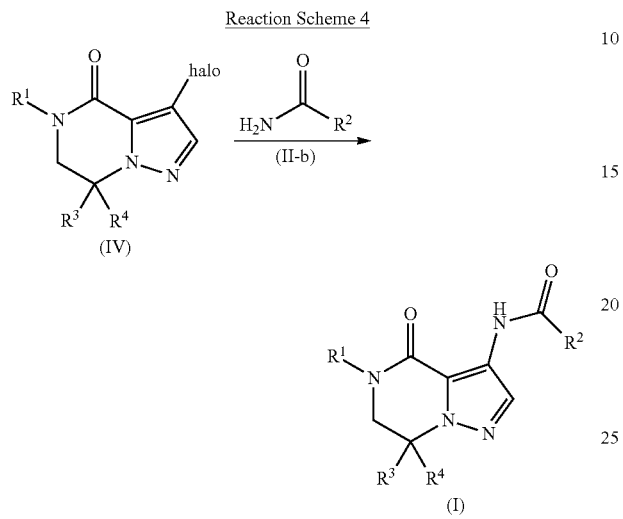

Experimental Procedure 5

Alternatively, final compounds according to Formula (I) can be prepared by a reaction of deprotection or cleavage of a compound of Formula (I-a) according to conditions known to the skilled person. A compound of Formula (I) can be obtained by removal of a protecting group such as for example (1) a Boc group (tert-butoxycarbonyl) in the compound of Formula (I-a), in the presence of acidic media, such as hydrochloric acid, in an inert solvent such as 1,4-dioxane, under suitable reaction conditions, such as at a convenient temperature, typically ranging between 60° C. and 80° C., in particular 70° C., for a period of time to ensure the completion of the reaction, or (2) a tert-butyl group in the presence of acidic media, such as trifluoroacetic acid, in an inert solvent such as 1,2-dichloroethane, under suitable reaction conditions, such as heating under microwave irradiation, at a convenient temperature, in particular at 120° C., for a period of time to ensure the completion of the reaction; or by cleavage of the following groups in (3) to (5): (3) an imidazolopyrimidine group by hydrazine hydrate-mediated cleavage, or (4) an acetyl group in the compound of Formula (I-a), in the presence of acidic media, such as a mixture of hydrochloric acid in 1,4-dioxane and hydrochloric acid in water, under suitable reaction conditions, such as at a convenient temperature, typically ranging between 70° C. and 90° C., in particular 80° C., for a period of time to ensure the completion of the reaction or (5) a diphenylimine group in the compound of Formula (I-a), in the presence of acidic media, such as an aqueous 1M hydrochloric acid solution, in an inert solvent such as 1,4-dioxane, under suitable reaction conditions, such as at a convenient temperature, typically at rt, for a period of time to ensure the completion of the reaction. In Reaction Scheme 5, all variables are defined as in Formula (I) and $R^{2'}$ include the residues indicated in the scope as $R^2$ as well as their protected forms or substituted forms discussed hereinabove.

Reaction Scheme 5

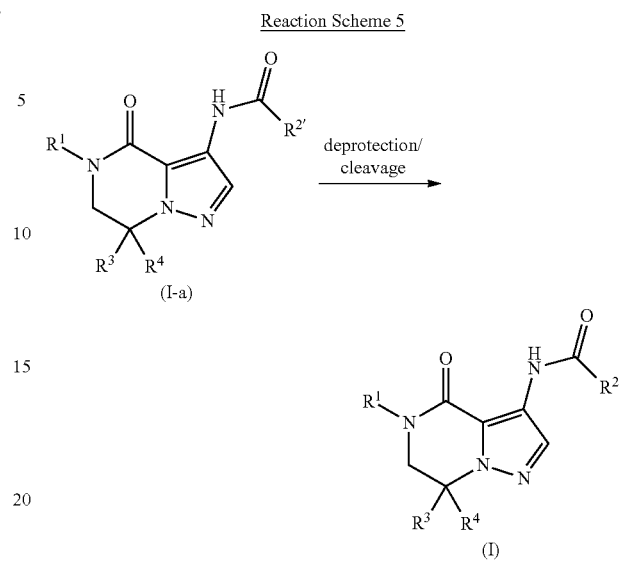

Experimental Procedure 6

Alternatively, final compounds according to Formula (I) can be prepared by a reaction of fluorination of a compound of Formula (I-b) wherein $R^{1'}$ is phenyl or 2-pyridinyl substituted with $C_{1-4}$alkyl-OH. A compound of Formula (I-b) can be treated in the presence of a fluorinating agent such as for example (diethylamino)sulfur trifluoride in a suitable solvent such as, for example DCM, and stirring the reaction mixture at rt. In Reaction Scheme 6, all variables are defined as in Formula (I).

Reaction Scheme 6

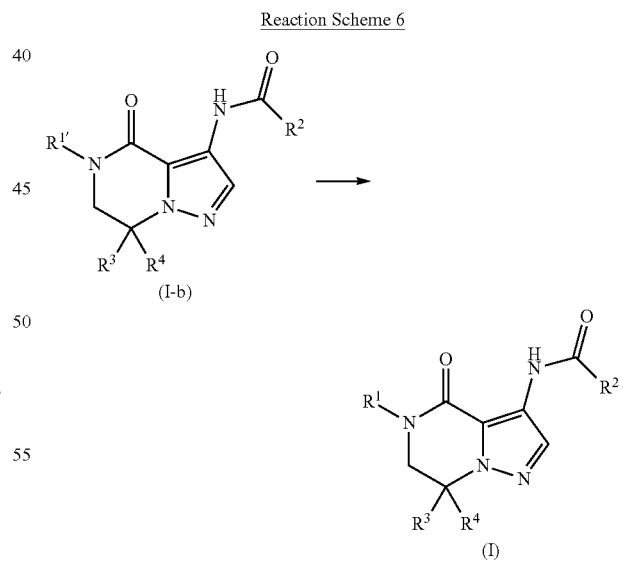

Experimental Procedure 7

Alternatively, final compounds according to Formula (I) can be prepared by a reaction of reduction of a compound of Formula (I-c) wherein $R^{2''}$ represents an $R^2$ precursor containing a nitro group. A compound of Formula (I) can be obtained for example by means of catalytic hydrogenation in the presence of an appropriate catalyst, such as palladium on charcoal, under hydrogen atmosphere, in an inert solvent such as EtOH, at a convenient temperature, typically ranging between rt to 40° C., for a period of time to ensure the completion of the reaction. In Reaction Scheme 7, all variables are defined as in Formula M.

Reaction Scheme 7

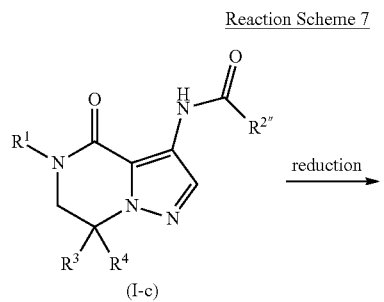

(I-c)

reduction

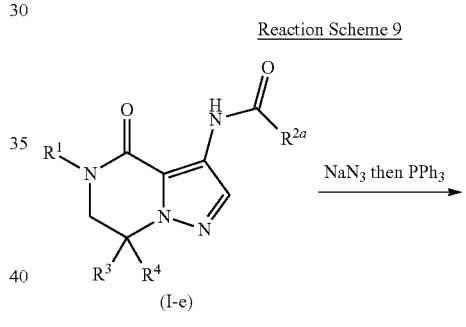

(I)

Experimental Procedure 8

Alternatively, final compounds according to Formula (I) can be prepared by a reaction of hydrolysis of a compound of Formula (I-d) wherein $R^{2'''}$ represents an $R^2$ precursor containing a nitrile group such as for example by means of a basic hydrolysis of a compound of Formula (I-d). The reaction can be performed for example by stirring a solution of nitrile of Formula (I-d), in the presence of a suitable base such as potassium carbonate ($K_2CO_3$) in a suitable solvent such as EtOH, under suitable reaction conditions, such as at a convenient temperature, in particular rt, for a period of time to ensure the completion of the reaction. In Reaction Scheme 8, all variables are defined as in Formula (I).

Reaction Scheme 8

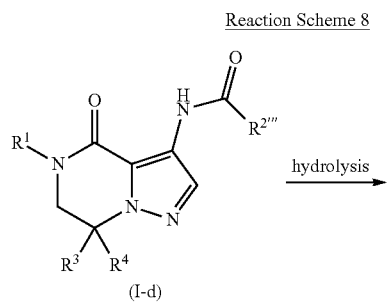

(I-d)

hydrolysis

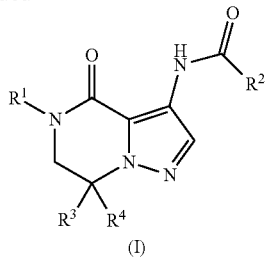

(I)

Experimental Procedure 9

Alternatively, final compounds according to Formula (I), wherein $R^2$ is an aromatic heterocyclyl group substituted with $NH_2$, can be prepared by a Staudinger reaction of a compound of Formula (I-e) wherein $R^{2a}$ is a halo group according to reaction conditions known to the skilled person. Such reaction conditions include the use of sodium azide in the presence of a phosphine, such as triphenylphosphine, in a suitable solvent such as dimethylsulfoxide, under suitable reaction conditions, such as at a convenient temperature, in particular at 120° C., for a period of time to ensure the completion of the reaction. In Reaction Scheme 9, all variables are defined as in Formula (I).

Reaction Scheme 9

(I-e)

NaN₃ then PPh₃ →

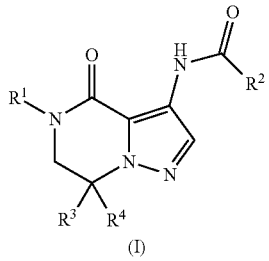

(I)

Experimental Procedure 10

Alternatively, final compounds according to Formula (I-f) can be converted to a final compound of Formula (I) wherein $R^2$ is the N-oxide of a nitrogen-containing aromatic heterocyclyl, by a reaction of oxidation of a compound of Formula (I-f) wherein $R^{2b}$ is an aromatic heterocyclyl with one or several nitrogen atoms that can be oxidized to the so called N-oxide, following procedures known to the skilled person. Such reaction conditions may generally be carried out by reacting the starting material of Formula (I-f) with an appropriate organic or inorganic peroxide, such as for example hydrogen peroxide, in the presence of a catalyst, such as methyltrioxorhenium(VII), in a suitable solvent such as DCM, such as at a convenient temperature, in particular at rt, for a period of time to ensure the completion of the reaction. In Reaction Scheme 10, all variables are defined as in Formula (I).

Reaction Scheme 10

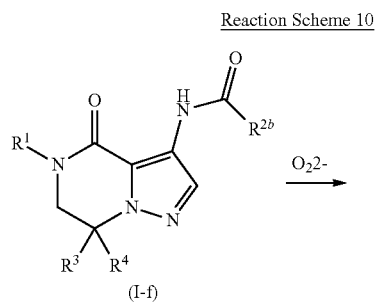
(I-f)

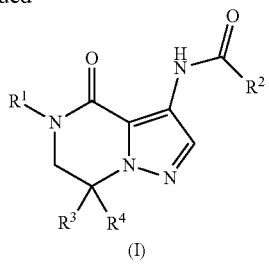
(I)

Experimental Procedure 11

Alternatively, final compounds according to Formula (I) wherein $R^2$ is an aromatic heterocyclyl substituted with NHR", wherein R" is $C_{1-4}$alkyl, can be prepared by a coupling reaction with a compound of Formula (II-c), wherein R" is $C_{1-4}$alkyl, to convert a final compound of Formula (I-g) to a final compound of Formula (I) according to reaction conditions known to the skilled person. A compound of Formula (I) can be obtained by a phosphonium coupling reaction of a final compound of Formula (I-g) wherein $R^{2c}$ is the N-oxide of a nitrogen-containing aromatic heterocyclyl. Such reaction conditions include the use of a suitable phosphonium salt such as bromotripyrrolidinophosphonium hexafluorophosphate (PyBroP®), in the presence of a suitable base such as DIPEA in a suitable solvent such as DCM under suitable reaction conditions, such as at a convenient temperature, in particular at rt, for a period of time to ensure the completion of the reaction. A compound of Formula (II-c) can be obtained commercially or made according to procedures known in the art. In Reaction Scheme 11, all variables are defined as in Formula (I).

Reaction Scheme 11

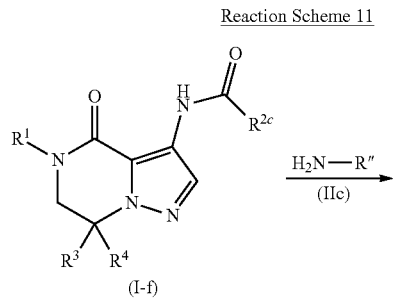
(I-f)

B. Preparation of the Intermediate Compounds

Experimental Procedure 12

Intermediate compounds according to Formula (III) can be prepared by a reaction of deprotection of a compound of Formula (V-a) or a compound of Formula (V-b) according to conditions known to the skilled person. A compound of Formula (III) can be obtained by removal of the protecting group such as for example a benzylideneamine group such as for example a diphenylimine group, in the compound of Formula (V-a), in the presence of acidic media, such as an aqueous 1M hydrochloric acid solution, in an inert solvent such as 1,4-dioxane, under suitable reaction conditions, such as at a convenient temperature, typically rt, for a period of time to ensure the completion of the reaction.

Alternatively a compound of Formula (III) can be obtained by removal of the protecting group such as for example a Boc group (tert-butoxycarbonyl) in the compound of Formula (V-b), in the presence of acidic media, such as hydrochloric acid, in an inert solvent such as 1,4-dioxane, under suitable reaction conditions, such as at a convenient temperature, typically ranging between 60° C. and 80° C., in particular 70° C., for a period of time to ensure the completion of the reaction.

Alternatively a compound of Formula (III) can be prepared by copper-catalyzed direct amination of a compound of Formula (IV) with sodium azide as the amino source. Such conditions for example include the use of sodium azide and a suitable copper catalyst such as copper(I) iodide, in the presence of a ligand such as N,N'-dimethylethylenediamine, in the presence of a suitable base such as sodium carbonate ($Na_2CO_3$) in a suitable solvent such as dimethylsulfoxide (DMSO), under suitable reaction conditions, such as at a convenient temperature, typically ranging between 30° C. and 50° C., in particular 40° C., for a period of time to ensure the completion of the reaction.

In Reaction Scheme 12, halo is defined as bromo or iodo and all other variables are defined as in Formula (I).

Reaction Scheme 12

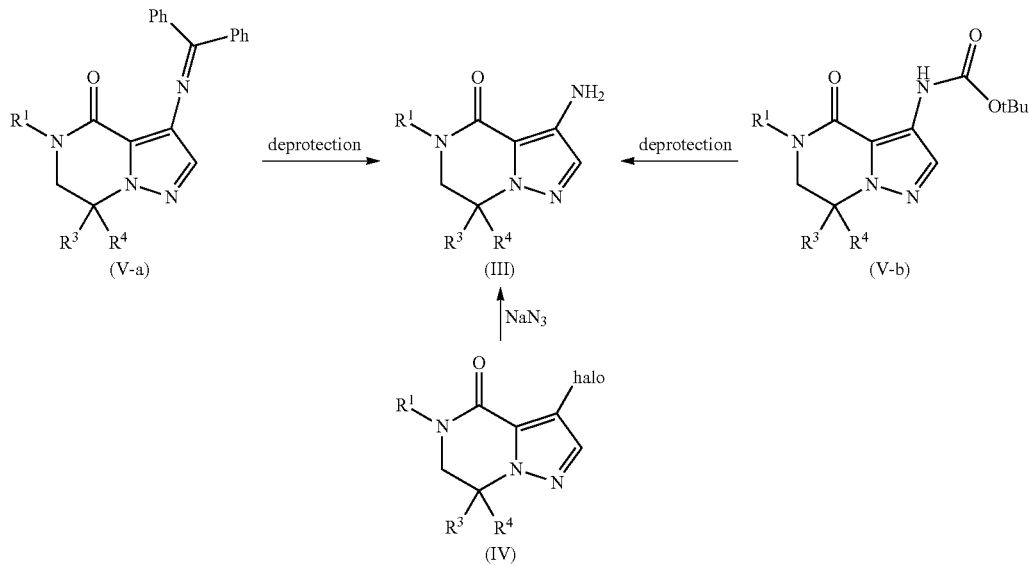

Experimental Procedure 13

Intermediate compounds according to Formula (V-a) can be prepared by a reaction of Buchwald-Hartwig amination between an intermediate compound of Formula (IV) and benzophenone imine. Such conditions for example include the use of a suitable palladium catalyst system such as tris(dibenzylideneacetone)dipalladium(0), in the presence of a ligand such as 2,2'-bis(diphenylphosphino)-1,1'-binaphthyl (BINAP), in the presence of a suitable base such as sodium tert-butoxide, in a suitable solvent such as toluene, under suitable reaction conditions, such as at a convenient temperature, typically ranging between 80° C. and 100° C., in particular 90° C., for a period of time to ensure the completion of the reaction.

Intermediate compounds according to Formula (V-b) can be prepared by a Goldberg coupling reaction of a compound of Formula (IV) with tert-butyl carbamate according to conditions known to the skilled person. Such conditions for example include the use of a suitable copper catalyst such as copper(I) iodide, in the presence of a ligand such as (+/−)-trans-1,2-cyclohexanediamine, in the presence of a suitable base such as $K_3PO_4$ in a suitable solvent such as 1,4-dioxane, under suitable reaction conditions, such as at a convenient temperature, typically ranging between 80° C. and 120° C., in particular 100° C., for a period of time to ensure the completion of the reaction.

In Reaction Scheme 13, halo is defined as Br or I and all other variables are defined as in Formula (I).

Reaction Scheme 13

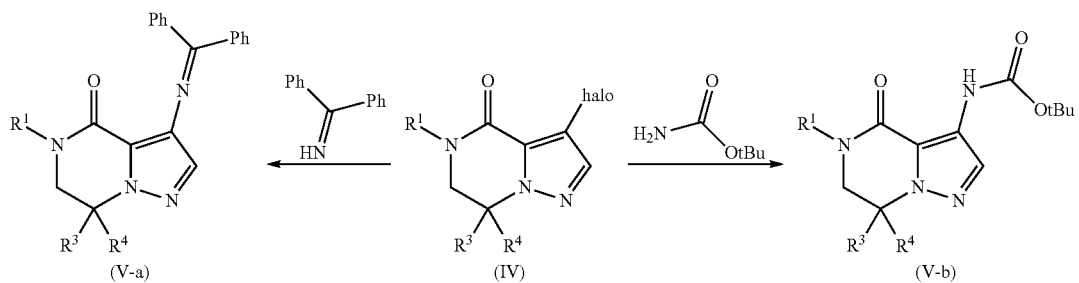

Experimental Procedure 14

Intermediate compounds according to Formula (IV) can be prepared by a Goldberg coupling reaction of a compound of Formula (VI) with an appropriate phenyl/2-pyridinyl halide of Formula (VII) where X is halo, in particular bromo or iodo, according to conditions known to the skilled person. Such conditions include for example the use of a suitable copper(I) catalyst such as copper(I) iodide, in the presence of a ligand, such as N,N'-dimethylethylenediamine, in the presence of a base, such as inorganic carbonates, for example sodium carbonate ($Na_2CO_3$) or potassium carbonate ($K_2CO_3$), in a suitable solvent, such as toluene or a mixture of toluene and DMF, under suitable reaction conditions, such as at a convenient temperature, typically ranging between 60 and 140° C., or between 100° C. and 140° C., or between 60 and 90° C., in particular 110 or 75° C., for a period of time to ensure the completion of the reaction. A compound of Formula (VII) can be obtained commercially or made according to procedures known in the art.

Alternatively intermediate compound according to Formula (IV) can be prepared via a reaction of halogenation of an intermediate of Formula (VIII) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction.

In Reaction Scheme 14, halo is defined as Br or I and all other variables are defined as in Formula (I).

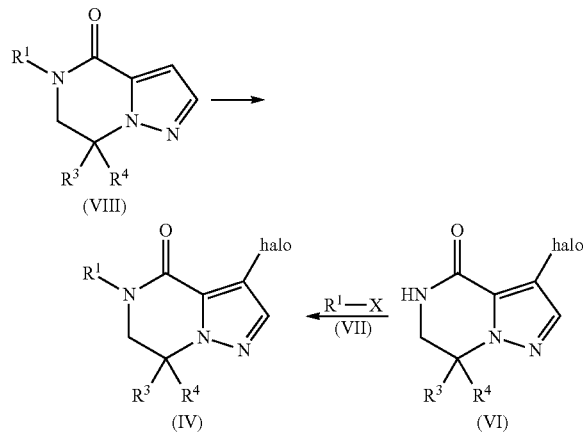

Reaction Scheme 14

Experimental Procedure 15

Intermediate compounds according to Formula (VIII) can be prepared by a Goldberg coupling reaction of a compound of Formula (IX-a) with an appropriate phenyl/2-pyridinyl halide of Formula (VII) where X is halo, in particular bromo or iodo, according to conditions known to the skilled person. Such conditions include for example the use of a suitable copper(I) catalyst such as copper(I) iodide, in the presence of a ligand, such as N,N-dimethylethylenediamine, in the presence of a base, such as inorganic carbonates, for example $Na_2CO_3$ or $K_2CO_3$, in a suitable solvent, such as toluene or a mixture of toluene and DMF, under suitable reaction conditions, such as at a convenient temperature, typically ranging between 100° C. and 140° C., in particular 110° C., for a period of time to ensure the completion of the reaction. A compound of Formula (VII) can be obtained commercially or made according to procedures known in the art.

Alternatively, intermediate compounds according to Formula (VIII) can be prepared by a Suzuki coupling reaction of a compound of Formula (IX-a) with an appropriate phenyl/2-pyridinyl halide of Formula (VII) where X is halo, in particular chloro, according to conditions known to the skilled person. Such conditions include for example the use of a suitable palladium catalyst such as tetrakis(triphenylphosphine)palladium(0), in the presence of a ligand, such 4,5-bis(diphenylphosphino)-9,9-dimethylxanthene (Xantphos), in the presence of a base, such as cesium carbonate, in a suitable solvent, such 1,4-dioxane, under suitable reaction conditions, such as at a convenient temperature, typically ranging between 100° C. and 140° C., in particular 100° C., for a period of time to ensure the completion of the reaction.

Intermediate compound according to Formula (IX-a) can be prepared by removal of the protecting group, for example a Boc group, in an intermediate of Formula (X-a), for example in the presence of acidic media, such as hydrochloric acid, in an inert solvent such as 1,4-dioxane or acetonitrile or ethyl acetate (EtOAc), under suitable reaction conditions, such as at a convenient temperature, such as from 15° C. to 80° C., typically 80° C. or from 15° C. to 30° C. depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15° C. to 30° C., for a period of time to ensure the completion of the reaction.

Intermediate compound according to Formula (X-a) wherein $R^x$ is $C_{1-4}$alkyl and PG is a protecting group, for example a Boc group, can be prepared by a Mitsunobu type reaction between an intermediate compound of Formula (XII-a) and an appropriate alcohol of Formula (XI), in the presence of a suitable triarylphosphine, such as triphenylphosphine or a suitable trialkylphosphine, and a suitable dialkyl azodicarboxylate reagent, such as di-tert-butyl azodicarboxylate or diethyl azodicarboxylate, in a suitable inert solvent, such as THF, under suitable reaction conditions, such as at a convenient temperature, typically ranging between 0° C. and rt, in particular, 20° C., for a period of time to ensure the completion of the reaction. Intermediate compounds of Formula (XI) and of Formula (XII-a) can be obtained commercially or synthesized according to literature procedures.

In Reaction Scheme 15, $R^x$ is $C_{1-4}$alkyl, PG is a protecting group, for example Boc, and all other variables are defined as in Formula (I).

Reaction Scheme 15

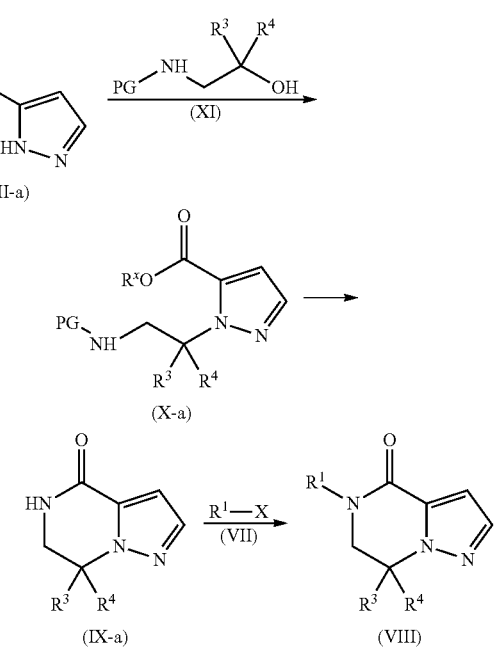

Experimental Procedure 16

Intermediate compounds according to Formula (VI) wherein halo is defined as Br or I can be prepared by removal of the protecting group, for example a Boc group, in an intermediate of Formula (X-b), for example in the presence of acidic media, such as hydrochloric acid, in an inert solvent such as 1,4-dioxane or acetonitrile or ethyl acetate (EtOAc), under suitable reaction conditions, such as at a convenient temperature, such as from 15 to 80° C., typically 80° C. or from 15-30° C., or rt, depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15 to 30° C., or rt, for a period of time to ensure the completion of the reaction.

Intermediate compound according to Formula (X-b) wherein halo is defined as Br or I, $R^x$ is $C_{1-4}$alkyl and PG is a protecting group, for example Boc, can be prepared by a Mitsunobu type reaction between an intermediate compound of Formula (XII-b) and an appropriate alcohol of Formula (XI), in the presence of a suitable triarylphosphine, such as triphenylphosphine, or a suitable trialkylphosphine, and a suitable dialkyl azodicarboxylate reagent, such as di-tert-butyl azodicarboxylate or diethyl azodicarboxylate, in a suitable inert solvent, such as THF, under suitable reaction conditions, such as at a convenient temperature, typically ranging from 0° C. to rt, e.g. 20° C., for a period of time to ensure the completion of the reaction. An intermediate compound of Formula (XI) can be obtained commercially or synthesized according to literature procedures.

Intermediate compound according to Formula (XII-b) wherein $R^x$ is $C_{1-4}$alkyl, can be prepared by means of a reaction of halogenation of intermediate of Formula (XII-a) with a halogenating reagent such as N-iodosuccinimide, in an inert solvent such as DCM, under suitable reaction conditions, such as at a convenient temperature, typically rt, for a period of time to ensure the completion of the reaction. Intermediate compound of Formula (XII-b), wherein $R^x$ is methyl and halo is bromo, can be obtained commercially and is a particularly preferred material for use in the synthesis, including large scale, of a variety of final compounds of Formula (I) according to the general procedures described herein. An intermediate compound of Formula (XII-a) can be obtained commercially or synthesized according to literature procedures.

In Reaction Scheme 16, halo is bromo or iodo, $R^x$ is $C_{1-4}$alkyl, PG is a protecting group, such as for example Boc, and all other variables are defined as in Formula (I).

Reaction Scheme 16

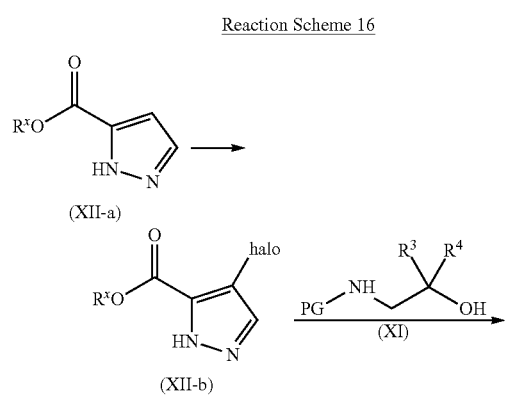

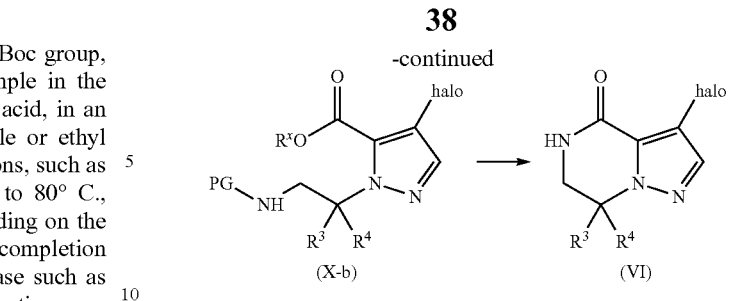

In order to obtain the HCl salt forms of the compounds, several procedures known to those skilled in the art can be used. In a typical procedure, for example, the free base can be dissolved in DIPE or $Et_2O$ and subsequently, a 6 N HCl solution in 2-propanol or a 1 N HCl solution in $Et_2O$ can be added dropwise. The mixture typically is stirred for 10 minutes after which the product can be filtered off. The HCl salt usually is dried in vacuo.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

The compounds provided in this invention are negative allosteric modulators (NAMs) of metabotropic glutamate receptors, in particular they are negative allosteric modulators of mGluR2. The compounds of the present invention do not appear to bind to the glutamate recognition site, the orthosteric ligand site, but instead to an allosteric site within the seven transmembrane region of the receptor. In the presence of glutamate, the compounds of this invention decrease the mGluR2 response. The compounds provided in this invention are expected to have their effect at mGluR2 by virtue of their ability to decrease the response of such receptors to glutamate, attenuating the response of the receptor.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

Hence, the present invention relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof for use as a medicament.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of negative allosteric modulators of mGluR2.

Also, the present invention relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of negative allosteric modulators of mGluR2.

In particular, the neurological and psychiatric disorders associated with glutamate dysfunction, include one or more of the following central nervous system conditions or diseases: mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

In particular, the central nervous system disorder is a psychotic disorder selected from the group of schizophrenia (in particular in antipsychotic-stabilized patients), schizophreniform disorder, schizoaffective disorder, delusional disorder, brief psychotic disorder, and substance-induced psychotic disorder.

In particular, the central nervous system disorder is a substance-related disorder selected from the group of alcohol dependence, alcohol abuse, amphetamine dependence, amphetamine abuse, caffeine dependence, caffeine abuse, cannabis dependence, cannabis abuse, cocaine dependence, cocaine abuse, hallucinogen dependence, hallucinogen abuse, nicotine dependence, nicotine abuse, opioid dependence, opioid abuse, phencyclidine dependence, and phencyclidine abuse.

In particular, the central nervous system disorder is a mood disorder selected from the group of major depressive disorder, depression, treatment resistant depression, dysthymic disorder, cyclothymic disorder, and substance-induced mood disorder.

In particular, the central nervous system disorder is a disorder usually first diagnosed in infancy, childhood, or adolescence selected from mental retardation, learning disorder, motor skills disorder, communication disorder, attention-deficit and disruptive behaviour disorders (such as Attention-Deficit/Hyperactivity Disorder (ADHD)). An additional disorder usually first diagnosed in infancy, childhood, or adolescence is autistic disorder.

In particular, the central nervous system disorder is a cognitive disorder selected from the group of dementia, in particular, dementia of the Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, and substance-induced persisting dementia.

In particular, the central nervous system disorder is an amnestic disorder, such as substance-induced persisting amnestic disorder.

As already mentioned hereinabove, the term "treatment" does not necessarily indicate a total elimination of all symptoms, but may also refer to symptomatic treatment in any of the disorders mentioned above. In particular, symptoms that may be treated include but are not limited to, memory impairment in particular in dementia or in major depressive disorder, age-related cognitive decline, mild cognitive impairment, and depressive symptoms.

Of the disorders mentioned above, the treatment of dementia, major depressive disorder, depression, treatment resistant depression, attention-deficit/hyperactivity disorder and schizophrenia, in particular in antipsychotic-stabilized patients, are of particular importance.

The fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

A skilled person will be familiar with alternative nomenclatures, nosologies, and classification systems for the diseases or conditions referred to herein. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, cannabis use disorder, cocaine use disorder, other hallucinogen use disorder, tobacco use disorder, opiod use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; somatic symptom disorders; hypersomnolence disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder. In particular, the disorder is autism. Specifiers associated with ASD include those where the individual has a genetic disorder, such as in Rett syndrome or Fragile X syndrome.

Therefore, the invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in the treatment of any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in treating any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the treatment or prevention, in particular treatment, of any one of the diseases mentioned hereinbefore.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof, or an N-oxide thereof, or a pharmaceutically acceptable salt or solvate thereof, in particular, a compound of Formula (I) or a stereoisomeric form thereof, or a pharmaceutically acceptable salt or a solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a subject in need thereof.

One skilled in the art will recognize that a therapeutically effective amount of the NAMs of the present invention is the amount sufficient to modulate the activity of the mGluR2 and that this amount varies inter alia, depending on the type of disease, the concentration of the compound in the therapeutic formulation, and the condition of the patient. Generally, an amount of NAM to be administered as a therapeutic agent for treating diseases in which modulation of the mGluR2 is beneficial, such as the disorders described herein, will be determined on a case by case by an attending physician.

Generally, a suitable dose is one that results in a concentration of the NAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone. Examples of such combinations include the compounds of the invention in combination with antipsychotic(s), NMDA receptor antagonists (e.g. memantine), NR2B antagonists, acetylcholinesterase inhibitors (e.g. donepezil, galantamine, physostigmine and rivastigmine) and/or antidepressant neurotransmitter reuptake inhibitors. Particular combinations include the compounds of the invention in combination with antipsychotics, or the compounds of the invention in combination with memantine and/or NR2B antagonists.

Pharmaceutical Compositions

The present invention also provides compositions for preventing or treating diseases in which modulation of the mGluR2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), an N-oxide, a pharmaceutically acceptable salt thereof, a solvate thereof or a stereochemically isomeric form thereof, more in particular, a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the N-oxides thereof, the pharmaceutically acceptable salts thereof, the solvates and the stereochemically isomeric forms thereof, more in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin or sulfobutyl-$\beta$-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility. The use of such a composition for the manufacture of a medicament as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional drug selected from the group of antipsychotics; NMDA receptor antagonists (e.g. memantine); NR2B antagonists; acetylcholinesterase inhibitors (e.g. donepezil, galantamine, physostigmine and rivastigmine) and/or antidepressant neurotransmitter reuptake inhibitors. In particular, the present invention also relates to a combination of a compound according to the present invention and antipsychotic(s), or to a combination of a compound according to the present invention and memantine and/or an NR2B antagonist. The present invention also relates to such a combination for use as a medicine. The present invention also relates to a product comprising (a) a compound according to the present invention, an N-oxide thereof, a pharmaceutically acceptable salt thereof or a solvate thereof, in particular, a pharmaceutically acceptable salt thereof or a solvate thereof, and (b) an additional component selected from antipsychotics, NMDA receptor antagonists (e.g. memantine), NR2B antagonists, acetylcholinesterase inhibitors and/or antidepressant neurotransmitter reuptake inhibitor(s), as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular negative mGluR2 allosteric modulators. More in particular the additional component (b) is selected from antipsychotic(s) or memantine and/or an NR2B antagonist. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "aq." means aqueous; "BEH" means bridged ethylsiloxane/silica hybrid; "Boc" or "BOC" means tert-butyloxycarbonyl; "BINAP" means (1,1'-binaphthalene-2,2'-diyl)bis(diphenylphosphine); "CI" means chemical ionisation; "CSH" means charged surface hybrid; "conc." means concentrated; "DAD" means diode-array detector; "DAST" means diethylaminosulfur trifluoride; "DIPEA" means diisopropylethylamine; "dil." means diluted; "THF" means tetrahydrofuran; "Et$_3$N" means triethylamine; "DIPE" means diisopropylether; "DMF" means N,N-dimethylformamide; "Et$_2$O" means diethylether; "EtOAc" means ethyl acetate; "DCM" means dichloromethane; "DMSO" means dimethylsulfoxide; "HSS" means high strength silica; "L" means liter; "LRMS" means low-resolution mass spectrometry/spectra; "Pd$_2$(dba)$_3$" means tris(dibenzylideneacetone)dipalladium(0); "Pd(PPh$_3$)$_4$" means tetrakis(triphenylphosphine)palladium(0); "Pd(OAc)$_2$" means palladium(II) acetate; "PyBOP®" means benzotriazole-1-yl-oxy-tris(pyrrolidino)phosphonium hexafluorophosphate and is a registered trademark of Merck KGaA; "Xantphos" means 4,5-bis(diphenylphosphino)-9,9-dimethylxanthene; "PyBrop®" means bromotripyrrolidinophosphonium hexafluorophosphate and is a registered trademark of Merck KGaA; "HATU" means 2-(7-aza-1H-benzotriazole-1-yl)-1,1,3,3-tetramethyluronium hexafluorophosphate; "HPLC" means high performance liquid chromatography; "HRMS" means high-resolution mass spectrometry/spectra; "mL" or "ml" means milliliter; "NH$_4$Ac" means ammonium acetate; "EtOH" means ethanol; "ES" means electrospray; "iPrOH" means isopropanol; "iPrNH$_2$" means isopropylamine; "MeOH" means methanol; "MeCN" means acetonitrile; "MSD" means Mass Selective Detector; "eq" means equivalent(s); "RP" means Reverse Phase; "rt" or "RT" mean room temperature; "M.p." means melting point; "min" means minutes; "h" means hour(s); "s" means second(s); "TOF" means time of flight; "TEA" means triethylamine; "QTOF" means Quadrupole-Time of Flight; "quant." means quantitative; "sat." means saturated; "SFC" means supercritical fluid chromatography; "SM" means starting material; "sol." means solution; "SQD" means Single Quadrupole Detector; "UPLC" means Ultra Performance Liquid Chromatography.

Microwave assisted reactions were performed in a single-mode reactor: Initiator™ Sixty EXP microwave reactor (Biotage AB), or in a multimode reactor: MicroSYNTH Labstation (Milestone, Inc.).

Hydrogenation reactions were performed in a continuous flow hydrogenator: H-CUBE® from ThalesNano Nanotechnology Inc.

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges from different vendors, on irregular silica gel, (normal phase disposable flash columns) on different flash systems.

Nuclear Magnetic Resonance (NMR): For a number of compounds, ¹H NMR spectra were recorded either on a Bruker Avance III, on a Bruker DPX-400 or on a Bruker AV-500 spectrometer with standard pulse sequences, operating at 400 MHz and 500 MHz, respectively. Chemical shifts (δ) are reported in parts per million (ppm) downfield from tetramethylsilane (TMS), which was used as internal standard.

IR and VCD spectra were recorded at 4 cm$^{-1}$ resolution on an FTIR Equinox spectrometer equipped with the VCD module PMA 37 (Bruker, Germany). A low-pass filter (<1830 cm$^{-1}$), BaF$_2$ polarizer, ZnSe Photoelastic Modulator (Hinds instruments PEM-90) oscillating at the frequency of 50 Hz and Lock-In Amplifier at 1 mV (SRS—SR830 DSP) were used. Samples were dissolved in CD$_2$Cl$_2$ and placed in a demountable KBr cell with a 0.09 mm Teflon spacer (1 h collection time). OPUS software (Bruker, Germany) was used for spectra processing.

A thorough conformational search was performed at molecular mechanics level using Macromodel to perform a mixed torsional/low-mode sampling with the OPLS-2005 force field. The located minima were optimized using Jaguar on the B3LYP/6-31G level with a Poisson-Boltzmann continuum solvation model to mimic a dichloromethane solvent. All conformations within 10 kJ/mol interval were used to simulate VCD and IR spectrum. Dipole and rotational strengths were calculated at the same B3LYP/6-31G level, using Jaguar.

Preparation of Intermediate Compounds

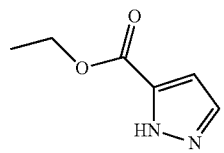

Intermediate 1 (I-1)

Sulfuric acid (10 mL, 187.6 mmol) was added to a solution of 1-H-pyrazole-3-carboxylic acid (1.93 g, 17.22 mmol) in EtOH (20 mL). The mixture was stirred at 90° C. for 15 h. Then it was allowed to cool to rt and the solvents were evaporated in vacuo. The residue was poured into water and the solution basified with K$_2$CO$_3$ and extracted with EtOAc. The organic layer was separated, dried (MgSO$_4$), filtered and the solvent evaporated in vacuo to yield intermediate compound I-1 as a white solid (2.28 g, 93% purity, 94%) which was used in the following step without further purification.

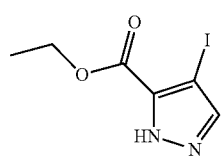

Intermediate 2 (I-2)

Intermediate I-1 (100 g, 0.68 mol) and N-iodosuccinimide (213.5 g, 0.95 mol) were dissolved in DCM (2 L). The mixture was stirred at rt for 24 h. The mixture was treated with a sat. sol. of Na$_2$S$_2$O$_3$ and a sat. sol. of Na$_2$CO$_3$ and extracted with DCM. The organic layer was separated, dried (MgSO$_4$), filtered and the solvent evaporated in vacuo to yield intermediate compound I-2 as a white solid (160 g, 85%).

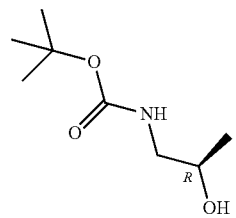

Intermediate 3 (I-3)

Di-tert-butyl dicarbonate (58.1 g, 266.3 mmol) in DCM (50 mL) was added to a stirred solution of (R)-(−)-1-amino-2-propanol in DCM (50 mL) at 0° C. under nitrogen. The mixture was stirred at rt for 2 h. The mixture was diluted with cooled water and extracted with DCM. The organic layer was separated, dried (Na$_2$SO$_4$), filtered and the solvents evaporated in vacuo to yield intermediate I-3 as a colorless oil (47 g, quant.). The product was used in the next step without further purification.

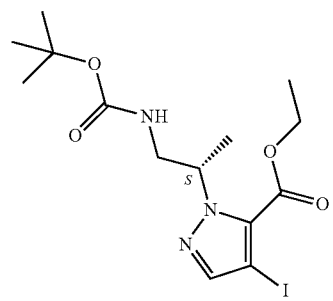

Intermediate 4 (I-4)

Di-tert-butyl azodicarboxylate (4.67 g, 20.3 mmol) was added to a stirred solution of intermediate I-2 (3 g, 11.28 mmol), intermediate I-3 (4.44 g, 22.55 mmol) and triphenylphosphine (5.32 g, 20.3 mmol) in THF (56 mL) under nitrogen. The mixture was stirred at rt for 5 h. The solvent was evaporated in vacuo and the crude product was triturated with DIPE. The solid was filtered and the filtrate was evaporated in vacuo. The crude product was purified by flash column chromatography (silica; EtOAc in heptane 0/100 to 30/70). The desired fractions were collected and the solvents evaporated in vacuo to give intermediate compound I-4 as a colorless oil (4.9 g, 91% purity, 93%).

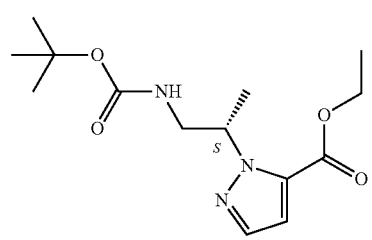

Intermediate 5 (I-5)

Intermediate compound I-5 was synthesized following a similar approach described for intermediate I-4. Starting from intermediate I-1 (25.82 g, 184.25 mmol) and intermediate I-3 (47.16 g, 239.5 mmol), intermediate compound I-5 was obtained as a yellow oil (123 g, quant) which was used in the following step without further purification.

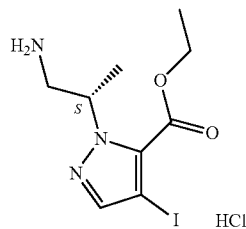

Intermediate 6 (I-6)

A 4 M solution of HCl in 1,4-dioxane (10 mL, 40 mmol) was added to a solution of intermediate I-4 (4.2 g, 9.63 mmol) in acetonitrile (20 mL). The mixture was stirred at 80° C. for 2 h. The solvent was evaporated in vacuo to yield intermediate compound I-6 (3.5 g, 97%).

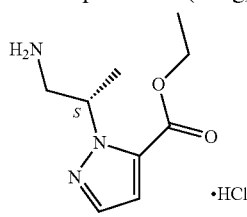

Intermediate 7 (I-7)

Intermediate compound I-7 was synthesized following a similar approach described for intermediate I-6. Starting from intermediate I-5 (54.79 g, 184.25 mmol) and a 4M solution of HCl in 1,4-dioxane (415 mL, 1.66 mol), intermediate compound I-7 was obtained as a white solid (32.5 g, 82% purity, 75%) which was used in the following step without further purification.

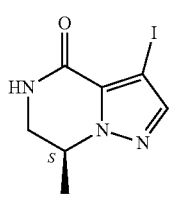

Intermediate 8 (I-8)

Intermediate I-6 as HCl salt (180 g, 350.4 mmol) was dissolved in a sat. sol. of NaHCO₃ (2 L). The mixture was stirred at rt for 12 h. The mixture was diluted with water and extracted with DCM. The organic layers were separated, dried (Na₂SO₄), filtered and the solvents evaporated in vacuo. Then the residue was washed with tert-butyl methyl ether to yield intermediate compound I-8 (92 g, 90%).

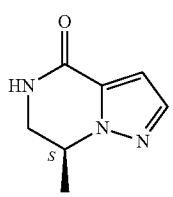

Intermediate 9 (I-9)

Intermediate compound I-9 was synthesized following a similar approach described for intermediate I-8. Starting from intermediate I-7 (32.5 g, 139.1 mmol), intermediate compound I-9 was obtained as a solid (14.8 g, 70%).

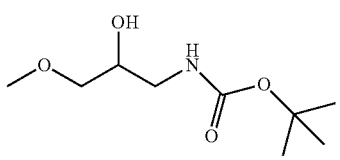

Intermediate 10 (I-10)

Intermediate compound I-10 was synthesized following a similar approach described for 1-3. Starting from 1-amino-3-methoxy-2-propanol (2.3 g, 21.876 mmol), and introducing a purification step (flash column chromatography (silica; MeOH in DCM 0/100 to 5/95)), I-10 (3.1 g, 69%) was obtained.

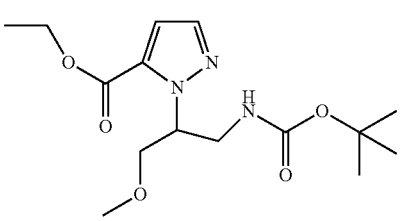

Intermediate 11 (I-11)

Di-tert-butyl azodicarboxylate (7.30 g, 31.68 mmol) was added to a stirred solution of I-1 (1.78 g, 12.671 mmol), intermediate I-10 (3.12 g, 15.21 mmol) and triphenylphosphine (8.31 g, 31.68 mmol) in THF (80 mL) under nitrogen at 0° C. The mixture was stirred at rt for 1 h. The solvent was evaporated and the residue was treated with DIPE, the solid was filtered and the filtrate was evaporated in vacuo. The crude product was purified by flash column chromatography (silica; EtOAc in heptane 0/100 to 50/50). The desired fractions were collected and the solvents evaporated in vacuo to give intermediate compound I-11 (4 g, 96%).

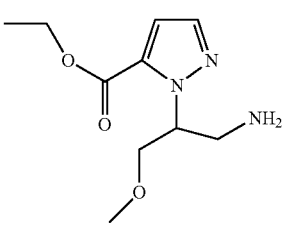

Intermediate 12 (I-12)

HCl (4 M in dioxane, 15.3 mL, 61.1 mmol) was added to a solution of I-11 (4 g, 12.22 mmol) in MeCN (55.3 mL). The mixture was stirred at rt for 1 h. The mixture was evaporated in vacuo to give intermediate compound I-12 (2.77 g) which was used in the next step without any further purification.

Intermediate 13 (I-13)

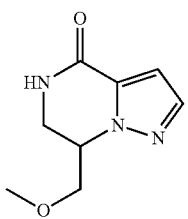

Intermediate 14(I-14)

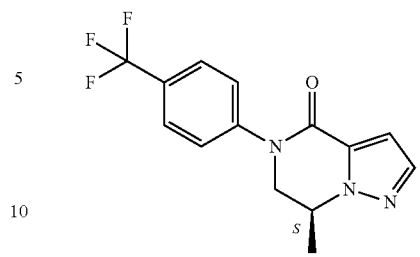

NaHCO$_3$ (sat. aq. sol., 40 mL) was added to a solution of intermediate I-12 (2.77 g, 12.19 mmol) in MeOH (14.20 mL). The mixture was stirred at rt for 16 h. The mixture was diluted with water and extracted with DCM, EtOAc and THF/EtOAc 1:1. The organic layer was separated, dried (Na$_2$SO$_4$), filtered and the solvents evaporated in vacuo to give intermediate compound I-13 (1.92 g) which was used in the next step without any further purification.

Intermediate I-13 was also prepared by reaction of intermediate I-12 (48 g, 52.44 mmol, 25% purity) and Na$_2$CO$_3$ (53 g, 0.5 mol) in a mixture of 1,4 dioxane (0.5 L) and water (0.2 L). The mixture was stirred at rt for 16 h. The mixture was diluted with water and extracted with DCM. The organic layer was separated, dried (Na$_2$SO$_4$), filtered and the solvents evaporated in vacuo. The crude product was purified by column chromatography (silica; EtOAc in petroleum ether 1/10 to 10/0). The desired fractions were collected and the solvents evaporated in vacuo to yield intermediate compound I-13 (6.22 g, 64%).

A mixture of intermediate I-9 (5 g, 33.01 mmol), copper (I) iodide (3.78 g, 19.85 mmol) and K$_2$CO$_3$ (9.14 g, 66.15 mmol) in toluene (150 mL) was nitrogen flushed for a few min. Then 4-bromobenzotrifluoride (9.3 mL, 66.1 mmol) and N,N'-dimethyl-ethylenediamine (2.1 mL, 19.8 mmol) were added. The mixture was stirred under nitrogen at rt for 10 min and then stirred at 100° C. for 16 h. Then, DMF (20 mL) was added and the mixture was stirred at 100° C. for 8 h. Then water, a conc. sol. of ammonia and DCM were added. The organic layer was separated, dried (Na$_2$SO$_4$), filtered and the solvents evaporated in vacuo. The crude product was purified by flash column chromatography (silica; EtOAc in DCM 0/100 to 50/50). The desired fractions were collected and the solvents evaporated in vacuo to yield intermediate compound I-14 as a pale yellow oil (9.6 g, 98%).

In a procedure analogous to that described for I-14, the following intermediates were synthesized:

| Starting Material | Reagent | Intermediate Product |
|---|---|---|
| I-9 | Br-(3,4-dichlorophenyl)<br>(solvent: toluene/DMF) | I-15 |
| I-9 | 6-bromo-2-methoxy-3-aminopyridine<br>(solvent: toluene/DMF) | I-16 |
| I-9 | 5-bromo-2-(trifluoromethyl)benzyl alcohol<br>(solvent: toluene) | I-17 |

-continued

| Starting Material | Reagent | Intermediate Product |
|---|---|---|
| I-9 | 4-bromo-2-methyl-1-(trifluoromethyl)benzene (solvent: toluene) | I-18 |
| I-9 | 4-bromo-2-fluoro-1-(trifluoromethyl)benzene (solvent: toluene/DMF) | I-19 |
| I-9 | 1-bromo-4-chlorobenzene (solvent: toluene) | I-20 |
| I-9 | 4-bromo-2-methoxy-1-(trifluoromethyl)benzene (solvent: toluene/DMF) | I-21 |
| I-9 | 5-bromo-2-(trifluoromethyl)benzonitrile (solvent: toluene) | I-22 |

-continued
| Starting Material | Reagent | Intermediate Product |
|---|---|---|
| I-9 | 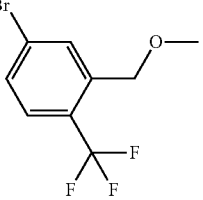<br>(solvent: toluene) | 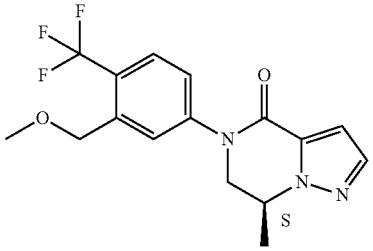<br>I-23 |
| I-9 | 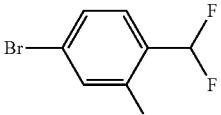<br>(solvent: toluene) | 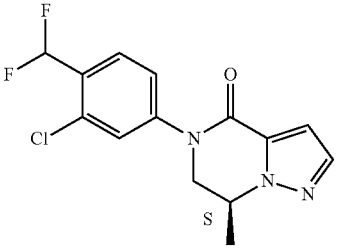<br>I-24 |
| I-9 | 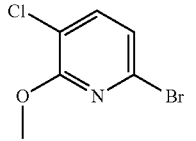<br>(solvent: toluene) | 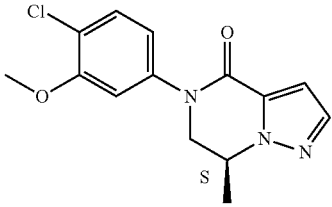<br>I-25 (*) |
| I-9 | 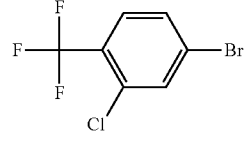<br>(solvent: toluene) | 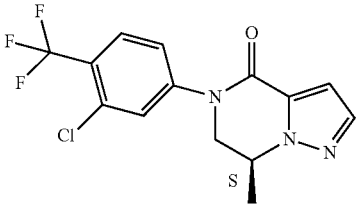<br>I-26 |
| I-9 | 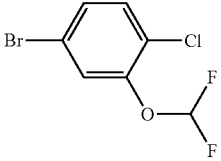 [SMILES: FC(F)Oc1cc(Br)ccc1Cl]<br>(solvent: toluene) | 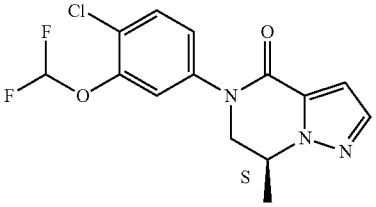<br>I-27 |
| I-9 | 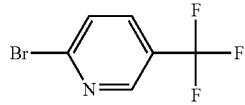<br>(solvent: toluene) | 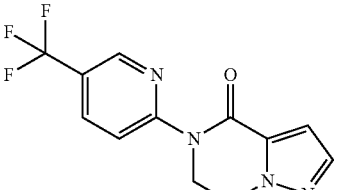<br>I-28 (**) |

-continued
| Starting Material | Reagent | Intermediate Product |
|---|---|---|
| I-9 | 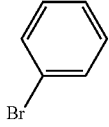<br>(solvent: toluene/DMF) | 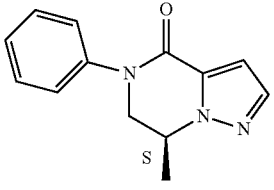<br>I-29 |
| I-13 | 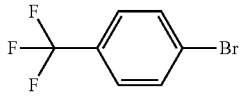<br>(solvent: toluene) | 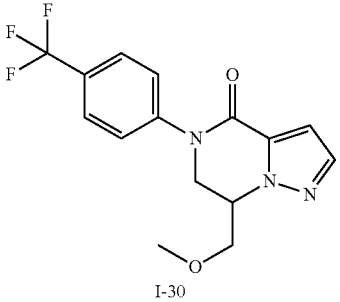<br>I-30 |
| I-13 | 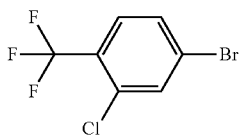 [SMILES: FC(F)(F)c1ccc(Br)cc1Cl]<br>(solvent: toluene) | 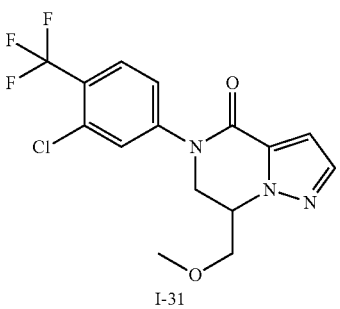<br>I-31 |
| I-9 | 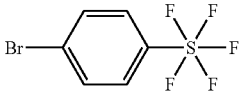 | 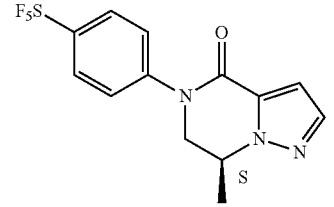<br>I-97 |
| I-9 | 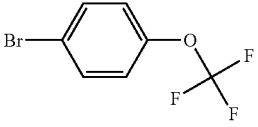 [SMILES: FC(F)(F)Oc1ccc(Br)cc1] | 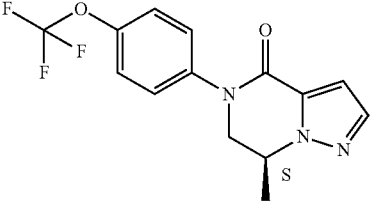<br>I-109 |
| I-9 | 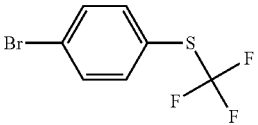 | 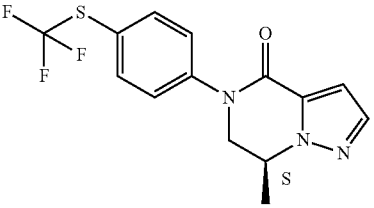<br>I-113 |

-continued

| Starting Material | Reagent | Intermediate Product |
|---|---|---|
| I-120 | 4-bromo-(trifluoromethyl)benzene | I-121 |
| I-9 | 4-iodo-2-chloro-1-(trifluoromethoxy)benzene | I-128 |
| I-132 | 4-bromo-2-chloro-1-(trifluoromethyl)benzene | I-134 |
| I-9 | 4-bromo-1-chloro-2-methylbenzene | I-136 |

(*) Intermediate I-25 was also made according to the procedure described below from I-16 using tert-butyl nitrite as the reagent.
(**) Intermediate I-28 was also made according to the procedure described below for I-35 using 2-bromo-5-(trifluoromethyl)pyridine as the reagent.

(*)Intermediate 25 (I-25)

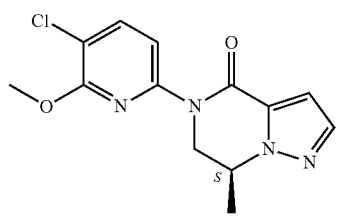

To a suspension of CuCl₂ (625 mg, 4.646 mmol) and LiCl (492 mg, 11.616 mmol) in MeCN (10 mL) at 60° C., was added tert-butyl nitrite (4.5 mL, 37.52 mmol) and the mixture was stirred at 60° C. for 10 min. Then intermediate I-16 (1.43 g, 3.872 mmol) in MeCN (20 mL) was added slowly. The reaction was stirred at 60° C. for 16 h. Then it was cooled to 0° C. and quenched with a dil. HCl sol. and extracted with DCM (2×). The combined organic phases were washed with sat. aq. NaCl sol, dried (Na₂SO₄), filtered and the solvent evaporated in vacuo. The crude product was purified by flash column chromatography (silica; EtOAc in DCM 0/100 to 20/80). The desired fractions were collected and the solvents concentrated in vacuo to yield intermediate I-25 (783 mg, 69%) as a yellow solid.

Intermediate 32 (I-32)

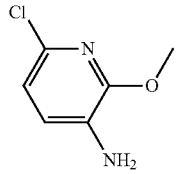

Sodium methoxide (25 wt. % in MeOH, 3.7 mL, 64.8 mmol) was added to a stirred solution of 3-amino-2,6-dichloropyridine (3 g, 18.4 mmol) in 1,4-dioxane (30 mL). The mixture was stirred at 140° C. for 20 min under microwave irradiation. The mixture was treated with a sat. sol. NH$_4$Cl and water and was stirred for 30 min. Then the mixture was extracted with Et$_2$O, washed with brine, dried (Na$_2$SO$_4$), filtered and the solvents concentrated in vacuo to yield intermediate compound I-32 (3.09 g, quant.) as a brown solid which was used in the following step without further purification.

Copper(I) iodide (8.44 g, 44.3 mmol) was added to a stirred suspension of intermediate I-33 (7.96 g, 29.53 mmol) and methyl fluorosulphonyldifluoroacetate (8.6 mL, 67.9 mmol) in DMF (60 mL). The mixture was stirred at 100° C. for 16 h. The crude was filtered through diatomaceous earth. The mixture was diluted with Et$_2$O and extracted with a sat. sol. of NH$_4$Cl. The organic layer was separated, dried (Na$_2$SO$_4$), filtered and the solvents concentrated in vacuo carefully (without heating) to yield intermediate compound I-34 (8.92 g, 55% pure, 78%).

Intermediate 33 (I-33)

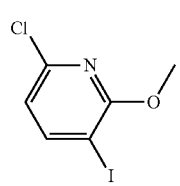

Intermediate 35 (I-35)

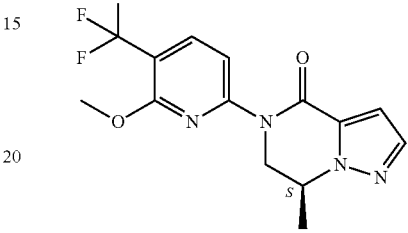

To a suspension of copper(I) iodide (7.86 g, 41.3 mmol) and tert-butyl nitrite (48 mL, 41.3 mmol) in MeCN (600 mL), intermediate I-32 in MeCN (600 mL) was added slowly at 0° C. for 5 min. The mixture was stirred at 0° C. for 1 h. Then it was stirred at 65° C. for 1 h. The crude was filtered over diatomaceous earth. The mixture was diluted with water and extracted with Et$_2$O. The organic phase was separated, dried (Na$_2$SO$_4$), filtered and the solvents concentrated in vacuo to yield intermediate compound I-33 (7.96 g, 71%) as a brown oil that was used in the next reaction step without any further purification.

Intermediate 34 (I-34)

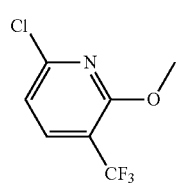

Pd(PPh$_3$)$_4$ (4.39 g, 3.798 mmol) was added to a stirred suspension of intermediate I-9 (5.74 g, 37.98 mmol), intermediate I-34 (14.88 g, 37.98 mmol), Xantphos (4.40 g, 7.60 mmol), Cs$_2$CO$_3$ (24.75 g, 75.958 mmol) in 1,4-dioxane (140 mL) in a sealed tube and under nitrogen. The mixture was stirred at 100° C. for 16 h. The mixture was filtered through a pad of diatomaceous earth and washed with DCM. The organic layer was evaporated in vacuo. The crude product was purified by flash column chromatography (silica, EtOAc in DCM 0/100 to 50/50). The desired fractions were collected and concentrated in vacuo. Then product was purified again by flash column chromatography (silica, EtOAc in DCM 0/100 to 20/80). The desired fractions were collected and concentrated in vacuo to yield intermediate compound I-35 (5.52 g, 44%) as a brown oil that solidified upon standing at rt.

In a procedure analogous to that described for I-35, the following intermediates were synthesized:

| Starting Material | Reagent | Intermediate Product |
|---|---|---|
| I-9 | ![Br-pyridine-CF3, solvent: toluene] (solvent: toluene) | I-28 |

Intermediate 36 (I-36)

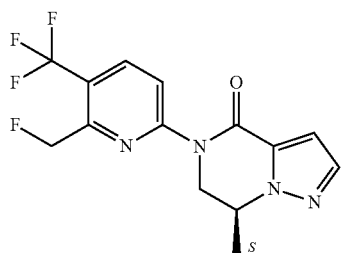

Bis(2-methoxyethyl)amino-sulfur trifluoride (4.85 mL, 26.33 mmol) was added to a stirred solution of intermediate I-17 (1.71 g, 5.26 mmol) in DCM (30 mL) at 0° C. and under nitrogen. The mixture was allowed to warm up to rt and stirred at rt for 17 h. Then it was treated with a sat. sol. NaHCO₃ at 0° C. and extracted with EtOAc. The organic layer was separated, dried (Na₂SO₄), filtered and concentrated in vacuo. The crude product was purified by flash column chromatography (silica; EtOAc in DCM 0/100 to 30/70). The desired fractions were collected and concentrated in vacuo to yield intermediate compound I-36 (1.1 g, 64%) as colorless oil that solidified upon standing at rt.

Intermediate 37 (I-37)

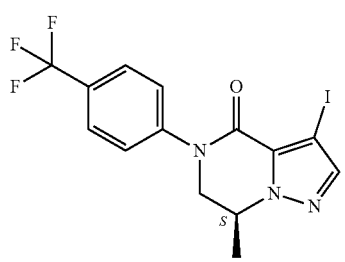

Iodine (11.55 g, 45.5 mmol) was added to a solution of intermediate I-14 (19.2 g, 65.0 mmol) and ammonium cerium(IV) nitrate (24.95 g, 45.5 mmol) in MeCN (350 mL). The mixture was stirred at 70° C. for 1 h. Then the mixture was diluted with EtOAc and washed with a sat. sol. of Na₂S₂O₃ and brine. The organic layer was separated, dried (Na₂SO₄), filtered and the solvents evaporated in vacuo. The residue was precipitated with DIPE and then was purified by short open column chromatography (silica, DCM) then by flash column chromatography (silica; DCM in heptane 50/50 to 100/0). The desired fractions were collected and the solvents evaporated in vacuo to yield intermediate compound I-37 as a solid (24.8 g, 90%).

In a procedure analogous to that described for intermediate I-37, the following intermediates were synthesized:

| Starting Material (SM) | Intermediate obtained |
|---|---|
| I-15 | ![I-38] I-38 |
| I-18 | ![I-39] I-39 |
| I-19 | ![I-40] I-40 |
| I-20 | ![I-41] I-41 |
| I-21 | ![I-42] I-42 |
| I-22 | ![I-43] I-43 |

-continued
| Starting Material (SM) | Intermediate obtained |
|---|---|
| I-23 | 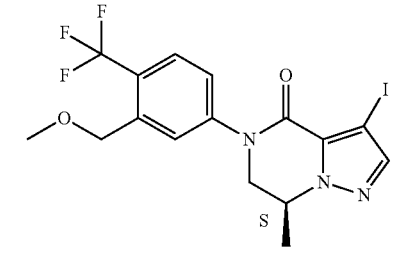<br>I-44 |
| I-24 | 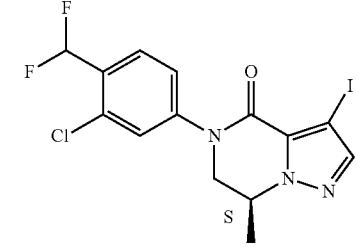<br>I-45 |
| I-25 | 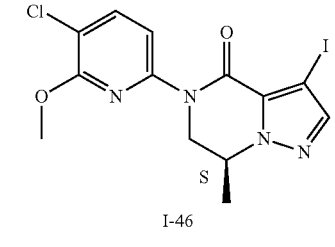<br>I-46 |
| I-26 | 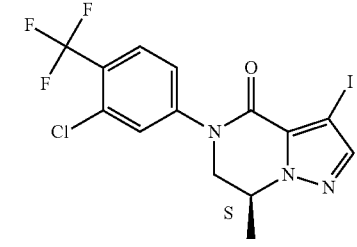<br>I-47 |
| I-27 | 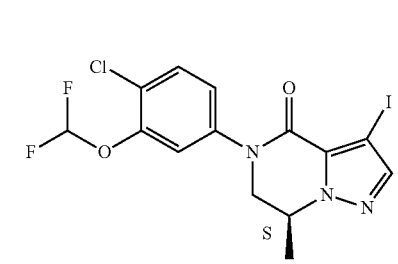<br>I-48 |
-continued
| Starting Material (SM) | Intermediate obtained |
|---|---|
| I-28 | 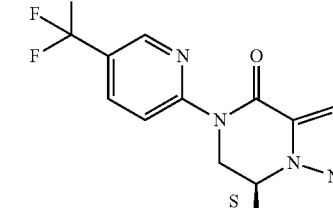<br>I-49 |
| I-29 | 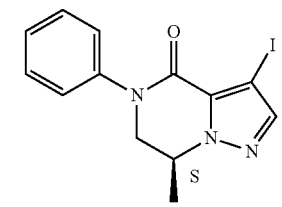<br>I-50 |
| I-30 | 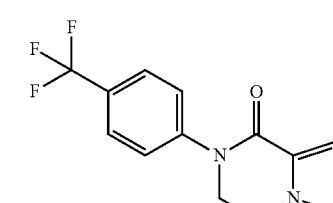<br>I-51 |
| I-31 | 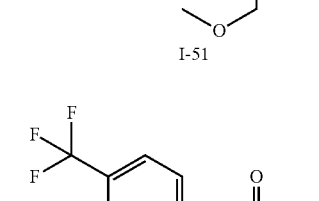<br>I-52 |
| I-35 | 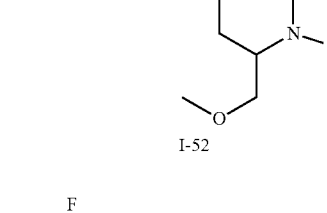<br>I-53 |

| Starting Material (SM) | Intermediate obtained |
|---|---|
| I-36 | I-54 |
| I-17 | I-55 |
| I-97 | I-108 |
| I-109 | I-110 |
| I-113 | I-114 |
| I-121 | I-122 |

| Starting Material (SM) | Intermediate obtained |
|---|---|
| I-128 | I-129 |
| I-134 | I-135 |
| I-136 | I-137 |

Intermediate 56 (I-56)

Benzophenone imine (0.398 mL, 2.374 mmol) was added to a stirred suspension of intermediate I-37 (500 mg, 1.187 mmol), Pd$_2$(dba)$_3$ (109 mg, 0.119 mmol), BINAP (221 mg, 0.356 mmol) and sodium tert-butoxide (205 mg, 2.137 mmol) in degassed toluene (10 mL) in a sealed tube and under nitrogen. The mixture was stirred at 90° C. for 7 h. The mixture was diluted with EtOAc and filtered through a pad of diatomaceous earth. The filtrate was evaporated in vacuo. The crude product was purified by flash column chromatography (silica; EtOAc in DCM 0/100 to 100/0 and 7M ammonia solution in MeOH in DCM 0/100 to 3/97). The desired fractions were collected and the solvents evaporated in vacuo. The residue was again purified by flash column chromatography (silica; EtOAc in Heptane 0/100 to 70/30).

The desired fractions were collected and the solvents evaporated in vacuo to yield intermediate compound I-56 (370 mg, 65%) as a yellow wax.

In a procedure analogous to that described for intermediate I-56, the following intermediates were synthesized:

| SM | Intermediate obtained |
|---|---|
| I-38 | 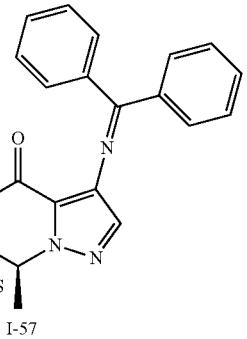<br>I-57 |
| I-40 | 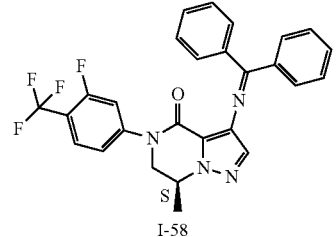<br>I-58 |
| I-41 | 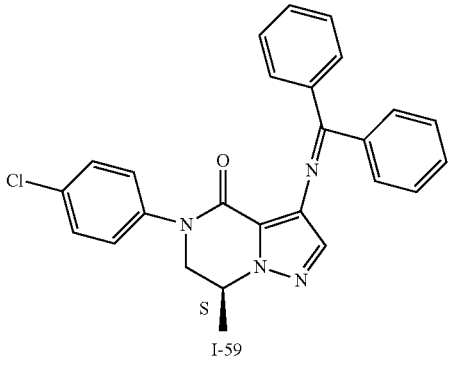<br>I-59 |
| I-42 | 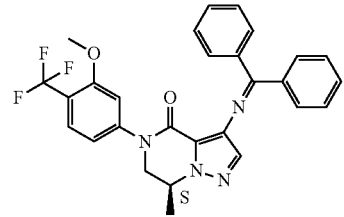<br>I-60 |
| I-43 | 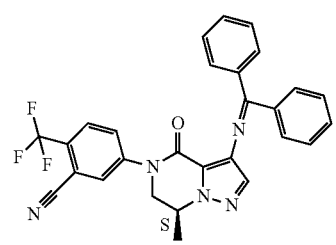<br>I-61 |

-continued

| SM | Intermediate obtained |
|---|---|
| I-44 | 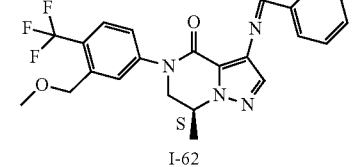<br>I-62 |
| I-45 | 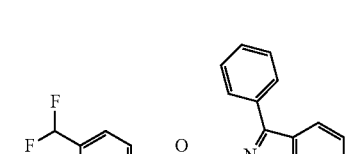<br>I-63 |
| I-47 | 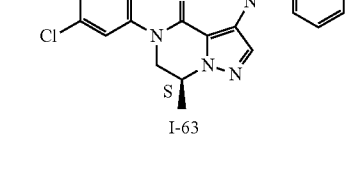<br>I-64 |
| I-48 | 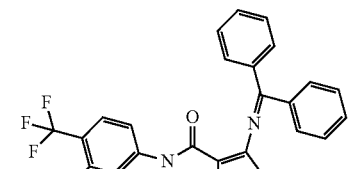<br>I-65 |
| I-49 | 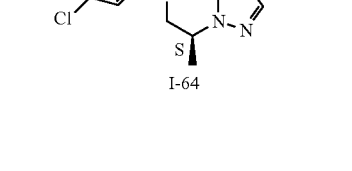<br>I-66 |

-continued

| SM | Intermediate obtained |
|---|---|
| I-50 | I-67 |
| I-51 | I-68 |
| I-52 | I-69 |
| I-110 | I-111 |
| I-114 | I-115 |

Intermediate 70 (I-70)

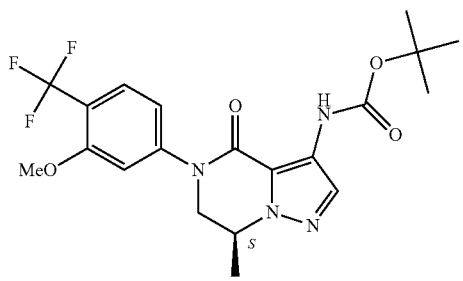

Copper(I) iodide (170 mg, 0.886 mmol) was added to a stirred suspension of intermediate I-53 (4 g, 8.865 mmol), tert-butyl carbamate (1.25 g, 10.64 mmol), (+/−)-trans-1,2-cyclohexanediamine (0.11 mL, 0.886 mmol) and $K_3PO_4$ (3.76 g, 17.73 mmol) in 1,4-dioxane (80 mL) under nitrogen in a sealed tube. The mixture was stirred at 100° C. for 16 h. Additional tert-butyl carbamate (0.52 g, 4.43 mmol), copper(I) iodide (68 mg, 0.354 mmol), (+/−)-trans-1,2-cyclohexanediamine (43 μL, 0.354 mmol) and $K_3PO_4$ (1.51 g, 7.092 mmol) were added and the mixture was stirred at 120° C. for 20 h. The mixture was filtered through a pad of diatomaceous earth, washed with EtOAc and the solvents evaporated in vacuo. The crude product was purified by flash column chromatography (silica; EtOAc in heptane 50/50 to 100/0). The desired fractions were collected and the solvents evaporated in vacuo to yield intermediate compound I-70 (2.15 g, 55%) as a beige solid.

In a procedure analogous to that described for intermediate I-70, the following intermediates were synthesized:

| Starting Material | Intermediate obtained |
|---|---|
| I-39 | I-71 |
| I-55 | I-72 |

Intermediate 73 (I-73)

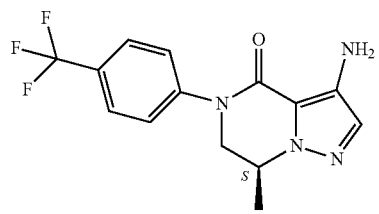

HCl (1 M aq. sol., 6.6 mL, 6.6 mmol) was added to a stirred solution of intermediate I-56 (370 mg, 0.780 mmol) in 1,4-dioxane (6 mL). The mixture was stirred at rt for 3 h. The mixture was diluted with EtOAc and basified with sat. sol. Na₂CO₃. The organic layer was separated, dried (Na₂SO₄), filtered and the solvents evaporated in vacuo. The crude product was purified by flash column chromatography (silica, EtOAc in DCM 0/100 to 80/20). The desired fractions were collected and the solvents evaporated in vacuo to yield intermediate compound I-73 (226 mg, 93% pure, 89%) as a yellow oil.

Following a procedure analogous to that described for intermediate I-73, the following compounds were also synthesized:

| SM | Intermediate obtained |
|---|---|
| I-57 | 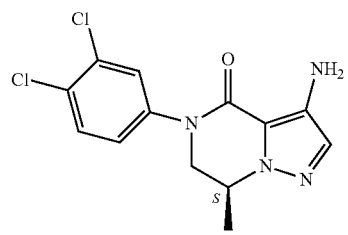<br>I-74 |
| I-58 | 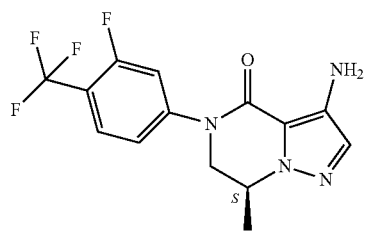<br>I-75 |
| I-59 | 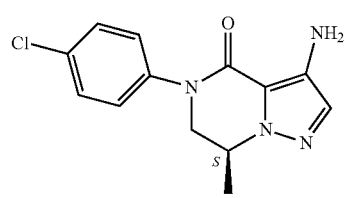<br>I-76 |
| I-60 | 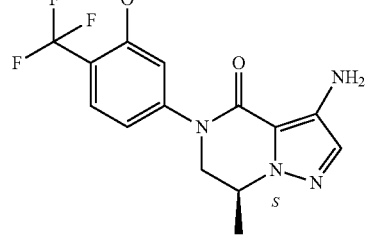<br>I-77 |
| I-61 | 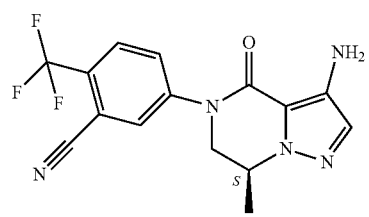<br>I-78 |
| I-62 | 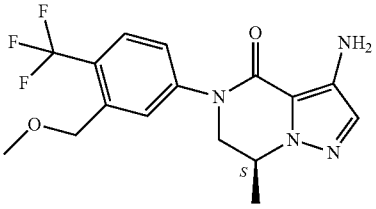<br>I-79 |
| I-63 | 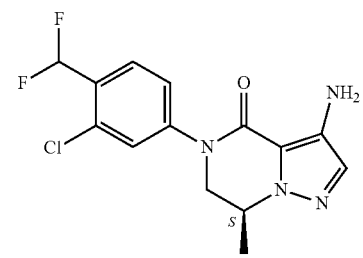<br>I-80 |
| I-64 | 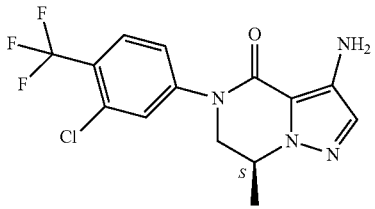<br>I-81 |

| SM | Intermediate obtained |
|---|---|
| I-65 | I-82 |
| I-66 | I-83 |
| I-67 | I-84 |
| I-68 | I-85 |
| I-69 | I-86 |
| I-111 | (structure) |

| SM | Intermediate obtained |
|---|---|
| I-115 | I-116 |

Intermediate 87 (I-87)

HCl (4 M in 1,4-dioxane, 12.2 mL, 48.817 mmol) was added to a stirred solution of intermediate I-70 (2.15 g, 4.88 mmol) in 1,4-dioxane (25 mL). The mixture was stirred at 70° C. for 1 h. The solvent was evaporated in vacuo. The residue was basified with sat. sol. Na$_2$CO$_3$ and extracted with EtOAc. The organic layer was separated, dried (Na$_2$SO$_4$), filtered and the solvents evaporated in vacuo. The crude product was purified by flash column chromatography (silica, EtOAc in DCM 0/100 to 80/20). The desired fractions were collected and the solvents evaporated in vacuo to yield intermediate compound I-87 (1.5 g, 90%) as a beige solid.

Following a procedure analogous to that described for intermediate I-87, the following compounds were also synthesized:

| Starting Material | Intermediate obtained |
|---|---|
| I-71 | I-88 |

-continued

| Starting Material | Intermediate obtained |
|---|---|
| I-72 | 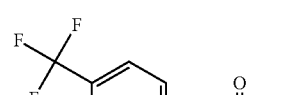<br>I-89 |

Intermediate 90 (I-90)

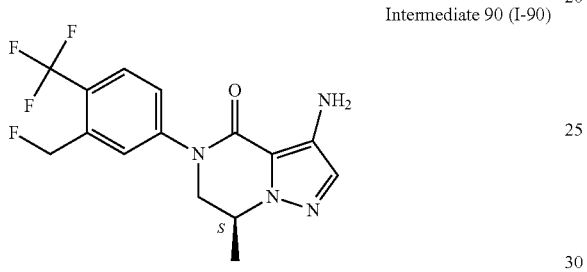

DMSO (1.9 mL) was added to a mixture of intermediate I-54 (150 mg, 0.331 mmol), sodium azide (64 mg, 0.993 mmol), copper(I) iodide (31 mg, 0.165 mmol) and sodium carbonate (70 mg, 0.662 mmol). The mixture was flushed with nitrogen for a few min. N,N-dimethylethylenediamine (35 μL, 0.331 mmol) was added and the mixture was stirred at 40° C. for 20 h. The mixture was poured into diluted NH$_4$OH sol. and extracted with EtOAc (×2). The combined organic layers were dried (Na$_2$SO$_4$), filtered and the solvents concentrated in vacuo. The crude product was purified by flash column chromatography (silica; EtOAc in DCM 0/100 to 40/60). The desired fractions were collected and the solvents evaporated in vacuo to yield intermediate compound I-90 (40 mg, 85% pure, 29%) as a yellow foam.

Following a procedure analogous to that described for intermediate I-90, the following compounds were also synthesized:

| Starting Material | Intermediate obtained |
|---|---|
| I-46 | 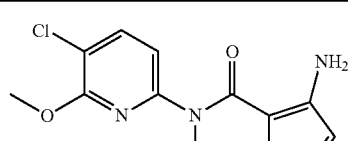<br>I-91 |

-continued

| Starting Material | Intermediate obtained |
|---|---|
| I-53 | 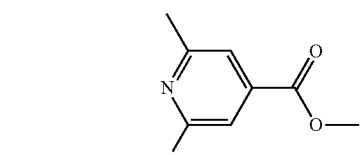<br>I-92 |

Intermediate 93 (I-93)

Di-tert-butyl dicarbonate (1.02 g, 4.693 mmol) was added to a stirred solution of methyl 6-amino-4-methylnicotinate (650 mg, 3.911 mmol) and 4-(dimethylamino)pyridine (33 mg, 0.274 mmol) in THF (50 mL) at 0° C. The mixture was allowed to warm to rt and stirred for 16 h. Additional di-tert-butyl dicarbonate (0.68 g, 0.683 mmol) was added at rt and the mixture was stirred at rt for 24 h more. The solvents were evaporated in vacuo and the residue was dissolved in DCM and washed with HCl 0.5 N, water and brine. The organic layer was dried (Na$_2$SO$_4$), filtered and the solvents evaporated in vacuo. The crude product was purified by flash column chromatography (silica; EtOAc in DCM 0/100 to 5/95). The desired fractions were collected and the solvents evaporated in vacuo to yield intermediate compound I-93 (0.8 g, 85% pure, 62%) as a white solid.

Intermediate 94 (I-94)

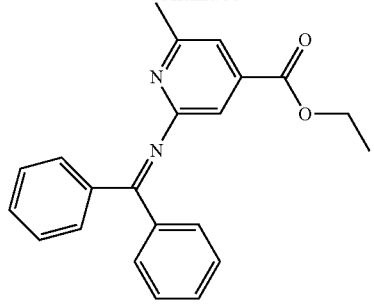

Intermediate 95 (I-95)

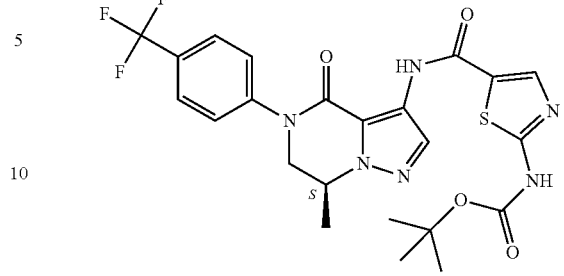

Benzophenone imine (0.904 mL, 5.387 mmol) was added to a stirred suspension of methyl 2-chloro-6-methylpyridine-4-carboxylate (500 mg, 2.694 mmol), Pd(OAc)$_2$ (121 mg, 0.538 mmol), BINAP (503 mg, 0.808 mmol) and Cs$_2$CO$_3$ (1.75 g, 5.387 mmol) in 1,4-dioxane degassed (10 mL), in a sealed tube and under nitrogen. The mixture was stirred at 80° C. for 4 h. The mixture was diluted with EtOAc/MeOH and filtered through diatomaceous earth and the solvents were evaporated in vacuo. The crude product was purified by flash column chromatography (silica, EtOAc in DCM 0/100 to 20/80 then silica, EtOAc in heptane 0/100 to 20/80). The desired fractions were collected and the solvents evaporated in vacuo to yield intermediate compound I-94 (790 mg) as a yellow oil.

Lithium bis(trimethylsilyl)amide (1M in THF, 1 mL, 1.015 mmol) was added to a stirred solution of intermediate I-73 (90 mg, 0.29 mmol) and ethyl 2-(tert-butoxycarbonylamino)thiazole-4-carboxylate (90 mg, 0.33 mmol) in anhydrous THF (3 mL) at 0° C. and under nitrogen. The mixture was stirred at 0° C. for 30 min and at rt for 3 h. The reaction was quenched by addition of sat. sol. NH$_4$Cl and extracted with EtOAc. The organic layer was separated, dried (Na$_2$SO$_4$), filtered and the solvents evaporated in vacuo. The crude product was purified by flash column chromatography (silica; EtOAc in DCM 0/100 to 70/30). The desired fractions were collected and the solvents evaporated in vacuo to yield intermediate compound I-95 (70 mg, 45%) as a white solid.

Following a procedure analogous to that described for intermediate I-95, the following compounds were also synthesized:

| Starting Material | Reagent | Intermediate Product |
|---|---|---|
| I-81 | | |

-continued
| Starting Material | Reagent | Intermediate Product |
|---|---|---|
| I-81 | I-93 | 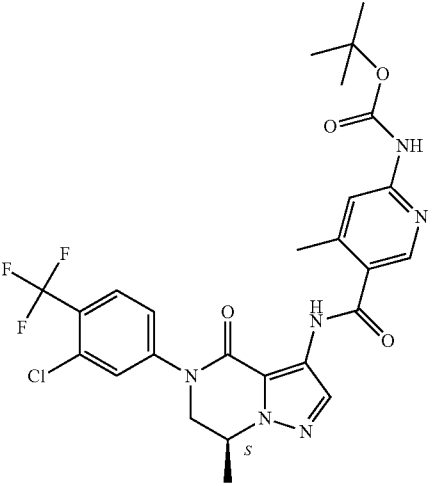<br>I-98 |
| I-73 | I-93 | 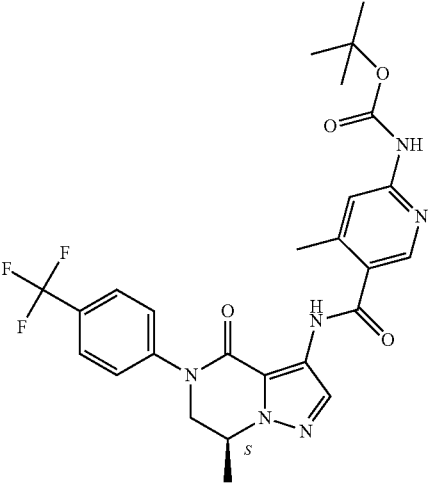<br>I-99 |
| I-73 | I-94 | 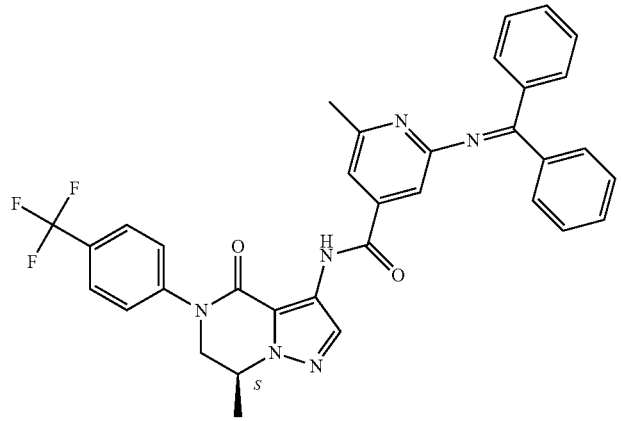<br>I-100 |

| Starting Material | Reagent | Intermediate Product |
|---|---|---|
| I-73 | 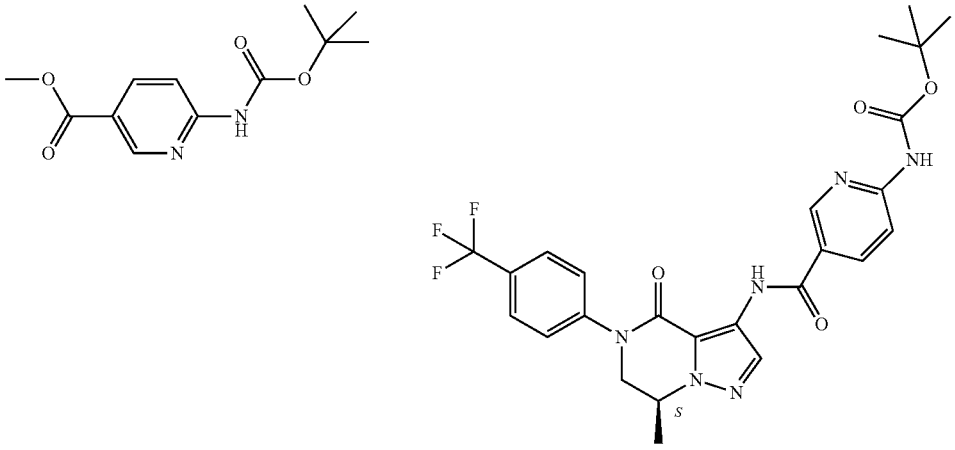 | 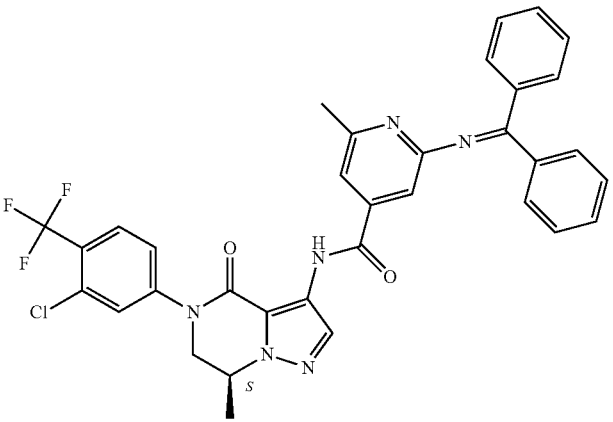<br>I-101 |
| I-81 | I-94 | 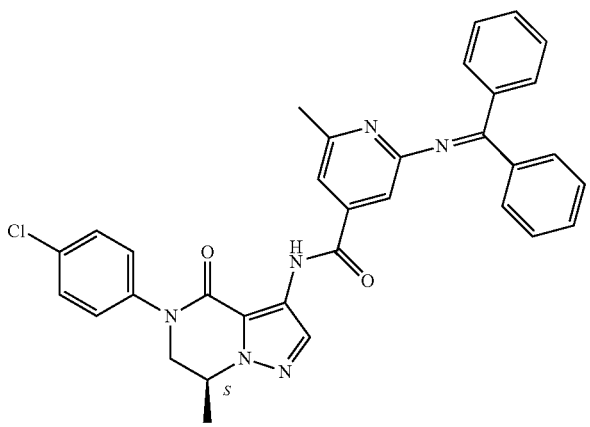<br>I-102 |
| I-76 | I-94 | I-130 |

Intermediate 102 (I-102)

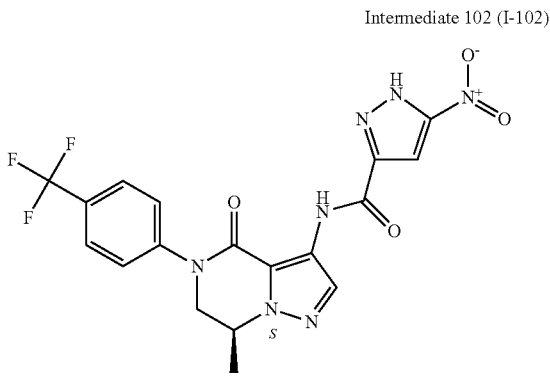

Intermediate 104 (I-104)

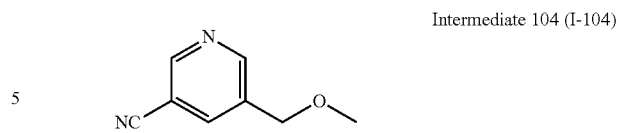

3-Bromo-5-(methoxymethyl)pyridine (173999-17-2, 591 mg, 2.926 mmol), zinc cyanide (687 mg, 5.852 mmol) and Pd(PPh$_3$)$_4$ (220 mg, 0.190 mmol) in MeCN (5 mL) were added to a sealed tube. The mixture was stirred at 150° C. for 30 min under microwave irradiation. The crude product was filtered through a pad of diatomaceous earth and the solvent was concentrated in vacuo. The crude product was purified by flash column chromatography (silica; EtOAc in DCM 0/100 to 50/50). The desired fractions were collected and the solvents evaporated in vacuo to yield intermediate compound I-104 (440 mg, 96%) as a white solid.

A mixture of intermediate I-73 (160 mg, 0.515 mmol), 5-nitro-3-pyrazolecarboxylic acid (97 mg, 0.619 mmol), HATU (333 mg, 0.876 mmol) and DIPEA (135 μL, 0.773 mmol) in DMF (4 mL) was stirred at rt for 20 h. The mixture was diluted in DCM and washed with sat. sol. NH$_4$Cl. The organic layer was separated, dried (Na$_2$SO$_4$), filtered and the solvents evaporated in vacuo. The crude product was purified by flash column chromatography (silica; 7 N solution ammonia in MeOH in DCM 0/100 to 10/90). The desired fractions were collected, the solvents evaporated in vacuo to yield intermediate compound I-102 (136 mg, 86% pure, 50%) as a yellow solid.

Following a procedure analogous to that described for intermediate I-102, the following compounds were also synthesized:

Intermediate 105 (I-105)

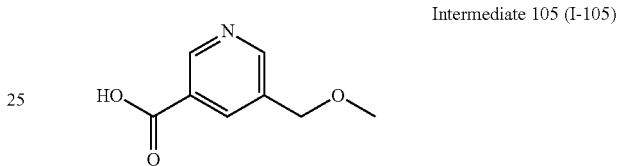

NaOH (10% in water, 5.4 mL) was added to a stirred suspension of intermediate I-104 (430 mg, 2.902 mmol) in

| Starting Material | Reagent | Intermediate Product |
|---|---|---|
| I-73 | ![](imidazo[1,2-a]pyrimidine-2-carboxylic acid) | I-103 |
| I-73 | benzoic acid) | I-131 |

EtOH (7.2 mL) in a sealed tube. The mixture was stirred at 115° C. for 3 h and the solvent evaporated in vacuo. The residue was diluted with DCM and washed with water. The aqueous layer was acidified with HCl 3 N till pH 2.0 and then extracted with EtOAc and butanol. The organic layers were combined, dried (MgSO$_4$), filtered and the solvents concentrated in vacuo to yield intermediate compound I-105 (227 mg, 41%) as a white solid, which was used in the next step without further purification.

Intermediate 106 (I-106)

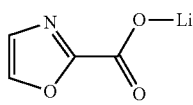

LiOH (34 mg, 1.417 mmol) was dissolved in distilled water (0.013 mL, 0.709 mmol) and added to a stirred solution of ethyl oxazole-2-carboxylate (100 mg, 0.709 mmol) in THF (1 mL) at rt. The mixture was stirred at rt for 4 h. The solvents were evaporated in vacuo to yield intermediate compound I-106 (84 mg, quant.) as a white solid, which was used in the next step without further purification.

Intermediate 107 (I-107)

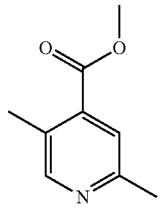

Two solutions of methyl 2,5-dichloroisonicotinate (623585-74-0, 894 mg, 4.34 mmol) in THF (18 mL) and dimethylzinc (2M in toluene, 5.3 mL, 10.6 mmol) in toluene (12.7 mL) were pumped using a syringe pump through a column containing SyliCat® DPP-Pd (800 mg, 0.26 mmol/g) at 80° C., 0.1 mL/min (each), Rt=5 min. The outlet solution was collected onto water and the solvent evaporated in vacuo. The crude was diluted with water and extracted with DCM and washed with water (3×). The organic layer was separated, dried (MgSO$_4$), filtered and the solvents evaporated in vacuo to yield intermediate compound I-107 (481 mg, 67%) as a colorless oil/solid.

Intermediate 117 (I-117)

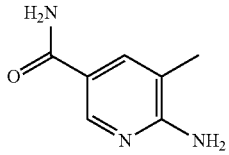

A solution of 6-amino-5-methyl-pyridine-3-carbonitrile (31 mg, 0.23 mmol) in sulfuric acid (0.37 mL) was stirred at rt for 3 days. The mixture was poured onto ice and then it was carefully basified with NH$_4$OH. The mixture was extracted with EtOAc. The organic layer was separated, dried (Na$_2$SO$_4$), filtered and the solvents evaporated in vacuo to yield intermediate compound I-117 (50 mg, 100%) as a beige solid.

Following a procedure analogous to that described for intermediate I-117, the following compounds were also synthesized.

| Starting Material | Intermediate Product |
|---|---|
| | I-126 |
| | I-127 |
| I-138 | I-139 |
| | I-140 |

Intermediate 118 (I-118)

Intermediate compound I-118 was synthesized following a similar approach described for intermediate I-3. Starting from (S)-(+)-1-amino-2-propanol (13.24 g, 176.31 mmol) intermediate compound I-118 was obtained as a colourless oil (32.4 g, quant.) which was used in the following step without further purification.

Intermediate 119 (I-119)

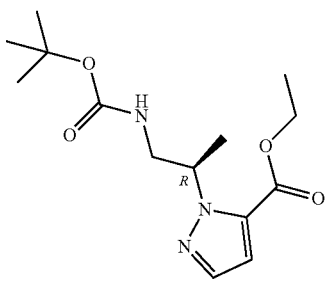

Intermediate compound I-119 was synthesized following a similar approach described for intermediate I-4. Starting from intermediate I-1 (10 g, 71.36 mmol) and intermediate I-118 (15.79 g, 85.63 mmol), intermediate compound I-119 was obtained as a yellow oil (42.86 g, 49% purity, quant.) which was used in the following step without further purification.

Intermediate 120

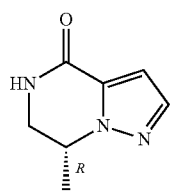
(I-120)

HCl (4 M in dioxane, 76 mL, 303.67 mmol) was added to a solution of I-119 (42.86 g, 70.62 mmol, 49% purity) in MeCN (154.6 mL). The mixture was stirred at rt for 18 h. The mixture was evaporated in vacuo. The residue was dissolved in 1,4-dioxane (50 mL) and additional HCl (4 M in dioxane, 57 mL, 229.52 mmol) was added. The resulting mixture was stirred at rt for 3 h and then evaporated in vacuo. The crude product was dissolved in NaHCO₃ (sat. aq. sol., 203 mL) and stirred at rt for 20 h. The mixture was extracted with DCM and the organic layer was separated, dried (Na₂SO₄), filtered and the solvent evaporated in vacuo. The residue was triturated with Et₂O to yield intermediate compound I-120 (7.41 g, 69%) as a white solid, which was used in next step without any further purification.

Intermediate 123

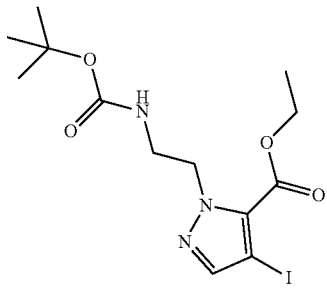
(I-123)

Intermediate compound I-123 was synthesized following a similar approach described for intermediate I-4. Starting from intermediate I-2 (2 g, 7.52 mmol) and N-(tert-butoxycarbonyl)ethanolamine (1.28 mL, 8.27 mmol), intermediate compound I-123 was obtained (3.5 g, 79% purity, quant.) which was used in the following step without further purification.

Intermediate 124

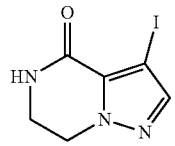
(I-124)

HCl (4 M in dioxane, 32.07 mL, 128.29 mmol) was added to a solution of I-123 (3.5 g, 8.55 mmol, 79% purity) in 1,4-dioxane (25 mL). The mixture was stirred at rt for 5 h. The mixture was partially evaporated in vacuo and the residue was diluted with NaHCO₃ (10% aq. sol., 40 mL) and stirred at rt for 2 h. The mixture was diluted with water and extracted with DCM. The organic layer was separated, dried (Na₂SO₄), filtered and the solvents evaporated in vacuo. The residue was triturated with Et₂O to yield intermediate compound I-124 (0.6 g, 27%) as a white solid, which was used in next step without any further purification.

Intermediate 125

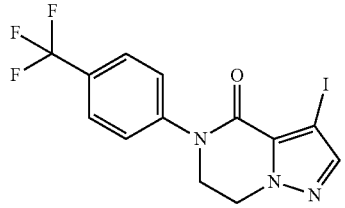
(I-125)

A mixture of intermediate I-124 (500 mg, 1.9 mmol), copper(I) iodide (110 mg, 0.57 mmol) and K₂CO₃ (530 mg, 3.8 mmol) in a mixture of toluene (8.6 mL) and DMF (1.15 mL) was nitrogen flushed for a few min. Then 4-iodobenzotrifluoride (1.03 g, 3.8 mmol) and N,N-dimethyl-ethylenediamine (0.061 mL, 0.57 mmol) were added. The mixture was stirred under nitrogen at 75° C. for 16 h. The mixture was filtered through diatomaceous earth and washed with DCM. The filtrate was evaporated in vacuo and the crude product was purified by flash column chromatography (silica; MeOH in DCM 0/100 to 5/95). The desired fractions were collected and the solvents evaporated in vacuo to yield intermediate compound I-125 (200 g, 26%).

Intermediates 132 (I-132)

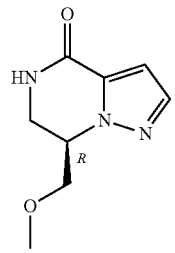
I-132 and 133 (I-133)

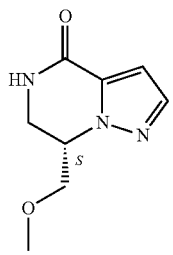

Intermediate compound I-13 (4.7 g, 25.94 mmol) was purified by chiral SFC (Stationary phase: Chiralpak AD-H 5 μm 250×30 mm, Mobile phase: 94.5% CO₂, 5.5% MeOH) to yield intermediate compound I-132 (2.16 g, 46%) and intermediate compound I-133 (2.11 g, 45%).

Intermediate 138

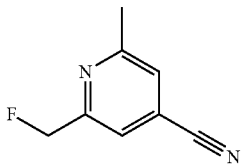

DAST (1.0 M in DCM, 75 μL, 0.61 mmol) was added to a stirred solution of 2-(hydroxymethyl)-6-methyl-pyridine-4-carbonitrile (70 mg, 0.47 mmol) in DCM (1 mL) at −35° C. The mixture was stirred at −35° C. for 30 min. Then, additional DAST (1.0 M in DCM, 40.5 μL, 0.33 mmol) was added and stirred at −35° C. for 1 h more. The mixture was treated at −35° C. with sat. sol. NaHCO₃ and extracted with DCM. The organic layer was separated, dried (Na₂SO₄), filtered and the solvents evaporated in vacuo. The crude product was purified by flash column chromatography (silica; EtOAc in heptane 5/95 to 60/40). The desired fractions were collected and the solvents evaporated in vacuo to yield intermediate compound I-138 (12 mg, 17%).

Preparation of Final Compounds

Example 1 (E-1) 6-Amino-N-[(7S)-5-[3-chloro-4-(trifluoromethyl)phenyl]-7-methyl-4-oxo-6,7-dihydropyrazolo[1,5-a]pyrazin-3-yl]pyridine-3-carboxamide (Co. No. 1)

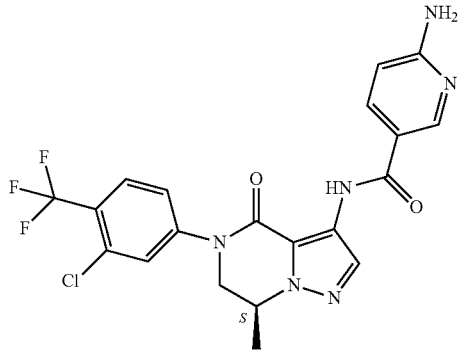

From intermediate I-81: To a solution of intermediate I-81 (310 mg, 0.899 mmol), PyBOP® (1169 mg, 2.248 mmol) and Et₃N (0.436 mL, 3.147 mmol) in DMF (5 mL) was added 6-aminonicotinic acid (310 mg, 2.248 mmol) portion-wise over 2 h. The reaction was stirred at rt for 6 h and then at 80° C. for 9 h. The mixture was diluted with water and extracted with DCM. The organic layer was dried (Na₂SO₄), filtered and the solvents concentrated in vacuo. The crude product was purified by flash column chromatography (silica; EtOAc in DCM 0/100 to 100/0). The desired fractions were collected and the solvents evaporated in vacuo to yield impure product, which was further purified by RP HPLC (Stationary phase: C18 XBridge® 30×100 mm 5 μm; mobile phase: Gradient from 60% 0.1% NH₄CO₃H/NH₄OH pH 9 solution in water, 40% MeCN to 43% 0.1% NH₄CO₃H/NH₄OH pH 9 solution in water, 57% MeCN), yielding final compound Co. No. 1 (161 mg, 38%) as a white solid.

From intermediate I-96: HCl (1 M in water, 39.6 mL, 39.6 mmol) was added to a stirred solution of intermediate I-96 (2.8 g, 4.95 mmol) in 1,4-dioxane (120 mL). The mixture was stirred at 70° C. for 2.5 h. The solvent was evaporated in vacuo and the residue was basified with sat. sol. Na₂CO₃ and extracted with DCM. The organic layer was separated, dried (Na₂SO₄), filtered and the solvents evaporated in vacuo. The crude product was purified by flash column chromatography (silica, EtOAc in DCM 0/100 to 100/0). The desired fractions were collected, the solvents evaporated in vacuo and the residue was triturated with DIPE, then triturated with MeOH at 50° C. The impure fraction was purified by flash column chromatography (silica, EtOAc in DCM 0/100 to 100/0). The desired fractions were collected and the solvents evaporated in vacuo and the residue was triturated with DIPE/MeOH to yield final compound Co. No. 1 (1.49 g, 64%) as a white solid. ¹H NMR (400 MHz, CDCl₃) δ ppm 1.72 (d, J=6.7 Hz, 3H) 4.01 (dd, J=12.5, 8.3 Hz, 1H) 4.20 (dd, J=12.5, 4.2 Hz, 1H) 4.66-4.76 (m, 1H) 5.00 (br. s., 2H) 6.52 (dd, J=8.8, 0.5 Hz, 1H) 7.39-7.44 (m, 1H) 7.59 (d, J=1.8 Hz, 1H) 7.79 (d, J=8.6 Hz, 1H) 7.95 (dd, J=8.7, 2.4 Hz, 1H) 8.45 (s, 1H) 8.70 (d, J=2.1 Hz, 1H) 9.56 (br. s, 1H).

Example 2 (E-2) N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide (Co. No. 101)

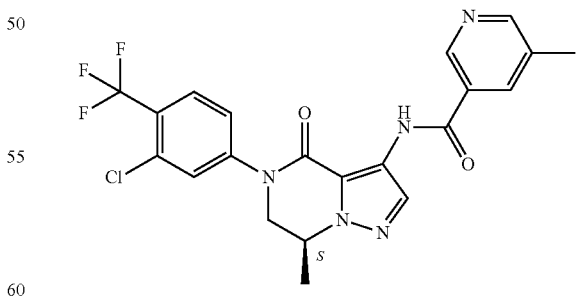

DIPEA (0.114 mL, 0.652 mmol) was added to a stirred solution of intermediate I-81 (150 mg, 0.435 mmol), 5-methylnicotinic acid (71 mg, 0.522 mmol) and HATU (281 mg, 0.739 mmol) in DMF (6 mL). The mixture was stirred at rt for 16 h. The solvent was evaporated in vacuo and the mixture was diluted DCM and washed with sat. sol.

NH₄Cl. The organic layer was separated, dried (Na₂SO₄), filtered and the solvents evaporated in vacuo. The crude product was purified by flash column chromatography (silica; EtOAc in heptane 0/100 to 100/0). The desired fractions were collected and the solvents evaporated in vacuo to yield a residue that was repurified by RP HPLC (Stationary phase: C18 XBridge® 30×100 mm 5 μm), Mobile phase: Gradient from 60% 0.1% NH₄CO₃H/NH₄OH pH 9 solution in Water, 40% MeCN to 43% 0.1% NH₄CO₃H/NH₄OH pH 9 solution in Water, 57% MeCN) and then triturated with Et₂O to yield final compound Co. No. 101 (95 mg, 47%) as a white solid. ¹H NMR (500 MHz, CDCl₃) δ ppm 1.74 (d, J=6.4 Hz, 3H) 2.46 (s, 3H) 4.03 (dd, J=12.6, 8.2 Hz, 1H) 4.22 (dd, J=12.6, 4.2 Hz, 1H) 4.69-4.78 (m, 1H) 7.43 (dd, J=8.5, 1.6 Hz, 1H) 7.60 (d, J=2.0 Hz, 1H) 7.80 (d, J=8.7 Hz, 1H) 8.08 (s, 1H) 8.47 (s, 1H) 8.63 (br. s., 1H) 9.00 (br. s., 1H) 9.74 (br. s, 1H).

Following a procedure analogous to that described for E-2, the following compounds were also synthesized:

| Starting Material | Reagent | Final Compound |
|---|---|---|
| I-81 | benzoic acid | Co. No. 2 |
| I-74 | 6-aminonicotinic acid | Co. No. 3 |
| I-71 | 6-aminonicotinic acid | Co. No. 4 |
| I-90 | 6-aminonicotinic acid | Co. No. 5 (*) |

-continued
| Starting Material | Reagent | Final Compound |
|---|---|---|
| I-80 | 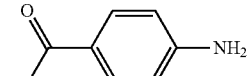 | 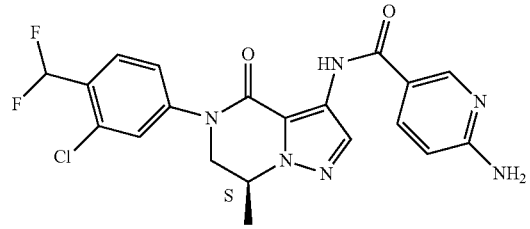<br>Co. No. 6 |
| I-71 | 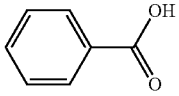 | 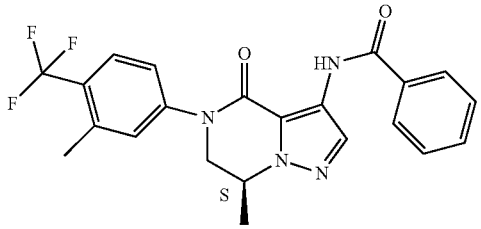<br>Co. No. 7 |
| I-73 | 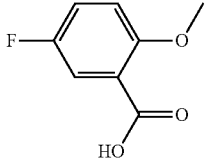 | 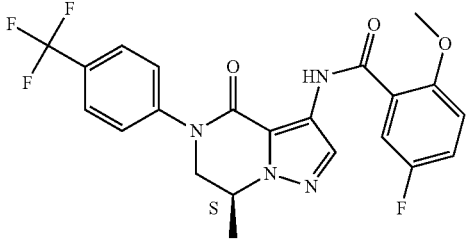<br>Co. No. 10 |
| I-73 |  | 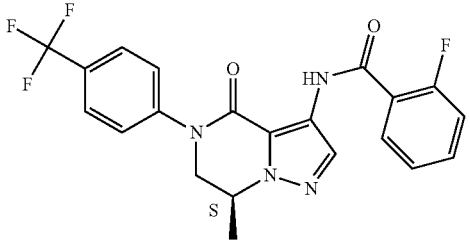<br>Co. No. 11 |
| I-81 | 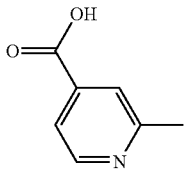 | 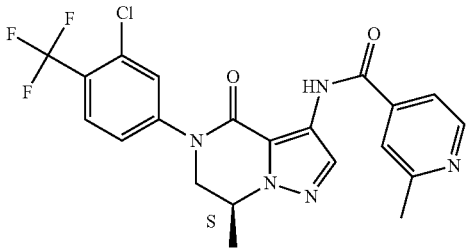<br>Co. No. 12 |

| Starting Material | Reagent | Final Compound |
|---|---|---|
| I-75 | 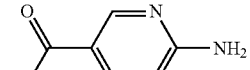 | 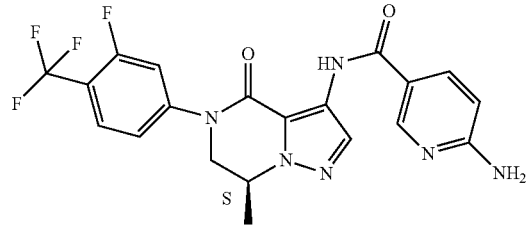<br>Co. No. 13 |
| I-73 | 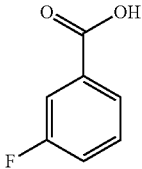 | 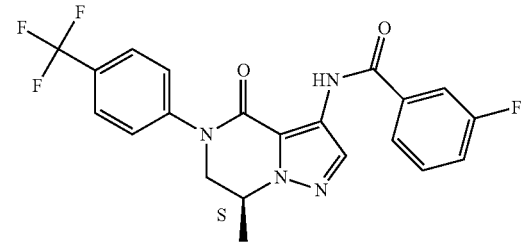<br>Co. No. 14 |
| I-73 | 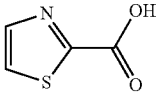 | 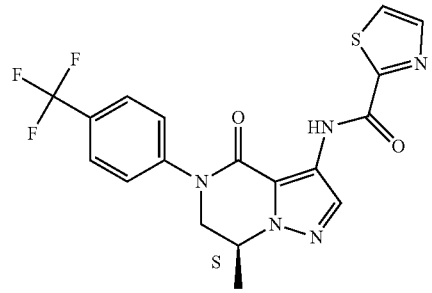<br>Co. No. 15 |
| I-73 | 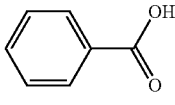 | 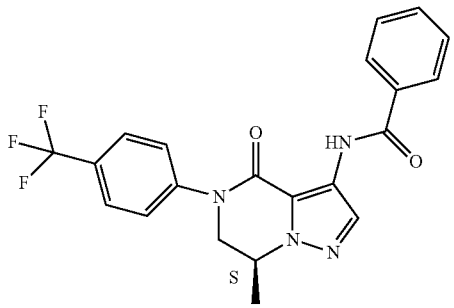<br>Co. No. 16 |

-continued
| Starting Material | Reagent | Final Compound |
|---|---|---|
| I-73 | 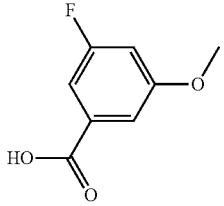 | 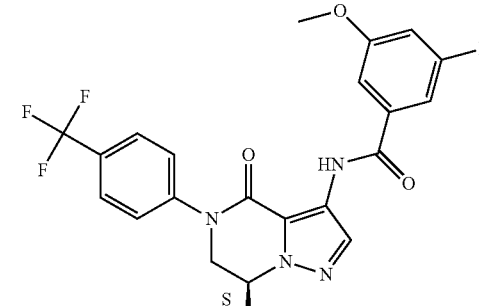
Co. No. 17 |
| I-82 | 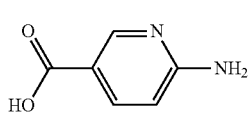 | 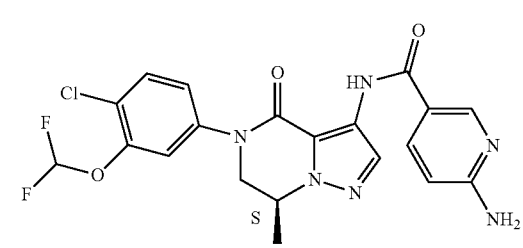
Co. No. 18 |
| I-73 | 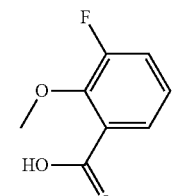 | 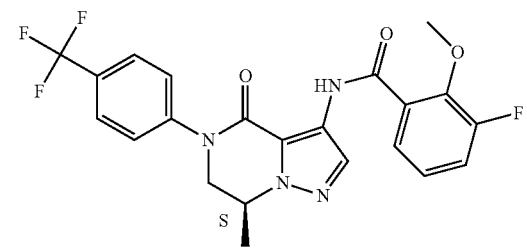
Co. No. 19 |
| I-79 | 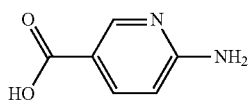 | 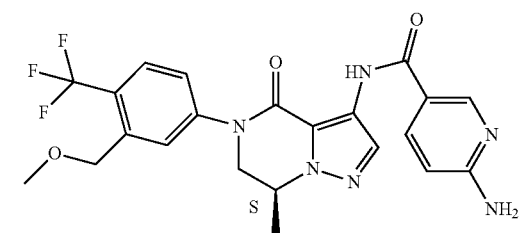
Co. No. 22 |
| I-73 | 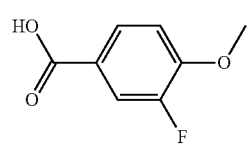 | 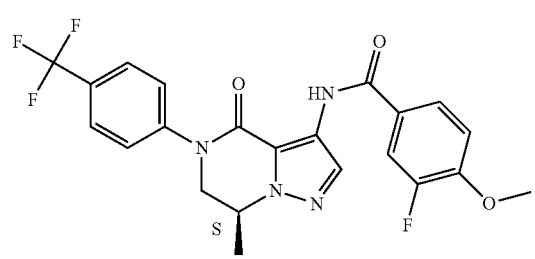
Co. No. 23 |

-continued
| Starting Material | Reagent | Final Compound |
|---|---|---|
| I-73 | 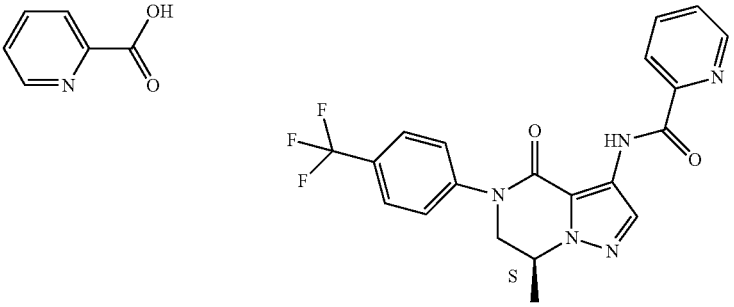 | 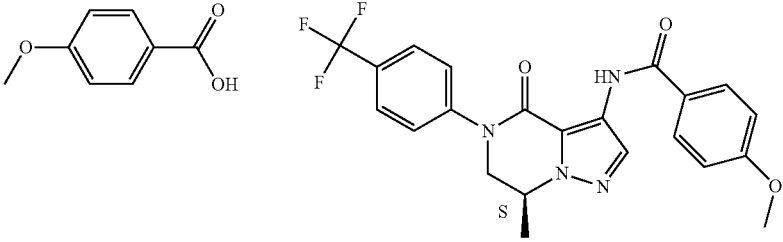
Co. No. 24 |
| I-73 | | Co. No. 25 |
| I-78 | 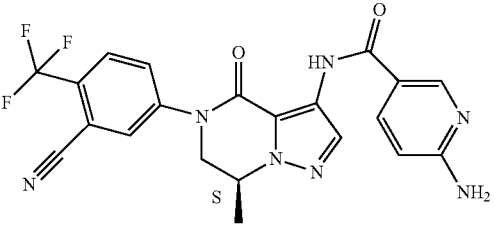 | Co. No. 26 |
| I-73 | | Co. No. 27 |
| I-73 | 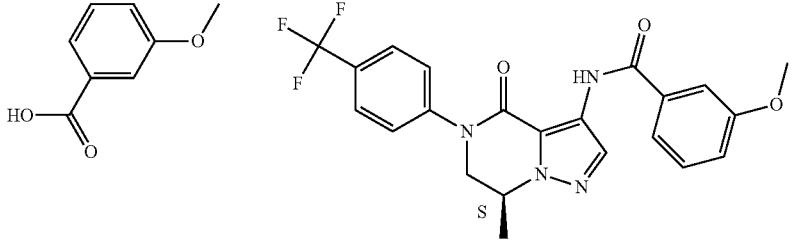 | 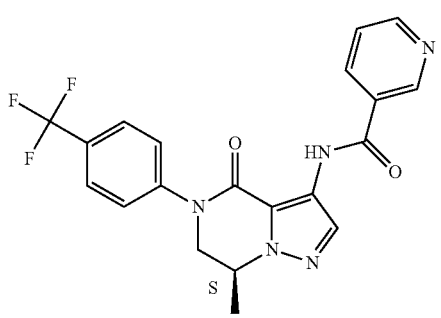
Co. No. 28 |

-continued

| Starting Material | Reagent | Final Compound |
|---|---|---|
| I-73 | 3-(methoxymethyl)benzoic acid | Co. No. 30 |
| I-73 | 5-fluoronicotinic acid | Co. No. 31 |
| I-92 | 6-aminonicotinic acid | Co. No. 33 |
| I-73 | 6-methylpicolinic acid | Co. No. 34 |

-continued

| Starting Material | Reagent | Final Compound |
|---|---|---|
| I-73 | pyrazine-2-carboxylic acid | Co. No. 35 |
| I-76 | 6-aminonicotinic acid | Co. No. 36 |
| I-73 | 2-fluoro-5-methoxybenzoic acid | Co. No. 37 |
| I-77 | 6-aminonicotinic acid | Co. No. 38 |
| I-73 | 5-methoxypyrazine-2-carboxylic acid | Co. No. 39 |

-continued
| Starting Material | Reagent | Final Compound |
|---|---|---|
| I-73 | 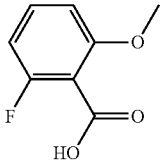 | 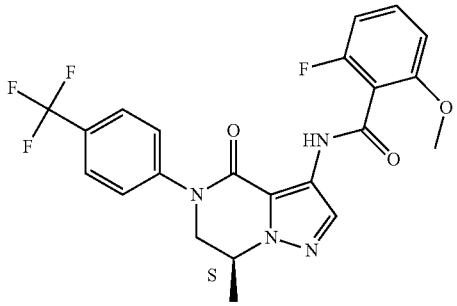<br>Co. No. 41 |
| I-73 | 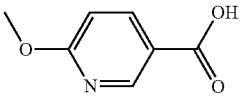 | 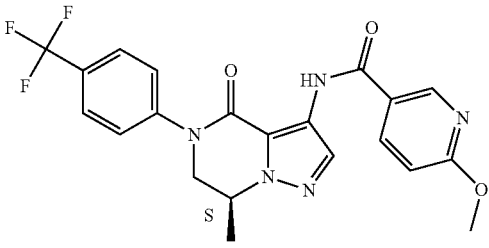<br>Co. No. 42 |
| I-73 | 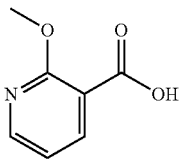 | 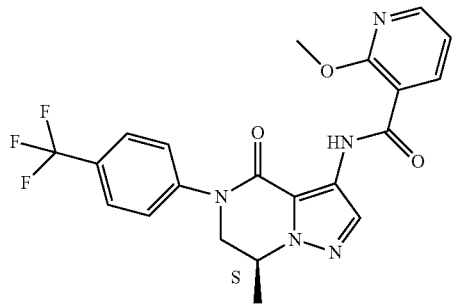<br>Co. No. 43 |
| I-73 | 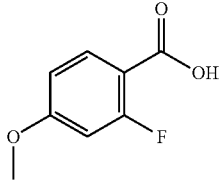 | 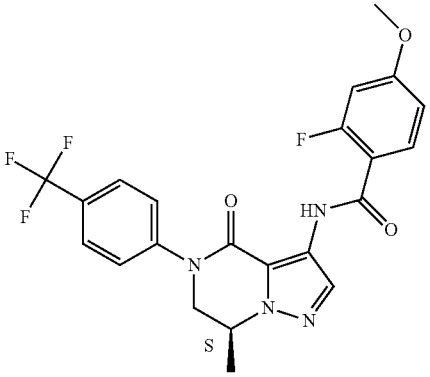<br>Co. No. 44 |

-continued

| Starting Material | Reagent | Final Compound |
|---|---|---|
| I-73 | 5-chloropyridine-2-carboxylic acid | Co. No. 46 |
| I-73 | 5-fluoropyridine-2-carboxylic acid | Co. No. 48 |
| I-73 | 4-fluorobenzoic acid | Co. No. 49 |
| I-73 | 2-aminoisonicotinic acid | Co. No. 50 |
| I-73 | 4-fluoro-3-methoxybenzoic acid | Co. No. 51 |

-continued

| Starting Material | Reagent | Final Compound |
|---|---|---|
| I-73 | 6-methylnicotinic acid | Co. No. 54 |
| I-73 | isonicotinic acid | Co. No. 55 |
| I-92 | 3-methoxybenzoic acid | Co. No. 56 |
| I-73 | 3-methylpicolinic acid | Co. No. 57 |
| I-73 | 4-methoxypicolinic acid | Co. No. 60 |

| Starting Material | Reagent | Final Compound |
|---|---|---|
| I-83 | 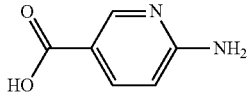 | 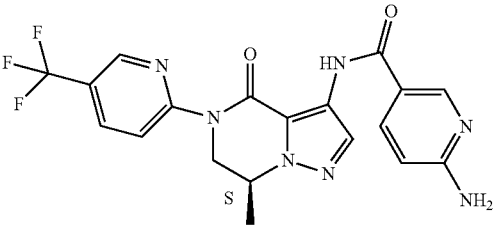
Co. No. 61 |
| I-85 | 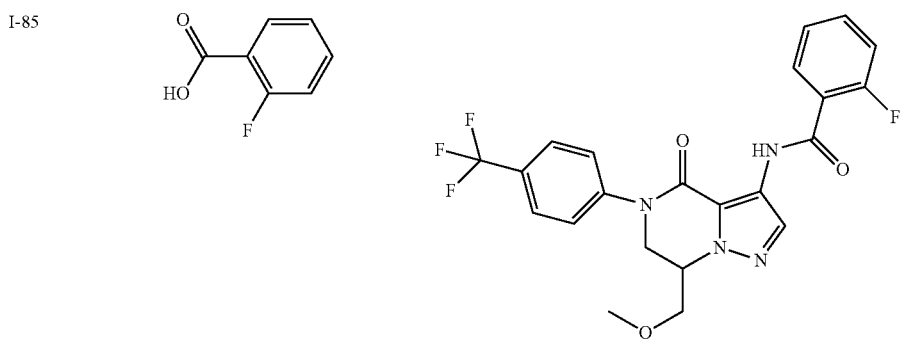 | 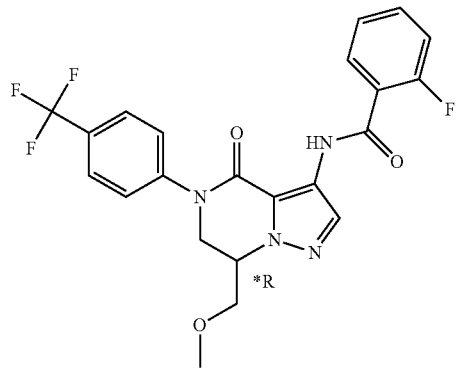
Co. No. 62
Co. No. 62 was purified by chiral SFC (Stationary phase: CHIRALPAK AD-H 5 μm 250 × 20 mm, Mobile phase: 65% CO$_2$, 35% EtOH) to yield
Co. No. 62a
and |

| Starting Material | Reagent | Final Compound |
|---|---|---|
| | | 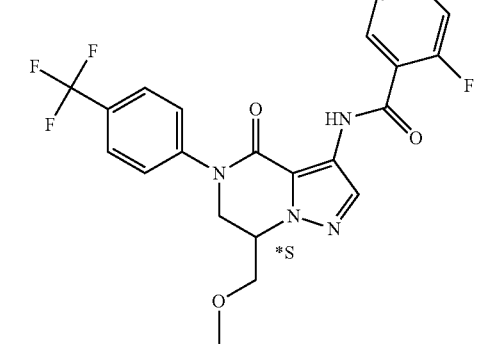
Co. No. 62b |
| I-85 | 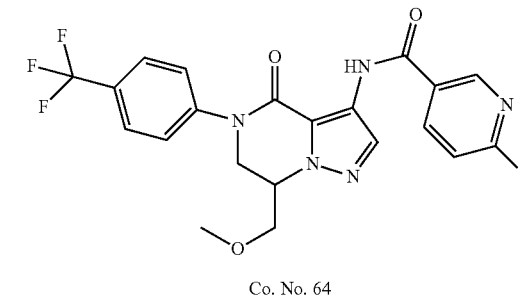 | 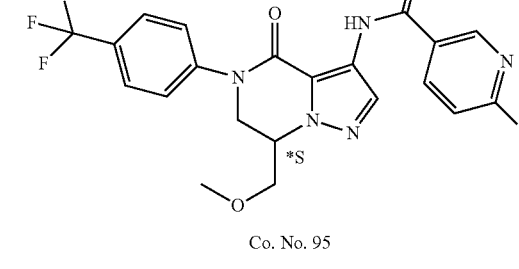
Co. No. 64
Co. No. 64 was purified by chiral SFC (Stationary phase: CHIRALPAK AD-H 5 μm 250 × 30 mm, Mobile phase: 50% CO$_2$, 50% EtOH) to yield Co. No. 95 and Co. No. 96, further purified by preparative LC (Stationary phase: irregular bare silica 40 g, Mobile phase: 99% DCM, 1% MEOH) to yield Co. No. 95 and Co. No. 96
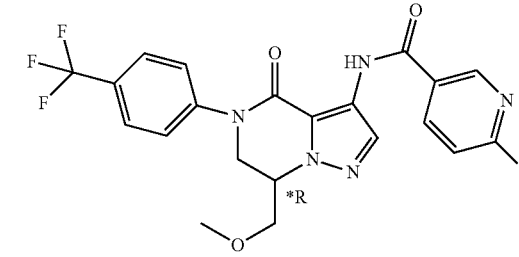
Co. No. 95
and
Co. No. 96 |

-continued
| Starting Material | Reagent | Final Compound |
|---|---|---|
| I-91 | 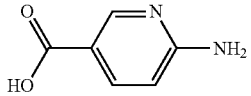 | 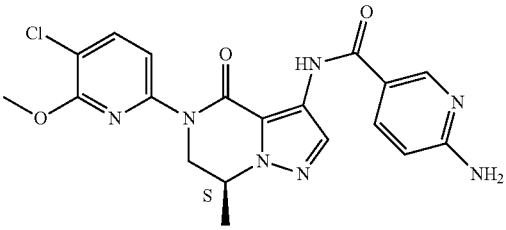
Co. No. 65 |
| I-73 | 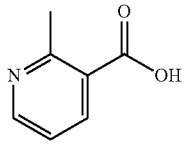 | 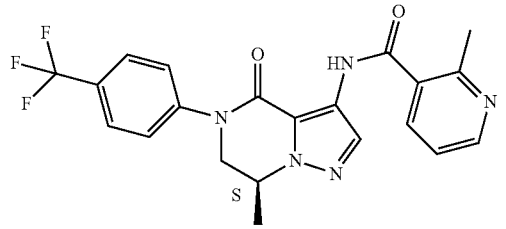
Co. No. 66 |
| I-73 | 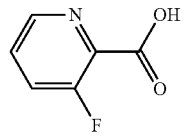 | 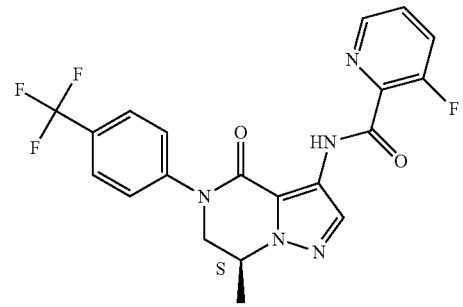
Co. No. 67 |
| I-92 | 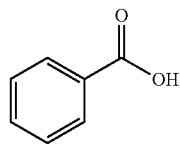 | 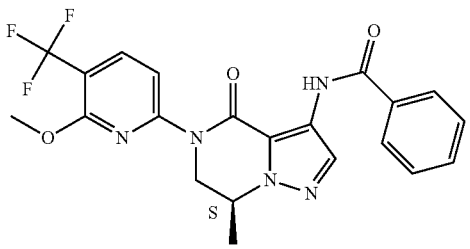
Co. No. 70 |
| I-73 | 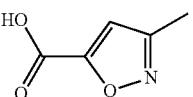 | 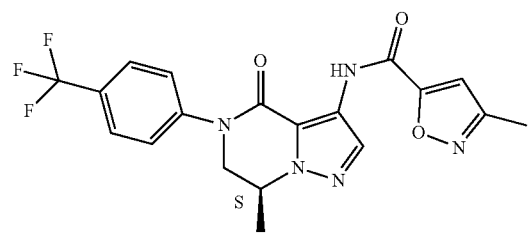
Co. No. 71 |

| Starting Material | Reagent | Final Compound |
|---|---|---|
| I-73 | 5-methylisoxazole-3-carboxylic acid | Co. No. 72 |
| I-73 | 2-cyclopropylacetic acid | Co. No. 73 |
| I-92 | 2-methoxybenzoic acid | Co. No. 75 |
| I-92 | 4-methoxybenzoic acid | Co. No. 77 |
| I-73 | 2-(methoxymethyl)benzoic acid | Co. No. 78 |

-continued
| Starting Material | Reagent | Final Compound |
|---|---|---|
| I-73 | 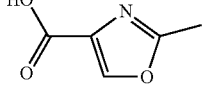 | 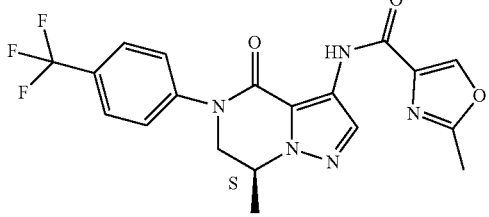<br>Co. No. 81 |
| I-73 | 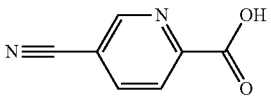 [SMILES: N#Cc1ccc(C(=O)O)nc1] | 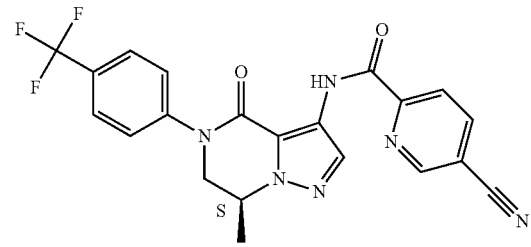<br>Co. No. 85 |
| I-73 | 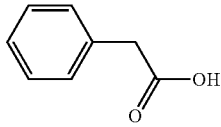 | 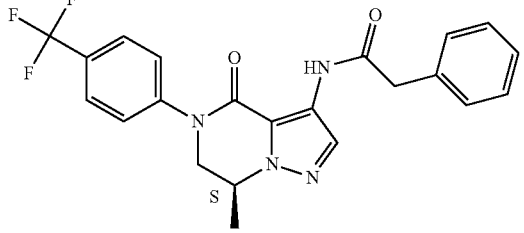<br>Co. No. 87 |
| I-73 | 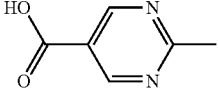 | 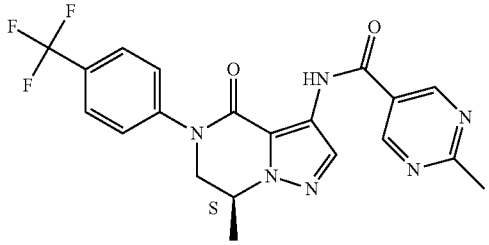<br>Co. No. 88 |
| I-73 | 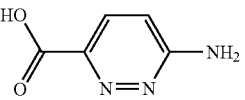 | 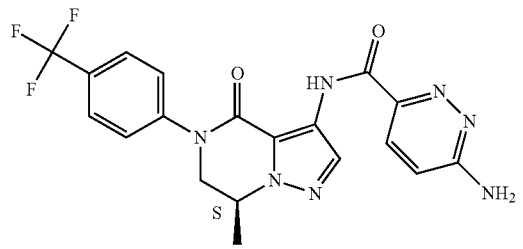<br>Co. No. 90 |

-continued
| Starting Material | Reagent | Final Compound |
|---|---|---|
| I-73 | 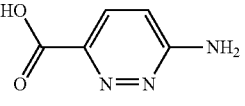 | 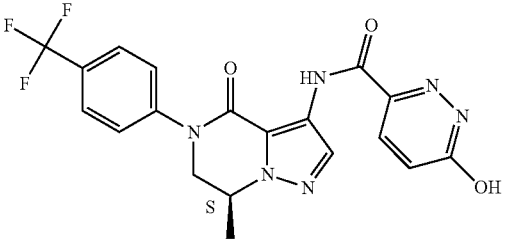
Co. No. 92 |
| I-73 | 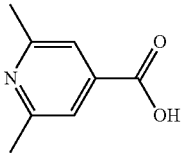 | 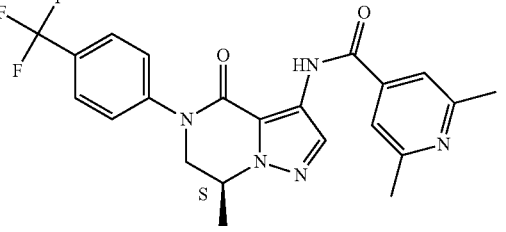
Co. No. 93 |
| I-84 | 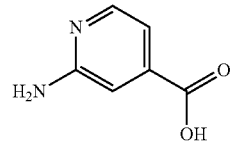 | 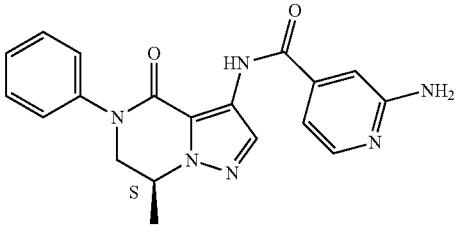
Co. No. 97 |
| I-73 | 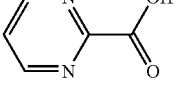 | 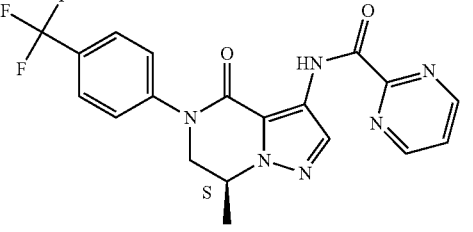
Co. No. 98 |
| I-73 | 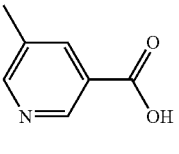 | 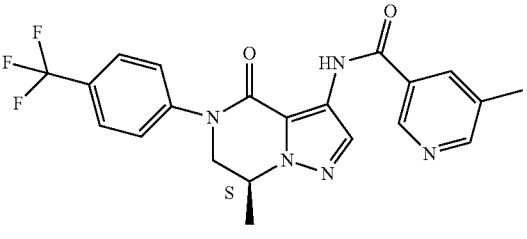
Co. No. 99 |

-continued
| Starting Material | Reagent | Final Compound |
|---|---|---|
| I-81 | 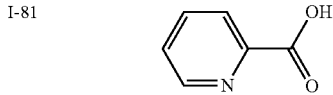 | 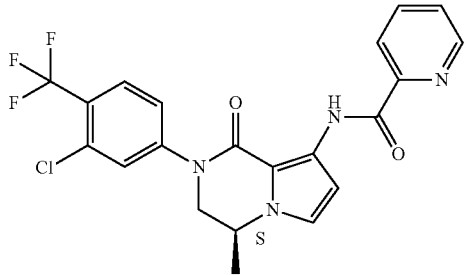<br>Co. No. 102 |
| I-81 | 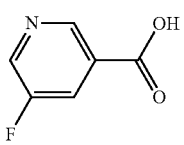 | 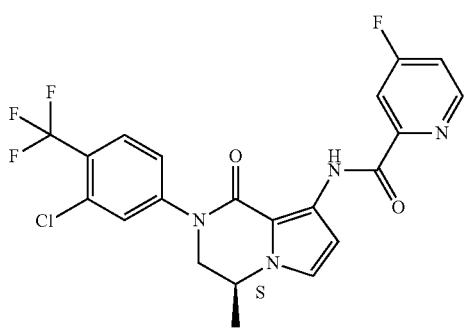<br>Co. No. 103 |
| I-74 | 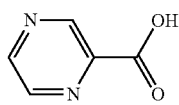 | 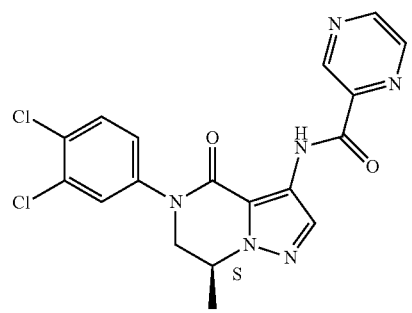<br>Co. No. 104 |
| I-74 | 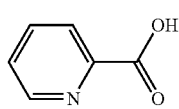 | 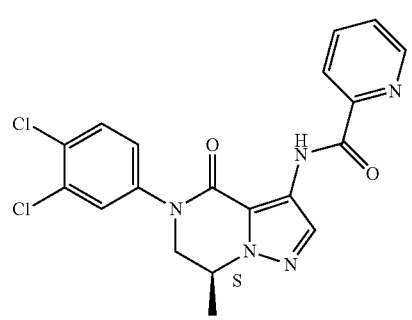<br>Co. No. 105 |

-continued
| Starting Material | Reagent | Final Compound |
|---|---|---|
| I-74 | 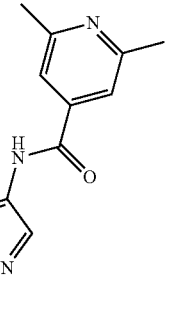 | 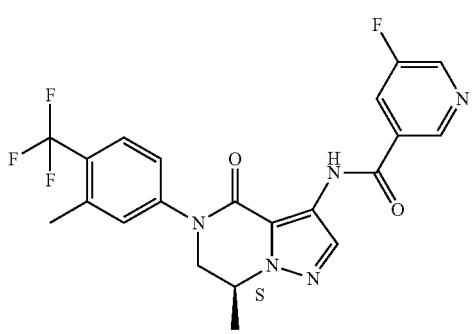
Co. No. 106 |
| I-71 | | 
Co. No. 107 |
| I-74 | 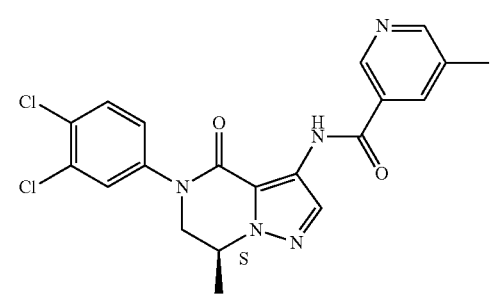 | 
Co. No. 108 |
| I-74 | 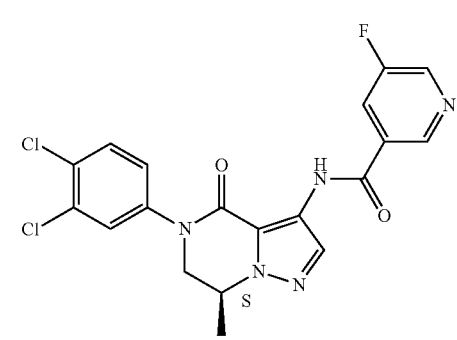 | 
Co. No. 109 |

| Starting Material | Reagent | Final Compound |
|---|---|---|
| I-71 | pyridine-2-carboxylic acid | Co. No. 110 |
| I-77 | pyridine-2-carboxylic acid | Co. No. 111 |
| I-71 | 2-methylpyridine-4-carboxylic acid | Co. No. 112 |
| I-71 | 2,6-dimethylpyridine-4-carboxylic acid | Co. No. 113 |

-continued

| Starting Material | Reagent | Final Compound |
|---|---|---|
| I-71 | pyrazine-2-carboxylic acid | Co. No. 114 |
| I-71 | 5-methylpyridine-3-carboxylic acid | Co. No. 115 |
| I-77 | 5-fluoropyridine-3-carboxylic acid | Co. No. 116 |
| I-77 | 5-methylpyridine-3-carboxylic acid | Co. No. 117 |

-continued

| Starting Material | Reagent | Final Compound |
|---|---|---|
| I-77 | pyrazine-2-carboxylic acid | Co. No. 118 |
| I-73 | 4-methylpyridine-3-carboxylic acid | Co. No. 119 |
| I-81 | 4-methylpyridine-3-carboxylic acid | Co. No. 120 |
| I-81 | 5-methoxy-4-methylpyridine-3-carboxylic acid | Co. No. 121 |

-continued
| Starting Material | Reagent | Final Compound |
|---|---|---|
| I-73 |  | 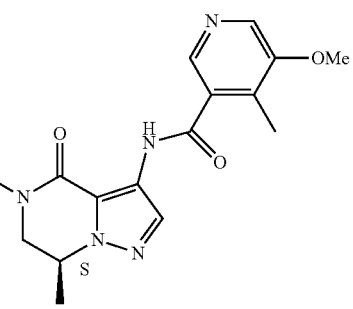
Co. No. 122 |
| I-77 | 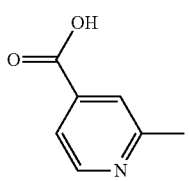 | 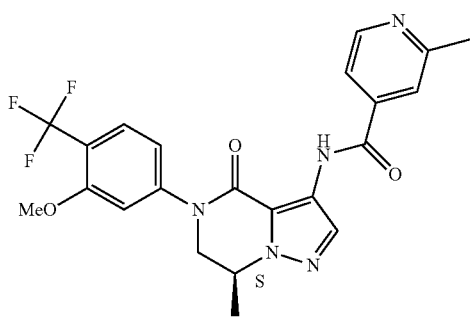
Co. No. 123 |
| I-75 | 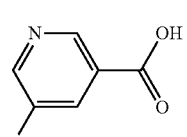 | 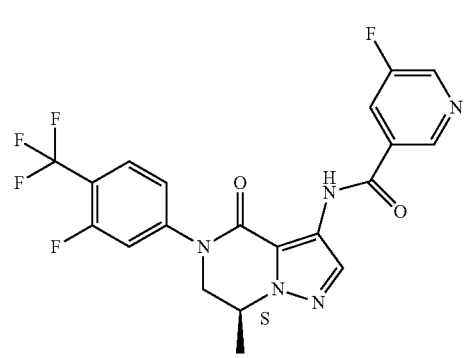
Co. No. 124 |
| I-77 | 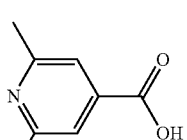 | 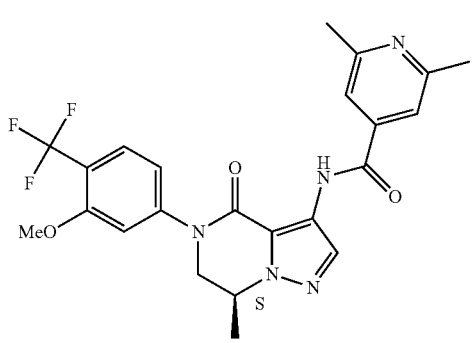
Co. No. 125 |

| Starting Material | Reagent | Final Compound |
|---|---|---|
| I-75 | 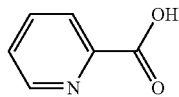 | 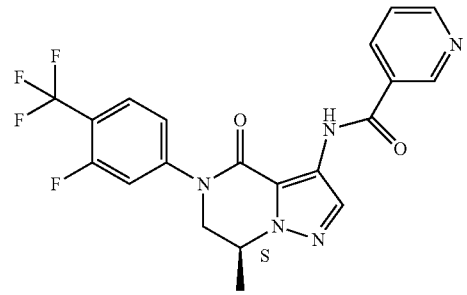<br>Co. No. 126 |
| I-75 | 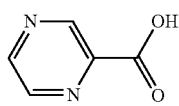 | 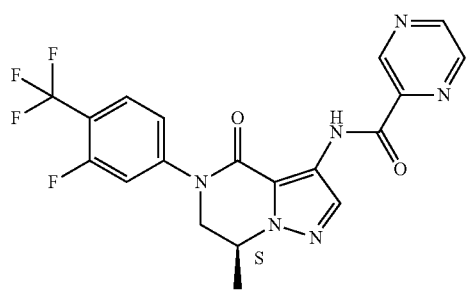<br>Co. No. 127 |
| I-75 | 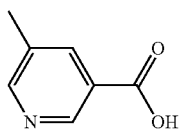 | 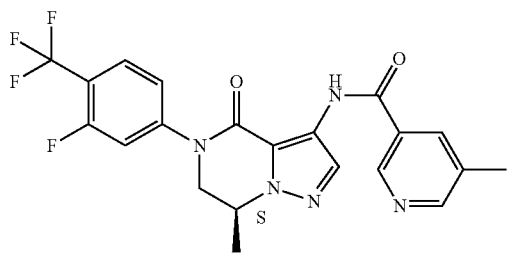<br>Co. No. 128 |
| I-75 | 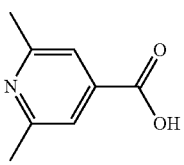 | 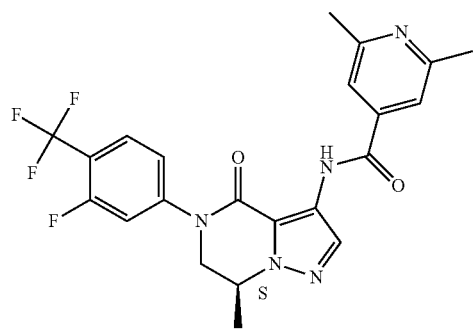<br>Co. No. 129 |

-continued
| Starting Material | Reagent | Final Compound |
|---|---|---|
| I-75 | 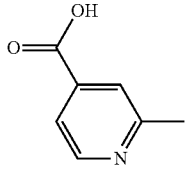 | 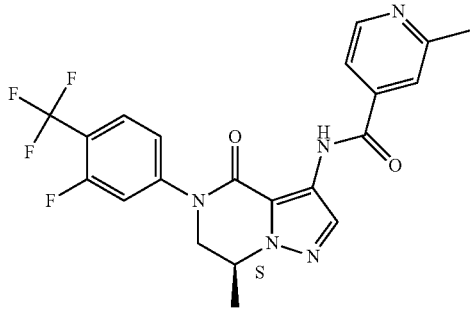
Co. No. 130 |
| I-76 | 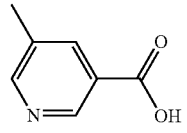 | 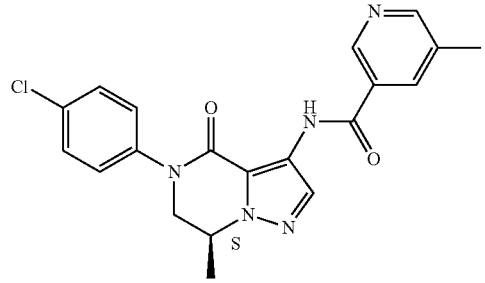
Co. No. 131 |
| I-76 | 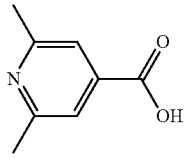 | 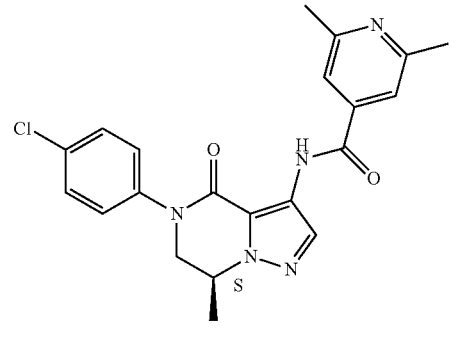
Co. No. 132 |
| I-81 | 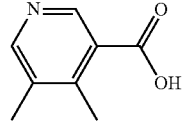 | 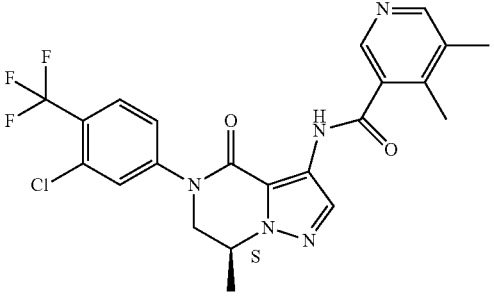
Co. No. 133 |

| Starting Material | Reagent | Final Compound |
|---|---|---|
| I-86 | 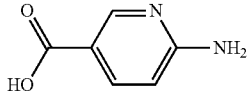 | 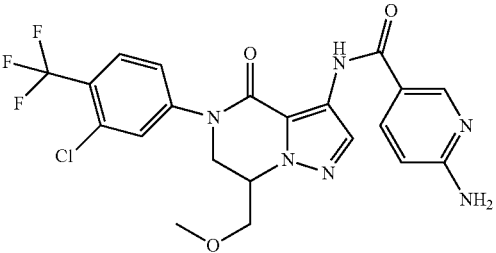
Co. No. 134
Co. No. 134 was purified by chiral SFC (Stationary phase: Chiralpak AD-H 5 μm 240 × 30 mm, Mobile phase: 55% CO$_2$, 45% EtOH) to yield Co. No. 140 and Co. No. 141
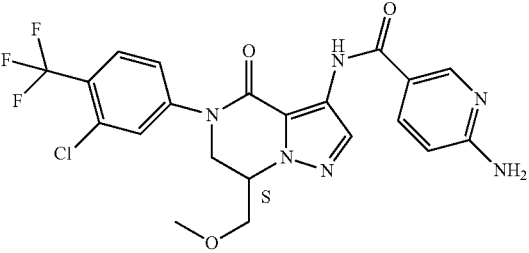
Co. No. 140
and
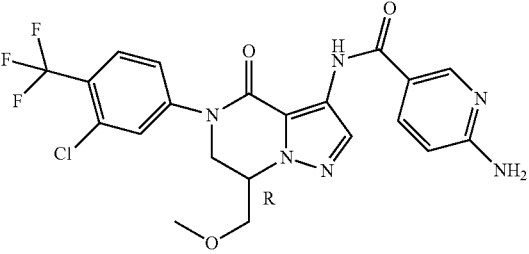
Co. No. 141 (***) |
| I-81 | 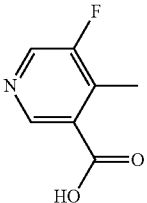 | 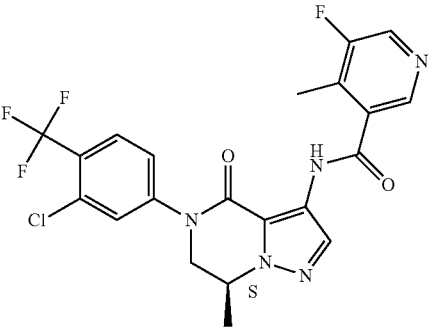
Co. No. 135 |

-continued
| Starting Material | Reagent | Final Compound |
|---|---|---|
| I-73 | 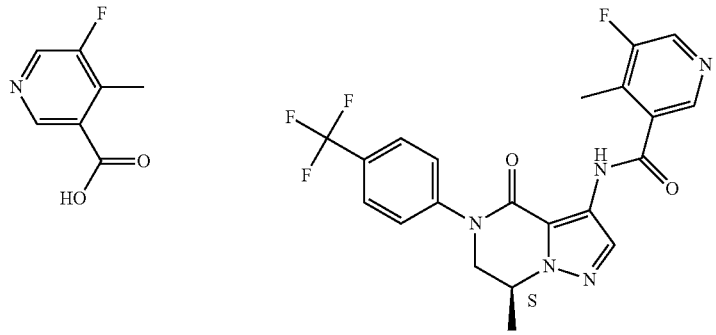 | 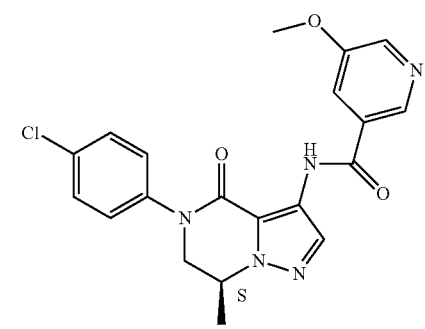
Co. No. 136 |
| I-76 | 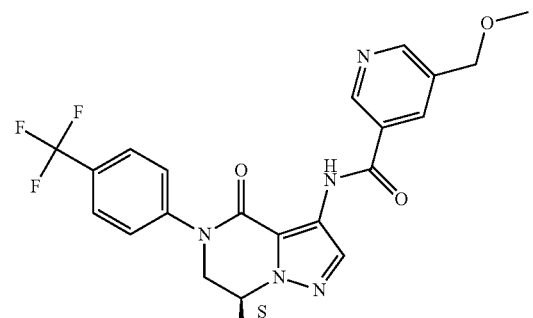 | Co. No. 137 |
| I-73 | I-105 | Co. No. 138 |
| I-81 | I-105 | 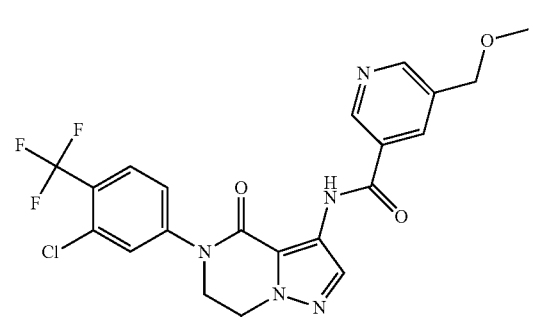
Co. No. 139 |

| Starting Material | Reagent | Final Compound |
|---|---|---|
| I-81 | 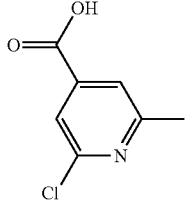 | 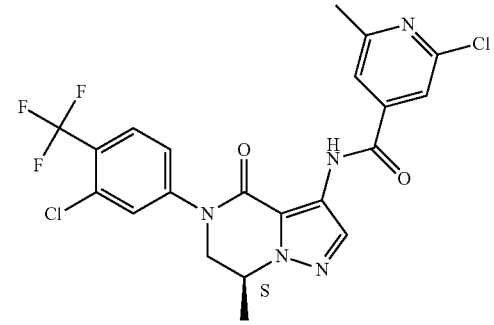<br>Co. No. 142 |
| I-73 | 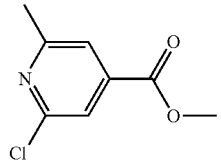 | 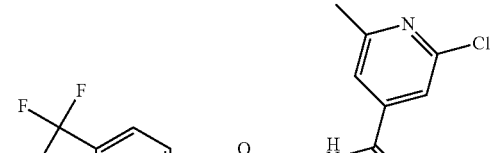<br>Co. No. 143 |
| I-81 | 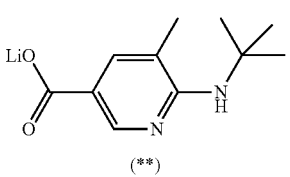<br>(**) | 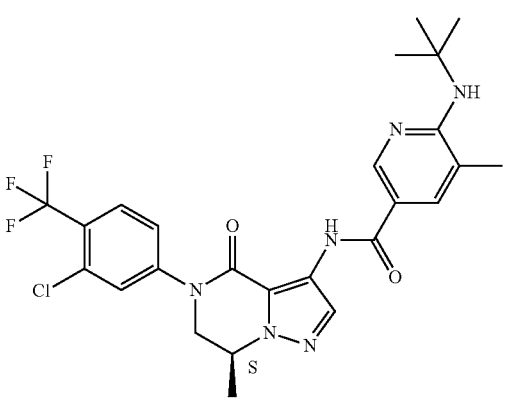<br>Co. No. 168 |
| I-71 | 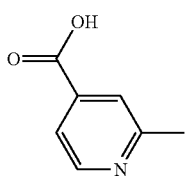 | 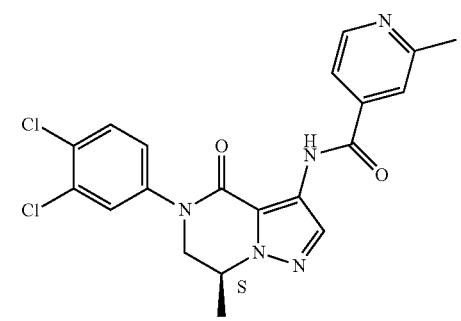<br>Co. No. 171 |

| Starting Material | Reagent | Final Compound |
|---|---|---|
| I-81 | 2,6-dimethylpyridine-4-carboxylic acid | Co. No. 172 |
| I-81 | pyrazine-2-carboxylic acid | Co. No. 176 |
| I-73 | 3-sulfamoylbenzoic acid | Co. No. 177 |
| I-112 | nicotinic acid | Co. No. 178 |

| Starting Material | Reagent | Final Compound |
|---|---|---|
| I-116 | 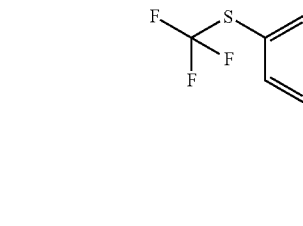 | 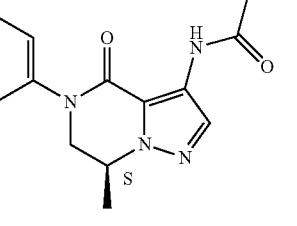
Co. No. 179 |
| I-73 | 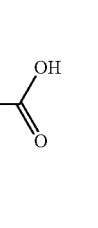 | 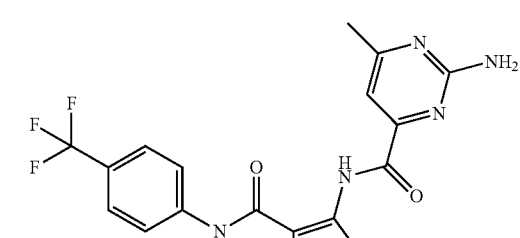
Co. No. 180 |
| I-81 | 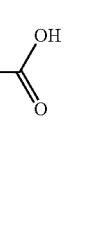 | 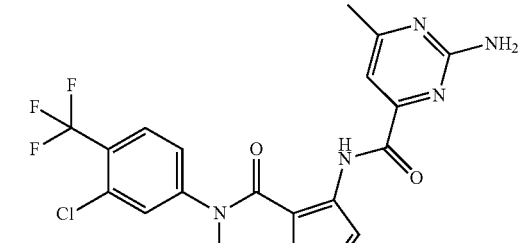
Co. No. 181 |
| I-81 |  | 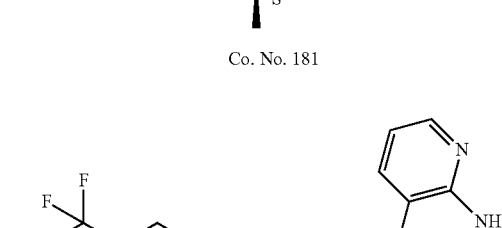
Co. No. 182 |

-continued

| Starting Material | Reagent | Final Compound |
|---|---|---|
| I-73 | 5-methoxypyrazine-2-carboxylic acid | Co. No. 183 |
| I-88 | 2-aminopyridine-3-carboxylic acid | Co. No. 184 |
| I-74 | 2-aminopyridine-3-carboxylic acid | Co. No. 185 |
| I-73 | 3-(fluorosulfonyl)benzoic acid | Co. No. 217 |

| Starting Material | Reagent | Final Compound |
|---|---|---|
| I-73 | 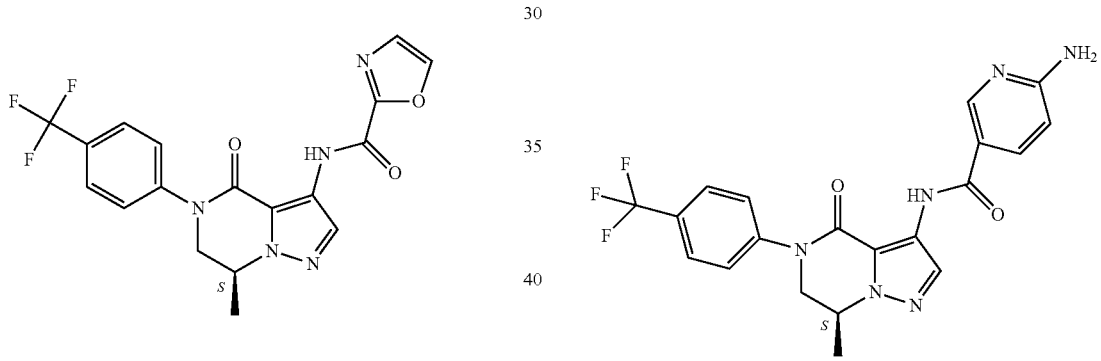 | Co. No. 218 |

(*) This compound was also prepared according to procedure E-14 by reaction of compound Co. No. 165; () prepared by reaction of 6-[(1,1-dimethylethyl)amino]-5-methyl-3-pyridinecarboxylic acid methyl ester with LiOH in THF/water; (*) this compound was also prepared according to procedure E-7 by reaction of intermediate I-135 and 6-aminonicotinamide.

Example 3 (E-3) N-[(7S)-7-Methyl-4-oxo-5-[4-(trifluoromethyl)phenyl]-6,7-dihydropyrazolo[1,5-a]pyrazin-3-yl]oxazole-2-carboxamide (Co. No. 63)

A mixture of intermediate I-73 (146 mg, 0.472 mmol), intermediate I-106 (84 mg, 0.709 mmol) and HATU (305 mg, 0.803 mmol) in DMF (4 mL) was stirred at rt for 20 h. The mixture was diluted with DCM and washed with sat. sol. NH$_4$Cl. The organic layer was separated, dried (Na$_2$SO$_4$), filtered and the solvents evaporated in vacuo. The crude product was purified by flash column chromatography (silica; EtOAc in heptane 30/70 to 70/30). The desired fractions were collected and the solvents evaporated in vacuo to yield final compound Co. No. 63 (62 mg, 32%) as a white solid. $^1$H NMR (400 MHz, CDCl$_3$) δ ppm 1.73 (d, J=6.5 Hz, 3H) 4.03 (dd, J=12.6, 8.0 Hz, 1H) 4.23 (dd, J=12.7, 4.2 Hz, 1H) 4.68-4.78 (m, 1H) 7.28 (d, J=0.7 Hz, 1H) 7.54 (br. d, J=8.3 Hz, 2H) 7.72 (br. d, J=8.6 Hz, 2H) 7.83 (d, J=0.7 Hz, 1H) 8.43 (s, 1H) 10.37 (br. s, 1H).

Example 4 (E-4) 6-Amino-N-[(7S)-7-methyl-4-oxo-5-[4-(trifluoromethyl)phenyl]-6,7-dihydropyrazolo[1,5-a]pyrazin-3-yl]pyridine-3-carboxamide (Co. No. 8)

From intermediate I-101: HCl (4 M in dioxane, 14 mL, 56 mmol) was added to a stirred solution of intermediate I-101 (3.158 g, 5.596 mmol) in 1,4-dioxane (50 mL). The mixture was stirred at 70° C. for 4 h. The solvent was evaporated in vacuo and the residue was basified with sat. sol. Na$_2$CO$_3$ and extracted with DCM. The organic layer was separated, dried (Na$_2$SO$_4$), filtered and the solvents evaporated in vacuo. The crude product was purified by flash column chromatography (silica; EtOAc in DCM 0/100 to 100/0). The desired fractions were collected, the solvents evaporated in vacuo and the residue was triturated with Et$_2$O and some drops of DCM. The impure fraction was purified by flash column chromatography (silica; EtOAc in DCM 0/100 to 90/10). The desired fractions were collected and the solvents evaporated in vacuo and the residue was triturated from a mixture of EtOAc/MeOH and crystallized from hot MeOH to yield final compound Co. No. 8 (1.098 g, 45%) as a white cotton. $^1$H NMR (500 MHz, CDCl$_3$) δ ppm 1.72 (d, J=6.6 Hz, 3H) 4.02 (dd, J=12.6, 7.9 Hz, 1H) 4.21 (dd, J=12.4, 4.0 Hz, 1H) 4.67-4.75 (m, 1H) 4.89 (br. s, 2H) 6.48 (d, J=8.7 Hz, 1H) 7.52 (br. d, J=8.1 Hz, 2H) 7.74 (br. d, J=8.4 Hz, 2H) 7.92 (dd, J=8.7, 2.3 Hz, 1H) 8.45 (s, 1H) 8.71 (d, J=2.0 Hz, 1H) 9.59 (br. s, 1H).

From compound Co. No. 159: Compound Co. No. 159 (1 g, 2.117 mmol) was dissolved in a mixture of HCl (4 M in dioxane, 20 mL, 80 mmol) and HCl (1 M in water, 20 mL, 20 mmol). The mixture was stirred at 80° C. for 1 h. Then the solvent was evaporated in vacuo and the resulting solid dissolved in 10% aq. Na₂CO₃ sol. and extracted with DCM. The organic layer was separated, dried (Na₂SO₄), filtered and the solvent evaporated in vacuo. The crude product was purified by flash column chromatography (silica, 7 N solution of ammonia in MeOH in DCM 0/100 to 100/0). The desired fractions were collected and the solvents concentrated in vacuo to yield final compound Co. No. 8 (600 mg, 66%) as a pale yellow solid. The solid can be triturated with MeCN and crystallized from MeOH to yield Co. No. 8 as white needles. This compound was also prepared according to procedure E-5 by reaction of intermediate I-73.

Example 5 (E-5) 6-Amino-N-[(7S)-7-methyl-4-oxo-5-[4-(trifluoromethyl)phenyl]-6,7-dihydropyrazolo[1,5-a]pyrazin-3-yl]pyridine-3-carboxamide (Co. No. 8); 6-acetamido-N-[(7S)-7-methyl-4-oxo-5-[4-(trifluoromethyl)phenyl]-6,7-dihydropyrazolo[1,5-a]pyrazin-3-yl]pyridine-3-carboxamide (Co. No. 159); and N-[(7S)-7-methyl-4-oxo-5-[4-(trifluoromethyl)phenyl]-6,7-dihydropyrazolo[1,5-a]pyrazin-3-yl]acetamide (Co. No. 160)

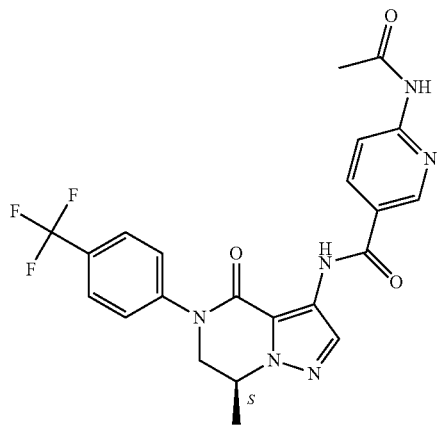

Co. No. 8

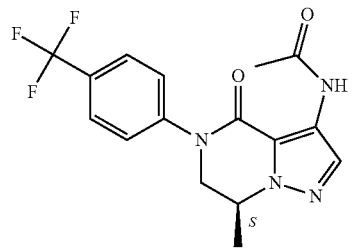

Co. No. 159

Co. No. 160

Lithium bis(trimethylsilyl)amide (1M in THF, 19.3 mL, 19.3 mmol) was added to a stirred solution of intermediate I-73 (2 g, 6.446 mmol) and methyl 6-aminopyridine-3-carboxylate (980 mg, 6.446 mmol) in anhydrous THF (50 mL) at 0° C. and under nitrogen. The mixture was allowed to reach rt and stirred for 3 days. Then the reaction was quenched with sat. sol. NH₄Cl and EtOAc. The organic layers were separated, combined, dried (Na₂SO₄), filtered and the solvents evaporated in vacuo. The crude product was purified by flash column chromatography (silica; EtOAc in DCM 20/80 to 80/20). The desired fractions were collected and the solvents evaporated in vacuo to yield final compounds Co. No. 8 (1.2 g, 43%), Co. No. 159 (1.2 g, 39%) as a white solid after triturating with Et₂O and Co. No. 160 (120 mg, 5%). Co. No. 159: ¹H NMR (500 MHz, CDCl₃) δ ppm 1.73 (d, J=6.4 Hz, 3H) 2.24 (s, 3H) 4.03 (dd, J=12.4, 8.1 Hz, 1H) 4.23 (dd, J=12.6, 4.2 Hz, 1H) 4.68-4.77 (m, 1H) 7.53 (d, J=8.4 Hz, 2H) 7.75 (d, J=8.4 Hz, 2H) 8.21 (dd, J=8.7, 2.6 Hz, 2H) 8.29 (d, J=8.7 Hz, 1H) 8.46 (s, 1H) 8.85 (d, J=1.7 Hz, 1H) 9.73 (s, 1H). Co. No. 160: ¹H NMR (500 MHz, CDCl₃) δ ppm 1.69 (d, J=6.4 Hz, 3H) 2.16 (s, 3H) 3.98 (dd, J=12.6, 7.9 Hz, 1H) 4.19 (dd, J=12.6, 4.2 Hz, 1H) 4.63-4.72 (m, 1H) 7.50 (d, J=8.4 Hz, 2H) 7.73 (d, J=8.4 Hz, 2H) 8.33 (s, 1H) 8.81 (br. s., 1H).

Following a procedure analogous to that described for E-5, the following compounds were also synthesized:

| Starting Material | Reagent | Final Compound |
| --- | --- | --- |
| I-73 | 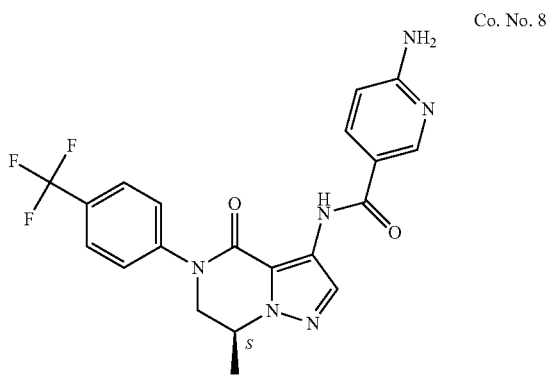 | |

Co. No. 9

| Starting Material | Reagent | Final Compound |
|---|---|---|
| I-73 | 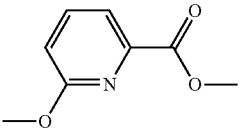 | 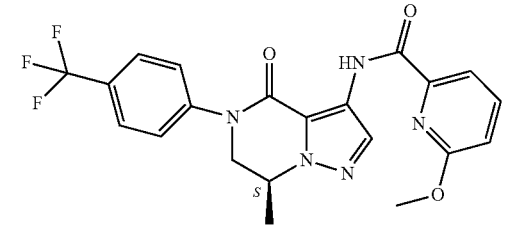<br>Co. No. 20 |
| I-73 | 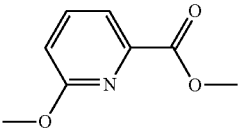 | 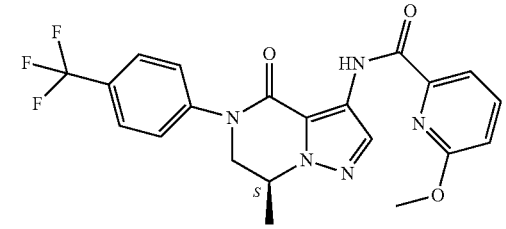<br>Co. No. 21 |
| I-73 | 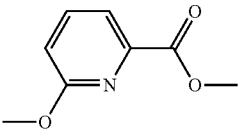 | 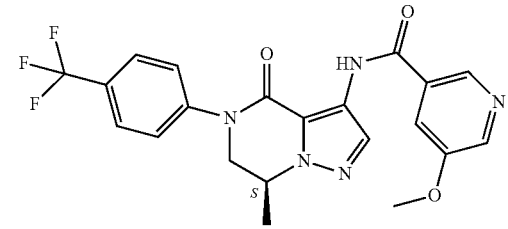<br>Co. No. 32 |
| I-80 | 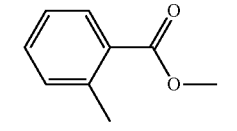 | 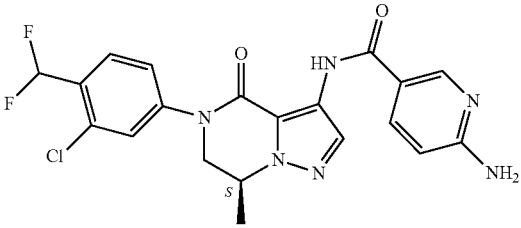<br>Co. No. 40 |
| I-73 | 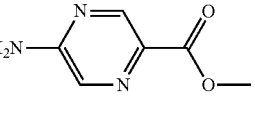 | 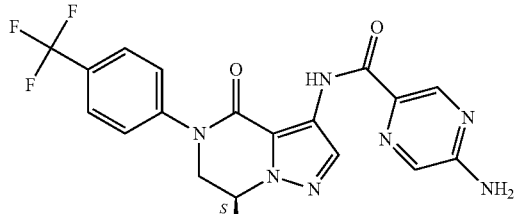<br>Co. No. 45 |

| Starting Material | Reagent | Final Compound |
|---|---|---|
| I-73 | methyl 6-methoxypyridine-2-carboxylate | Co. No. 47 |
| I-73 | ethyl 2-aminopyrimidine-5-carboxylate | Co. No. 52 |
| I-73 | ethyl 4-methylbenzoate | Co. No. 53 |
| I-73 | ethyl 1H-pyrazole-4-carboxylate | Co. No. 79 |
| I-73 | ethyl 1H-imidazole-2-carboxylate | Co. No. 80 |

-continued

| Starting Material | Reagent | Final Compound |
|---|---|---|
| I-73 | methyl 1H-imidazole-4-carboxylate | Co. No. 83 |
| I-73 | ethyl 1-methyl-1H-pyrazole-4-carboxylate | Co. No. 86 |
| I-73 | ethyl 3-methyl-1H-pyrazole-5-carboxylate | Co. No. 89 |
| I-73 | methyl 1-methyl-1H-imidazole-5-carboxylate | Co. No. 91 |
| I-81 | ethyl benzoate | Co. No. 100 (*) |

-continued
| Starting Material | Reagent | Final Compound |
|---|---|---|
| I-73 | 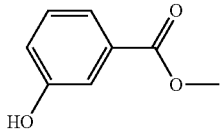 | 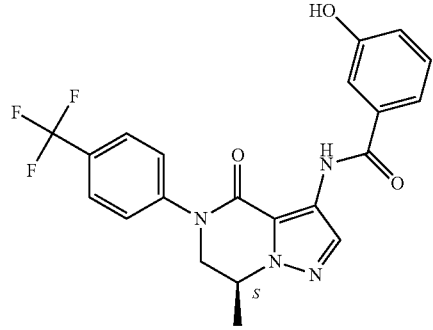<br>Co. No. 144 |
| I-71 | 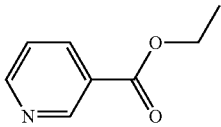 | 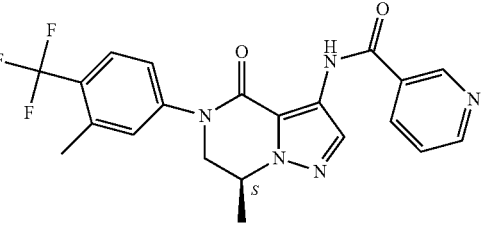<br>Co. No. 145 |
| I-81 | 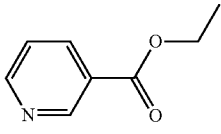 | 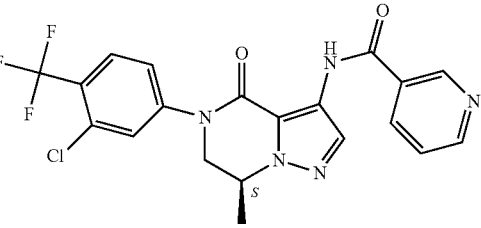<br>Co. No. 146 |
| I-77 | 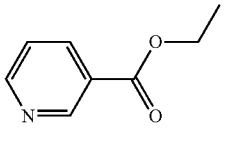 | 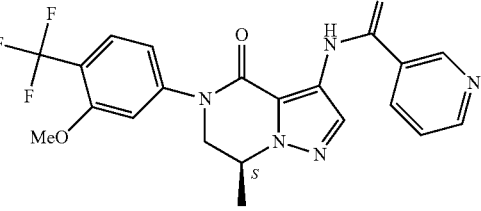<br>Co. No. 147 |
| I-75 | 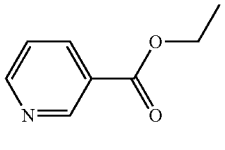 | 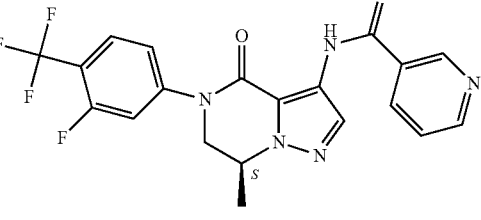<br>Co. No. 148 |

| Starting Material | Reagent | Final Compound |
|---|---|---|
| I-74 | 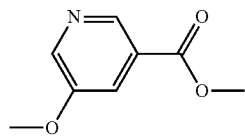 | 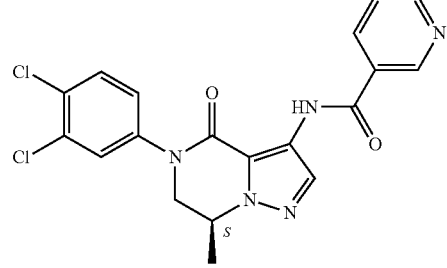
Co. No. 149 |
| I-81 | 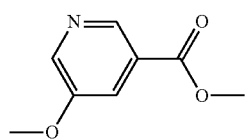 | 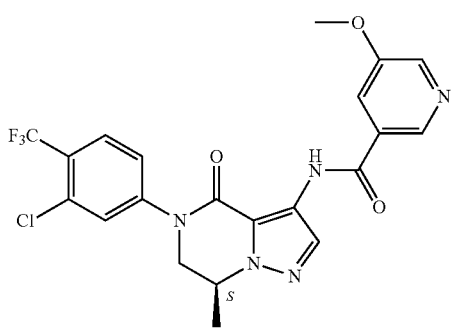
Co. No. 150 |
| I-71 | 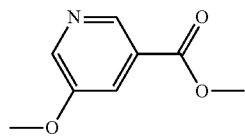 | 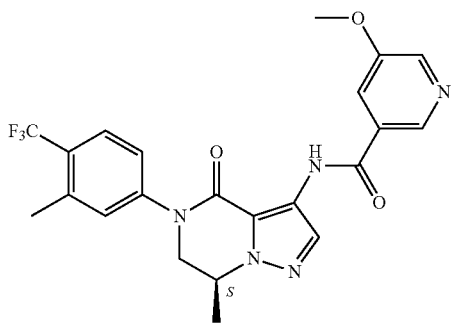
Co. No. 151 |
| I-77 | 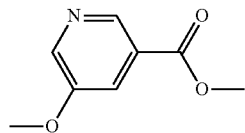 | 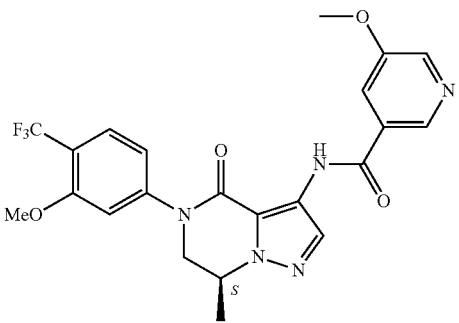
Co. No. 152 |

| Starting Material | Reagent | Final Compound |
|---|---|---|
| I-75 | 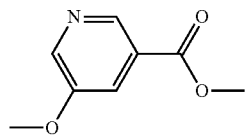 | 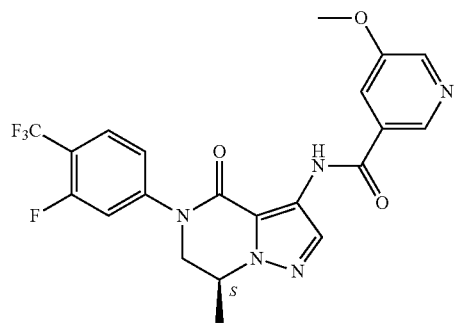
Co. No. 153 |
| I-73 | 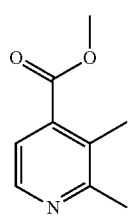 | 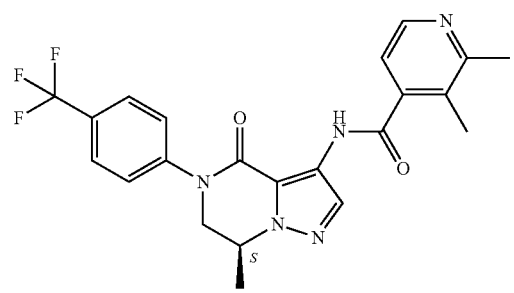
Co. No. 154 |
| I-81 | 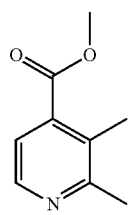 | 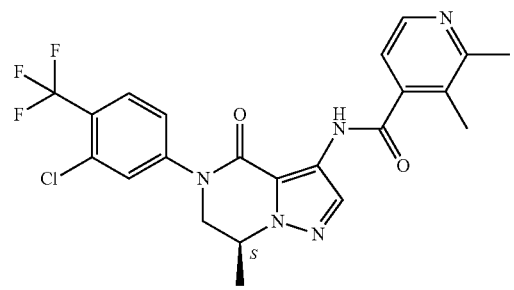
Co. No. 155 |
| I-73 | 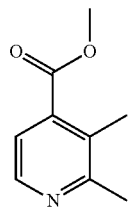 | 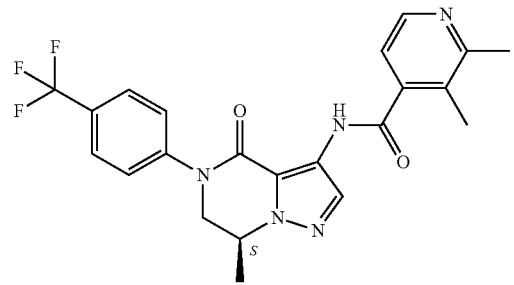
Co. No. 156 |

-continued

| Starting Material | Reagent | Final Compound |
|---|---|---|
| I-73 | I-107 | Co. No. 157 |
| I-81 | I-107 | Co. No. 158 |
| I-73 | | Co. No. 161 |
| I-73 | | Co. No. 186 |

(*) This compound was also prepared according to procedure E-1 by reaction of intermediate I-81 and nicotinic acid.

Example 6 (E-6) 5-Amino-N-[(7S)-7-methyl-4-oxo-5-[4-(trifluoromethyl)phenyl]-6,7-dihydropyrazolo[1,5-a]pyrazin-3-yl]pyridine-2-carboxamide (Co. No. 68)

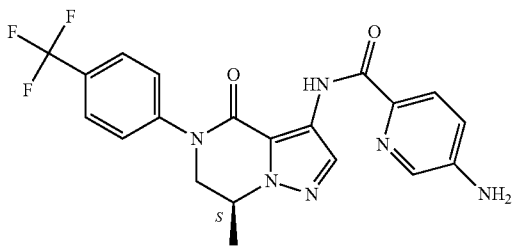

A mixture of compound Co. No. 46 (88 mg, 0.196 mmol), NaN$_3$ (25 mg, 0.391 mmol) and PPh$_3$ (103 mg, 0.391 mmol) in DMSO (1.35 mL) was stirred at 120° C. for 24 h. Then, HCl (1 M in H$_2$O, 0.27 mL, 0.27 mmol) was added to the mixture and stirring was continued at 120° C. for an additional h. The mixture was cooled to rt and diluted with HCl (1 M in H$_2$O, 0.27 mL, 0.27 mmol). The resulting mixture was poured into distilled water and the aqueous layer was washed with EtOAc to remove triphenylphosphine oxide and the majority of DMSO thus allowing easy removal of solvent at the end of work-up. The aqueous layer was slowly neutralized with sat. aq. NaHCO$_3$. The aqueous layer was extracted with EtOAc. The combined organic layers were washed with water, brine, dried (Na$_2$SO$_4$), filtered and the solvents evaporated in vacuo. A purification was performed by RP HPLC (Stationary phase: C18 Sunfire 30×100 mm 5 µm, Mobile phase: Gradient from 80% Water, 20% MeOH to 40% Water, 60% MeOH), to yield final compound Co. No. 68 (35 mg, 42%) as a white solid. $^1$H NMR (400 MHz, CDCl$_3$) δ ppm 1.71 (d, J=6.5 Hz, 3H) 4.01 (dd, J=12.5, 7.9 Hz, 1H) 4.06 (br. s, 2H) 4.21 (dd, J=12.5, 4.2 Hz, 1H) 4.66-4.76 (m, 1H) 7.03 (dd, J=8.6, 2.8 Hz, 1H) 7.54 (br. d, J=8.3 Hz, 2H) 7.72 (br. d, J=8.3 Hz, 2H) 8.01 (d, J=2.3 Hz, 1H) 8.03 (d, J=8.6 Hz, 1H) 8.53 (s, 1H) 10.98 (br. s, 1H).

Example 7 (E-7) N-[(7S)-5-(5-Chloro-6-methoxy-2-pyridyl)-7-methyl-4-oxo-6,7-dihydropyrazolo[1,5-a]pyrazin-3-yl]benzamide (Co. No. 76)

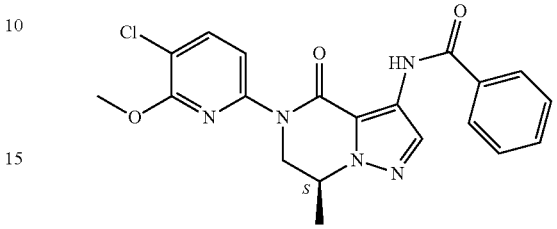

Copper(I) iodide (34 mg, 0.179 mmol) was added to a stirred suspension of intermediate I-46 (125 mg, 0.299 mmol), benzamide (54 mg, 0.448 mmol), N,N'-dimethylethylenediamine (19 µL, 0.179 mmol) and K$_2$CO$_3$ (103 mg, 0.746 mmol) in toluene (1 mL) and DMF (0.5 mL), under nitrogen and in a sealed tube. The mixture was stirred at 100° C. for 16 h. Then the mixture was filtered through a pad of diatomaceous earth and washed with DCM. The organic layer was evaporated in vacuo. The crude product was purified by flash column chromatography (silica; EtOAc in DCM 0/100 to 20/80). The desired fractions were collected and the solvents concentrated in vacuo. The crude product was triturated twice with MeOH to yield final compound Co. No. 76 (27 mg, 22%) as a white solid. $^1$H NMR (500 MHz, CDCl$_3$) δ ppm 1.70 (d, J=6.4 Hz, 3H) 4.03 (s, 3H) 4.25 (dd, J=13.6, 8.1 Hz, 1H) 4.60 (dd, J=13.3, 4.0 Hz, 1H) 4.63-4.71 (m, 1H) 7.46-7.53 (m, 2H) 7.54-7.59 (m, 1H) 7.62 (d, J=8.1 Hz, 1H) 7.72 (d, J=8.4 Hz, 1H) 7.94-7.99 (m, 2H) 8.49 (s, 1H) 9.84 (br. s, 1H).

Following a procedure analogous to that described for E-7, the following compounds were also synthesized:

| Starting Material | Reagent | Final Compound |
|---|---|---|
| I-55 | ![reagent: 6-aminonicotinamide] H$_2$N-pyridine-C(O)NH$_2$<br>K$_3$PO$_4$, (+/−)-trans-1,2-cyclohexanediamine, 1,4-dioxane | Co. No. 165 |

-continued

| Starting Material | Reagent | Final Compound |
|---|---|---|
| I-108 | nicotinamide<br><br>K₃PO₄, (+/−)-trans-1,2-cyclohexanediamine, 1,4-dioxane | Co. No. 175 |
| I-37 | I-117<br>K₃PO₄, (+/−)-trans-1,2-cyclohexanediamine, 1,4-dioxane | Co. No. 187 |
| I-122 | nicotinamide<br><br>K₃PO₄, (+/−)-trans-1,2-cyclohexanediamine, 1,4-dioxane | Co. No. 188 |
| I-37 | 2-aminonicotinamide<br><br>K₃PO₄, (+/−)-trans-1,2-cyclohexanediamine, 1,4-dioxane | Co. No. 189 |

-continued
| Starting Material | Reagent | Final Compound |
|---|---|---|
| I-125 | 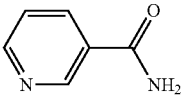<br>K₃PO₄, (+/−)-trans-1,2-cyclohexanediamine, 1,4-dioxane | 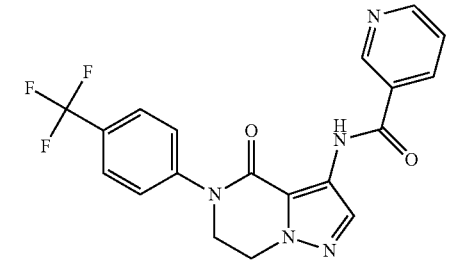 [SMILES: O=C(Nc1cnn2c1C(=O)N(c1ccc(C(F)(F)F)cc1)CC2)c1cccnc1]<br>Co. No. 190 |
| I-37 | 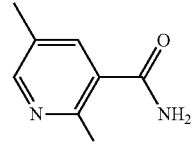<br>K₃PO₄, (+/−)-trans-1,2-cyclohexanediamine, 1,4-dioxane | 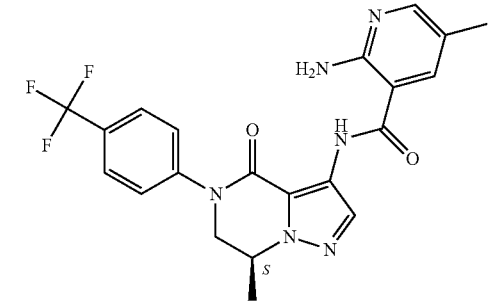<br>Co. No. 191 |
| I-37 | I-126<br>K₃PO₄, (+/−)-trans-1,2-cyclohexanediamine, 1,4-dioxane | 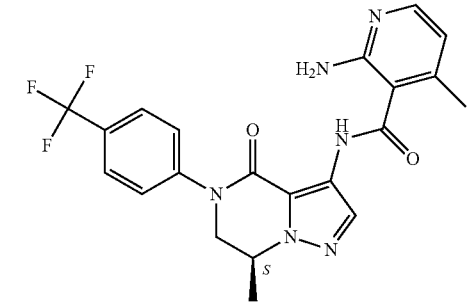<br>Co. No. 192 |
| I-37 | I-127<br>K₃PO₄, (+/−)-trans-1,2-cyclohexanediamine, 1,4-dioxane | 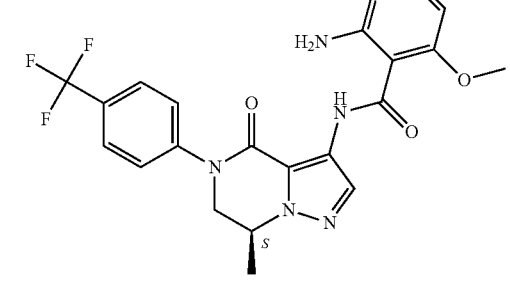<br>Co. No. 193 |

-continued

| Starting Material | Reagent | Final Compound |
|---|---|---|
| I-37 | K₃PO₄, (+/−)-trans-1,2-cyclohexanediamine, 1,4-dioxane | Co. No. 194 |
| I-129 | K₃PO₄, (+/−)-trans-1,2-cyclohexanediamine, 1,4-dioxane | Co. No. 195 |
| I-110 | K₃PO₄, (+/−)-trans-1,2-cyclohexanediamine, 1,4-dioxane | Co. No. 196 |
| I-39 | K₃PO₄, (+/−)-trans-1,2-cyclohexanediamine, 1,4-dioxane | Co. No. 197 |

-continued
| Starting Material | Reagent | Final Compound |
|---|---|---|
| I-41 | 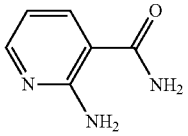<br>K₃PO₄, (+/−)-trans-1,2-cyclohexanediamine, 1,4-dioxane | 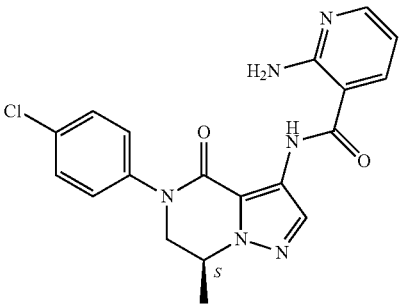<br>Co. No. 198 |
| I-38 | 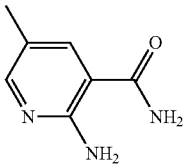<br>K₃PO₄, (+/−)-trans-1,2-cyclohexanediamine, 1,4-dioxane | 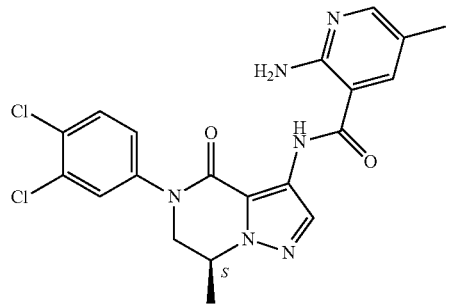<br>Co. No. 199 |
| I-108 | 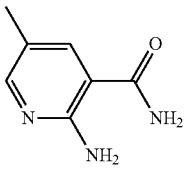<br>K₃PO₄, (+/−)-trans-1,2-cyclohexanediamine, 1,4-dioxane | 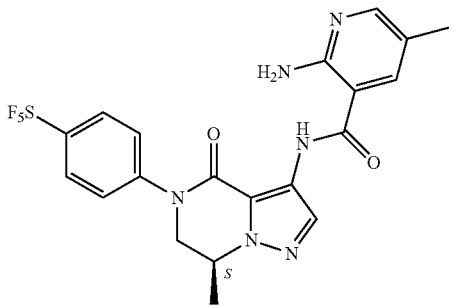<br>Co. No. 200 |
| I-41 | 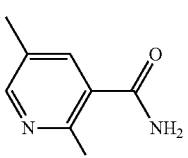<br>K₃PO₄, (+/−)-trans-1,2-cyclohexanediamine, 1,4-dioxane | 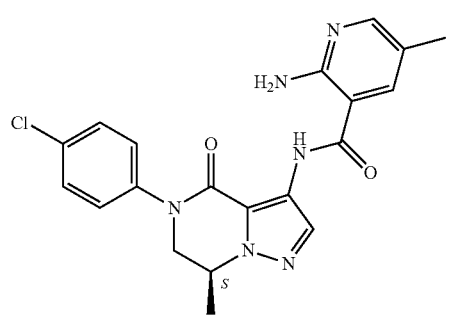<br>Co. No. 201 |

-continued

| Starting Material | Reagent | Final Compound |
|---|---|---|
| I-108 | 2-amino-nicotinamide<br><br>K₃PO₄, (+/−)-trans-1,2-cyclohexanediamine, 1,4-dioxane | Co. No. 202 |
| I-114 | 2-amino-5-methyl-nicotinamide<br><br>K₃PO₄, (+/−)-trans-1,2-cyclohexanediamine, 1,4-dioxane | Co. No. 207 |
| I-137 | 2-amino-nicotinamide<br><br>K₃PO₄, (+/−)-trans-1,2-cyclohexanediamine, 1,4-dioxane | Co. No. 208<br>Co. No. 208 was purified by achiral SFC (Stationary phase: Chiralpak IC 5 μm 250 × 20 mm, Mobile phase: 55% CO₂, 45% iPrOH(0.3% iPrNH₂). |
| I-37 | I-139<br>K₃PO₄, (+/−)-trans-1,2-cyclohexanediamine, 1,4-dioxane | Co. No. 209 |

-continued

| Starting Material | Reagent | Final Compound |
|---|---|---|
| I-54 | 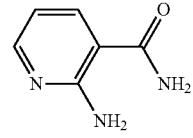 K₃PO₄, (+/−)-trans-1,2-cyclohexanediamine, 1,4-dioxane | 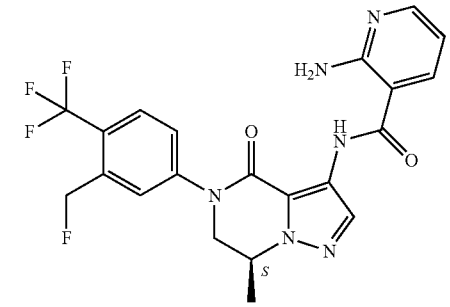 Co. No. 210 |
| I-137 | 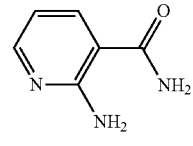 K₃PO₄, (+/−)-trans-1,2-cyclohexanediamine, 1,4-dioxane | 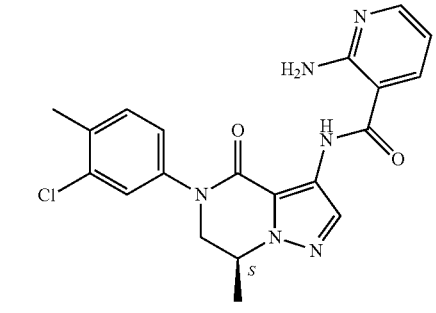 Co. No. 211<br>Co. No. 211 was purified by achiral SFC (Stationary phase: Chiralpak IC 5 μm 250 × 20 mm, Mobile phase: 55% CO₂, 45% iPrOH(0.3% iPrNH₂). (82% purity) |
| I-110 | 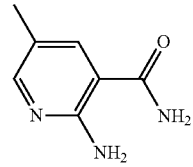 K₃PO₄, (+/−)-trans-1,2-cyclohexanediamine, 1,4-dioxane | 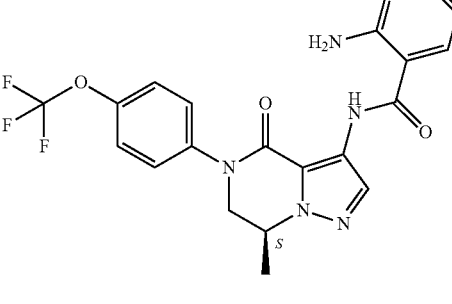 Co. No. 212 (75-80% purity) |
| I-37 | I-140 K₃PO₄, (+/−)-trans-1,2-cyclohexanediamine, TEA, 1,4-dioxane | 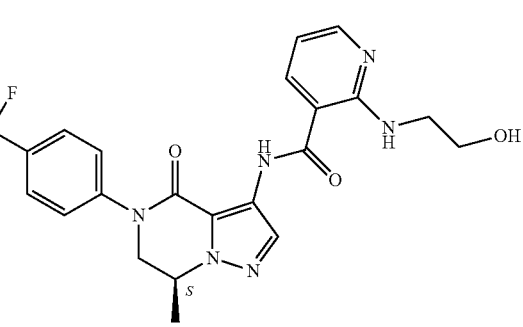 Co. No. 213 |

-continued
| Starting Material | Reagent | Final Compound |
|---|---|---|
| I-47 | I-140 K$_3$PO$_4$, (+/−)-trans-1,2-cyclohexanediamine, TEA, 1,4-dioxane | 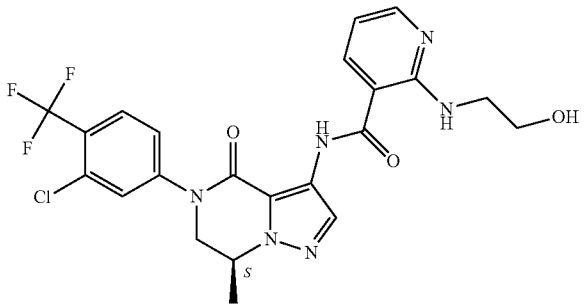<br>Co. No. 214 |
| I-37 | 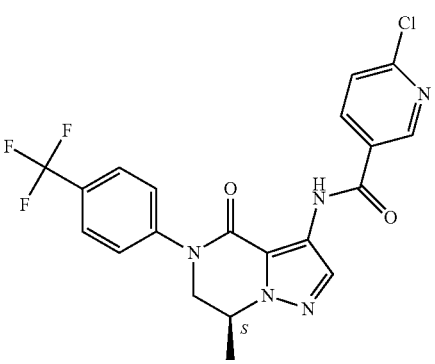<br>K$_3$PO$_4$, (+/−)-trans-1,2-cyclohexanediamine, 1,4-dioxane | Co. No. 215 |
| I-55 | 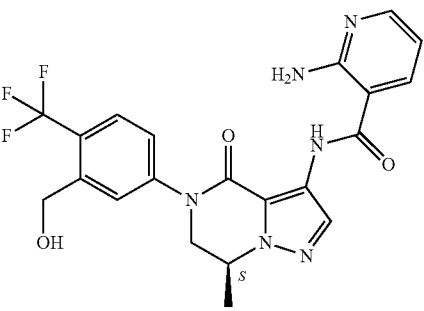<br>K$_3$PO$_4$, (+/−)-trans-1,2-cyclohexanediamine, 1,4-dioxane | Co. No. 216 |
| I-37 | 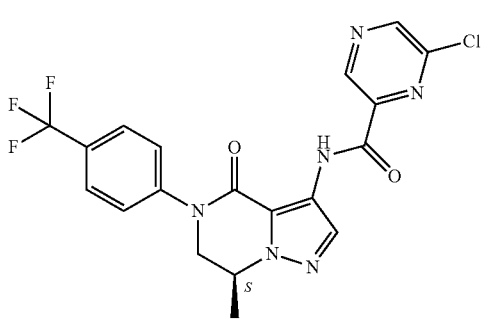<br>K$_3$PO$_4$, (+/−)-trans-1,2-cyclohexanediamine, 1,4-dioxane | Co. No. 221 |

| Starting Material | Reagent | Final Compound |
|---|---|---|
| I-38 | 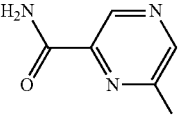<br>K₃PO₄, (+/−)-trans-1,2-cyclohexanediamine, 1,4-dioxane | 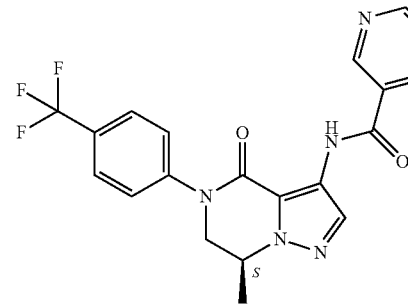<br>Co. No. 222 |

Example 8 (E-8) 2-Methyl-N-[(7S)-7-methyl-4-oxo-5-[4-(trifluoromethyl)phenyl]-6,7-dihydropyrazolo[1,5-a]pyrazin-3-yl]pyridine-4-carboxamide (Co. No. 29)

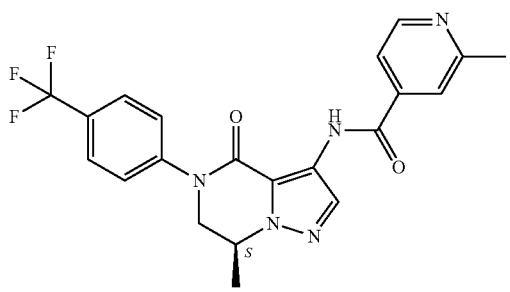

Intermediate I-73 (130 mg, 0.419 mmol) followed by DIPEA (0.217 mL, 1.257 mmol) was added to a stirred solution of 2-methylisonicotinoyl chloride (117 mg, 0.754 mmol) in DCM (3 mL) and DMF (1 mL) at 0° C. The mixture was stirred at rt for 18 h. The mixture was diluted with sat. sol. NH₄Cl and extracted with DCM. The organic layer was separated, washed with brine, dried (Na₂SO₄), filtered and the solvents evaporated in vacuo. The crude product was purified by flash column chromatography (silica, EtOAc in DCM 0/100 to 80/20). The desired fractions were collected and the solvents evaporated in vacuo. The residue was triturated with a mixture DIPE/heptane to yield final compound Co. No. 29 (161 mg, 89%) as a white foam. ¹H NMR (500 MHz, CDCl₃) δ ppm 1.73 (d, J=6.4 Hz, 3H) 2.64 (s, 3H) 4.04 (dd, J=12.4, 8.1 Hz, 1H) 4.23 (dd, J=12.4, 4.0 Hz, 1H) 4.70-4.78 (m, 1H) 7.50-7.56 (m, 3H) 7.61 (s, 1H) 7.76 (d, J=8.4 Hz, 2H) 8.47 (s, 1H) 8.64 (d, J=5.2 Hz, 1H) 9.81 (br. s, 1H).

Following a procedure analogous to that described for E-7, the following compounds were also synthesized:

| Starting Material | Reagent | Final Compound |
|---|---|---|
| I-73 | 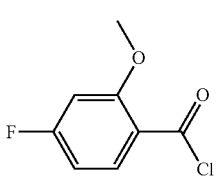<br>Solvent: DCM | 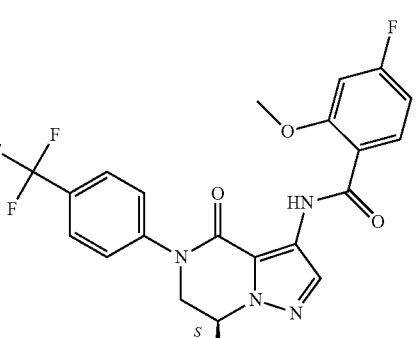<br>Co. No. 58 |

| Starting Material | Reagent | Final Compound |
|---|---|---|
| I-73 | Solvent: DCM | Co. No. 59 |
| I-73 | Solvent: DCM | Co. No. 69 |

Example 9 (E-9) 2-Amino-N-[(7S)-7-methyl-4-oxo-5-[4-(trifluoromethyl)phenyl]-6,7-dihydropyrazolo[1,5-a]pyrazin-3-yl]thiazole-5-carboxamide (Co. No. 74)

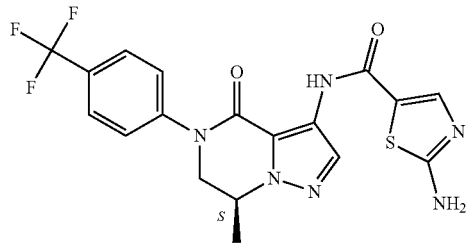

HCl (1 M in water, 3.4 mL, 3.459 mmol) was added to a stirred solution of intermediate I-95 (116 mg, 0.216 mmol) in dioxane (15 mL). The mixture was stirred at 70° C. for 16 h. The solvent was evaporated in vacuo and the residue was basified with sat. sol. $Na_2CO_3$ and extracted with DCM. The organic layer was separated, dried ($Na_2SO_4$), filtered and the solvents evaporated in vacuo. The crude product was triturated with $Et_2O$ to yield final compound Co. No. 74 (79 mg, 84%) as a white solid. $^1$H NMR (500 MHz, DMSO-$d_6$) δ ppm 1.54 (d, J=6.4 Hz, 3H) 4.11 (dd, J=12.7, 8.1 Hz, 1H) 4.33 (dd, J=12.7, 4.0 Hz, 1H) 4.67-4.78 (m, 1H) 7.63 (s, 1H) 7.69 (d, J=8.4 Hz, 2H) 7.78 (br. s, 2H) 7.84 (d, J=8.7 Hz, 2H) 8.05 (s, 1H) 9.35 (br. s, 1H).

Following a procedure analogous to that described for E-9, the following compound was also synthesized:

| Starting Material | Final Compound |
|---|---|
| I-100 | Co. No. 162 |

| Starting Material | Final Compound |
|---|---|
| I-102 | 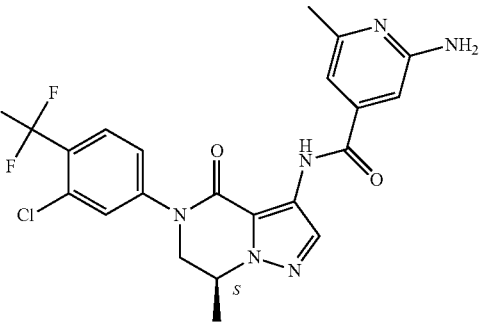<br>Co. No. 174 |
| I-130 | 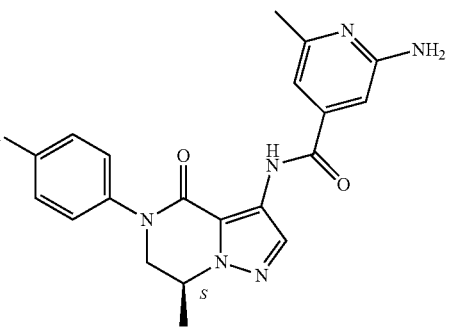<br>Co. No. 203 |

Example 10 (E-10) 6-Amino-4-methyl-N-[(7S)-7-methyl-4-oxo-5-[4-(trifluoromethyl)phenyl]-6,7-dihydropyrazolo[1,5-a]pyrazin-3-yl]pyridine-3-carboxamide (Co. No. 163)

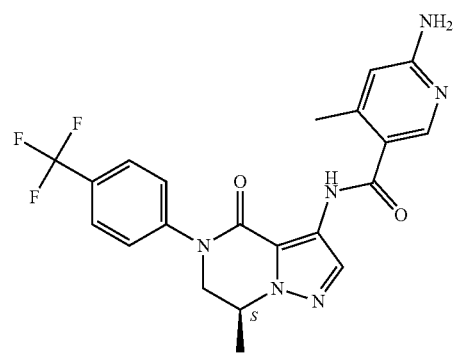

HCl (4 M in 1,4-dioxane, 1.3 mL, 5.209 mmol) was added to a stirred solution of intermediate I-99 (183 mg, 0.336 mmol) in 1,4-dioxane (2 mL). The mixture was stirred at 70° C. for 3 h. The solvent was evaporated in vacuo and the residue was basified with sat. sol. $Na_2CO_3$ and extracted with DCM. The organic layer was separated, dried ($Na_2SO_4$), filtered and the solvents evaporated in vacuo. The crude product was purified by flash column chromatography (silica; EtOAc in DCM 0/100 to 100/0). The desired fractions were collected and the solvents evaporated in vacuo and the residue was triturated with $Et_2O$ to yield final compound Co. No. 163 (130 mg, 87%) as a white solid. $^1$H NMR (400 MHz, $CDCl_3$) δ ppm 1.71 (d, J=6.5 Hz, 3H) 2.50 (d, J=0.5 Hz, 3H) 4.00 (dd, J=12.6, 8.0 Hz, 1H) 4.21 (dd, J=12.5, 4.2 Hz, 1H) 4.66-4.75 (m, 1H) 4.89 (br. s., 2H) 6.36 (s, 1H) 7.50 (br. d, J=8.3 Hz, 2H) 7.72 (br. d, J=8.3 Hz, 2H) 8.33 (s, 1H) 8.44 (s, 1H) 9.30 (br. s, 1H).

Following a procedure analogous to that described for E-10, the following compounds were also synthesized:

| Starting Material | Final Compound |
|---|---|
| I-98 | 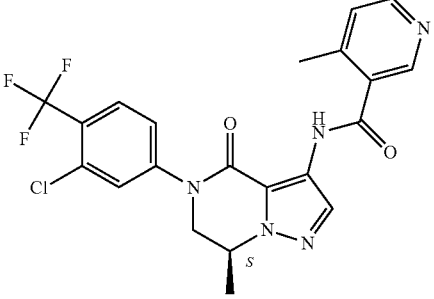<br>Co. No. 164 |
| I-131 | 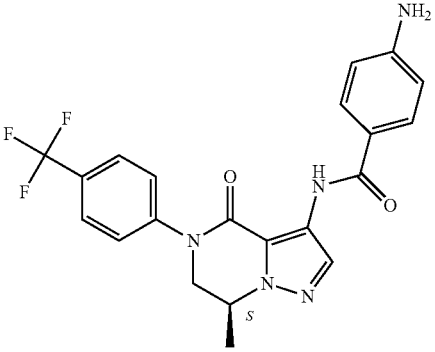<br>Co. No. 204 |

Example 11 (E-11) N2-[(7S)-7-Methyl-4-oxo-5-[4-(trifluoromethyl)phenyl]-6,7-dihydropyrazolo[1,5-a]pyrazin-3-yl]pyridine-2,5-dicarboxamide (Co. No. 82)

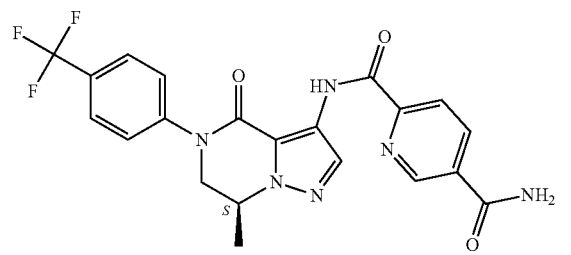

$K_2CO_3$ (7.532 mg, 0.0545 mmol) was added to a stirred suspension of compound Co. No. 85 (80 mg, 0.182 mmol) in EtOH (6.7 mL). The mixture was stirred at rt for 36 h. The reaction was quenched with water and extracted with DCM.

The organic layer was separated, dried (Na$_2$SO$_4$), filtered and the solvents evaporated in vacuo to yield a fraction which was purified by RP HPLC (Stationary phase: C18 XBridge® 30×100 mm 5 um; mobile phase: Gradient from 67% 0.1% NH$_4$CO$_3$H/NH$_4$OH pH 9 solution in water, 33% MeCN to 50% 0.1% NH$_4$CO$_3$H/NH$_4$OH pH 9 solution in water, 50% MeCN), to yield final compound Co. No. 82 (40 mg, 48%) as a white solid. $^1$H NMR (400 MHz, DMSO-d$_6$) δ ppm 1.57 (d, J=6.5 Hz, 3H) 4.15 (dd, J=12.7, 8.6 Hz, 1H) 4.36 (dd, J=12.7, 4.2 Hz, 1H) 4.73-4.84 (m, 1H) 7.73 (br. d, J=8.6 Hz, 2H) 7.82 (s, 1H) 7.86 (br. d, J=8.8 Hz, 2H) 8.25 (dd, J=8.1, 0.5 Hz, 1H) 8.33 (br. s., 1H) 8.34 (s, 1H) 8.46 (dd, J=8.1, 2.1 Hz, 1H) 9.07 (d, J=1.4 Hz, 1H) 11.09 (s, 1H).

Example 12 (E-12) 5-Amino-N-[(7S)-7-methyl-4-oxo-5-[4-(trifluoromethyl)phenyl]-6,7-dihydropyrazolo[1,5-a]pyrazin-3-yl]-1H-pyrazole-3-carboxamide (Co. No. 84)

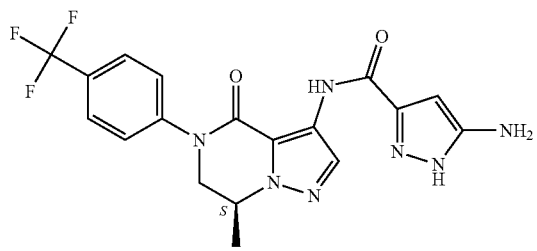

A 0.05 M solution of intermediate I-102 (80 mg, 0.178 mmol) in EtOH (3.529 mL) was hydrogenated in an H-Cube® reactor (1.0 ml/min, Pd/C 10% cartridge, full H$_2$ mode, 20° C., 1 cycle). Then, the solvent was evaporated in vacuo and the crude product was purified by flash column chromatography (silica; 90% DCM and 10% NH$_4$OH/MeOH in heptane 0/100 to 100/0). The desired fractions were collected and the solvents evaporated in vacuo. The residue was triturated with Et$_2$O to yield final compound Co. No. 84 (28 mg, 38%) as a white solid. $^1$H NMR (400 MHz, DMSO-d$_6$) δ ppm 1.55 (d, J=6.5 Hz, 3H) 4.11 (dd, J=12.7, 8.3 Hz, 1H) 4.32 (dd, J=12.7, 4.2 Hz, 1H) 4.67-4.78 (m, 1H) 5.28 (br. s, 2H) 5.70 (d, J=1.8 Hz, 1H) 7.70 (br. d, J=8.6 Hz, 2H) 7.83 (br. d, J=8.6 Hz, 2H) 8.20 (s, 1H) 10.05 (br. s, 1H) 12.09 (d, J=1.6 Hz, 1H).

Example 13 (E-13) 2-Amino-N-[(7S)-7-methyl-4-oxo-5-[4-(trifluoromethyl)phenyl]-6,7-dihydropyrazolo[1,5-a]pyrazin-3-yl]-1H-imidazole-4-carboxamide (Co. No. 94)

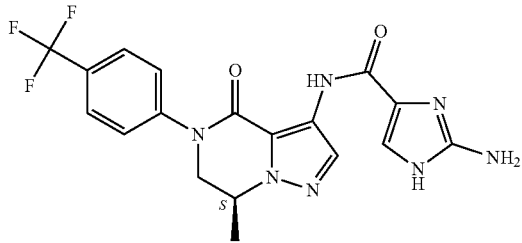

To a stirred solution of intermediate I-103 (177 mg, 0.388 mmol) in EtOH (5 mL) was added hydrazine monohydrate (23 μL, 0.465 mmol). The mixture was stirred at 75° C. for 5 h in a sealed tube. Then the solvent was evaporated in vacuo and the residue was triturated with Et$_2$O to yield a pale yellow solid, which was then purified by RP HPLC (Stationary phase: C18 XBridge® 30×100 mm 5 μm; mobile phase: Gradient from 67% 0.1% NH$_4$CO$_3$H/NH$_4$OH pH 9 solution in water, 33% MeCN to 50% 0.1% NH$_4$CO$_3$H/NH$_4$OH pH 9 solution in water, 50% MeCN), to yield final compound Co. No. 94 (87 mg, 54%) as a white solid. $^1$H NMR (400 MHz, DMSO-d$_6$) δ ppm 1.54 (d, J=6.5 Hz, 3H) 4.10 (dd, J=12.6, 8.4 Hz, 1H) 4.31 (dd, J=12.7, 4.2 Hz, 1H) 4.66-4.77 (m, 1H) 5.55 (br. s, 2H) 7.21 (s, 1H) 7.69 (br. d, J=8.3 Hz, 2H) 7.83 (br. d, J=8.6 Hz, 2H) 8.22 (s, 1H) 9.96 (br. s, 1H) 10.88 (br. s., 1H).

Example 14 (E-14) 6-Amino-N-[(7S)-5-[3-(fluoromethyl)-4-(trifluoromethyl)phenyl]-7-methyl-4-oxo-6,7-dihydropyrazolo[1,5-a]pyrazin-3-yl]pyridine-3-carboxamide (Co. No. 5)

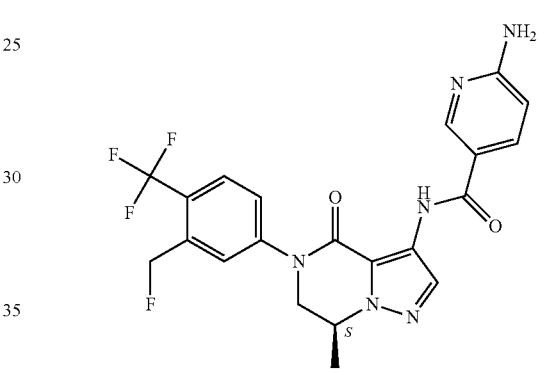

Diethylaminosulfur trifluoride (80 μL, 0.651 mmol) was added dropwise to a stirred solution of compound Co. No. 165 (100 mg, 0.217 mmol) in DCM (2 mL) at 0° C. and under nitrogen. The mixture was allowed to warm up to rt and stirred for 30 min. The mixture was treated with sat. sol. NaHCO$_3$ and extracted with DCM. The organic layer was separated, dried (Na$_2$SO$_4$), filtered and the solvents evaporated in vacuo. The crude product was purified by flash column chromatography (silica; MeOH in DCM 0/100 to 3/97). The desired fractions were collected and the solvents evaporated in vacuo and then was repurified by RP HPLC (Stationary phase: C18 XBridge® 30×100 mm 5 μm, Mobile phase: Gradient from 67% 10 mM NH$_4$CO$_3$H pH 9 solution in Water, 33% MeCN to 50% 10 mM NH$_4$CO$_3$H pH 9 solution in Water, 50% MeCN). This residue was triturated with Et$_2$O to yield final compound Co. No. 5 (17 mg, 17%) as a white solid. $^1$H NMR (500 MHz, CDCl$_3$) δ ppm 1.73 (d, J=6.4 Hz, 3H) 4.04 (dd, J=12.4, 8.1 Hz, 1H) 4.23 (dd, J=12.6, 4.2 Hz, 1H) 4.68-4.76 (m, 1H) 5.26 (br. s., 2H) 5.66 (d, J=46.8 Hz, 2H) 6.56 (d, J=8.7 Hz, 1H) 7.50 (d, J=8.1 Hz, 1H) 7.68 (br. s, 1H) 7.78 (s, 1H) 7.98 (dd, J=8.7, 2.3 Hz, 1H) 8.44 (s, 1H) 8.67 (br. s., 1H) 9.60 (s, 1H).

Example 15 (E-15) N-[(7S)-5-[3-Chloro-4-(trifluoromethyl)phenyl]-7-methyl-4-oxo-6,7-dihydropyrazolo[1,5-a]pyrazin-3-yl]-5-methyl-1-oxido-pyridin-1-ium-3-carboxamide (Co. No. 166)

Example 16 (E-16) 2-(tert-Butylamino)-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide and 6-(tert-butylamino)-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide (Co. No. 167 and Co. No. 168)

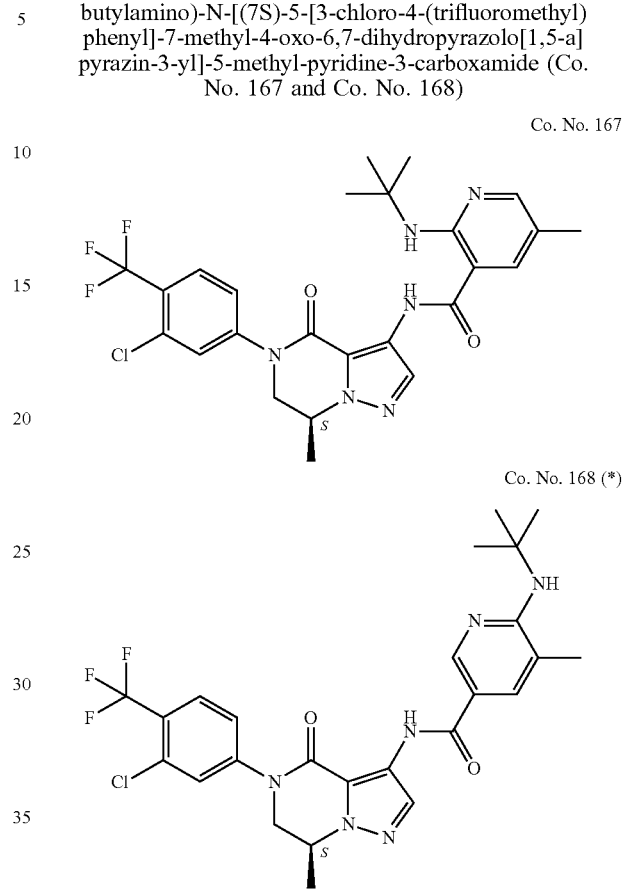

Methyltrioxorhenium(VII) (1 mg, 0.005 mmol) was added to a solution of compound Co. No. 101 (100 mg, 0.215 mmol) in H₂O₂ (30% sol., 0.5 mL) and DCM (1.5 mL) under nitrogen. The mixture was stirred at rt for 3 h. Then the mixture was washed with NaHCO₃ sat. The organic layer was separated, dried (Na₂SO₄), filtered and the solvent evaporated in vacuo to yield final compound Co. No. 166 (103 mg, quant.) as a yellow solid.

Following a procedure analogous to that described for E-15, the following compound was also synthesized:

| Starting Material | Final Compound |
| --- | --- |
| Co. No. 28 | 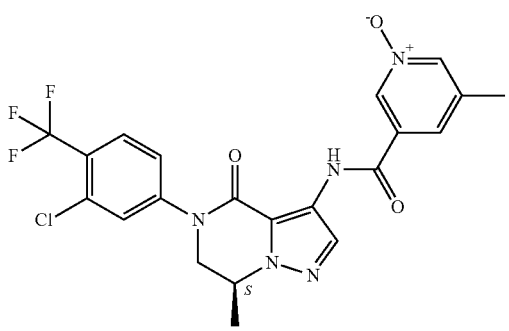 Co. No. 205 |

PyBroP® (130 mg, 0.280 mmol) was added to a stirred solution of compound Co. No. 166 (103 mg, 0.215 mmol), tert-butylamine (28 µL, 0.269 mmol) and DIPEA (139 µL, 0.808 mmol) in DCM (2 mL). The mixture was stirred at rt for 16 h. Then additional tert-butylamine (28 µL, 269 mmol), DIPEA (139 µL, 0.808 mmol) and PyBroP® (130 mg, 0.280 mmol) were added and the mixture was stirred at rt for 48 h. Then the mixture was poured into NaHCO₃ sat. and extracted with DCM. The combined organic phase was washed with brine, dried (Na₂SO₄) and the solvents evaporated in vacuo. The crude product was purified by flash column chromatography (EtOAc in DCM 0/100 to 20/80). The desired fractions were collected and the solvents concentrated in vacuo to yield final compound Co. No. 167 (15 mg, 13%) as a yellow solid and final compound Co. No. 168 (38 mg, 33%) as a colorless oil. Co. No. 167: ¹H NMR (400 MHz, CDCl₃) δ ppm 1.50 (s, 9H) 1.72 (d, J=6.7 Hz, 3H) 2.18 (s, 3H) 4.00 (dd, J=12.5, 7.9 Hz, 1H) 4.20 (dd, J=12.5, 4.2 Hz, 1H) 4.66-4.75 (m, 1H) 7.42 (dd, J=8.4, 1.5 Hz, 1H) 7.49 (d, J=2.1 Hz, 1H) 7.59 (d, J=1.8 Hz, 1H) 7.79 (d, J=8.6 Hz, 1H) 8.09 (d, J=1.8 Hz, 1H) 8.21 (br. s, 1H) 8.43 (s, 1H) 9.54 (br. s, 1H). Co. No. 168: ¹H NMR (500 MHz, CDCl₃) δ ppm 1.50 (s, 9H) 1.71 (d, J=6.6 Hz, 3H) 2.08 (s, 3H) 4.00 (dd, J=12.4, 8.1 Hz, 1H) 4.19 (dd, J=12.4, 4.0 Hz, 1H) 4.43 (br. s., 1H) 4.64-4.74 (m, 1H) 7.42 (dd, J=8.4, 1.2 Hz, 1H) 7.59 (d, J=1.4 Hz, 1H) 7.71 (d, J=1.4 Hz, 1H) 7.78 (d, J=8.4 Hz, 1H) 8.46 (s, 1H) 8.61 (d, J=2.0 Hz, 1H) 9.53 (br. s, 1H).

(*) Co. No. 168 was also prepared according to procedure E-2 by reaction of intermediate I-81 with 6-(tert-butylamino)-5-methyl-pyridine-3-carboxylic acid.

Example 17 (E-17) 6-Amino-N-[(7S)-5-[3-chloro-4-(trifluoromethyl)phenyl]-7-methyl-4-oxo-6,7-dihydropyrazolo[1,5-a]pyrazin-3-yl]-5-methyl-pyridine-3-carboxamide (Co. No. 169)

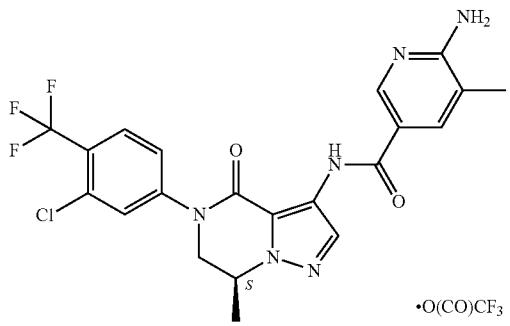

Compound Co. No. 168 (38 mg, 0.071 mmol) in trifluoroacetic acid (1 mL) and 1,2-dichloroethane (1 mL) was stirred twice at 120° C. for 10 min under microwave irradiation. The solvents were evaporated in vacuo. The residue was triturated with Et₂O. The solid filtered and dried in vacuo to yield final compound Co. No. 169 (10 mg, 24%) as an off white solid. $^1$H NMR (500 MHz, DMSO-$d_6$) δ ppm 1.56 (d, J=6.6 Hz, 3H) 2.18 (s, 3H) 3.73 (br. s., 1H) 4.14 (dd, J=12.7, 8.1 Hz, 1H) 4.38 (dd, J=12.7, 4.0 Hz, 1H) 4.72-4.80 (m, 1H) 7.67 (br. s, 2H) 7.66 (dd, J=8.5, 1.6 Hz, 1H) 7.90 (d, J=1.7 Hz, 1H) 7.94-7.99 (m, 2H) 8.15 (s, 1H) 8.38 (d, J=2.0 Hz, 1H) 9.74 (br. s, 1H).

Following a procedure analogous to that described for E-17, the following compound was also synthesized:

Pentafluorophenyl trifluoroacetate (0.126 mL, 0.723 mmol) was added slowly to a solution of 5-methylnicotinic acid (66 mg, 0.482 mmol) and DIPEA (0.183 mL, 1.060 mmol) in DMF (3 mL) at 0° C. The reaction mixture was stirred at 0° C. for 30 min. A solution of intermediate I-74 (150 mg, 0.482 mmol) in DMF (2 mL) was then added and the mixture stirred at rt for 10 days. The solvent was evaporated in vacuo. The mixture was diluted EtOAc and washed first with sat. sol. NH₄Cl and then with 10% sol Na₂CO₃. The organic layers were separated, combined, dried (Na₂SO₄), filtered and the solvents evaporated in vacuo. The crude product was purified by flash column chromatography (silica; EtOAc in heptane 0/100 to 80/20). The desired fractions were collected and the solvents evaporated in vacuo to yield an impure fraction which was performed by RP HPLC (Stationary phase: C18 XSelect 19×100 mm 5 μm, Mobile phase: Gradient from 60% 10 mM NH₄CO₃H pH 9 solution in Water, 40% MeCN to 0% 10 mM NH₄CO₃H pH 9 solution in Water, 100% MeCN), to yield final compound Co. No. 173 (22 mg, 11%). $^1$H NMR (500 MHz, CDCl₃) δ ppm 1.71 (d, J=6.4 Hz, 3H) 3.96 (dd, J=12.7, 8.1 Hz, 1H) 4.17 (dd, J=12.7, 4.3 Hz, 1H) 4.67-4.75 (m, 1H) 7.24 (dd, J=8.5, 2.5 Hz, 1H) 7.49 (d, J=2.3 Hz, 1H) 7.54 (d, J=8.7 Hz, 1H) 8.30 (s, 1H) 9.68 (br. s., 1H).

| Starting Material | Final Compound |
|---|---|
| Co. No. 167 | 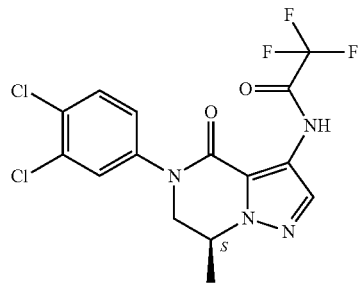 Co. No. 170 |

Example 18 (E-18) N-[(7S)-5-(3,4-Dichlorophenyl)-7-methyl-4-oxo-6,7-dihydropyrazolo[1,5-a]pyrazin-3-yl]-2,2,2-trifluoro-acetamide (Co. No. 173)

Example 19 (E-19) 3-Amino-N-[(7S)-7-methyl-4-oxo-5-[4-(trifluoromethyl)phenyl]-6,7-dihydropyrazolo[1,5-a]pyrazin-3-yl]pyrazine-2-carboxamide (Co. No. 206)

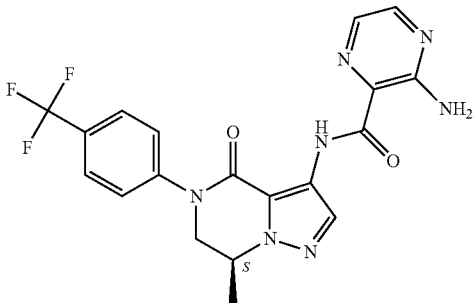

Isopropylmagnesium chloride lithium chloride complex solution (1.3 M, 0.446 mL, 0.58 mmol) was added slowly to a solution of intermediate I-73 (150 mg, 0.48 mmol) and methyl 3-aminopyrazine-2-carboxylate (74 mg, 0.48 mmol) in THF (2 mL). The reaction mixture was stirred at rt for 1 h and at 60° C. for 18 h. The mixture was diluted with sat. sol. NH$_4$Cl and extracted with DCM. The organic layer was separated, dried (Na$_2$SO$_4$), filtered and the solvents evaporated in vacuo. The crude product was purified by flash column chromatography (silica; MeOH in DCM 0/100 to 3/97). The desired fractions were collected and the solvents evaporated in vacuo and the residue was then purified by flash column chromatography (silica; EtOAc in DCM 0/100 to 80/20). The desired fractions were collected and the solvents evaporated in vacuo. The impure product was performed by RP HPLC (Stationary phase: C18 XBridge® 30×100 mm 5 μm, Mobile phase: Gradient from 60% 0.1% NH$_4$CO$_3$H/NH$_4$OH pH 9 solution in Water, 40% MeCN to 43% 0.1% NH$_4$CO$_3$H/NH$_4$OH pH 9 solution in Water, 57% MeCN), to yield final compound Co. No. 206 (46 mg, 22%). $^1$H NMR (400 MHz, DMSO-d$_6$) δ ppm 1.59 (d, J=6.5 Hz, 3H) 4.16 (dd, J=13.2, 8.8 Hz, 1H) 4.37 (dd, J=12.7, 4.2 Hz, 1H) 4.74-4.87 (m, 1H) 7.68 (br. s., 2H) 7.72 (d, J=8.3 Hz, 2H) 7.85 (d, J=8.6 Hz, 2H) 8.05 (d, J=2.3 Hz, 1H) 8.34 (s, 1H) 8.37 (d, J=2.1 Hz, 1H) 8.48 (d, J=2.3 Hz, 1H) 8.75 (d, J=2.3 Hz, 1H) 11.22 (s, 1H) 13.14 (s, 1H).

Example 20 (E-20) 6-fluoro-N-[(7S)-7-methyl-4-oxo-5-[4-(trifluoromethyl)phenyl]-6,7-dihydropyrazolo[1,5-a]pyrazin-3-yl]pyrazine-2-carboxamide (Co. No. 219)

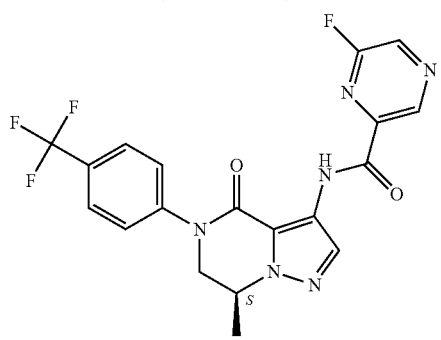

Potassium fluoride (31.393 mg; 0.54 mmol) was added to a stirred solution of Co. No. 221 (prepared according to E-7) (81.2 mg; 0.18 mmol) in DMSO (8 mL). The mixture was stirred at 150° C. for 15 minutes under microwave irradiation. The mixture was treated with water and extracted with ethyl acetate. The organic layer was separated, washed with brine, dried (Na$_2$SO$_4$), filtered and evaporated in vacuo. The residue was purified by flash column chromatography (silica; ethyl acetate in DCM 0/100 to 30/70). The desired fractions were collected and evaporated in vacuo. The product was triturated with diisopropyl ether to yield Co. No. 219 (47.9 mg; 61%) as a white solid.

Following a procedure analogous to that described for E-20, the following compound was also synthesized:

| Starting Material | Final Compound |
|---|---|
| Co. No. 222 | 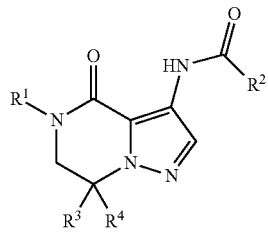 I-115 |

Table 1 below lists additional compounds of Formula (I).

TABLE 1

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R$^1$ | R$^2$ | >CR$^3$R$^4$ | Salt Form |
|---|---|---|---|---|
| 1 | ![Cl, F$_3$C phenyl] | ![pyridine-NH$_2$] | >CH(CH$_3$) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

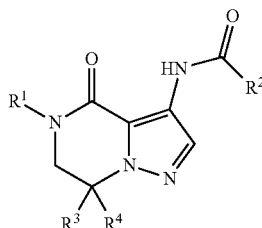

| Co. No. | R¹ | R² | >CR³R⁴ | Salt Form |
|---|---|---|---|---|
| 2 | 3-Cl, 4-CF₃-phenyl | phenyl | >CH(CH₃) (S) | |
| 3 | 3,4-diCl-phenyl | 6-aminopyridin-3-yl | >CH(CH₃) (S) | |
| 4 | 3-CH₃, 4-CF₃-phenyl | 6-aminopyridin-3-yl | >CH(CH₃) (S) | |
| 5 | 3-CH₂F, 4-CF₃-phenyl | 6-aminopyridin-3-yl | >CH(CH₃) (S) | |
| 6 | 3-CHF₂, 4-Cl-phenyl | 6-aminopyridin-3-yl | >CH(CH₃) (S) | |
| 7 | 3-CH₃, 4-CF₃-phenyl | phenyl | >CH(CH₃) (S) | |
| 8 | 4-CF₃-phenyl | 6-aminopyridin-3-yl | >CH(CH₃) (S) | |
| 9 | 4-CF₃-phenyl | 3-CH₃-phenyl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

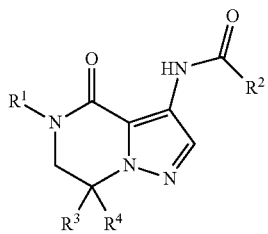

| Co. No. | R¹ | R² | >CR³R⁴ | Salt Form |
|---|---|---|---|---|
| 10 | 4-CF₃-phenyl | 2-methoxy-5-fluoro-phenyl | >CH(CH₃) (S) | |
| 11 | 4-CF₃-phenyl | 2-fluoro-phenyl | >CH(CH₃) (S) | |
| 12 | 3-Cl-4-CF₃-phenyl | 2-methyl-pyridin-4-yl | >CH(CH₃) (S) | |
| 13 | 3-F-4-CF₃-phenyl | 6-amino-pyridin-3-yl | >CH(CH₃) (S) | |
| 14 | 4-CF₃-phenyl | 3-fluoro-phenyl | >CH(CH₃) (S) | |
| 15 | 4-CF₃-phenyl | thiazol-2-yl | >CH(CH₃) (S) | |
| 16 | 4-CF₃-phenyl | phenyl | >CH(CH₃) (S) | |
| 17 | 4-CF₃-phenyl | 3-methoxy-5-fluoro-phenyl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

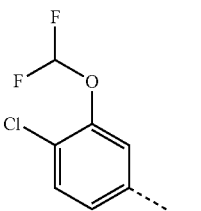

| Co. No. | R¹ | R² | >CR³R⁴ | Salt Form |
|---|---|---|---|---|
| 18 | 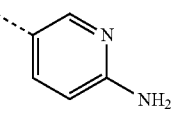 | 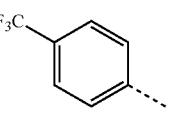 | >CH(CH₃) (S) | |
| 19 | 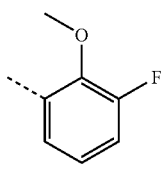 | 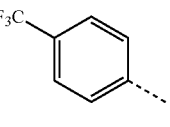 | >CH(CH₃) (S) | |
| 20 | 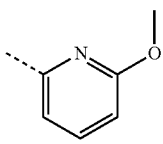 | 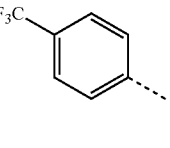 | >CH(CH₃) (S) | |
| 21 | 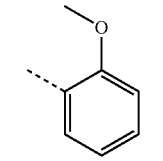 | 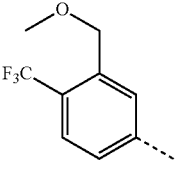 | >CH(CH₃) (S) | |
| 22 | 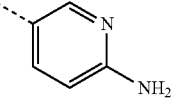 | 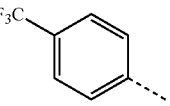 | >CH(CH₃) (S) | |
| 23 | 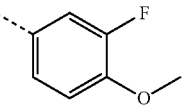 | 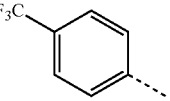 | >CH(CH₃) (S) | |
| 24 | 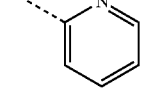 | | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 25 | 4-CF$_3$-phenyl | 4-methoxyphenyl | >CH(CH$_3$) (S) | |
| 26 | 2-CF$_3$-5-CN-phenyl | 6-amino-pyridin-3-yl | >CH(CH$_3$) (S) | |
| 27 | 4-CF$_3$-phenyl | 3-methoxyphenyl | >CH(CH$_3$) (S) | |
| 28 | 4-CF$_3$-phenyl | pyridin-3-yl | >CH(CH$_3$) (S) | |
| 29 | 4-CF$_3$-phenyl | 2-methylpyridin-4-yl | >CH(CH$_3$) (S) | |
| 30 | 4-CF$_3$-phenyl | 3-(methoxymethyl)phenyl | >CH(CH$_3$) (S) | |
| 31 | 4-CF$_3$-phenyl | 5-fluoropyridin-3-yl | >CH(CH$_3$) (S) | |
| 32 | 4-CF$_3$-phenyl | 5-methoxypyridin-3-yl | >CH(CH$_3$) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

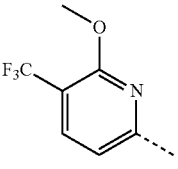

| Co. No. | R¹ | R² | >CR³R⁴ | Salt Form |
|---|---|---|---|---|
| 33 | 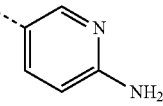 | 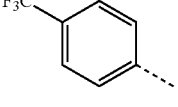 | >CH(CH₃) (S) | |
| 34 | 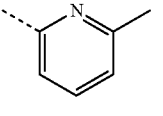 | 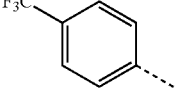 | >CH(CH₃) (S) | |
| 35 | 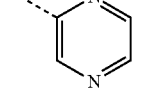 | 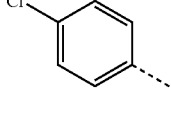 | >CH(CH₃) (S) | |
| 36 | 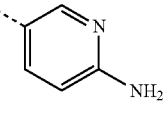 | 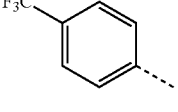 | >CH(CH₃) (S) | |
| 37 | 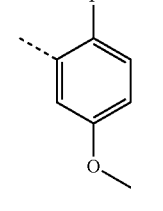 | 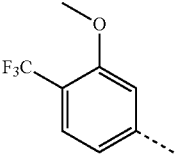 | >CH(CH₃) (S) | |
| 38 | 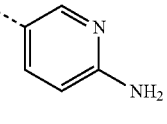 | 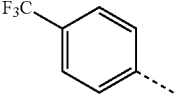 | >CH(CH₃) (S) | |
| 39 | 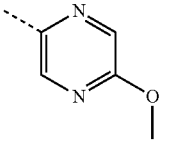 | 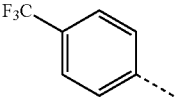 | >CH(CH₃) (S) | |
| 40 | 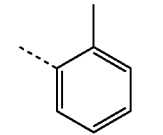 | | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

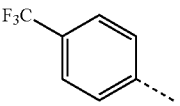

| Co. No. | R¹ | R² | >CR³R⁴ | Salt Form |
|---|---|---|---|---|
| 41 | F₃C-C₆H₄- | 3-F-2-OMe-C₆H₃- | >CH(CH₃) (S) | |
| 42 | F₃C-C₆H₄- | 6-OMe-pyridin-3-yl | >CH(CH₃) (S) | |
| 43 | F₃C-C₆H₄- | 2-OMe-pyridin-3-yl | >CH(CH₃) (S) | |
| 44 | F₃C-C₆H₄- | 3-F-4-OMe-C₆H₃- | >CH(CH₃) (S) | |
| 45 | F₃C-C₆H₄- | 5-NH₂-pyrazin-2-yl | >CH(CH₃) (S) | |
| 46 | F₃C-C₆H₄- | 3-Cl-pyridin-5-yl | >CH(CH₃) (S) | |
| 47 | F₃C-C₆H₄- | 2-OMe-pyridin-4-yl | >CH(CH₃) (S) | |
| 48 | F₃C-C₆H₄- | 5-F-pyridin-2-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

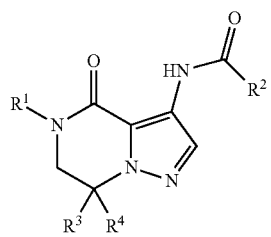

| Co. No. | $R^1$ | $R^2$ | $>CR^3R^4$ | Salt Form |
|---|---|---|---|---|
| 49 | 4-CF3-phenyl | 4-F-phenyl | >CH(CH3) (S) | |
| 50 | 4-CF3-phenyl | 2-NH2-pyridin-4-yl | >CH(CH3) (S) | |
| 51 | 4-CF3-phenyl | 2-OMe-3-F-phenyl | >CH(CH3) (S) | |
| 52 | 4-CF3-phenyl | 2-NH2-pyrimidin-5-yl | >CH(CH3) (S) | |
| 53 | 4-CF3-phenyl | 4-Me-phenyl | >CH(CH3) (S) | |
| 54 | 4-CF3-phenyl | 6-Me-pyridin-3-yl | >CH(CH3) (S) | |
| 55 | 4-CF3-phenyl | pyridin-4-yl | >CH(CH3) (S) | |
| 56 | 3-CF3-2-OMe-pyridin-6-yl | 3-OMe-phenyl | >CH(CH3) (S) | |
| 57 | 4-CF3-phenyl | 3-Me-pyridin-2-yl | >CH(CH3) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

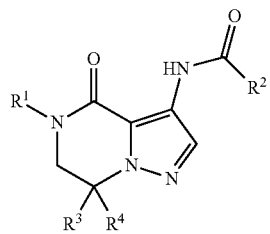

| Co. No. | $R^1$ | $R^2$ | $>CR^3R^4$ | Salt Form |
|---|---|---|---|---|
| 58 | 4-F$_3$C-phenyl | 2-methoxy-5-fluoro-phenyl | >CH(CH$_3$) (S) | |
| 59 | 4-F$_3$C-phenyl | 2-fluoro-3-methoxy-phenyl | >CH(CH$_3$) (S) | |
| 60 | 4-F$_3$C-phenyl | 4-methoxy-pyridin-2-yl | >CH(CH$_3$) (S) | |
| 61 | 5-F$_3$C-pyridin-2-yl | 6-amino-pyridin-3-yl | >CH(CH$_3$) (S) | |
| 62 | 4-F$_3$C-phenyl | 2-fluoro-phenyl | >CH(CH$_2$OCH$_3$) | |
| 63 | 4-F$_3$C-phenyl | oxazol-2-yl | >CH(CH$_3$) (S) | |
| 64 | 4-F$_3$C-phenyl | 6-amino-pyridazin-3-yl | >CH(CH$_2$OCH$_3$) | |
| 65 | 3-chloro-2-methoxy-pyridin-6-yl | 6-amino-pyridin-3-yl | >CH(CH$_3$) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | $R^1$ | $R^2$ | $>CR^3R^4$ | Salt Form |
|---|---|---|---|---|
| 66 | 4-(F$_3$C)phenyl | 2-methylpyridin-3-yl | $>CH(CH_3)$ (S) | |
| 67 | 4-(F$_3$C)phenyl | 3-fluoropyridin-2-yl | $>CH(CH_3)$ (S) | |
| 68 | 4-(F$_3$C)phenyl | 5-aminopyridin-2-yl | $>CH(CH_3)$ (S) | |
| 69 | 4-(F$_3$C)phenyl | isoxazol-5-yl | $>CH(CH_3)$ (S) | |
| 70 | 2-methoxy-3-(F$_3$C)pyridin-6-yl | phenyl | $>CH(CH_3)$ (S) | |
| 71 | 4-(F$_3$C)phenyl | 3-methylisoxazol-5-yl | $>CH(CH_3)$ (S) | |
| 72 | 4-(F$_3$C)phenyl | 5-methylisoxazol-3-yl | $>CH(CH_3)$ (S) | |
| 73 | 4-(F$_3$C)phenyl | cyclopropylmethyl | $>CH(CH_3)$ (S) | |
| 74 | 4-(F$_3$C)phenyl | 2-aminothiazol-5-yl | $>CH(CH_3)$ (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 75 | 3-CF₃-2-methoxypyridin-6-yl | 2-methoxyphenyl | >CH(CH₃) (S) | |
| 76 | 3-Cl-2-methoxypyridin-6-yl | phenyl | >CH(CH₃) (S) | |
| 77 | 3-CF₃-2-methoxypyridin-6-yl | 4-methoxyphenyl | >CH(CH₃) (S) | |
| 78 | 4-CF₃-phenyl | 2-(methoxymethyl)phenyl | >CH(CH₃) (S) | |
| 79 | 4-CF₃-phenyl | 1H-pyrazol-4-yl | >CH(CH₃) (S) | |
| 80 | 4-CF₃-phenyl | 1H-imidazol-2-yl | >CH(CH₃) (S) | |
| 81 | 4-CF₃-phenyl | 2-methyloxazol-4-yl | >CH(CH₃) (S) | |
| 82 | 4-CF₃-phenyl | 5-carbamoylpyridin-2-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 83 | 4-CF₃-phenyl | 1H-imidazol-4-yl | >CH(CH₃) (S) | |
| 84 | 4-CF₃-phenyl | 5-amino-1H-pyrazol-3-yl | >CH(CH₃) (S) | |
| 85 | 4-CF₃-phenyl | 5-cyanopyridin-2-yl | >CH(CH₃) (S) | |
| 86 | 4-CF₃-phenyl | 1-methyl-1H-pyrazol-4-yl | >CH(CH₃) (S) | |
| 87 | 4-CF₃-phenyl | benzyl | >CH(CH₃) (S) | |
| 88 | 4-CF₃-phenyl | 2-methylpyrimidin-5-yl | >CH(CH₃) (S) | |
| 89 | 4-CF₃-phenyl | 3-methyl-1H-pyrazol-5-yl | >CH(CH₃) (S) | |
| 90 | 4-CF₃-phenyl | 6-amino-3-methylpyridazin-? | >CH(CH₃) (S) | |
| 91 | 4-CF₃-phenyl | 1-methyl-1H-imidazol-5-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 92 | 4-CF₃-phenyl | 6-hydroxypyridazin-3-yl | >CH(CH₃) (S) | |
| 93 | 4-CF₃-phenyl | 2,6-dimethylpyridin-4-yl | >CH(CH₃) (S) | |
| 94 | 4-CF₃-phenyl | 2-amino-1H-imidazol-4-yl | >CH(CH₃) (S) | |
| 95 | 4-CF₃-phenyl | 6-aminopyridin-3-yl | >CH(CH₂OCH₃) (*S) | |
| 96 | 4-CF₃-phenyl | 6-aminopyridin-3-yl | >CH(CH₂OCH₃) (*R) | |
| 97 | phenyl | 2-aminopyridin-4-yl | >CH(CH₃) (S) | |
| 98 | 4-CF₃-phenyl | pyrimidin-2-yl | >CH(CH₃) (S) | |
| 99 | 4-CF₃-phenyl | 5-methylpyrazin-2-yl | >CH(CH₃) (S) | |
| 100 | 3-chloro-4-CF₃-phenyl | pyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

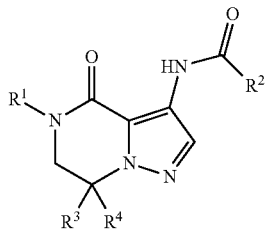

| Co. No. | R¹ | R² | >CR³R⁴ | Salt Form |
|---|---|---|---|---|
| 62a | 4-CF₃-phenyl | 2-F-phenyl | >CH(CH₂OCH₃) (*R) | |
| 62b | 4-CF₃-phenyl | 2-F-phenyl | >CH(CH₂OCH₃) (*S) | |
| 144 | 4-CF₃-phenyl | 3-OH-phenyl | >CH(CH₃) (S) | |
| 102 | 3-Cl-4-CF₃-phenyl | pyridin-2-yl | >CH(CH₃) (S) | |
| 101 | 3-Cl-4-CF₃-phenyl | 5-methyl-pyridin-3-yl | >CH(CH₃) (S) | |
| 103 | 3-Cl-4-CF₃-phenyl | 5-fluoro-pyridin-3-yl | >CH(CH₃) (S) | |
| 150 | 3-Cl-4-CF₃-phenyl | 6-methoxy-pyridin-4-yl | >CH(CH₃) (S) | |
| 149 | 3,4-dichloro-phenyl | 5-methoxy-pyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

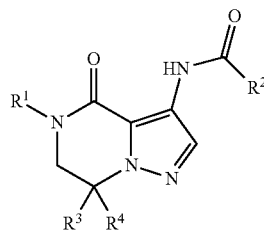

| Co. No. | R¹ | R² | >CR³R⁴ | Salt Form |
|---|---|---|---|---|
| 146 146a | 3,4-diCl-phenyl | pyridin-3-yl | >CH(CH₃) (S) | •HCl |
| 176 | 3-Cl-4-CF₃-phenyl | pyrazin-2-yl | >CH(CH₃) (S) | |
| 104 | 3,4-diCl-phenyl | pyrazin-2-yl | >CH(CH₃) (S) | |
| 105 | 3,4-diCl-phenyl | pyridin-2-yl | >CH(CH₃) (S) | |
| 106 | 3,4-diCl-phenyl | 2,6-dimethylpyridin-4-yl | >CH(CH₃) (S) | |
| 107 | 4-CF₃-3-methyl-phenyl | 6-fluoropyridin-4-yl | >CH(CH₃) (S) | |
| 108 | 3,4-diCl-phenyl | 5-methylpyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

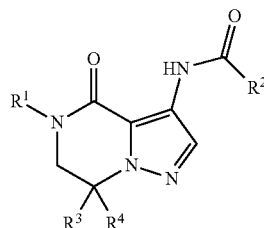

| Co. No. | R¹ | R² | >CR³R⁴ | Salt Form |
|---|---|---|---|---|
| 109 | 3,4-diCl-phenyl | 5-F-pyridin-3-yl | >CH(CH$_3$) (S) | |
| 172 | 3-Cl-4-CF$_3$-phenyl | 2,6-diMe-pyridin-4-yl | >CH(CH$_3$) (S) | |
| 110 | 3-Me-4-CF$_3$-phenyl | pyridin-2-yl | >CH(CH$_3$) (S) | |
| 111 | 2-OMe-4-CF$_3$-phenyl | pyridin-2-yl | >CH(CH$_3$) (S) | |
| 112 | 3-Me-4-CF$_3$-phenyl | 2-Me-pyridin-4-yl | >CH(CH$_3$) (S) | |
| 113 | 3-Me-4-CF$_3$-phenyl | 3,6-diMe-pyridazin-4-yl | >CH(CH$_3$) (S) | |
| 114 | 3-Me-4-CF$_3$-phenyl | pyrazin-2-yl | >CH(CH$_3$) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

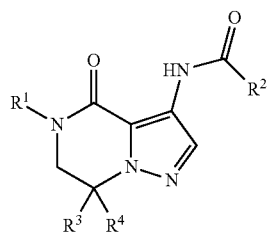

| Co. No. | R¹ | R² | >CR³R⁴ | Salt Form |
|---|---|---|---|---|
| 145 | 2-methyl-4-(trifluoromethyl)phenyl (F₃C, CH₃ on phenyl) | pyridin-3-yl | >CH(CH₃) (S) | |
| 173 | 3,4-dichlorophenyl | CF₃ | >CH(CH₃) (S) | |
| 151 | 2-methyl-4-(trifluoromethyl)phenyl | 5-methoxypyridin-3-yl | >CH(CH₃) (S) | |
| 115 | 2-methyl-4-(trifluoromethyl)phenyl | 5-methylpyridin-3-yl | >CH(CH₃) (S) | |
| 147 | 2-methoxy-4-(trifluoromethyl)phenyl | pyridin-3-yl | >CH(CH₃) (S) | |
| 152 | 2-methoxy-4-(trifluoromethyl)phenyl | 5-methoxypyridin-3-yl | >CH(CH₃) (S) | |
| 116 | 2-methoxy-4-(trifluoromethyl)phenyl | 5-fluoropyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

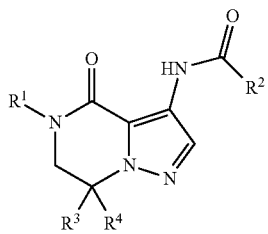

| Co. No. | R¹ | R² | >CR³R⁴ | Salt Form |
|---|---|---|---|---|
| 117 | 2-CF₃, 4-(OMe)-phenyl (O-methyl on position with OMe ortho to CF₃) | 5-methylpyridin-3-yl | >CH(CH₃) (S) | |
| 118 | 2-CF₃, 4-(OMe)-phenyl | pyrazin-2-yl | >CH(CH₃) (S) | |
| 119 | 4-CF₃-phenyl | 4-methylpyridin-3-yl | >CH(CH₃) (S) | |
| 120 | 3-Cl, 4-CF₃-phenyl | 4-methylpyridin-3-yl | >CH(CH₃) (S) | |
| 154 / 154a | 4-CF₃-phenyl | 2,3-dimethylpyridin-4-yl | >CH(CH₃) (S) | •HCl |
| 121 | 3-Cl, 4-CF₃-phenyl | 4-methyl-6-methoxypyridin-3-yl | >CH(CH₃) (S) | |
| 122 | 4-CF₃-phenyl | 4-methyl-5-methoxypyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

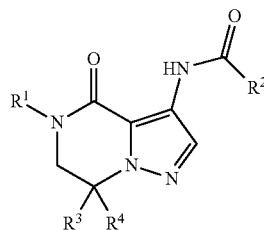

| Co. No. | R¹ | R² | >CR³R⁴ | Salt Form |
|---|---|---|---|---|
| 123 | 2-OMe-4-(F₃C)phenyl | 2-methylpyridin-4-yl | >CH(CH₃) (S) | |
| 157 | 4-(F₃C)phenyl | 2,5-dimethylpyridin-4-yl | >CH(CH₃) (S) | |
| 158 | 2-Cl-4-(F₃C)phenyl | 2,5-dimethylpyridin-4-yl | >CH(CH₃) (S) | |
| 148 | 2-F-4-(F₃C)phenyl | pyridin-3-yl | >CH(CH₃) (S) | |
| 153 | 2-F-4-(F₃C)phenyl | 5-methoxypyridin-3-yl | >CH(CH₃) (S) | |
| 124 | 2-F-4-(F₃C)phenyl | 5-fluoropyridazin-3-yl | >CH(CH₃) (S) | |
| 155 | 2-Cl-4-(F₃C)phenyl | 2,3-dimethylpyridin-4-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R$^1$ | R$^2$ | >CR$^3$R$^4$ | Salt Form |
|---|---|---|---|---|
| 125 | 2-(trifluoromethyl)-5-methoxyphenyl (F$_3$C, O-Me on phenyl) | 2,6-dimethylpyridin-4-yl | >CH(CH$_3$) (S) | |
| 126 | 4-(trifluoromethyl)-3-fluorophenyl | pyridin-2-yl | >CH(CH$_3$) (S) | |
| 127 | 4-(trifluoromethyl)-3-fluorophenyl | pyrazin-2-yl | >CH(CH$_3$) (S) | |
| 171 | 3,4-dichlorophenyl | 2-methylpyridin-4-yl | >CH(CH$_3$) (S) | |
| 128 | 4-(trifluoromethyl)-3-fluorophenyl | 5-methylpyridin-3-yl | >CH(CH$_3$) (S) | |
| 159 | 4-(trifluoromethyl)phenyl | 6-acetamidopyridin-3-yl | >CH(CH$_3$) (S) | |
| 160 | 4-(trifluoromethyl)phenyl | CH$_3$ | >CH(CH$_3$) (S) | |
| 129 | 4-(trifluoromethyl)-3-fluorophenyl | 2,6-dimethylpyridin-4-yl | >CH(CH$_3$) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

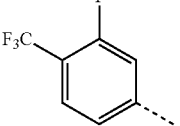

| Co. No. | R¹ | R² | >CR³R⁴ | Salt Form |
|---|---|---|---|---|
| 130 | 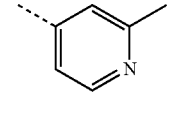 | 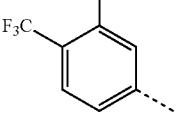 | >CH(CH₃) (S) | |
| 165 | 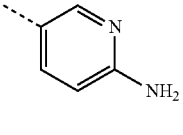 | 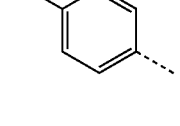 | >CH(CH₃) (S) | |
| 156 | 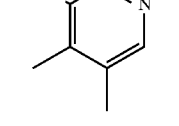 | 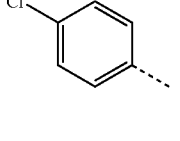 | >CH(CH₃) (S) | |
| 131 | 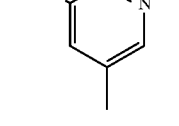 | 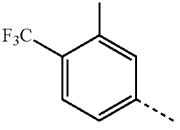 | >CH(CH₃) (S) | |
| 142 | 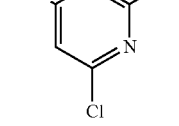 | 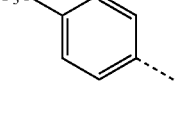 | >CH(CH₃) (S) | |
| 162 | 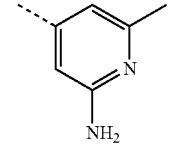 | 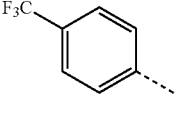 | >CH(CH₃) (S) | |
| 163 | 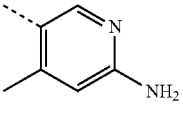 | | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 167 | 3-Cl-4-CF₃-phenyl | 2-(tert-butylamino)-5-methylpyridin-3-yl | >CH(CH₃) (S) | |
| 132 | 4-Cl-phenyl | 2,6-dimethylpyridin-4-yl | >CH(CH₃) (S) | |
| 174 | 3-Cl-4-CF₃-phenyl | 6-amino-2-methylpyridin-4-yl | >CH(CH₃) (S) | |
| 133 | 3-Cl-4-CF₃-phenyl | 4,5-dimethylpyridin-3-yl | >CH(CH₃) (S) | |
| 134 | 3-Cl-4-CF₃-phenyl | 6-aminopyridin-3-yl | >CH(CH₂OCH₃) | |
| 168 | 3-Cl-4-CF₃-phenyl | 2-(tert-butylamino)-3-methylpyridin-5-yl | >CH(CH₃) (S) | |
| 135 | 3-Cl-4-CF₃-phenyl | 5-fluoro-4-methylpyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

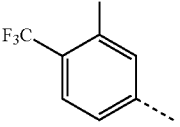

| Co. No. | R¹ | R² | >CR³R⁴ | Salt Form |
|---|---|---|---|---|
| 164 | 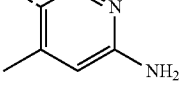 | 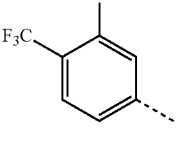 | >CH(CH₃) (S) | |
| 170 | 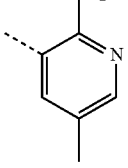 | 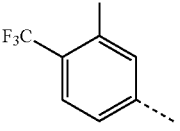 | >CH(CH₃) (S) | •O(CO)CF₃ |
| 169 | 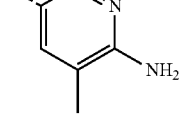 | 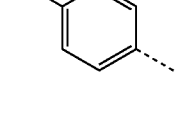 | >CH(CH₃) (S) | •O(CO)CF₃ |
| 136 | 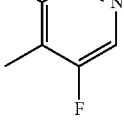 | 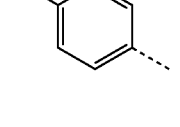 | >CH(CH₃) (S) | |
| 137 | 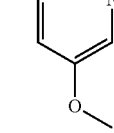 | 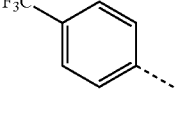 | >CH(CH₃) (S) | |
| 138 | 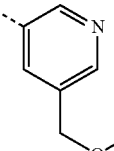 | 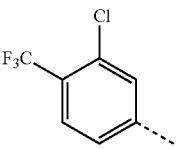 | >CH(CH₃) (S) | |
| 139 | 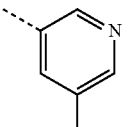 | | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 140 | 3-Cl-4-CF₃-phenyl | 6-amino-pyridin-3-yl | >CH(CH₂OCH₃) (S) | |
| 141 | 3-Cl-4-CF₃-phenyl | 6-amino-pyridin-3-yl | >CH(CH₂OCH₃) (R) | |
| 143 | 4-CF₃-phenyl | 6-methyl-2-chloro-pyridin-4-yl | >CH(CH₃) (S) | |
| 175 | 4-SF₅-phenyl | pyridin-3-yl | >CH(CH₃) (S) | |
| 161 | 4-CF₃-phenyl | 2-amino-thiazol-4-yl | >CH(CH₃) (S) | |
| 166 | 3-Cl-4-CF₃-phenyl | 5-methyl-pyridin-3-yl N-oxide | >CH(CH₃) (S) | |
| 177 | 4-CF₃-phenyl | 3-sulfamoyl-phenyl | >CH(CH₃) (S) | |
| 178 | 4-OCF₃-phenyl | pyridin-3-yl | >CH(CH₃) (S) | |
| 179 | 4-SCF₃-phenyl | pyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

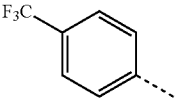

| Co. No. | R¹ | R² | >CR³R⁴ | Salt Form |
|---|---|---|---|---|
| 180 | 4-CF₃-phenyl | 2-amino-pyrimidin-4-yl (6-methyl) | >CH(CH₃) (S) | |
| 181 | 3-Cl-4-CF₃-phenyl | 2-amino-pyrimidin-4-yl (6-methyl) | >CH(CH₃) (S) | |
| 182 | 3-Cl-4-CF₃-phenyl | 2-amino-pyridin-3-yl | >CH(CH₃) (S) | |
| 183 | 4-CF₃-phenyl | 3-OMe-pyrazin-5-yl | >CH(CH₃) (S) | |
| 184 | 2-methyl-4-CF₃-phenyl | 2-amino-pyridin-3-yl | >CH(CH₃) (S) | |
| 185 | 3,4-dichloro-phenyl | 2-amino-pyridin-3-yl | >CH(CH₃) (S) | |
| 186 | 4-CF₃-phenyl | tetrahydropyran-4-yl | >CH(CH₃) (S) | |
| 187 | 4-CF₃-phenyl | 2-amino-3-methyl-pyridin-5-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 188 | 4-CF₃-phenyl | pyridin-3-yl | >CH(CH₃) (R) | |
| 189 | 4-CF₃-phenyl | 2-aminopyridin-3-yl | >CH(CH₃) (S) | |
| 190 | 4-CF₃-phenyl | pyridin-3-yl | >CH₂ | |
| 191 | 4-CF₃-phenyl | 2-amino-5-methylpyridin-3-yl | >CH(CH₃) (S) | |
| 192 | 4-CF₃-phenyl | 2-amino-4-methylpyridin-3-yl | >CH(CH₃) (S) | |
| 193 | 4-CF₃-phenyl | 2-amino-4-methoxypyridin-3-yl | >CH(CH₃) (S) | |
| 194 | 4-CF₃-phenyl | 2-(methylamino)pyridin-3-yl | >CH(CH₃) (S) | |
| 195 | 3-chloro-4-CF₃-phenyl | pyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 196 | 4-CF₃-phenyl | 2-aminopyridin-3-yl | >CH(CH₃) (S) | |
| 197 | 4-CF₃-2-methylphenyl | 2-amino-5-methylpyridin-3-yl | >CH(CH₃) (S) | |
| 198 | 4-Cl-phenyl | 2-aminopyridin-3-yl | >CH(CH₃) (S) | |
| 199 | 3,4-diCl-phenyl | 2-amino-5-methylpyridin-3-yl | >CH(CH₃) (S) | |
| 200 | 4-SF₅-phenyl | 2-amino-5-methylpyridin-3-yl | >CH(CH₃) (S) | |
| 201 | 4-Cl-phenyl | 2-amino-5-methylpyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

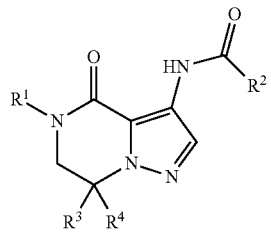

| Co. No. | R¹ | R² | >CR³R⁴ | Salt Form |
|---|---|---|---|---|
| 202 | F₅S-C₆H₄- | 2-amino-pyridin-3-yl | >CH(CH₃) (S) | |
| 203 | 4-Cl-C₆H₄- | 2-amino-6-methyl-pyridin-4-yl | >CH(CH₃) (S) | |
| 204 | 4-F₃C-C₆H₄- | 4-amino-phenyl | >CH(CH₃) (S) | |
| 205 | 4-F₃C-C₆H₄- | pyridin-3-yl N-oxide | >CH(CH₃) (S) | |
| 206 | 4-F₃C-C₆H₄- | 3-amino-pyrazin-2-yl | >CH(CH₃) (S) | |
| 207 | 4-F₃CS-C₆H₄- | 2-amino-5-methyl-pyridin-3-yl | >CH(CH₃) (S) | |
| 208 | 4-Cl-3-methyl-C₆H₃- | 2-amino-pyridin-3-yl | >CH(CH₃) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

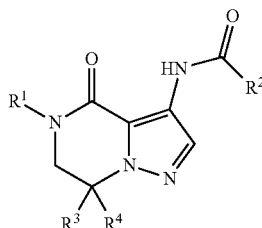

| Co. No. | $R^1$ | $R^2$ | $>CR^3R^4$ | Salt Form |
|---|---|---|---|---|
| 209 | 4-F$_3$C-phenyl | 4-F,6-CH$_3$-pyridin-2-yl (via CH$_2$) | >CH(CH$_3$) (S) | |
| 210 | 2-F,4-F$_3$C-benzyl | 2-NH$_2$-pyridin-3-yl | >CH(CH$_3$) (S) | |
| 211 | 2-Cl,4-CH$_3$-phenyl | 2-CH$_3$-pyridin-3-yl | >CH(CH$_3$) (S) | |
| 212 | 4-F$_3$CO-phenyl | 2-NH$_2$,5-CH$_3$-pyridin-3-yl | >CH(CH$_3$) (S) | |
| 213 | 4-F$_3$C-phenyl | 2-(2-hydroxyethylamino)-pyridin-3-yl | >CH(CH$_3$) (S) | |
| 214 | 3-Cl,4-F$_3$C-phenyl | 2-(2-hydroxyethylamino)-pyridin-3-yl | >CH(CH$_3$) (S) | |

TABLE 1-continued

The following compounds were prepared following the methods exemplified in the Experimental Part (Ex. No.). For some compounds the stereochemical configuration has been designated as *R or *S when the absolute stereochemistry is undetermined although the compound itself has been isolated as a single stereoisomer and is enantiomerically pure.

| Co. No. | R¹ | R² | >CR³R⁴ | Salt Form |
|---|---|---|---|---|
| 215 | 4-(F₃C)-phenyl | 2-Cl-pyridin-5-yl | >CH(CH₃) (S) | |
| 216 | 2-(F₃C)-5-(HOCH₂)-phenyl | 2-NH₂-pyridin-3-yl | >CH(CH₃) (S) | |
| 217 | 4-(F₃C)-phenyl | 3-(SO₂F)-phenyl | >CH(CH₃) (S) | |
| 218 | 4-(F₃C)-phenyl | 3-(SO₂F)-phenyl | >CH(CH₃) (S) | |
| 219 | 4-(F₃C)-phenyl | 6-F-pyrazin-2-yl | >CH(CH₃) (S) | |
| 220 | 3,4-diCl-phenyl | 6-F-pyrazin-2-yl | >CH(CH₃) (S) | |
| 221 | 4-(F₃C)-phenyl | 3-Cl-pyrazin-5-yl | >CH(CH₃) (S) | |
| 222 | 3,4-diCl-phenyl | 3-Cl-pyrazin-5-yl | >CH(CH₃) (S) | |

The values of salt stoichiometry or acid content in the compounds as provided herein, are those obtained experimentally and may vary when using different analytical methods. The content of hydrochloric acid reported herein was determined by $^1$H NMR integration and/or elemental analysis.

Analytical Part

Melting Points

Values are peak values, and are obtained with experimental uncertainties that are commonly associated with this analytical method.

DSC823e (A):

For a number of compounds, melting points (m.p.) were determined with a DSC823e (Mettler-Toledo) apparatus. Melting points were measured with a temperature gradient of 10° C./minute. Maximum temperature was 300° C. Peak values were recorded.

Mettler FP 81HT/FP90 Apparatus (B):

For a number of compounds, melting points were determined in open capillary tubes on a Mettler FP 81HT/FP90 apparatus. Melting points were measured with a temperature gradient of 1, 3, 5 or 10° C./minute. Maximum temperature was 300° C. The melting point was read from a digital display.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). For molecules with multiple isotopic patterns (Br, Cl), the reported value is the one obtained for the lowest isotope mass. All results were obtained with experimental uncertainties that are commonly associated with the method used.

TABLE 2

LC-MS Methods (Flow expressed in mL/min; column temperature (T) in ° C.; Run time in minutes).

| Method | Instrument | Column | Mobile phase | Gradient | Flow Col T | Run time |
|---|---|---|---|---|---|---|
| 1 | Waters: Acquity ® UPLC ®-DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 50 | 5 |
| 2 | Waters: Acquity ® IClass UPLC ®-DAD/ Xevo G2-S QTOF | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 50 | 5 |
| 3 | Waters: Acquity ® IClass UPLC ®-DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 50 | 5 |
| 4 | Agilent: HP1100-DAD, MSD G1956B | Agilent: Eclipse Plus C18 (3.5 μm, 2.1 × 30 mm) | A: 95% $CH_3COONH_4$ 6.5 mM + 5% $CH_3CN$, B: $CH_3CN$ | 95% A for 0.2 min, to 0% A in 2.8 min, held for 0.15 min, back to 95% A in 0.15 min, held for 1.7 min | 1 60 | 5 |
| 5 | Waters: Acquity ® IClass UPLC ®-DAD/Xevo G2-S QTOF | Waters: CSH ™ C18 (1.7 μm, 2.1 × 50 mm) | A: 95% $CH_3COONH_4$ 6.5 mM + 5% CH3CN, B: CH3CN | From 95% A to 40% A in 1.2 min, to 5% A in 0.6 min, held for 0.2 min | 1 50 | 2 |
| 6 | Agilent: HP1100-DAD, Waters: SQD | Agilent: Eclipse Plus C18 (3.5 μm, 2.1 × 30 mm) | A: 95% $CH_3COONH_4$ 6.5 mM + 5% $CH_3CN$, B: 1/1 $CH_3CN$/ $CH_3OH$ | 95% A kept for 0.2 min, to 0% A in 2.8 min, held for 0.15 min, back to 95% A in 0.15 min, held for 1.7 min | 1 60 | 5 |
| 7 | Waters: Acquity UPLC ®-DAD/ Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |

TABLE 2-continued

LC-MS Methods (Flow expressed in mL/min; column temperature (T) in °C.; Run time in minutes).

| Method | Instrument | Column | Mobile phase | Gradient | Flow Col T | Run time |
|---|---|---|---|---|---|---|
| 8 | Waters: Acquity ® UPLC ®-DAD/SQD | Waters: CSH ™ C18 (1.7 µm, 2.1 × 50 mm) | A: 95% CH₃COONH₄ 6.5 mM + 5% CH₃CN, B: CH₃CN | From 95% A to 40% A in 1.2 min, to 5% A in 0.6 min, held for 0.2 min | 1 50 | 2 |
| 9 | Waters: Acquity ® IClass UPLC ®-DAD/Xevo G2-S QTOF | Waters: CSH ™ C18 (1.7 µm, 2.1 × 50 mm) | A: 95% CH₃COONH₄ 6.5 mM + 5% CH3CN, B: CH3CN | From 95% A to 5% A in 4.6 min, held for 0.4 min | 1 50 | 5 |
| 10 | Waters: Acquity ® IClass UPLC ®-DAD and SQD | Waters: CSH ™ C18 (1.7 µm, 2.1 × 50 mm) | A: 95% CH₃COONH₄ 6.5 mM + 5% CH₃CN, B: CH₃CN | From 95% A to 40% A in 1.2 min, to 5% A in 0.6 min, held for 0.2 min | 1 50 | 2 |
| 11 | Waters: Acquity ® IClass UPLC ®-DAD/Xevo G2-S QTOF | Waters: HSS T3 (1.7 µm, 2.1 × 50 mm) | A: 98% CH₃CO₂NH₄ 6.5 mM + 2% CH₃CN, B: CH₃CN | 99% A kept for 1.0 min to 0% A in 1.8 min, held for 1.2 min | 1 50 | 5 |
| 12 | Waters: Acquity ® IClass UPLC ®-DAD/Xevo G2-S QTOF | Waters: CSH ™ C18 (1.7 µm, 2.1 × 50 mm) | A: 95% CH₃COONH₄ 6.5 mM + 5% CH₃CN, B: CH₃CN | From 95% A to 5% A in 4.6 min, held for 0.4 min | 1 50 | 5 |

(*) Different MS tuning parameters between S7* methods

TABLE 3

Analytical data - melting point (M.p.) and LCMS: [M + H]⁺ means the protonated mass of the free base of the compound, $R_t$ means retention time (in min), method refers to the method used for LCMS. For some compounds, high resolution exact mass was determined.

| Co. No. | M.p. (°C.) | [M + H]⁺ | $R_t$ | LCMS Method |
|---|---|---|---|---|
| 1 | 219.62 (A) | 465 | 2.11 | 1 |
| 2 | 161.54 (A) | 449 | 2.87 | 1 |
| 3 | 189.94 (A) | 431 | 1.95 | 1 |
| 4 | 202.24 (A) | 445 | 2.03 | 1 |
| 5 | n.d. | 463.1506 (+0.1 mDa) | 2.08 | 2 |
| 6 | 177.00 (A) | 447 | 2.02 | 1 |
| 7 | 154.53 (A) | 429 | 2.88 | 2 |
| 8 | 240.39 (A) | 431 | 1.85 | 1 |
| 9 | 147.40 (A) | 429 | 2.85 | 1 |
| 10 | 204.35 (A) | 463 | 2.81 | 1 |
| 11 | 241.79 (A) | 433 | 2.63 | 1 |
| 12 | 159.96 (A) | 464.1106 (+0.5 mDa) | 2.48 | 2 |
| 13 | 207.25 (A) | 449 | 1.96 | 1 |
| 14 | 161.84 (A) | 433 | 2.74 | 1 |
| 15 | 213.94 (A) | 422 | 2.61 | 2 |
| 16 | 201.48 (A) | 415 | 2.63 | 1 |
| 17 | 136.53 (A) | 463 | 2.84 | 1 |
| 18 | n.d. | 463.1096 (−0.1 mDa) | 1.91 | 2 |
| 19 | 170.98 (A) | 463 | 2.87 | 1 |
| 20 | 190.00 (A) | 446 | 2.77 | 1 |
| 21 | 199.24 (A) | 445 | 2.73 | 1 |
| 22 | 213.77 (A) | 475 | 2.09 | 1 |
| 23 | 152.43 (A) | 463 | 2.81 | 2 |
| 24 | n.d. | 416 | 2.44 | 1 |
| 25 | 164.82 (A) | 445 | 2.65 | 1 |
| 26 | 216.96 (A) | 456 | 1.75 | 1 |
| 27 | 136.91 (A) | 445 | 2.70 | 1 |
| 28 | 152.59 (A) | 415 | 2.04 | 1 |
| 29 | 145.1 (B) | 430 | 2.21 | 1 |
| 30 | 160.03 (A) | 459 | 2.63 | 2 |
| 31 | 185.29 (A) | 434.1240 (−0.0 mDa) | 2.3 | 2 |
| 32 | 174.59 (A) | 446 | 2.2 | 1 |
| 33 | 250.03 (A) | 462 | 2.31 | 1 |
| 34 | 214.97 (A) | 430 | 2.64 | 1 |
| 35 | 219.91 (A) | 417.1285 (−0.2 mDa) | 2.23 | 2 |
| 36 | n.d. | 397 | 1.64 | 1 |
| 37 | 185.41 (A) | 463 | 2.77 | 1 |
| 38 | 179.66 (A) | 461 | 1.9 | 1 |
| 39 | 191.33 (A) | 447 | 2.56 | 1 |
| 40 | 133.34 (A) | 429 | 2.63 | 1 |
| 41 | n.d. | 463 | 2.55 | 1 |
| 42 | 127.02 (A) | 446 | 2.48 | 1 |
| 43 | 213.83 (A) | 446 | 2.64 | 2 |
| 44 | 214.58 (A) | 463 | 2.74 | 1 |
| 45 | 287.45 (A) | 432 | 1.97 | 1 |
| 46 | 237.65 (A) | 450 | 2.77 | 1 |
| 47 | 128.68 (A) | 446 | 2.52 | 1 |
| 48 | 221.22 (A) | 434 | 2.55 | 1 |
| 49 | 119.36 (A) | 433 | 2.71 | 1 |
| 50 | 225.63 (A) | 431 | 2.49 | 4 |
| 51 | 140.98 (A) | 463 | 2.73 | 1 |
| 52 | n.d. | 432 | 1.6 | 1 |
| 53 | 198.98 (A) | 429 | 2.83 | 1 |
| 54 | 175.17 (A) | 430 | 2.66 | 4 |
| 55 | 145.26 (A) | 416 | 2.04 | 1 |
| 56 | 160.66 (A) | 476 | 3.12 | 1 |
| 57 | 292.16 (A) | 430 | 2.7 | 1 |
| 58 | 240.77 (A) | 463 | 2.94 | 2 |
| 59 | 205.32 (A) | 463 | 2.66 | 1 |
| 60 | 227.69 (A) | 446.1439 (−0.1 mDa) | 2.61 | 2 |
| 61 | 223.46 (A) | 432 | 1.95 | 1 |
| 62 | n.d. | 463 | 2.65 | 1 |
| 63 | 204.97 (A) | 406 | 2.07 | 1 |
| 64 | n.d. | 461.1550 (+0.1 mDa) | 1.11 | 5 |
| 65 | n.d. | 428 | 2.09 | 1 |
| 66 | 120.37 (A) | 430 | 2.06 | 1 |

TABLE 3-continued

Analytical data - melting point (M.p.) and LCMS: [M + H]⁺ means the protonated mass of the free base of the compound, $R_t$ means retention time (in min), method refers to the method used for LCMS. For some compounds, high resolution exact mass was determined.

| Co. No. | M.p. (° C.) | [M + H]⁺ | $R_t$ | LCMS Method |
|---|---|---|---|---|
| 67 | n.d. | 434 | 2.38 | 1 |
| 68 | 289.40 (A) | 431 | 2.13 | 1 |
| 69 | n.d. | 406 | 2.68 | 4 |
| 70 | 201.06 (A) | 446 | 3.07 | 1 |
| 71 | 243.14 (A) | 420 | 2.38 | 1 |
| 72 | 209.27 (A) | 420 | 2.53 | 1 |
| 73 | 152.20 (A) | 393 | 2.34 | 1 |
| 74 | 283.48 (A) | 437 | 1.84 | 1 |
| 75 | 231.11 (A) | 476 | 3.17 | 1 |
| 76 | 188.77 (A) | 412 | 2.81 | 1 |
| 77 | 194.90 (A) | 476 | 3.06 | 1 |
| 78 | 88.18 (A) | 459.1651 (+0.7 mDa) | 2.61 | 2 |
| 79 | 240.10 (A) | 405 | 1.88 | 2 |
| 80 | 275.03 (A) | 405 | 2.01 | 1 |
| 81 | 189.92 (A) | 420 | 2.34 | 1 |
| 82 | 278.58 (A) | 459 | 1.93 | 1 |
| 83 | 277.42 (A) | 405 | 1.80 | 1 |
| 84 | n.d. | 420 | 1.73 | 1 |
| 85 | 291.58 (A) | 441 | 2.5 | 1 |
| 86 | 167.59 (A) | 419 | 2.72 | 6 |
| 87 | 135.05 (A) | 429 | 2.52 | 1 |
| 88 | 231.10 (A) | 431 | 1.96 | 1 |
| 89 | 285.92 (A) | 419 | 2.10 | 1 |
| 90 | n.d. | 432 | 1.74 | 1 |
| 91 | 162.27 (A) | 419 | 1.87 | 1 |
| 92 | n.d. | 431 [M − H]⁻(**) | 1.79 | 1 |
| 93 | 154.26 (A) | 444 | 2.41 | 2 |
| 94 | 272.72 (A) | 420 | 1.66 | 2 |
| 95 | 225.94 (A) | 461 | 2.59 | 7 |
| 96 | 225.83 (A) | 461 | 2.59 | 7 |
| 97 | 153.01 (A) | 363.1570 (+0.1 mDa) | 1.45 | 2 |
| 98 | n.d. | 417.1288 (0.1 mDa) | 1.98 | 2 |
| 99 | 165.21 (A) | 430 | 2.2 | 1 |
| 100 | 157.47 (A) | 450.0950 (+0.6 mDa) | 2.36 | 2 |
| 62a | 162.59 (A) | 463 | 3.21 | 7 |
| 62b | 162.51 (A) | 463 | 3.21 | 7 |
| 144 | 240.46 (A) | 431.1334 (+0.3 mDa) | 2.32 | 2 |
| 102 | 216.62 (A) | 450.0950 (+0.6 mDa) | 2.83 | 2 |
| 101 | 160.38 (A) | 464.1108 (+0.7 mDa) | 2.56 | 2 |
| 103 | 198.12 (A) | 466 [M − H]⁻(**) | 2.59 | 2 |
| 150 | 133.07 (A) | 480.1061 (+1.1 mDa) | 2.54 | 2 |
| 149 | 184.46 (A) | 446.0788 (+0.2 mDa) | 2.41 | 2 |
| 146 | n.d. | 416.0681 (+0.0 mDa) | 2.23 | 2 |
| 146a | 196.42 (A) | 416.0685 (+0.4 mDa) | 2.2 | 2 |
| 176 | 230.53 (A) | 451.0899 (+0.2 mDa) | 2.56 | 2 |
| 104 | 201.39 (A) | 417.0634 (+0.1 mDa) | 2.37 | 2 |
| 105 | 155.04 (A) | 448.1399 (+0.3 mDa) | 2.51 | 2 |
| 106 | 186.11 (A) | 444.1000 (+0.6 mDa) | 2.49 | 2 |
| 107 | 155.04 (A) | 448.1399 (+0.3 mDa) | 2.51 | 2 |
| 108 | 185.71 (A) | 430.0844 (+0.7 mDa) | 2.4 | 2 |
| 109 | 128.16 (A) | 434.0589 (+0.2 mDa) | 2.4 | 2 |
| 172 | n.d. | 478.1270 (+1.3 mDa) | 2.65 | 2 |
| 110 | 217.95 (A) | 446.1448 (+0.8 mDa) | 2.57 | 2 |
| 111 | 217.95 (A) | 446.1448 (+0.8 mDa) | 2.57 | 2 |
| 112 | 128.97 (A) | 444.1644 (−0.3 mDa) | 2.45 | 2 |
| 113 | 164.61 (A) | 458.1805 (+0.1 mDa) | 2.6 | 2 |
| 114 | 225.49 (A) | 431 | 2.41 | 3 |
| 145 | 120.33 (A) | 430 | 2.23 | 2 |
| 173 | n.d. | 405 [M − H]⁻(**) | 2.74 | 2 |
| 151 | 135.98 (A) | 460 | 2.39 | 3 |
| 115 | 151.53 (A) | 444.1650 (+0.3 mDa) | 2.45 | 2 |
| 147 | 186.11 (A) | 446.1444 (+0.4 mDa) | 2.14 | 2 |
| 152 | 115.19 (A) | 476.1547 (+0.2 mDa) | 2.28 | 2 |
| 116 | 162.96 (A) | 464.1344 (−0.2 mDa) | 2.35 | 2 |
| 117 | 166.32 (A) | 460.1602 (+0.6 mDa) | 2.32 | 2 |
| 118 | 191.55 (A) | 447 | 2.25 | 3 |
| 119 | 200.30 (A) | 430.1493 (+0.2 mDa) | 2.14 | 2 |
| 120 | 145.92 (A) | 464.1107 (+0.6 mDa) | 2.4 | 2 |
| 154 | n.d. | 444 | 2.18 | 3 |
| 154a | n.d. | 444.1646 (−0.1 mDa) | 2.24 | 2 |
| 121 | 160.45 (A) | 494.1215 (+0.9 mDa) | 2.55 | 2 |
| 122 | 181.87 (A) | 460.1596 (+0.0 mDa) | 2.31 | 2 |
| 123 | 157.12 (A) | 460.1608 (+1.2 mDa) | 2.3 | 2 |
| 157 | n.d. | 444.1647 (+0.0 mDa) | 2.3 | 2 |
| 158 | 130.79 (A) | 478.1262 (+0.5 mDa) | 2.55 | 2 |
| 148 | 166.06 (A) | 434.1244 (+0.4 mDa) | 2.2 | 2 |
| 153 | 143.17 (A) | 464.1350 (+0.4 mDa) | 2.36 | 2 |
| 124 | 217.01 (A) | 452.1148 (+0.2 mDa) | 2.41 | 2 |
| 155 | n.d. | 478.1266 (+0.9 mDa) | 2.51 | 2 |
| 125 | 226.99 (A) | 474.1754 (+0.1 mDa) | 2.44 | 2 |
| 126 | 226.14 (A) | 434.1241 (+0.1 mDa) | 2.65 | 2 |
| 127 | 236.55 (A) | 435.1193 (+0.1 mDa) | 2.38 | 2 |
| 171 | 108.41 (A) | 430.0837 (0.0 mDa) | 2.38 | 2 |
| 128 | 163.67 (A) | 446.1242 (+0.2 mDa) | 2.4 | 2 |
| 159 | 265 (A) | 473.1547 (−0.2 mDa) | 2.09 | 2 |
| 160 | 142.82 (A) | 353.1224 (−0.1 mDa) | 1.87 | 2 |
| 129 | 148.36 (A) | 462.1552 (−0.1 mDa) | 2.51 | 2 |
| 130 | 134.44 (A) | 448.1394 (−0.2 mDa) | 2.35 | 2 |
| 165 | 238.83 (A) | 461.1553 (+0.4 mDa) | 1.58 | 2 |
| 156 | 182.69 (A) | 444.1653 (+0.6 mDa) | 2.29 | 2 |
| 131 | n.d. | 396.1234 (+0.7 mDa) | 2.1 | 2 |
| 142 | 124.01 (A) | 498.0713 (+0.2 mDa) | 2.99 | 2 |
| 162 | 196.39 (A) | 445.1605 (+0.5 mDa) | 2.15 | 2 |
| 163 | 226.06 (A) | 445.16 (+0.0 mDa) | 1.99 | 2 |
| 167 | n.d. | 535.1848 (+1.2 mDa) | 3.91 | 2 |
| 132 | n.d. | 410 | 2.18 | 3 |
| 174 | 192.47 (A) | 479.1216 (+0.6 mDa) | 2.37 | 3 |
| 133 | 172.80 (A) | 478 | 2.48 | 3 |
| 134 | n.d. | 495 | 2.12 | 3 |
| 168 | n.d. | 535.1839 (+0.3 mDa) | 3.51 | 2 |
| 135 | 97.90 (A) | 482.1009 (+0.2 mDa) | 2.63 | 2 |
| 164 | 233.32 (A) | 479.1205 (−0.6 mDa) | 2.25 | 2 |
| 170 | n.d. | 479.1216 (+0.6 mDa) | 2.67 | 2 |
| 169 | n.d. | 479.1211 (+0.1 mDa) | 2.31 | 2 |
| 136 | 89.55 (A) | 448.1398 (+0.2 mDa) | 2.37 | 2 |
| 137 | 153.40 (A) | 412.1183 (+0.7 mDa) | 2.09 | 2 |
| 138 | 149.93 (A) | 460.1606 (+1.0 mDa) | 2.21 | 2 |
| 139 | 170.75 (A) | 492 [M − H]⁻(**) | 2.45 | 9 |
| 140 | 230.27 (A) | 495.1156 (−0.3 mDa) | 2.16 | 2 |
| 141 | 230.40 (A) | 495.1162 (−0.3 mDa) | 2.18 | 2 |
| 143 | n.d. | 464 | 1.46 | 8 |
| 175 | 205.19 (A) | 474.1026 (0.3 mDa) | 2.28 | 2 |
| 161 | n.d. | n.d. | n.d. | |
| 166 | n.d. | 480 | 1.09 | 10 |
| 177 | 280.43 (A) | 494.1109 (−0.1 mDa) | 2.11 | 2 |
| 178 | 125.45 (A) | 432 | 2.15 | 1 |
| 179 | 110.73 (A) | 448.1061 (+0.6 mDa) | 2.35 | 2 |
| 180 | 265.47 (A) | 446.1557 (+0.5 mDa) | 2.17 | 2 |
| 181 | 258.12 (A) | 480.1167 (+0.5 mDa) | 2.40 | 2 |
| 182 | 142.58 (A) | 465.1058 (+0.5 mDa) | 2.52 | 2 |
| 183 | 185.23 (A) | 447.1393 (+0.1 mDa) | 2.55 | 2 |
| 184 | 175.63 (A) | 445.1604 (+0.4 mDa) | 2.43 | 2 |
| 185 | 193.17 (A) | 431.0788 (−0.2 mDa) | 2.37 | 2 |
| 186 | 142.94 (A) | 423.1644 (0.0 mDa) | 2.07 | 2 |
| 187 | 277.76 (A) | 445.1604 (+0.4 mDa) | 2.05 | 2 |
| 188 | 152.20 (A) | 416.1335 (+0.1 mDa) | 2.09 | 2 |
| 189 | 214.96 (A) | 431.1452 (+0.9 mDa) | 2.25 | 2 |
| 190 | 162.12 (A) | 402.1181 (+0.4 mDa) | 1.87 | 2 |
| 191 | 222.34 (A) | 445.1605 (+0.5 mDa) | 2.42 | 2 |
| 192 | 122.92, 177.39 (A)-(*) | 445.1604 (+0.4 mDa) | 2.21 | 2 |
| 193 | 248.21 (A) | 461.1552 (+0.3 mDa) | 2.38 | 2 |
| 194 | 161.97 (A) | 445.1607 (+0.7 mDa) | 2.62 | 2 |
| 195 | 181.21 (A) | 466.0901 (+0.7 mDa) | 2.43 | 2 |
| 196 | 188.46 (A) | 447.1396 (+0.4 mDa) | 2.33 | 2 |
| 197 | 190.13 (A) | 459.1764 (+0.8 mDa) | 2.60 | 2 |
| 198 | 209.11 (A) | 397.1184 (+0.4 mDa) | 2.07 | 2 |
| 199 | 220.49 (A) | 445.0947 (+0.1 mDa) | 2.52 | 2 |
| 200 | 197.51 (A) | 503.1291 (+0.3 mDa) | 2.60 | 2 |
| 201 | n.d. | 411.1340 (+0.4 mDa) | 2.25 | 2 |
| 202 | 223.96 (A) | 489.1143 (+1.1 mDa) | 2.45 | 2 |
| 203 | 223.01 (A) | 411.1338 (+0.2 mDa) | 1.96 | 2 |

TABLE 3-continued

Analytical data - melting point (M.p.) and LCMS:
[M + H]+ means the protonated mass of the free base of the compound, $R_t$ means retention time (in min), method refers to the method used for LCMS. For some compounds, high resolution exact mass was determined.

| Co. No. | M.p. (° C.) | [M + H]+ | $R_t$ | LCMS Method |
|---|---|---|---|---|
| 204 | 250.78 (A) | 430.1492 (+0.1 mDa) | 2.20 | 2 |
| 205 | 257.47 (A) | 432.1291 (+0.8 mDa) | 1.59 | 2 |
| 206 | 205.79 (A) | 432.1395 (−0.1 mDa) | 3.55 | 11 |
| 207 | 172.90 (A) | 477.1321 (+0.1 mDa) | 2.69 | 2 |
| 208 | 174.32 (A) | 411.1 | 2.93 | 7 |
| 209 | 157.37 (A) | 462.1554 (+0.1 mDa) | 2.50 | 2 |
| 210 | 176.26 (A) | 463.1505 (+0.0 mDa) | 2.30 | 2 |
| 211 | n.d. | 411.1 | 2.94 | 7 |
| 212 | n.d. | 461.1557 (−0.2 mDa) | 2.49 | 2 |
| 213 | 168.55 (A) | 475.1701 (−0.4 mDa) | 2.25 | 2 |
| 214 | n.d. | 509.1324 (+0.8 mDa) | 2.54 | 2 |
| 215 | n.d. | 450 | 1.36 | 8 |
| 216 | n.d. | 461.1547 (−0.2 mDa) | 1.87 | 2 |
| 217 | 161.88 (A) | 495.0751 (+0.1 mDa)(**) | 2.82 | 9 |
| 218 | 163.64 (A) | 495.0756 (+0.6 mDa)(**) | 2.83 | 9 |
| 219 | 183.54 (A) | 435.1193 (+0.1 mDa) | 2.48 | 12 |
| 220 | 211.35 (A) | 433.0380 (−0.3 mDa) | 2.57 | 9 |
| 221 | n.d. | 451 | 1.39 | 8 |
| 222 | n.d. | 451 | 1.45 | 8 | n.d. means not determined.
(*)Multiple crystalline forms detected. The reported M.p. corresponds to two crystalline forms or to the main/highest peak
(**)The reported molecular ion corresponds to the [M − H]−(deprotonated molecule).

Optical Rotations

Optical rotations were measured on a Perkin-Elmer 341 polarimeter with a sodium lamp and reported as follows: [α]° (λ, c g/100 ml, solvent, T° C.).

$[α]_λ^T = (100α)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 4

Optical Rotation data.

| Co. No. | $α_D$ (°) | Wavelength (nm) | Concentration w/v % | Solvent | Temp. (° C.) |
|---|---|---|---|---|---|
| 8 | +14.3 | 589 | 0.63 | DMF | 20 |
| 29 | +24.1 | 589 | 0.71 | DMF | 25 |
| 47 | +17.9 | 589 | 0.56 | DMF | 20 |
| 89 | +22.4 | 589 | 0.6 | DMF | 20 |
| 69 | +24.3 | 589 | 0.57 | DMF | 20 |
| 86 | +21.1 | 589 | 0.6 | DMF | 20 |
| 54 | +18.4 | 589 | 0.53 | DMF | 20 |
| 50 | +25.6 | 589 | 0.53 | DMF | 20 |
| 1 | +22.5 | 589 | 0.66 | DMF | 20 |
| 16 | +23.7 | 589 | 0.58 | DMF | 20 |
| 2 | +25.9 | 589 | 0.63 | DMF | 20 |
| 12 | +21.2 | 589 | 0.65 | DMF | 20 |
| 24 | +27.0 | 589 | 0.55 | DMF | 20 |
| 49 | +20.9 | 589 | 0.5 | DMF | 20 |
| 73 | +30.6 | 589 | 0.48 | DMF | 20 |
| 88 | +18.2 | 589 | 0.48 | DMF | 20 |
| 83 | +22.6 | 589 | 0.6 | DMF | 20 |
| 91 | +21.9 | 589 | 0.56 | DMF | 20 |
| 27 | +20.7 | 589 | 0.48 | DMF | 20 |
| 25 | +19.6 | 589 | 0.48 | DMF | 20 |
| 71 | +26.5 | 589 | 0.6 | DMF | 20 |
| 9 | +21.6 | 589 | 0.52 | DMF | 20 |
| 21 | +22.9 | 589 | 0.51 | DMF | 20 |
| 72 | +20.7 | 589 | 0.59 | DMF | 20 |
| 53 | +16.3 | 589 | 0.49 | DMF | 20 |
| 45 | +15.4 | 589 | 0.51 | DMF | 20 |
| 87 | +19.2 | 589 | 0.49 | DMF | 20 |
| 55 | +26.4 | 589 | 0.5 | DMF | 20 |
| 28 | +23.8 | 589 | 0.53 | DMF | 20 |
| 4 | +11.8 | 589 | 0.49 | DMF | 20 |
| 26 | +14.8 | 589 | 0.86 | DMF | 20 |
| 46 | +22.4 | 589 | 0.54 | DMF | 20 |
| 48 | +25.4 | 589 | 0.52 | DMF | 20 |
| 36 | +18.8 | 589 | 0.9 | DMF | 20 |
| 61 | +23.7 | 589 | 0.8 | DMF | 20 |
| 38 | +45.4 | 589 | 0.46 | DMF | 20 |
| 85 | +21.6 | 589 | 0.5 | DMF | 20 |
| 82 | +19.3 | 589 | 0.54 | DMF | 20 |
| 20 | +25.8 | 589 | 0.57 | DMF | 20 |
| 4 | +18.3 | 589 | 0.4 | DMF | 20 |
| 13 | +15.5 | 589 | 0.41 | DMF | 20 |
| 66 | +17.6 | 589 | 0.61 | DMF | 20 |
| 57 | +26.6 | 589 | 0.62 | DMF | 20 |
| 68 | +14.2 | 589 | 0.5 | DMF | 20 |
| 42 | +15.4 | 589 | 0.51 | DMF | 20 |
| 67 | +20.2 | 589 | 0.5 | DMF | 20 |
| 52 | +17.0 | 589 | 0.5 | DMF | 20 |
| 32 | +24.4 | 589 | 0.62 | DMF | 20 |
| 34 | +123.3 | 589 | 0.52 | DMF | 20 |
| 76 | +10.5 | 589 | 0.48 | DMF | 20 |
| 43 | +23.1 | 589 | 0.66 | DMF | 20 |
| 70 | +17.2 | 589 | 0.46 | DMF | 20 |
| 56 | +13.4 | 589 | 0.55 | DMF | 20 |
| 77 | +9.0 | 589 | 0.52 | DMF | 20 |
| 33 | +5.4 | 589 | 0.46 | DMF | 20 |
| 22 | +3.4 | 589 | 0.48 | DMF | 20 |
| 75 | +17.5 | 589 | 0.53 | DMF | 20 |
| 40 | +17.3 | 589 | 0.5 | DMF | 20 |
| 90 | −264.6 | 589 | 0.52 | DMF | 20 |
| 63 | +26.1 | 589 | 0.5 | DMF | 20 |
| 30 | +21.6 | 589 | 0.6 | DMF | 20 |
| 79 | +19.1 | 589 | 0.51 | DMF | 20 |
| 15 | +22.8 | 589 | 0.49 | DMF | 20 |
| 23 | +18.3 | 589 | 0.47 | DMF | 20 |
| 58 | +21.9 | 589 | 0.55 | DMF | 20 |
| 10 | +22.0 | 589 | 0.44 | DMF | 20 |
| 41 | +14.5 | 589 | 0.45 | DMF | 20 |
| 44 | +16.1 | 589 | 0.55 | DMF | 20 |
| 51 | +20.8 | 589 | 0.56 | DMF | 20 |
| 37 | +15.9 | 589 | 0.5 | DMF | 20 |
| 17 | +16.4 | 589 | 0.53 | DMF | 20 |
| 19 | +20.1 | 589 | 0.58 | DMF | 20 |
| 84 | +21.8 | 589 | 0.5 | DMF | 20 |
| 80 | +20.1 | 589 | 0.5 | DMF | 20 |
| 59 | +15.0 | 589 | 0.48 | DMF | 20 |
| 31 | +16.4 | 589 | 0.58 | DMF | 20 |
| 35 | +21.8 | 589 | 0.5 | DMF | 20 |
| 78 | +19.2 | 589 | 0.61 | DMF | 20 |
| 5 | +15.3 | 589 | 0.44 | DMF | 20 |
| 74 | +17.7 | 589 | 0.49 | DMF | 20 |
| 100 | +24.4 | 589 | 0.59 | DMF | 20 |
| 99 | +21.1 | 589 | 0.67 | DMF | 20 |
| 98 | +22.2 | 589 | 0.5 | DMF | 20 |
| 97 | +26.1 | 589 | 0.5 | DMF | 20 |
| 96 | +7.1 | 589 | 0.45 | DMF | 20 |
| 95 | −12 | 589 | 0.3 | DMF | 20 |
| 94 | +23.9 | 589 | 0.53 | DMF | 20 |
| 93 | +18.8 | 589 | 0.57 | DMF | 20 |
| 62a | −16.2 | 589 | 0.51 | DMF | 20 |
| 62b | +12.3 | 589 | 0.51 | DMF | 20 |
| 144 | +20.9 | 589 | 0.52 | DMF | 20 |
| 102 | +27.6 | 589 | 0.55 | DMF | 20 |
| 101 | +27.7 | 589 | 0.77 | DMF | 20 |
| 150 | +19.6 | 589 | 0.59 | DMF | 20 |
| 149 | +22.3 | 589 | 0.87 | DMF | 20 |

TABLE 4-continued

Optical Rotation data.

| Co. No. | α_D (°) | Wavelength (nm) | Concentration w/v % | Solvent | Temp. (° C.) |
|---|---|---|---|---|---|
| 146 | +22.4 | 589 | 0.82 | DMF | 20 |
| 146a | +17.6 | 589 | 0.59 | DMF | 20 |
| 176 | +26.6 | 589 | 0.6 | DMF | 20 |
| 104 | +21.6 | 589 | 0.48 | DMF | 20 |
| 105 | +13.4 | 589 | 0.52 | DMF | 20 |
| 108 | +22.5 | 589 | 1.04 | DMF | 20 |
| 109 | +20.8 | 589 | 0.93 | DMF | 20 |
| 172 | +24.9 | 589 | 0.53 | DMF | 20 |
| 110 | +20.9 | 589 | 0.69 | DMF | 20 |
| 165 | +18.7 | 589 | 0.5 | DMF | 20 |
| 112 | +20.0 | 589 | 0.5 | DMF | 20 |
| 113 | +24.3 | 589 | 0.5 | DMF | 20 |
| 114 | +23.2 | 589 | 0.49 | DMF | 20 |
| 145 | +17.7 | 589 | 0.86 | DMF | 20 |
| 151 | +17.7 | 589 | 0.7 | DMF | 20 |
| 115 | +17.8 | 589 | 0.64 | DMF | 20 |
| 147 | +8.2 | 589 | 1.3 | DMF | 20 |
| 152 | +3.2 | 589 | 1.32 | DMF | 20 |
| 116 | +17.3 | 589 | 0.73 | DMF | 20 |
| 117 | +8.1 | 589 | 0.52 | DMF | 20 |
| 118 | +18.7 | 589 | 0.49 | DMF | 20 |
| 119 | +17.8 | 589 | 0.62 | DMF | 20 |
| 120 | +20.7 | 589 | 0.58 | DMF | 20 |
| 154 | +16.4 | 589 | 0.5 | DMF | 20 |
| 154a | +12.5 | 589 | 0.48 | DMF | 20 |
| 121 | +16.4 | 589 | 0.65 | DMF | 20 |
| 122 | +15.0 | 589 | 0.6 | DMF | 20 |
| 123 | +20.1 | 589 | 0.5 | DMF | 20 |
| 157 | +18.0. | 589 | 0.51 | DMF | 20 |
| 158 | +21.9 | 589 | 0.51 | DMF | 20 |
| 148 | +17.9 | 589 | 0.74 | DMF | 20 |
| 153 | +16.7 | 589 | 0.87 | DMF | 20 |
| 124 | +16.2 | 589 | 0.74 | DMF | 20 |
| 155 | +16.8 | 589 | 0.5 | DMF | 20 |
| 125 | +22.0 | 589 | 0.5 | DMF | 20 |
| 126 | +20.4 | 589 | 0.56 | DMF | 20 |
| 171 | +21.3 | 589 | 0.48 | DMF | 20 |
| 128 | +18.7 | 589 | 0.96 | DMF | 20 |
| 159 | +16.3 | 589 | 0.51 | DMF | 20 |
| 160 | +29.3 | 589 | 0.68 | DMF | 20 |
| 129 | +19.2 | 589 | 0.51 | DMF | 20 |
| 130 | +19.9 | 589 | 0.53 | DMF | 20 |
| 156 | +16.3 | 589 | 0.5 | DMF | 20 |
| 142 | +21.3 | 589 | 0.58 | DMF | 20 |
| 162 | +20.6 | 589 | 0.74 | DMF | 20 |
| 163 | +8.7 | 589 | 0.55 | DMF | 20 |
| 174 | +22.3 | 589 | 0.52 | DMF | 20 |
| 133 | +19.3 | 589 | 0.5 | DMF | 20 |
| 135 | +18.6 | 589 | 0.55 | DMF | 20 |
| 164 | +17.9 | 589 | 0.54 | DMF | 20 |
| 136 | +13.1 | 589 | 0.69 | DMF | 20 |
| 138 | +18.3 | 589 | 0.56 | DMF | 20 |
| 139 | +20.0 | 589 | 0.56 | DMF | 20 |
| 140 | +18.8 | 589 | 0.49 | DMF | 20 |
| 141 | −19.9 | 589 | 0.49 | DMF | 20 |
| 81 | +24.2 | 589 | 0.48 | DMF | 20 |
| 106 | +21.2 | 589 | 0.52 | DMF | 20 |
| 14 | +19.3 | 589 | 0.51 | DMF | 20 |
| 107 | +13.4 | 589 | 0.52 | DMF | 20 |
| 175 | +17.8 | 589 | 0.57 | DMF | 20 |
| 177 | +19.5 | 589 | 0.50 | DMF | 20 |
| 178 | +17.4 | 589 | 0.54 | DMF | 20 |
| 179 | +13.3 | 589 | 0.60 | DMF | 20 |
| 180 | +36.6 | 589 | 0.49 | DMF | 20 |
| 181 | +31.8 | 589 | 0.51 | DMF | 20 |
| 182 | +26.2 | 589 | 1.00 | DMF | 20 |
| 183 | +26.3 | 589 | 0.51 | DMF | 20 |
| 184 | +20.3 | 589 | 0.44 | DMF | 20 |
| 185 | +25.4 | 589 | 0.53 | DMF | 20 |
| 186 | +24.3 | 589 | 0.50 | DMF | 20 |
| 187 | +20.7 | 589 | 0.56 | DMF | 20 |
| 188 | −23.3 | 589 | 0.56 | DMF | 20 |
| 189 | +25.9 | 589 | 0.57 | DMF | 20 |
| 191 | +24.9 | 589 | 0.53 | DMF | 20 |
| 192 | +21.1 | 589 | 0.55 | DMF | 20 |
| 193 | +30.1 | 589 | 0.56 | DMF | 20 |
| 195 | +22.9 | 589 | 0.57 | DMF | 20 |
| 196 | +20.1 | 589 | 0.57 | DMF | 20 |
| 197 | +20.1 | 589 | 0.54 | DMF | 20 |
| 198 | +23.8 | 589 | 0.50 | DMF | 20 |
| 199 | +19.9 | 589 | 0.45 | DMF | 20 |
| 200 | +3.2 | 589 | 0.49 | DMF | 20 |
| 202 | +21.3 | 589 | 0.55 | DMF | 20 |
| 203 | +20.5 | 589 | 0.76 | DMF | 20 |
| 204 | +12.4 | 589 | 0.50 | DMF | 20 |
| 205 | +21.7 | 589 | 0.57 | DMF | 20 |
| 206 | +14.7 | 589 | 0.65 | DMF | 20 |
| 208 | +23.7 | 589 | 0.54 | DMF | 20 |
| 210 | +27.9 | 589 | 0.55 | DMF | 20 |
| 213 | +22.5 | 589 | 0.51 | DMF | 20 |
| 214 | +27.4 | 589 | 0.60 | DMF | 20 |
| 217 | +234.5 | 589 | 0.51 | DMF | 20 |
| 218 | +14.9 | 589 | 0.67 | DMF | 20 |
| 219 | +23.1 | 589 | 0.53 | DMF | 20 |
| 220 | +21.0 | 589 | 0.57 | DMF | 20 |
| 221 | n.d. | | | | |
| 222 | n.d. | | | | |

SFC-MS

General Procedure

The SFC measurement was performed using Analytical system from Berger instrument comprising a FCM-1200 dual pump fluid control module for delivering carbon dioxide ($CO_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 μa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

TABLE 5

Analytical SFC-MS Methods (Flow expressed in mL/min; column temperature (T) in ° C.; Pressure in MPa).

| Method | Column | Mobile Phase | Flow | T | Pressure |
|---|---|---|---|---|---|
| 1 | Chiralpak AD-H 150 × 4.6 mm, 5 μm Daicel | $CO_2$/EtOH (0.3% $iPrNH_2$) 60/40 | 3 | 35 | 100 |

TABLE 6

Analytical SFC data - $R_t$ means retention time (in minutes), [M + H]$^+$ means the protonated mass of the compound, method refers to the method used for SFC/MS analysis of enantiomerically pure compounds. The measurement was compared against the mixture.

| Co. No. | $R_t$ | [M + H]$^+$ | UV Area % | Isomer Elution Order | Method |
|---|---|---|---|---|---|
| 96 | 2.62 | 461 | 100 | A | 1 |
| 95 | 4.05 | 461 | 100 | B | 1 |
| 62a | 2.76 | 463 | 100 | A | 1 |
| 62b | 5.09 | 463 | 100 | B | 1 |

TABLE 6-continued

Analytical SFC data - $R_t$ means retention time (in minutes), [M + H]$^+$ means the protonated mass of the compound, method refers to the method used for SFC/MS analysis of enantiomerically pure compounds. The measurement was compared against the mixture.

| Co. No. | $R_t$ | [M + H]$^+$ | UV Area % | Isomer Elution Order | Method |
|---|---|---|---|---|---|
| 140 | 3.44 | 495 | 100 | A | 1 |
| 141 | 6.92 | 495 | 100 | B | 1 |

Pharmalogical Examples

The compounds provided in the present invention are negative allosteric modulators of mGluR2. These compounds appear to inhibit glutamate responses by binding to an allosteric site other than the glutamate binding site. The response of mGluR2 to a concentration of glutamate is decreased when compounds of Formula (I) are present. Compounds of Formula (I) are expected to have their effect substantially at mGluR2 by virtue of their ability to reduce the function of the receptor. The effects of negative allosteric modulators tested at mGluR2 using the [$^{35}$S]GTPγS binding assay method described below and which is suitable for the identification of such compounds, and more particularly the compounds according to Formula (I), are shown in Table 7.

1) [$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein α subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the antagonist can be determined. mGlu2 receptors are shown to be preferentially coupled to Gαi-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the negative allosteric modulation (NAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with an Ultra Turrax homogenizer. The suspension was centrifuged at 12,400 RPM (Sorvall F14S-6x250Y) for 10 minutes and the supernatant discarded. The pellet was homogenized in 5 mM Tris-HCl, pH 7.4 using an Ultra Turrax homogenizer and centrifuged again (13,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 negative allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 mM GDP. Human mGlu2 receptor-containing membranes were thawed on ice and diluted in assay buffer supplemented with 18 µg/ml saponin. Membranes were pre-incubated with compound together with a predefined (~EC$_{80}$) concentration of glutamate (60 µM) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 µg of membrane protein in 10 mM HEPES acid, 10 mM HEPES salt, pH 7.4, 100 mM NaCl, 3 mM MgCl$_2$, 10 µM GDP and 10 µg/ml saponin. Total reaction volume was 200 µl. Reactions were terminated by rapid filtration through Unifilter-96 GF/B plates (Perkin Elmer, Massachusetts, USA) using a 96-well filtermate universal harvester. Filters were washed 6 times with ice-cold 10 mM NaH$_2$PO$_4$/10 mM Na$_2$HPO$_4$, pH 7.4. Filters were then air-dried, and 30 µl of liquid scintillation cocktail (Microscint-O) was added to each well. Membrane-bound radioactivity was counted in a Topcount.

Data Analysis

The concentration-response curves of representative compounds of the present invention were generated using the Lexis software interface (developed at J&J). Data were calculated as % of the control glutamate response, defined as the response that is generated upon addition of an EC$_{80}$-equivalent concentration of glutamate. Sigmoid concentration-response curves plotting these percentages versus the log concentration of the test compound were analyzed using non-linear regression analysis. The concentration producing half-maximal inhibition was calculated as the IC$_{50}$. The pIC$_{50}$ values were calculated as the −log IC$_{50}$, when the IC$_{50}$ is expressed in M. E$_{max}$ is defined as the relative maximal effect (i.e. maximal % inhibition relative to the control glutamate response).

TABLE 7

Pharmacological data for compounds according to the invention.

| Co. No. | GTPγS-hmGluR2 anGT pIC$_{50}$ | GTPγS-hmGluR2 anGT Emax |
|---|---|---|
| 8 | 8.67 | 110 |
| 29 | 8.16 | 100 |
| 47 | 7.89 | 101 |
| 89 | 6.61 | 100 |
| 69 | 7.53 | 103 |
| 86 | 6.72 | 103 |
| 54 | 7.75 | 104 |
| 50 | 7.86 | 104 |
| 1 | 8.94 | 109 |
| 16 | 8.47 | 108 |
| 2 | 8.88 | 105 |
| 12 | 8.67 | 107 |
| 24 | 8.23 | 102 |
| 11 | 8.59 | 104 |
| 49 | 7.88 | 101 |
| 14 | 8.56 | 102 |
| 81 | 6.99 | 103 |
| 73 | 7.32 | 98 |
| 88 | 6.65 | 99 |
| 83 | 6.95 | 101 |
| 91 | 6.46 | 101 |
| 27 | 8.18 | 106 |

TABLE 7-continued

Pharmacological data for compounds according to the invention.

| Co. No. | GTPγS-hmGluR2 anGT pIC$_{50}$ | GTPγS-hmGluR2 anGT Emax |
|---|---|---|
| 25 | 8.21 | 104 |
| 71 | 7.42 | 97 |
| 9 | 8.61 | 106 |
| 21 | 8.33 | 106 |
| 72 | 7.37 | 99 |
| 53 | 7.75 | 104 |
| 45 | 7.92 | 106 |
| 92 | 5.9 | 101 |
| 87 | 6.7 | 103 |
| 55 | 7.7 | 105 |
| 28 | 8.12 | 107 |
| 4 | 8.78 | 106 |
| 26 | 8.19 | 106 |
| 7 | 8.64 | 108 |
| 46 | 7.9 | 104 |
| 48 | 7.88 | 108 |
| 36 | 8.05 | 110 |
| 61 | 7.61 | 103 |
| 38 | 8.04 | 109 |
| 39 | 8.03 | 111 |
| 85 | 6.78 | 106 |
| 82 | 6.95 | 104 |
| 20 | 8.34 | 103 |
| 3 | 8.79 | 110 |
| 13 | 8.58 | 109 |
| 66 | 7.56 | 104 |
| 57 | 7.69 | 103 |
| 68 | 7.55 | 107 |
| 42 | 7.96 | 105 |
| 67 | 7.55 | 102 |
| 52 | 7.81 | 113 |
| 32 | 8.13 | 112 |
| 34 | 8.08 | 116 |
| 76 | 7.23 | 106 |
| 43 | 7.95 | 114 |
| 70 | 7.42 | 108 |
| 56 | 7.69 | 107 |
| 77 | 7.11 | 103 |
| 33 | 8.12 | 117 |
| 22 | 8.32 | 111 |
| 6 | 8.64 | 114 |
| 75 | 7.27 | 103 |
| 40 | 8.02 | 113 |
| 90 | 6.54 | 97 |
| 63 | 7.58 | 109 |
| 30 | 8.15 | 113 |
| 65 | 7.57 | 111 |
| 79 | 7.07 | 107 |
| 15 | 8.49 | 111 |
| 23 | 8.26 | 105 |
| 58 | 7.66 | 101 |
| 10 | 8.59 | 113 |
| 41 | 7.98 | 109 |
| 44 | 7.95 | 115 |
| 51 | 7.84 | 113 |
| 37 | 8.04 | 116 |
| 17 | 8.43 | 114 |
| 19 | 8.36 | 117 |
| 18 | 8.37 | 117 |
| 84 | 6.86 | 109 |
| 80 | 7 | 111 |
| 60 | 7.61 | 111 |
| 59 | 7.65 | 110 |
| 31 | 8.14 | 114 |
| 64 | 7.57 | 110 |
| 35 | 8.09 | 112 |
| 78 | 7.25 | 105 |
| 5 | 8.62 | 107 |
| 74 | 7.47 | 113 |
| 62 | 7.52 | 108 |
| 100 | 8.66 | 106 |
| 99 | 8.4 | 114 |
| 98 | 6.82 | 106 |
| 97 | 6.5 | 111 |
| 96 | 5.84 | 95 |
| 95 | 8.2 | 114 |
| 94 | 6.34 | 98 |
| 93 | 8.56 | 110 |
| 62a | 7.9 | 111 |
| 62b | 5.32 | 66 |
| 144 | 8.69 | 115 |
| 102 | 8.76 | 110 |
| 101 | 8.95 | 107 |
| 103 | 8.63 | 106 |
| 150 | 8.78 | 107 |
| 149 | 8.78 | 107 |
| 146a | 8.53 | 108 |
| 176 | 8.77 | 108 |
| 104 | 8.74 | 107 |
| 105 | 8.58 | 109 |
| 106 | 8.97 | 108 |
| 107 | 8.57 | 108 |
| 108 | 9.01 | 109 |
| 109 | 8.86 | 105 |
| 172 | 8.88 | 110 |
| 110 | 8.63 | 107 |
| 111 | 7.99 | 105 |
| 112 | 8.33 | 106 |
| 113 | 8.69 | 107 |
| 114 | 8.6 | 106 |
| 145 | 8.34 | 105 |
| 173 | 7.64 | 104 |
| 151 | 8.5 | 106 |
| 115 | 8.47 | 107 |
| 147 | 7.97 | 106 |
| 152 | 8.01 | 106 |
| 116 | 8 | 104 |
| 117 | 8.07 | 104 |
| 118 | 8.37 | 108 |
| 119 | 8.08 | 107 |
| 120 | 8.74 | 109 |
| 154 | 7.22 | 105 |
| 154a | 7.03 | 105 |
| 121 | 7.68 | 106 |
| 122 | 6.72 | 105 |
| 123 | 7.58 | 107 |
| 157 | 7.73 | 106 |
| 158 | 8.39 | 112 |
| 148 | 8.07 | 105 |
| 153 | 7.87 | 106 |
| 124 | 8.02 | 109 |
| 155 | 8.26 | 104 |
| 125 | 8.39 | 104 |
| 126 | 8.38 | 110 |
| 127 | 8.18 | 104 |
| 171 | 8.64 | 104 |
| 128 | 8.16 | 103 |
| 159 | 8.22 | 106 |
| 160 | 6.2 | 101 |
| 129 | 8.25 | 108 |
| 130 | 8.13 | 107 |
| 141 | 8.73 | 108 |
| 140 | 6.79 | 105 |
| 139 | 8.52 | 108 |
| 138 | 7.53 | 106 |
| 137 | 7.76 | 106 |
| 136 | 7.61 | 106 |
| 169 | 9.23 | 108 |
| 170 | 9.15 | 108 |
| 164 | 8.87 | 108 |
| 135 | 8.64 | 108 |
| 168 | 7.54 | 105 |
| 167 | 6.55 | 103 |
| 134 | 8.38 | 111 |
| 133 | 8.48 | 109 |
| 174 | 8.78 | 106 |

TABLE 7-continued

Pharmacological data for compounds according to the invention.

| Co. No. | GTPγS-hmGluR2 anGT pIC$_{50}$ | GTPγS-hmGluR2 anGT Emax |
|---|---|---|
| 132 | 8.06 | 112 |
| 163 | 8.59 | 106 |
| 162 | 8.56 | 107 |
| 142 | 8.61 | 109 |
| 131 | 7.78 | 107 |
| 156 | 7.62 | 113 |
| 175 | 8.5 | 108 |
| 186 | 6.15 | 106 |
| 177 | 8.78 | 109 |
| 205 | 7.48 | 109 |
| 187 | 8.82 | 109 |
| 188 | 6.61 | 105 |
| 178 | 7.83 | 105 |
| 203 | 7.95 | 105 |
| 189 | 8.74 | 109 |
| 179 | 8.23 | 106 |
| 180 | 7.36 | 107 |
| 190 | 5.97 | 102 |
| 181 | 8.24 | 101 |
| 182 | 9.15 | 110 |
| 191 | 8.71 | 112 |
| 183 | 8.65 | 114 |
| 192 | 7.57 | 110 |
| 204 | 8.55 | 107 |
| 193 | 8.54 | 106 |
| 194 | 8.89 | 113 |
| 206 | 8.52 | 110 |
| 195 | 8.8 | 105 |
| 184 | 8.91 | 110 |
| 196 | 8.58 | 109 |
| 197 | 8.88 | 108 |
| 185 | 8.97 | 113 |
| 198 | 8.39 | 109 |
| 199 | 9.01 | 109 |
| 200 | 8.83 | 111 |
| 201 | 8.31 | 108 |
| 202 | 8.94 | 108 |
| 210 | 8.68 | 106 |
| 213 | 8.99 | 103 |
| 214 | 9.28 | 112 |
| 217 | 7.97 | 110 |
| 218 | 7.36 | 112 |
| 219 | 8.48 | 107 |
| 220 | 8.47 | 104 |

B) In Vivo Pharmacology

1) Reversal of LY-404039-Induced Decrease of Palpebral Opening in Apomorphine-Challenged Rats.

Male Wiga Wistar rats (Crl:WI; Charles River Germany; 220±40 g) were housed under standard laboratory conditions (21±2° C.; 50-65% relative humidity; light-dark cycle set at 12 h; lights on at 6.00 h) and fasted overnight prior to the start of the experiments (tap water remained available ad libitum). During the test period, they were housed in individual cages. Palpebral opening was scored every 5 min over the first hour after injection of apomorphine (1.0 mg/kg, i.v.) in animals either pretreated or not pretreated with LY-404039 (2.5 mg/kg, s.c.) at 1 h prior to the apomorphine injection. The animals were also pretreated with test compound or solvent at a predefined interval before apomorphine challenge. The score system was: (5) exophthalmos, (4) wide open, (3) open for three-quarters, (2) half open, (1) open for one-quarter, (0) closed. The scores for palpebral opening were cumulated over the 60-min observation period. A cumulative palpebral opening score >26 was selected for drug-induced reversal of the LY-404039-induced decrease of palpebral opening (occurrence in 3.2% of control animals pretreated with LY-404039 (n=154) versus in 99.5% of control rats not pretreated with LY-404039 (n=6335)).

Table 8 shows the palpebral opening score in control animals receiving apomorphine alone and in animals receiving apomorphine and LY-404039. In animals receiving apomorphine alone the median palpebral opening is 43 whereas in animals receiving apomorphine and LY-404039, the median palpebral opening is 17. In animals treated with apomorphine alone, the palpebral opening score is almost always (in 95.5% of the rats) greater than 34, whereas in animals treated with the combination (apomorphine+LY-404039) only 3.2% of the animals show a palpebral opening greater than 26.

TABLE 8

Palpebral opening score in control animals.

| Measurement | Apomorphine alone (n = 6335) | Apomorphine + LY-404039 (n = 154) |
|---|---|---|
| Palpebral opening score | | |
| Median score: | 43 | 17 |
| Occurrence score > 26 (%): | 99.5 | 3.2 |
| Occurrence score > 34 (%): | 95.9 | 0.0 |

2) Reversal of the Effect of the mGluR2 PAM JNJ-42153605-Induced Inhibition of Scopolamine-Induced Hyperlocomotion Apparatus Motor activity was measured in microprocessor-based motor activity arenas (closed gray PVC cylinders with a height of 39 cm and a diameter of 31 cm). Each arena was placed on an infrared LED (8×8 LEDs) lit box (white PVC squared box; 40×40 cm$^2$; height 12.5 cm. An infrared-sensitive tube camera and a white light source were mounted to the ceiling above the observation chamber to track the animal. The total distance traveled (cm) was recorded and analyzed using the Noldus Ethovision XT Video Tracking System (Version 7.0.418; Noldus, Wageningen, The Netherlands). The intensity of the light within the activity cages (measured in the centre at the level of the floor) ranged between 4 and 8 LUX.

General Procedure

The rats were pretreated with test compound or vehicle at 60 min before the start of the activity recordings and placed into individual cages. The rats were challenged with JNJ-42153605 (3-(cyclopropylmethyl)-7-(4-phenylpiperidin-1-yl)-8-(trifluoromethyl)[1,2,4]triazolo[4,3-a]pyridine; WO2010/130424; Cid et al. J. Med. Chem. 2012, 55, 8770-8789) (20 mg/kg, i.v.) 30 min before the start of the activity recording combined with scopolamine (0.16 mg/kg, i.v.) just before the start of the activity measurements. Immediately after the injection of scopolamine, the rats were placed into the activity monitors and total distance travelled over the first 30 min was measured.

Solvent-Pretreated Control Rats.

Frequency distributions obtained in a historical series of solvent-pretreated control rats are given in Table 9 below. Animals receiving the combination of JNJ-42153605 and scopolamine (n=433) almost always travelled a distance of less than 1500 cm (<1500 cm) (only 2.5% of the control rats travelled a distance of more than 1500 cm (>1500 cm)). On the other hand, animals challenged with scopolamine alone (n=215) always travelled a total distance of more than 1500 cm (>1500 cm) and almost always (in 95.8% of the rats) a distance of more than 4400 cm (>4400 cm). Rats that did not receive any challenge travelled almost always a distance of more than 1500 cm (>1500 cm) (in 93.3% of the rats) and less than 4400 cm (<4400 cm) (in 98.9% of the rats). For reversal of the inhibitory effect of JNJ-42153605 on the scopolamine-induced hyperlocomotion, the following all-or-none criteria were adopted: (1) reversal: total distance >1500 cm.

TABLE 9

Frequency distributions obtained in historical series of solvent-pretreated control rats. $N_{tested}$ means number of animals tested.

| | Median (cm) | >1500 cm (%) | >4400 cm (%) | $N_{tested}$ |
|---|---|---|---|---|
| Combination | 480 | 2.5 | 0.0 | 433 |
| No challenge | 2618 | 93.3 | 1.1 | 638 |
| Scopolamine | 7246 | 100 | 95.8 | 215 |

3) Induction of Mydriasis

The pupil diameter of Wiga rats was measured with a microscopic micrometer (1 unit=1/24 mm). Criteria for drug-induced effects: pupil diameter >25 units for mydriasis (in controls: 1.9%) 1, 2 or 3 h post-administration of the test compound (wherein the maximum pupil diameter over the full 3 h period is reported).

Table 10 below provides the data obtained in the tests 1)-3) described above:

TABLE 10

Summary of data in tests 1)-3). In the table: SCOP JNJ-42153605 means Reversal of the effect of JNJ 42153605 on scopolamine-induced hyperlocomotion, APO LY-404039 means Reversal of LY-404039-induced decrease of palpebral opening in apomorphine challenged rats, MYD means Induction of mydriasis, $ED_{50}$ means median effective dose; PO means oral route; SC means subcutaneous route.
$ED_{50}$ (mg/kg)

| Co. No. | Route | SCOP JNJ-42153605 | APO LY-404039 | MYD |
|---|---|---|---|---|
| 8 | PO | 0.13 | 0.19 | 8.7 |
|  | SC | 0.13 | 0.34 | 7.1 |
| 29 | PO | >2.5 | | |
| 1 | PO | 0.26 | 0.39 | 14.1 |
| 16 | PO | >2.5 | | |
| 2 | PO | >2.5 | | |
| 12 | PO | 0.32 | 0.42 | 21.5 |
| 11 | PO | >2.5 | | |
| 14 | PO | >2.5 | | |
| 27 | PO | >2.5 | | |
| 45 | PO | >2.5 | | |
| 28 | PO | 0.39 | 0.78 | 25 |
| 4 | PO | 0.5 | 1.26 | |
| 26 | PO | >2.5 | | |
| 36 | PO | 0.5 | | |
| 38 | PO | >2.5 | | |
| 39 | PO | >2.5 | | |
| 20 | PO | >2.5 | | |
| 3 | PO | 0.32 | | |
| 13 | PO | 0.32 | 0.2 | |
| 52 | PO | >2.5 | | |
| 32 | PO | 1.26 | | |
| 34 | PO | >2.5 | | |
| 22 | PO | >2.5 | | |
| 6 | PO | >2.5 | | |
| 30 | PO | >2.5 | | |
| 15 | PO | >2.5 | | |
| 18 | PO | >2.5 | | |
| 35 | PO | 1.26 | | |
| 100 | PO | 0.8 | | >2.5 |
| 99 | PO | >2.5 | | |

TABLE 10-continued

Summary of data in tests 1)-3). In the table: SCOP JNJ-42153605 means Reversal of the effect of JNJ 42153605 on scopolamine-induced hyperlocomotion, APO LY-404039 means Reversal of LY-404039-induced decrease of palpebral opening in apomorphine challenged rats, MYD means Induction of mydriasis, $ED_{50}$ means median effective dose; PO means oral route; SC means subcutaneous route.
$ED_{50}$ (mg/kg)

| Co. No. | Route | SCOP JNJ-42153605 | APO LY-404039 | MYD |
|---|---|---|---|---|
| 95 | PO | 1.26 | >2.5 | |
| 93 | PO | 0.5 | 0.79 | |
| 62a | PO | >2.5 | >2.5 | |
| 102 | PO | >0.63 | | |
| 101 | PO | >0.63 | 0.18 | 5 |
| 103 | PO | >0.63 | | |
| 150 | PO | >0.63 | | |
| 149 | PO | >0.63 | | |
| 146a | PO | >0.63 | >0.63 | |
| 176 | PO | 0.32 | | >10 |
| 104 | PO | 0.32 | | 6.6 |
| 105 | PO | >0.63 | | |
| 106 | PO | >0.63 | >0.63 | |
| 107 | PO | >0.63 | | |
| 108 | PO | >0.63 | | |
| 109 | PO | >0.63 | | |
| 172 | PO | 0.32 | | >40 |
| 110 | PO | >0.63 | | |
| 111 | PO | >0.63 | | |
| 112 | PO | >0.63 | | |
| 113 | PO | 0.5 | | >40 |
| 114 | PO | >0.63 | | |
| 145 | PO | >0.63 | 0.5 | 6.6 |
| 151 | PO | >0.63 | | |
| 115 | PO | >0.63 | | |
| 147 | PO | >0.63 | | |
| 152 | PO | >0.63 | | |
| 116 | PO | >0.63 | | |
| 117 | PO | >0.63 | | |
| 118 | PO | >0.63 | | |
| 119 | PO | >0.63 | | |
| 120 | PO | >0.63 | >0.63 | |
| 121 | PO | >0.63 | | |
| 122 | PO | >0.63 | | |
| 123 | PO | >0.63 | | |
| 148 | PO | >0.63 | >0.63 | |
| 153 | PO | >0.63 | | |
| 124 | PO | >0.63 | | |
| 126 | PO | >0.63 | | |
| 127 | PO | >0.63 | | |
| 171 | PO | >0.63 | >0.63 | |
| 128 | PO | >0.63 | | |
| 175 | PO | 0.318 | | >10 |
| 187 | PO | 0.0794 | | >10 |
| 178 | PO | 0.318 | | >10 |
| 189 | PO | 0.2 | | >10 |
| 141 | PO | <0.63 | | >10 |
| 182 | PO | 0.0985 | | >10 |
| 191 | PO | 0.318 | | >10 |
| 177 | PO | >0.63 | | |
| 205 | PO | >0.63 | | |
| 203 | PO | >0.63 | | |
| 179 | PO | >0.63 | | |
| 181 | PO | >0.63 | | |
| 183 | PO | 0.318 | | |
| 192 | PO | >0.63 | | |
| 204 | PO | 0.318 | | |
| 193 | PO | >0.63 | | |
| 194 | PO | 0.318 | | |
| 206 | PO | 0.505 | | |
| 184 | PO | 0.20 | | >10 |
| 196 | PO | 0.32 | | >10 |
| 197 | PO | 0.13 | | >10 |
| 185 | PO | 0.08 | | >10 |
| 198 | PO | >0.63 | | |
| 199 | PO | 0.08 | | |
| 200 | PO | >0.63 | | |
| 201 | PO | >0.63 | | |

TABLE 10-continued

Summary of data in tests 1)-3). In the table: SCOP JNJ-42153605 means Reversal of the effect of JNJ 42153605 on scopolamine-induced hyperlocomotion, APO LY-404039 means Reversal of LY-404039-induced decrease of palpebral opening in apomorphine challenged rats, MYD means Induction of mydriasis, $ED_{50}$ means median effective dose; PO means oral route; SC means subcutaneous route.
$ED_{50}$ (mg/kg)

| Co. No. | Route | SCOP JNJ-42153605 | APO LY-404039 | MYD |
|---|---|---|---|---|
| 202 | PO | 0.20 | | |
| 210 | PO | 0.32 | | |
| 213 | PO | 1.12 | | |
| 214 | PO | 0.32 | | |

4) V-Maze Test

The V-maze-test is a two-trial short term visual-spatial working memory task based on spontaneous exploration of a new and a familiar arm in a 2-arm maze (Embrechts et al. (2013) "Longitudinal characterization of the TauPS2APP mouse model of Alzheimer's disease in a two trial discrimination task of visuo-spatial recognition memory", 45th European Brain and Behaviour Society Meeting 6-9 Sep. 2013, Munich, Abstract P202). Performance in this task can be disrupted by a low dose of PCP, such that the animals do not discriminate anymore between the new and a familiar arm.

Method

Male Long Evans rats (Janvier, France, body weight 280 to 295 g) were group housed in enriched individually ventilated cages and habituated to environmental conditions for 5 days. After acclimatization, animals were single housed for 4 days until testing. During this period animals were handled for 2 min per day and received sham dosing once a day for 3 days prior to the test. The V-maze consisted of two arms (L×W×H: 70×10×30 cm) at a 90° angle to each other to form a V-shaped maze connected by guillotine doors to a center zone. The walls of each arm were of a different context displaying horizontally black and white striped in one arm vs. uniform black walls in the other. Background infra-red illumination was provided via the bottom of the maze and a top view video camera above the platform was used for video recording of the experiments. The animal's exploration of each arm was automatically quantified using Ethovision XT 7.0 (Noldus, The Netherlands). Animals were treated with Co. No. 8 or its vehicle (10% cyclodextrin+1 eq. HCl+NaCl) administered p.o. 4 h before the start of the test. PCP (0.75 mg/kg s.c.) or its vehicle (0.9% NaCl solution) was administered 30 min prior to the test. The test consisted of 2 sessions of 5 min each: in the first session (exploration) the animal was placed in the center zone and given access to one of both arms (=familiar). After 5 min, the animal was taken out of the maze, the door of the other arm (new) was also opened, and the animal was put back in the center zone for a second session (choice). The time spent in the familiar and new arm respectively during the choice session was recorded for 5 min.

Results

Co. No. 8 was evaluated in rats in a series of dose-response studies evaluating doses from 0.16 to 0.63 mg/kg. While control animals (treated with vehicle of the test compound and the vehicle of PCP) displayed a strong preference for exploration of the new vs. the familiar arm in the second session, the PCP-treated rats did not discriminate anymore between both arms in each of these studies. PCP-challenged rats that were pretreated with Co. No. 8 at doses 0.16 and 0.31 mg/kg showed again a clear preference for the new arm (FIG. 1) and significantly reversed the PCP deficit.

Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

We claim:

1. A method for modulating metabotropic glutamate receptor 2 activity in a patient suffering from a disorder involving metabotropic glutamate receptor 2 activity, comprising administering to a patient in need thereof a compound of Formula (I):

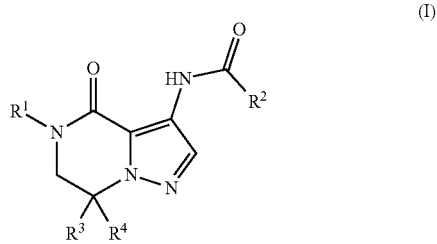

or a stereoisomeric form thereof, wherein:
R$^1$ is phenyl or 2-pyridinyl, each optionally substituted with one or more substituents each independently selected from the group consisting of halo, C$_{1-4}$alkyl, monohalo-C$_{1-4}$alkyl, polyhalo-C$_{1-4}$alkyl, —C$_{1-4}$alkyl-OH, —CN, —C$_{1-4}$alkyl-O—C$_{1-4}$alkyl, C$_{3-7}$cycloalkyl, —O—C$_{1-4}$alkyl, monohalo-C$_{1-4}$alkyloxy, polyhalo-C$_{1-4}$alkyloxy, SF$_5$, C$_{1-4}$alkylthio, monohalo-C$_{1-4}$alkylthio and polyhalo-C$_{1-4}$alkylthio;
R$^2$ is selected from the group consisting of C$_{1-4}$alkyl; C$_{3-7}$cycloalkyl; Het$^1$; Aryl; Het$^2$; and C$_{1-4}$alkyl substituted with one or more substituents each independently selected from the group consisting of halo, C$_{3-7}$cycloalkyl, Aryl, Het$^1$ and Het$^2$; wherein
Aryl is phenyl optionally substituted with one or more substituents each independently selected from the group consisting of halo, C$_{1-4}$alkyl, —C$_{1-4}$alkyl-OH, monohalo-C$_{1-4}$alkyl, polyhalo-C$_{1-4}$alkyl, —CN, —O—C$_{1-4}$alkyl, —OH, —C$_{1-4}$alkyl-O—C$_{1-4}$alkyl, —NR'R", —NHC(O)C$_{1-4}$alkyl, —C(O)NR'R", —C(O)NH[C(O)C$_{1-4}$alkyl], —S(O)$_2$NR'R", —S(O)$_2$NH[C(O)C$_{1-4}$alkyl] and —S(O)$_2$—C$_{1-4}$alkyl;
Het$^1$ is selected from the group consisting of oxetanyl, tetrahydrofuranyl and tetrahydropyranyl;
Het$^2$ is (a) a 6-membered aromatic heterocyclyl substituent selected from the group consisting of pyridinyl, pyrimidinyl, pyrazinyl and pyridazinyl, each of which may be optionally substituted with one or more substituents each independently selected from the group consisting of halo, C$_{1-4}$alkyl, —C$_{1-4}$alkyl-OH, monohalo-C$_{1-4}$alkyl, polyhalo-C$_{1-4}$alkyl, —CN, —O—C$_{1-4}$alkyl, —OH, —C$_{1-4}$alkyl-O—C$_{1-4}$alkyl, —NR'R", —NHC(O)C$_{1-4}$alkyl, —C(O)NR'R", —C(O)NH[C(O)C$_{1-4}$alkyl], —S(O)$_2$NR'R", —S(O)$_2$NH[C(O)C$_{1-4}$alkyl] and —S(O)$_2$—C$_{1-4}$alkyl;
or (b) a 5-membered aromatic heterocyclyl selected from the group consisting of thiazolyl, oxazolyl, 1H-pyrazolyl and 1H-imidazolyl, each of which may be optionally substituted with one or more substituents each independently selected from the group consisting of halo, C$_{1-4}$alkyl, —C$_{1-4}$alkyl-OH, monohalo-C$_{1-4}$alkyl, polyhalo-C$_{1-4}$alkyl, —CN, —O—C$_{1-4}$alkyl, —OH, —C$_{1-4}$alkyl-O—C$_{1-4}$alkyl, —NR'R", —NHC(O)C$_{1-4}$alkyl, —C(O)NR'R", —C(O)NH[C(O)C$_{1-4}$alkyl], —S(O)$_2$NR'R", —S(O)$_2$NH[C(O)C$_{1-4}$alkyl] and —S(O)$_2$—C$_{1-4}$alkyl;
R' and R" are each independently selected from the group consisting of hydrogen, C$_{1-4}$alkyl and —C$_{2-4}$alkyl-OH;
R$^3$ is selected from the group consisting of hydrogen and C$_{1-4}$alkyl; and
R$^4$ is selected from the group consisting of hydrogen, C$_{1-4}$alkyl, monohalo-C$_{1-4}$alkyl, polyhalo-C$_{1-4}$alkyl, —C$_{1-4}$alkyl-O—C$_{1-4}$alkyl and —C$_{1-4}$alkyl-OH;
or a N-oxide, or a pharmaceutically acceptable salt thereof.

2. The method according to claim 1, wherein
R$^1$ is phenyl or 2-pyridinyl, each optionally substituted with one, two or three substituents each independently selected from the group consisting of halo, C$_{1-4}$alkyl, monohalo-C$_{1-4}$alkyl, polyhalo-C$_{1-4}$alkyl, —C$_{1-4}$alkyl-OH, —CN, —C$_{1-4}$alkyl-O—C$_{1-4}$alkyl, —O—C$_{1-4}$alkyl, monohalo-C$_{1-4}$alkyloxy and polyhalo-C$_{1-4}$alkyloxy;
R$^2$ is selected from the group consisting of C$_{1-4}$alkyl; Aryl; Het$^2$; and C$_{1-4}$alkyl substituted with one, two or three substituents each independently selected from the group consisting of halo, C$_{3-7}$cycloalkyl and Aryl; wherein
Aryl is phenyl optionally substituted with one, two or three substituents each independently selected from the group consisting of halo, C$_{1-4}$alkyl, —O—C$_{1-4}$alkyl, —OH and —C$_{1-4}$alkyl-O—C$_{1-4}$alkyl;
Het$^2$ is (a) a 6-membered aromatic heterocyclyl substituent selected from the group consisting of pyridinyl, pyrimidinyl, pyrazinyl and pyridazinyl, each of which may be optionally substituted with one or two substituents each independently selected from the group consisting of halo, C$_{1-4}$alkyl, —CN, —OH, —O—C$_{1-4}$alkyl, —C$_{1-4}$alkyl-O—C$_{1-4}$alkyl, —C(O)NR'R", —NHC(O)C$_{1-4}$alkyl and —NR'R";
or (b) a 5-membered aromatic heterocyclyl selected from the group consisting of thiazolyl, oxazolyl, 1H-pyrazolyl and 1H-imidazolyl, each of which may be optionally substituted with one or two substituents each independently selected from the group consisting of halo, C$_{1-4}$alkyl and NR'R";
R' and R" are each independently selected from the group consisting of hydrogen and C$_{1-4}$alkyl;
R$^3$ is hydrogen; and
R$^4$ is hydrogen, C$_{1-4}$alkyl or —C$_{1-4}$alkyl-O—C$_{1-4}$alkyl;
or a N-oxide, or a pharmaceutically acceptable salt thereof.

3. The method according to claim 1, wherein
R$^1$ is phenyl or 2-pyridinyl, each optionally substituted with one or two substituents each independently selected from the group consisting of halo, C$_{1-4}$alkyl, monohalo-C$_{1-4}$alkyl, polyhalo-C$_{1-4}$alkyl, —CN, —C$_{1-4}$alkyl-O—C$_{1-4}$alkyl, —O—C$_{1-4}$alkyl, monohalo-C$_{1-4}$alkyloxy and polyhalo-C$_{1-4}$alkyloxy;
R$^2$ is selected from the group consisting of C$_{1-4}$alkyl; Aryl; Het$^2$; and C$_{1-4}$alkyl substituted with one, two or three substituents each independently selected from the group consisting of halo, C$_{3-7}$cycloalkyl and Aryl; wherein
Aryl is phenyl optionally substituted with one or two substituents each independently selected from the group consisting of halo, C$_{1-4}$alkyl, —O—C$_{1-4}$alkyl, —OH and —C$_{1-4}$alkyl-O—C$_{1-4}$alkyl;
Het$^2$ is (a) a 6-membered aromatic heterocyclyl substituent selected from the group consisting of pyridinyl, pyrimidinyl, pyrazinyl and pyridazinyl, each of which may be optionally substituted with one or two substituents each independently selected from the group consisting of halo, C$_{1-4}$alkyl, —CN, —OH, —O—C$_{1-4}$alkyl, —C(O)NR'R", —NHC(O)C$_{1-4}$alkyl and —NR'R"; or (b) a 5-membered aromatic heterocyclyl selected from the group consisting of thiazolyl, oxazolyl, 1H-pyrazolyl and 1H-imidazolyl, each of which may be optionally substituted with one or two substituents each independently selected from the group consisting of halo, C$_{1-4}$alkyl and NR'R";
R' and R" are each independently selected from the group consisting of hydrogen and C$_{1-4}$alkyl;
R$^3$ is hydrogen; and
R$^4$ is selected from the group consisting of hydrogen, C$_{1-4}$alkyl and —C$_{1-4}$alkyl-O—C$_{1-4}$alkyl;
or a N-oxide, or a pharmaceutically acceptable salt thereof.

4. The method according to claim 1, wherein
R$^1$ is phenyl, optionally substituted with one or two substituents each independently selected from the group consisting of halo, C$_{1-4}$alkyl, monohalo- C$_{1-4}$alkyl, polyhalo-C$_{1-4}$alkyl, —CN, —C$_{1-4}$alkyl-O—C$_{1-4}$alkyl, —O—C$_{1-4}$alkyl, monohalo-C$_{1-4}$alkyloxy and polyhalo-C$_{1-4}$alkyloxy;

or R$^1$ is 2-pyridinyl, optionally substituted with one or two substituents each independently selected from the group consisting of halo, monohalo-C$_{1-4}$alkyl, polyhalo-C$_{1-4}$alkyl and —O—C$_{1-4}$alkyl;

R$^2$ is selected from the group consisting of C$_{1-4}$alkyl; Aryl; Het$^2$; and C$_{1-4}$alkyl substituted with one, two or three substituents each independently selected from the group consisting of halo, C$_{3-7}$cycloalkyl and Aryl; wherein Aryl is phenyl optionally substituted with one or two substituents each independently selected from the group consisting of halo, C$_{1-4}$alkyl, —O—C$_{1-4}$alkyl, —OH and —C$_{1-4}$alkyl-O—C$_{1-4}$alkyl;

Het$^2$ is (a) a 6-membered aromatic heterocyclyl substituent selected from the group consisting of pyridinyl, pyrimidinyl, pyrazinyl and pyridazinyl, each of which may be optionally substituted with one or two substituents each independently selected from the group consisting of halo, C$_{1-4}$alkyl, —CN, —OH, —O—C$_{1-4}$alkyl, —C(O)NR'R", —NHC(O)C$_{1-4}$alkyl and —NR'R"; or (b) a 5-membered aromatic heterocyclyl selected from the group consisting of thiazolyl, oxazolyl, 1H-pyrazolyl and 1H-imidazolyl, each of which may be optionally substituted with one or two substituents each independently selected from the group consisting of halo, C$_{1-4}$alkyl and NR'R";

R' and R" are each independently selected from hydrogen and C$_{1-4}$alkyl;

R$^3$ is hydrogen; and

R$^4$ is selected from the group consisting of C$_{1-4}$alkyl and —C$_{1-4}$alkyl-O—C$_{1-4}$alkyl;

or a N-oxide, or a pharmaceutically acceptable salt thereof.

5. The method according to claim 1, wherein

R$^1$ is phenyl, optionally substituted with one or two substituents each independently selected from the group consisting of halo, C$_{1-4}$alkyl, monohalo-C$_{1-4}$alkyl, polyhalo-C$_{1-4}$alkyl, —CN, —C$_{1-4}$alkyl-O—C$_{1-4}$alkyl, —O—C$_{1-4}$alkyl, monohalo-C$_{1-4}$alkyloxy and polyhalo-C$_{1-4}$alkyloxy;

or R$^1$ is 2-pyridinyl, optionally substituted with one or two substituents each independently selected from the group consisting of polyhalo-C$_{1-4}$alkyl and —O—C$_{1-4}$alkyl;

R$^2$ is selected from the group consisting of Aryl and Het$^2$; wherein

Aryl is phenyl optionally substituted with one or two substituents each independently selected from the group consisting of halo, C$_{1-4}$alkyl, —O—C$_{1-4}$alkyl, —OH and —C$_{1-4}$alkyl-O—C$_{1-4}$alkyl;

Het$^2$ is (a) a 6-membered aromatic heterocyclyl substituent selected from the group consisting of pyridinyl and pyrazinyl, each of which may be optionally substituted with one or two substituents each independently selected from the group consisting of halo, C$_{1-4}$alkyl, —O—C$_{1-4}$alkyl, —NHC(O)C$_{1-4}$alkyl and —NR'R"; or (b) thiazolyl;

R' and R" are each independently hydrogen;

R$^3$ is hydrogen; and

R$^4$ is selected from the group consisting of C$_{1-4}$alkyl and —C$_{1-4}$alkyl-O—C$_{1-4}$alkyl;

or a N-oxide, or a pharmaceutically acceptable salt thereof.

6. The method according to claim 1, wherein

R' and R" are each independently selected from the group consisting of hydrogen and C$_{1-4}$alkyl;

or a N-oxide, or a pharmaceutically acceptable salt thereof.

7. The method according to claim 1, wherein the compound is of Formula (I'):

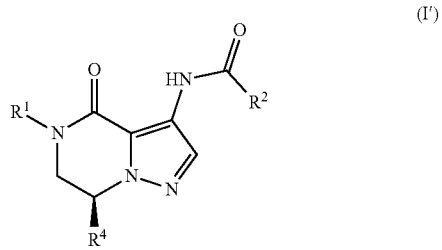

wherein R$^4$ is selected from the group consisting of C$_{1-4}$alkyl, monohalo-C$_{1-4}$alkyl, polyhalo-C$_{1-4}$alkyl, —C$_{1-4}$alkyl-O—C$_{1-4}$alkyl and —C$_{1-4}$alkyl-OH.

8. The method according to claim 1, wherein the compound is

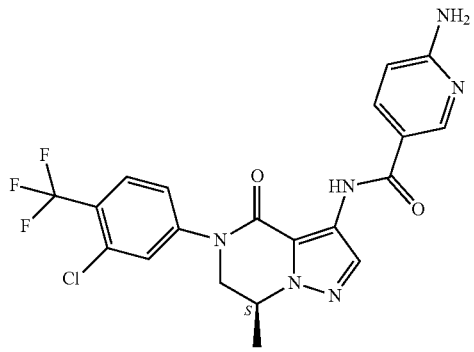

or a pharmaceutically acceptable salt thereof.

9. The method according to claim 1, wherein the compound is

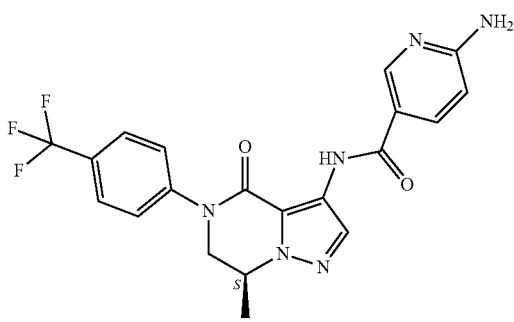

or a pharmaceutically acceptable salt thereof.

10. The method according to claim 1, wherein the compound is

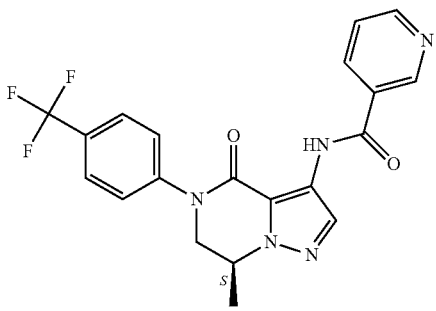

or a pharmaceutically acceptable salt thereof.

11. The method according to claim 1, wherein the compound is or a pharmaceutically acceptable salt thereof.

12. The method according to claim 1, wherein the compound is or a pharmaceutically acceptable salt thereof.

13. The method according to claim 1, wherein the disorder is a neurocognitive disorder.

14. The method according to claim 13, wherein the neurocognitive disorder is selected from the group consisting of a neurocognitive disorder due to Alzheimer's disease, a neurocognitive disorder due to Parkinson's disease, a neurocognitive disorder due to Huntington's disease and a frontotemporal neurocognitive disorder.

15. The method according to claim 14, wherein the neurocognitive disorder is a neurocognitive disorder due to Alzheimer's disease.

16. The method according to claim 15, wherein the neurocognitive disorder due to Alzheimer's disease is dementia.

17. The method according to claim 1, wherein the disorder is a depressive disorder.

18. The method according to claim 17, wherein the depressive disorder is selected form the group consisting of major depressive disorder, treatment resistant depression, persistent depressive disorder and substance-medication-induced depressive disorder.

19. The method according to claim 18, wherein the depressive disorder is major depressive disorder.

20. The method according to claim 18, wherein the depressive disorder is treatment resistant depression.

* * * * *